US011242375B2

(12) United States Patent
Adusumilli et al.

(10) Patent No.: US 11,242,375 B2
(45) Date of Patent: Feb. 8, 2022

(54) IMMUNE CELL COMPOSITIONS AND METHODS OF USE

(71) Applicant: Memorial Sloan Kettering Cancer Center, New York, NY (US)

(72) Inventors: Prasad S. Adusumilli, New York, NY (US); Michel Sadelain, New York, NY (US)

(73) Assignee: Memorial Sloan Kettering Cancer Center, New York, NY (US)

(*) Notice: Subject to any disclaimer, the term of this patent is extended or adjusted under 35 U.S.C. 154(b) by 193 days.

(21) Appl. No.: 15/757,276

(22) PCT Filed: Sep. 2, 2016

(86) PCT No.: PCT/US2016/050128
§ 371 (c)(1),
(2) Date: Mar. 2, 2018

(87) PCT Pub. No.: WO2017/040945
PCT Pub. Date: Mar. 9, 2017

(65) Prior Publication Data
US 2018/0273601 A1    Sep. 27, 2018

Related U.S. Application Data

(60) Provisional application No. 62/214,809, filed on Sep. 4, 2015.

(51) Int. Cl.
*C07K 14/725* (2006.01)
*A61K 35/17* (2015.01)
*C07K 14/705* (2006.01)
*A61K 38/20* (2006.01)
*C07K 16/30* (2006.01)
*C12N 5/0783* (2010.01)
*A61K 39/00* (2006.01)
*A61K 38/19* (2006.01)
(Continued)

(52) U.S. Cl.
CPC .......... *C07K 14/7051* (2013.01); *A61K 35/17* (2013.01); *A61K 35/28* (2013.01); *A61K 38/177* (2013.01); *A61K 38/1774* (2013.01); *A61K 38/193* (2013.01); *A61K 38/2013* (2013.01); *A61K 38/4873* (2013.01); *A61K 39/0011* (2013.01); *A61K 39/00117* (2018.08); *A61K 39/00118* (2018.08); *A61K 39/001104* (2018.08); *A61K 39/001106* (2018.08); *A61K 39/001109* (2018.08); *A61K 39/001112* (2018.08); *A61K 39/001113* (2018.08); *A61K 39/001114* (2018.08); *A61K 39/001119* (2018.08); *A61K 39/001122* (2018.08); *A61K 39/001124* (2018.08); *A61K 39/001126* (2018.08); *A61K 39/001128* (2018.08); *A61K 39/001129* (2018.08); *A61K 39/001153* (2018.08); *A61K 39/001157* (2018.08); *A61K 39/001166* (2018.08); *A61K 39/001168* (2018.08); *A61K 39/001171* (2018.08); *A61K 39/001174* (2018.08); *A61K 39/001182* (2018.08); *A61K 39/001186* (2018.08); *A61K 39/001188* (2018.08); *A61K 39/001192* (2018.08); *A61K 39/001193* (2018.08); *A61K 39/001195* (2018.08); *A61K 39/39558* (2013.01); *A61P 35/00* (2018.01); *C07K 14/70503* (2013.01); *C07K 14/70517* (2013.01); *C07K 14/70521* (2013.01); *C07K 14/70578* (2013.01); *C07K 16/30* (2013.01); *C07K 16/3069* (2013.01); *C12N 5/0636* (2013.01); *C12N 5/0638* (2013.01); *C12N 9/6472* (2013.01); *C12Y 304/22062* (2013.01); *A61K 38/00* (2013.01); *C07K 2317/622* (2013.01); *C07K 2319/02* (2013.01); *C07K 2319/03* (2013.01); *C07K 2319/33* (2013.01); *C07K 2319/74* (2013.01); *C12N 2510/00* (2013.01)

(58) Field of Classification Search
None
See application file for complete search history.

(56) References Cited

U.S. PATENT DOCUMENTS 4,956,778 A    9/1990  Naito
5,091,513 A    2/1992  Huston et al.
(Continued)

FOREIGN PATENT DOCUMENTS

WO    WO 2013/019615 A2    7/2013
WO    WO 2014/055668 A1    4/2014
(Continued)

OTHER PUBLICATIONS

Moon EK et al. (Mol. Therapy May 2014 22(Suppl. 1): S201, Ab. No. 520) (Year: 2014).*
(Continued)

*Primary Examiner* — Peter J Reddig
(74) *Attorney, Agent, or Firm* — Jones Day

(57) ABSTRACT

Disclosed herein are cells that are immune cells or precursor cells thereof, which cells recombinantly express a chimeric antigen receptor (CAR), and a dominant negative form of an inhibitor of a cell-mediated immune response of the immune cell, wherein the CAR binds to a cancer antigen. Also disclosed herein are T cells that recognize and are sensitized to a cancer antigen, which T cells recombinantly express a dominant negative form of an inhibitor of a T cell-mediated immune response. Additionally provided are methods of using such cells to treat cancer in a subject in need thereof.

Figure 1A:
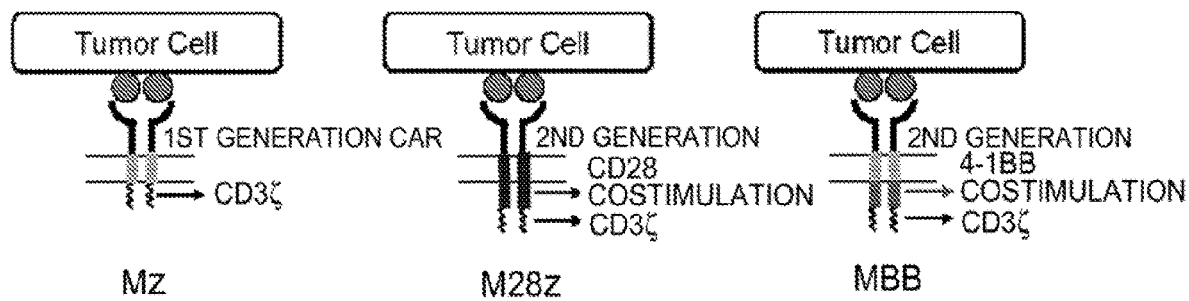

58 Claims, 54 Drawing Sheets
Specification includes a Sequence Listing.

(51) Int. Cl.

| | |
|---|---|
| A61K 35/28 | (2015.01) |
| A61P 35/00 | (2006.01) |
| A61K 38/17 | (2006.01) |
| A61K 38/48 | (2006.01) |
| A61K 39/395 | (2006.01) |
| C12N 9/64 | (2006.01) |
| A61K 38/00 | (2006.01) |

(56) References Cited

U.S. PATENT DOCUMENTS

| | | | |
|---|---|---|---|
| 5,132,405 | A | 7/1992 | Huston et al. |
| 5,399,346 | A | 3/1995 | Anderson et al. |
| 7,446,190 | B2 | 11/2008 | Sadelain et al. |
| 8,357,783 | B2 | 1/2013 | Dimitrov et al. |
| 8,802,374 | B2 | 8/2014 | Jensen |
| 2003/0105000 | A1* | 6/2003 | Pero ............... C07K 14/47 514/19.3 |
| 2005/0196754 | A1 | 9/2005 | Drmanac et al. |
| 2013/0071414 | A1* | 3/2013 | Dotti ............... C12N 5/0636 424/184.1 |
| 2015/0031624 | A1* | 1/2015 | Feldman ......... C07K 14/70517 514/19.3 |
| 2015/0376296 | A1 | 12/2015 | Fedorov et al. |
| 2016/0256488 | A1* | 9/2016 | Wu ................. C07K 16/2803 |
| 2018/0360884 | A1 | 12/2018 | Adusumilli |
| 2020/0010803 | A1 | 1/2020 | Adusumilli |

FOREIGN PATENT DOCUMENTS

| | | |
|---|---|---|
| WO | WO 2014/184744 A1 | 11/2014 |
| WO | WO 2015/188141 A2 | 12/2015 |
| WO | WO 2016/113203 A1 | 7/2016 |
| WO | WO 2016/138846 A1 | 9/2016 |
| WO | WO 2017/040945 A1 | 3/2017 |
| WO | WO 2017/100428 A1 | 6/2017 |
| WO | WO 2018/044866 A1 | 3/2018 |
| WO | WO 2018/165228 A1 | 9/2018 |

OTHER PUBLICATIONS

Zakraweski et al. (Nature Biotechnology Apr. 2008 26(4): 453-461) (Year: 2008).*
Rudikoff et al. (PNAS USA, 1982, 79: 1979-1983) (Year: 1982).*
Coleman et al. (Research in Immunology, 1994; 145(1): 33-36) (Year: 1994).*
Thomas et al., "High mesothelin expression in advanced lung adenocarcinoma is associated with KRAS mutations and a poor prognosis," *Oncotarget*, 6:11694-11703 (2015).
U.S. Appl. No. 16/060,899, filed Jun. 8, 2018, Adusumilli.
Abate-Daga et al., "A novel chimeric antigen receptor against prostate stem cell antigen mediates tumor destruction in a humanized mouse model of pancreatic cancer," *Hum. Gene Ther.*, 25:1003-1012 (2014).
Adusumilli et al., "Imaging and therapy of malignant pleural mesothelioma using replication-competent herpes simplex viruses," *J Gene Med.*, 8(5):603-615 (2006).
Adusumilli et al., "Regional delivery of mesothelin-targeted CAR T cell therapy generates potent and long-lasting CD4-dependent tumor immunity," *Sci. Transl. Med.*, 6(261):261ra151 (2014).
Agarwal et al., "Scaffold attachment region-mediated enhancement of retroviral vector expression in primary T cells," *J. Virol.*, 72:3720-3728 (1998).
Ahmad et al., "scFv antibody: principles and clinical application," *Clin. Dev. Immunol.*, 2012: ID980250 (2012).
Ahmed et al., "HER2-specific T cells target primary glioblastoma stem cells and induce regression of autologous experimental tumors," *Clin. Cancer Res.*, 16:474-485 (2010).
Ahmed et al., "Human Epidermal Growth Factor Receptor 2 (HER2)-Specific Chimeric Antigen Receptor-Modified T Cells for the Immunotherapy of HER2-Positive Sarcoma," *J Clin. Oncol.*, 33:1688-1696 (2015).
Ahmed et al., "Immunotherapy for osteosarcoma: genetic modification of T cells overcomes low levels of tumor antigen expression," *Mol. Ther.*, 17:1779-1787 (2009).
Ahmed et al., "Regression of experimental medulloblastoma following transfer of HER2-specific T cells," *Cancer Res.*, 67:5957-5964 (2007).
Ali et al., "Hiv-1-Specific Chimeric Antigen Receptors Based on Broadly Neutralizing Antibodies," *J Virol.*, 90(15):6999-7006 (2016).
Alvarez et al., "Mesothelin is a specific biomarker of invasive cancer in the Barrett-associated adenocarcinoma progression model: translational implications for diagnosis and therapy," *Nanomedicine*, 4:295-301 (2008).
Amati et al., "Profiling tumor-associated markers for early detection of malignant mesothelioma: an epidemiologic study," *Cancer Epidemiol. Biomarkers Prev.*, 17:163-170 (2008).
Anderson, "Prospects for human gene therapy," *Science*, 226:401-409 (1984).
Ankri et al., "Human T cells engineered to express a programmed death 1/28 costimulatory retargeting molecule display enhanced antitumor activity," *J. Immunol.*, 191(8):4121-4129 (2013).
Arakawa et al., "Targeting of T cells to CEA-expressing tumor cells by chimeric immune receptors with a highly specific single-chain anti-CEA activity," *Anticancer Res.*, 22:4285-4289 (2002).
Argani et al., "Mesothelin is overexpressed in the vast majority of ductal adenocarcinomas of the pancreas: identification of a new pancreatic cancer marker by serial analysis of gene expression (SAGE).," *Clin. Cancer Res.*, 7(12):3862-3868 (2001).
Assenmacher et al., *Cytometric Cytokine Secretion Assay, in Analyzing T Cell Responses: How to Analyze Cellular Immune Responses Against Tumor Associated Antigens*, Nagorsen et al., eds., Springer, The Netherlands, Ch. 10, pp. 183-195 (2005).
Ataca et al., "Chimeric Antigen Receptor T Cell Therapy in Hematology," *Turk. J. Hematol.*, 32:285-294 (2015).
Baba et al., "Mesothelin expression correlates with prolonged patient survival in gastric cancer," *J Surg. Oncol.*, 105:195-199 (2012).
Bakhtiari et al., "Anti-MUC1 nanobody can redirect T-body cytotoxic effector function," *Hybridoma*, 28:85-92 (2009).
Bally et al., "NF-κB regulates PD-1 expression in macrophages," *J Immunol.*, 194:4545-4554 (2015).
Barber et al., "Chimeric NKG2D expressing T cells eliminate immunosuppression and activate immunity within the ovarian tumor microenvironment," *J. Immunol.*, 183:6939-6947 (2009).
Barber et al., "Restoring function in exhausted CD8 T cells during chronic viral infection," *Nature*, 439(7077):682-687 (2006).
Barese et al., "Thymidine kinase suicide gene-mediated ganciclovir ablation of autologous gene-modified rhesus hematopoiesis," *Mol. Therapy*, 20:1932-1943 (2012).
Bayoglu et al., "Prognostic value of mesothelin expression in patients with triple negative and HER2-positive breast cancers," *Biomed. Pharmacother.*, 70:190-195 (2015).
Beard et al., "Multiple chimeric antigen receptors successfully target chondroitin sulfate proteoglycan 4 in several different cancer histologies and cancer stem cells," *J Immunother. Cancer*, 2:25 (2014).
Beatty et al., "Mesothelin-specific chimeric antigen receptor mRNA-engineered T cells induce anti-tumor activity in solid malignancies," *Cancer Immunol. Res.*, 2(2):112-120 (2014).
Beatty, "Engineered chimeric antigen receptor-expressing T cells for the treatment of pancreatic ductal adenocarcinoma," *Oncoimmunology*, 3:e28327 (2014).
Bekaii-Saab et al., "A phase I trial of paclitaxel and trastuzumab in combination with interleukin-12 in patients with HER2/neu-expressing malignancies," *Mol. Cancer Ther.*, 8:2983-2991 (2009).
Bera et al., "Mesothelin is not required for normal mouse development or reproduction," *Mol. Cell. Biol.*, 20:2902-2906 (2000).
Bharadwaj et al., "Mesothelin-induced pancreatic cancer cell proliferation involves alteration of cyclin E via activation of signal transducer and activator of transcription protein 3," *Mol. Cancer Res.*, 6:1755-1765 (2008).
Blomer et al., "Highly efficient and sustained gene transfer in adult neurons with a lentivirus vector," *J. Virol.*, 71:6641-6649 (1997).

(56) References Cited

OTHER PUBLICATIONS

Boggio et al., "Ability of systemic interleukin-12 to hamper progressive stages of mammary carcinogenesis in HER2/neu transgenic mice," *Cancer Res.*, 60:359-364 (2000).
Bollard et al., "Adapting a transforming growth factor beta-related tumor protection strategy to enhance antitumor immunity," *Blood*, 99:3179-3187 (2002).
Borkner et al., "RNA interference targeting programmed death receptor-1 improves immune functions of tumor-specific T cells," *Cancer Immunol. Immunother.*, 59(8):1173-1183 (2010).
Bottinger et al., "Expression of a dominant-negative mutant TGF-beta type II receptor in transgenic mice reveals essential roles for TGF-beta in regulation of growth and differentiation in the exocrine pancreas," *EMBO J.*, 16:2621-2633 (1997).
Bramson et al., "Direct intratumoral injection of an adenovirus expressing interleukin-12 induces regression and long-lasting immunity that is associated with highly localized expression of interleukin-12," *Hum. Gene Ther.*, 7:1995-2002 (1996).
Bregni et al., "Human peripheral blood hematopoietic progenitors are optimal targets of retroviral-mediated gene transfer," *Blood*, 80:1418-1422 (1992).
Brentjens et al., "CD19-targeted T cells rapidly induce molecular remissions in adults with chemotherapy-refractory acute lymphoblastic leukemia," *Sci. Transl. Med.*, 5(177):177ra38 (2013).
Brentjens et al., "Eradication of systemic B-cell tumors by genetically targeted human T lymphocytes co-stimulated by CD80 and interleukin-15," *Nature Medicine*, 9:279-286 (2003).
Brentjens et al., "Genetically targeted T cells eradicate systemic acute lymphoblastic leukemia xenografts," *Clin. Cancer Res.*, 13:5426-5435 (2007).
Brentjens et al., "Safety and persistence of adoptively transferred autologous CD19-targeted T cells in patients with relapsed or chemotherapy refractory B-cell leukemias," *Blood*, 118(18):4817-4828 (2011).
Brown et al., "Bioactivity and Safety of IL13Rα2-Redirected Chimeric Antigen Receptor CD8+ T Cells in Patients with Recurrent Glioblastoma," *Clin. Cancer Res.*, 21(18):4062-4072 (2015).
Brunda et al., "Antitumor and antimetastatic activity of interleukin 12 against murine tumors," *J Exp. Med.*, 178:1223-1230 (1993).
Bunos et al., "Automated isolation of primary antigen-specific T cells from donor lymphocyte concentrates: results of a feasibility exercise," *Vox Sanguinis*, 109:387-393 (2015).
Burga et al., "Liver myeloid-derived suppressor cells expand in response to liver metastases in mice and inhibit the anti-tumor efficacy of anti-CEA CAR-T," *Cancer Immunol. Immunother.*, 64(7):817-829 (2015).
Burns et al., "A high molecular weight melanoma-associated antigen-specific chimeric antigen receptor redirects lymphocytes to target human melanomas," *Cancer Res.*, 70:3027-3033 (2010).
Cao et al., "Expression of mesothelin, fascin, and prostate stem cell antigen in primary ovarian mucinous tumors and their utility in differentiating primary ovarian mucinous tumors from metastatic pancreatic mucinous carcinomas in the ovary," *Int. J Gynecol. Pathol.*, 24:67-72 (2005).
Carpenito et al., "Control of large, established tumor xenografts with genetically retargeted human T cells containing CD28 and CD137 domains," *Proc. Natl. Acad. Sci. U.S.A.*, 106:3360-3365 (2009).
Carter et al., "PD-1:PD-L inhibitory pathway affects both CD4(+) and CD8(+) T cells and is overcome by IL-2," *Eur. J Immunol.*, 32(3):634-643 (2002).
Cayouette et al., "Adenovirus-mediated gene transfer of ciliary neurotrophic factor can prevent photoreceptor degeneration in the retinal degeneration (rd) mouse," *Hum. Gene Ther.*, 8:423-430 (1997).
Chang et al., "Transgene-enforced co-stimulation of CD4+ T cells leads to enhanced and sustained anti-tumor effector functioning," *Cytotherapy*, 9:771-784 (2007).
Chekmasova et al., "Adoptive T cell immunotherapy strategies for the treatment of patients with ovarian cancer," *Discov. Med.*, 9:62-70 (2010).
Chekmasova et al., "Successful eradication of established peritoneal ovarian tumors in SCID-Beige mice following adoptive transfer of T cells genetically targeted to the MUC16 antigen," *Clin. Cancer Res.*, 16(14):3594-3606 (2010).
Chen et al., "Molecular mechanisms of T cell co-stimulation and co-inhibition," *Nat. Rev. Immunol.*, 13(4):227-242 (2013).
Chen, "Mesothelin expression in thymic epithelial tumors (TETs)," *J Clin. Oncol.*, 32:503s, abstract 7607 (2014).
Chen et al., "CAR T-cell intrinsic PD-1 checkpoint blockade: A two-in-one approach for solid tumor immunotherapy," *Oncoimmunology*, 6(2):e1273302 (2017).
Cherkassky et al., "Genetic-Engineering Strategies to Enhance CAR T-Cell Therapy Efficacy against PD-L1 Expressing Lung Adenocarcinoma and Mesothelioma," *J. Thorac. Oncol.*, 10:S794, presented at the World Conference on Lung Cancer, Sep. 6-9, 2015.
Cherkassky et al., "Human CAR T cells with cell-intrinsic PD-1 checkpoint blockade resist tumor-mediated inhibition," *J Clin. Invest.*, 126(8):3130-3144 (2016).
Cheung et al., "Anti-idiotypic antibody facilitates scFv chimeric immune receptor gene transduction and clonal expansion of human lymphocytes for tumor therapy," *Hybrid Hybridomics*, 22:209-218 (2003).
Chicaybam et al., "Chimeric antigen receptors in cancer immuno-gene therapy: current status and future directions," *Int. Rev. Immunol.*, 30(5-6):294-311 (2011).
Chinnasamy et al., "Local delivery of interleukin-12 using T cells targeting VEGF receptor-2 eradicates multiple vascularized tumors in mice," *Clin. Cancer Res.*, 18:1672-1683 (2012).
Chinnasamy et al., "Simultaneous targeting of tumor antigens and the tumor vasculature using T lymphocyte transfer synergize to induce regression of established tumors in mice," *Cancer Res.*, 73:3371-3380 (2013).
Chmielewski et al., "IL-12 release by engineered T cells expressing chimeric antigen receptors can effectively Muster an antigen-independent macrophage response on tumor cells that have shut down tumor antigen expression," *Cancer Res.*, 71:5697-5706 (2011).
Chmielewski et al., "T cell activation by antibody-like immunoreceptors: increase in affinity of the single-chain fragment domain above threshold does not increase T cell activation against antigen-positive target cells but decreases selectivity," *J Immunol.*, 173(12):7647-7653 (2004).
Chmielewski et al., "T cells redirected by a CD3ζ chimeric antigen receptor can establish self-antigen-specific tumour protection in the long term," *Gene Ther.*, 20:177-186 (2013).
Chmielewski et al., "T cells that target carcinoembryonic antigen eradicate orthotopic pancreatic carcinomas without inducing autoimmune colitis in mice.," *Gastroenterology*, 143:1095-1107 (2012).
Chmielewski et al., "TRUCKs: the fourth generation of CARs," *Exp. Opin. Biolog. Ther.*, 15(8):1145-1154 (2015).
Choi et al., "Intracerebral delivery of a third generation EGFRvIII-specific chimeric antigen receptor is efficacious against human glioma," *J Clin. Neurosci.*, 21:189-190 (2014).
Chow et al., "T cells redirected to EphA2 for the immunotherapy of glioblastoma," *Mol. Ther.*, 21:629-637 (2013).
Chuang et al., "The CD28 and CTLA-4 receptors associate with the serine/threonine phosphatase PP2A," *Immunity*, 13(3):313-322 (2000).
Cornetta et al., "Gene transfer into primates and prospects for gene therapy in humans," *Prog. Nucleic Acid Res. Mol. Biol.*, 36:311-322 (1989).
Curran et al., "PD-1 and CTLA-4 combination blockade expands infiltrating T cells and reduces regulatory T and myeloid cells within B16 melanoma tumors," *Proc. Natl. Acad. Sci. U.S.A.*, 107(9):4275-4280 (2010).
Curran et al., "Systemic 4-1BB activation induces a novel T cell phenotype driven by high expression of Eomesodermin," *J Exp. Med.*, 210(4):743-755 (2013).
Curtsinger et al., "Signal 3 determines tolerance versus full activation of naive CD8 T cells: dissociating proliferation and development of effector function," *J Exp. Med.*, 197:1141-1151 (2003).

(56) References Cited

OTHER PUBLICATIONS

Czerniecki et al., "Targeting HER-2/neu in early breast cancer development using dendritic cells with staged interleukin-12 burst secretion," *Cancer Res.*, 67:1842-1852 (2007).
Dainty et al., "Overexpression of folate binding protein and mesothelin are associated with uterine serous carcinoma," *Gynecol. Oncol.*, 105:563-570 (2007).
Danos et al., "Safe and efficient generation of recombinant retroviruses with amphotropic and ecotropic host ranges," *Proc. Natl. Acad. Sci. USA*, 85:6460-6464 (1988).
Darcy et al., "Expression in cytotoxic T lymphocytes of a single-chain anti-carcinoembryonic antigen antibody. Redirected Fas ligand-mediated lysis of colon carcinoma," *Eur J Immunol.*, 28:1663-1672 (1998).
Darcy et al., "Redirected perforin-dependent lysis of colon carcinoma by ex vivo genetically engineered CTL," *J Immunol.*, 164:3705-3712 (2000).
Davies et al., "Flexible targeting of ErbB dimers that drive tumorigenesis by using genetically engineered T cells," *Mol. Med.*, 18:565-576 (2012).
Davila et al., "Efficacy and toxicity management of 19-28z CAR T cell therapy in B cell acute lymphoblastic leukemia," *Sci. Transl. Med.*, 6(224):224ra25 (2014).
Davila et al., "How do CARs work?: Early insights from recent clinical studies targeting CD19," *Oncoimmunol.* 1(9):1577-1583 (2012).
Del Vecchio et al., "Interleukin-12: biological properties and clinical application," *Clin. Cancer Res.*, 13:4677-4685 (2007).
Deng et al., "Adoptive T-cell therapy of prostate cancer targeting the cancer stem cell antigen EpCAM," *BMC Immunol.*, 16:1 (2015).
Deniger et al., "Sleeping Beauty Transposition of Chimeric Antigen Receptors Targeting Receptor Tyrosine Kinase-Like Orphan Receptor-1 (ROR1) into Diverse Memory T-Cell Populations," *PLoS One*, 10:e0128151 (2015).
Dennis et al., "Markers of adenocarcinoma characteristic of the site of origin: development of a diagnostic algorithm," *Clin. Cancer Res.*, 11:3766-3772 (2005).
Di Stasi et al., "Inducible apoptosis as a safety switch for adoptive cell therapy," *N. Engl. J. Med.*, 365:1673-1683 (2011).
Dotti et al., "Design and development of therapies using chimeric antigen receptor-expressing T cells," *Immunol. Reviews*, 257(1):107-126 (2013).
Drapkin et al., "Expression of candidate tumor markers in ovarian carcinoma and benign ovary: evidence for a link between epithelial phenotype and neoplasia" *Hum. Pathol.*, 35:1014-1021 (2004).
Duong et al., "Enhancing the specificity of T-cell cultures for adoptive immunotherapy of cancer," *Immunotherapy*, 3:33-48 (2011).
Dupont et al., "Artificial antigen-presenting cells transduced with telomerase efficiently expand epitope-specific, human leukocyte antigen-restricted cytotoxic T cells," *Cancer Res.*, 65:5417-5427 (2005).
Eglitis et al., "Retroviral vectors for introduction of genes into mammalian cells," *BioTechniques*, 6:608-614 (1988).
Einama et al., "Luminal membrane expression of mesothelin is a prominent poor prognostic factor for gastric cancer," *Br. J Cancer*, 107:137-142 (2012).
Eliopoulos et al., "Neo-organoid of marrow mesenchymal stromal cells secreting interleukin-12 for breast cancer therapy," *Cancer Res.*, 68:4810-4818 (2008).
Emtage et al., "Second-generation anti-carcinoembryonic antigen designer T cells resist activation-induced cell death, proliferate on tumor contact, secrete cytokines, and exhibit superior antitumor activity in vivo: a preclinical evaluation," *Clin. Cancer Res.*, 14:8112-8122 (2008).
Fedorov et al., "PD-1- and CTLA-4-based inhibitory chimeric antigen receptors (iCARs) divert off-target immunotherapy responses," *Sci. Transl. Med.*, 5(215):215ra172 (2013).

Feng et al., "A novel human monoclonal antibody that binds with high affinity to mesothelin-expressing cells and kills them by antibody-dependent cell-mediated cytotoxicity," *Mol. Cancer Ther.*, 8:1113-1118 (2009).
Finney et al., "Chimeric receptors providing both primary and costimulatory signaling in T cells from a single gene product," *J. Immunol.*, 161:2791-2797 (1998).
Foster et al., "Antitumor activity of EBV-specific T lymphocytes transduced with a dominant negative TGF-beta receptor," *J. Immunother.*, 31:500-505 (2008).
Frank et al., "Mesothelin expression in pancreatic mucinous cysts.," *Am. J Clin. Pathol.*, 142:313-319 (2014).
Fransson et al., "CAR/FoxP3-engineered T regulatory cells target the CNS and suppress EAE upon intranasal delivery," *J. Neuroinflammation*, 9:112 (2012).
Freeman et al., "Engagement of the PD-1 immunoinhibitory receptor by a novel B7 family member leads to negative regulation of lymphocyte activation," *J Exp. Med.*, 192(7):1027-1034 (2000).
Friedman, "Progress toward human gene therapy," *Science*, 244:1275-1281 (1989).
Frierson et al., "Large-scale molecular and tissue microarray analysis of mesothelin expression in common human carcinomas," *Hum. Pathol.*, 34(6):605-609 (2003).
Gade et al., "Targeted elimination of prostate cancer by genetically directed human T lymphocytes," *Cancer Res.*, 65:9080-9088 (2005).
Galloway et al., "The use of the monoclonal antibody mesothelin in the diagnosis of malignant mesothelioma in pleural biopsies," *Histopathology*, 48:767-769 (2006).
Gao et al., "Development of T cells redirected to glypican-3 for the treatment of hepatocellular carcinoma," *Clin. Cancer Res.*, 20:6418-6428 (2014).
Geldres et al., "T lymphocytes redirected against the chondroitin sulfate proteoglycan-4 control the growth of multiple solid tumors both in vitro and in vivo," *Clin. Cancer Res.*, 20:962-971 (2014).
GenBank Accession No. AAH69566.1, "Cytotoxic T-lymphocyte-associated protein 4 [*Homo sapiens*]," (Jul. 15, 2006).
GenBank Accession No. AAP44003.1, "B and T lymphocyte attenuator [*Homo sapiens*]," (Jun. 18, 2003).
GenBank Accession No. AAV87530.1, "mesothelin precursor [*Homo sapiens*]," (Jan. 7, 2009).
GenBank Accession No. AH002818.2, "*Homo sapiens* FKBP12C (FKBP12) gene, FK506-binding protein 12 (FKBP12) gene, complete cds; and FKBP12A (FKBP12) gene, complete sequence," (Jun. 10, 2016).
GenBank Accession No. CAA36243.3, "LAG-3 protein precursor [*Homo sapiens*]," (Sep. 12, 2001).
GenBank Accession No. NM_001229.4, "*Homo sapiens* caspase 9, apoptosis-related cysteine peptidase (CASP9), transcript variant alpha, mRNA," (Mar. 15, 2015).
GenBank Accession No. NP_000607.1, "T-cell surface glycoprotein CD4 isoform 1 precursor [*Homo sapiens*]," (Apr. 23, 2016).
GenBank Accession No. NP_001020018.1, "TGF-beta receptor type-2 isoform A precursor [*Homo sapiens*]," (Apr. 30, 2016).
GenBank Accession No. NP_001139345.1, "T-cell surface glycoprotein CD8 alpha chain isoform 1 precursor [*Homo sapiens*]," (Mar. 15, 2015).
GenBank Accession No. NP_001160135.1, "natural killer cell receptor 2B4 isoform 2 precursor [*Homo sapiens*]," (Jan. 8, 2016).
GenBank Accession No. NP_001181943.1, "T-cell surface glycoprotein CD4 isoform 2 [*Homo sapiens*]," (Mar. 15, 2015).
GenBank Accession No. NP_001181944.1, "T-cell surface glycoprotein CD4 isoform 3 [*Homo sapiens*]," (Mar. 15, 2015).
GenBank Accession No. NP_001181945.1, "T-cell surface glycoprotein CD4 isoform 3 [*Homo sapiens*]," (Mar. 15, 2015).
GenBank Accession No. NP_001181946.1, "T-cell surface glycoprotein CD4 isoform 3 [*Homo sapiens*]," (Mar. 15, 2015).
GenBank Accession No. NP_001275952.2, "leukocyte-associated immunoglobulin-like receptor 1 isoform c precursor [*Homo sapiens*]," (Aug. 28, 2016).
GenBank Accession No. NP_001275954.2, "leukocyte-associated immunoglobulin-like receptor 1 isoform e precursor [*Homo sapiens*]," (Aug. 28, 2016).

(56) References Cited

OTHER PUBLICATIONS

GenBank Accession No. NP_001275955.2, "leukocyte-associated immunoglobulin-like receptor 1 isoform f [*Homo sapiens*]," (Aug. 28, 2016).
GenBank Accession No. NP_001275956.2, "leukocyte-associated immunoglobulin-like receptor 1 isoform g [*Homo sapiens*]," (Aug. 28, 2016).
GenBank Accession No. NP_001552.2, "tumor necrosis factor receptor superfamily member 9 precursor [*Homo sapiens*]," (Sep. 1, 2016).
GenBank Accession No. NP_002277.4, "lymphocyte activation gene 3 protein precursor [*Homo sapiens*]," (Jan. 23, 2016).
GenBank Accession No. NP_002278.2, "leukocyte-associated immunoglobulin-like receptor 1 isoform a precursor [*Homo sapiens*]," (Aug. 28, 2016).
GenBank Accession No. NP_003318.1, "tumor necrosis factor receptor superfamily member 4 precursor [*Homo sapiens*]," (Sep. 1, 2016).
GenBank Accession No. NP_005009.2, "programmed cell death protein 1 precursor [*Homo sapiens*]," (Mar. 15, 2015).
GenBank Accession No. NP_005205.2, "cytotoxic T-lymphocyte protein 4 isoform CTLA4-TM precursor [*Homo sapiens*]," (Aug. 28, 2016).
GenBank Accession No. NP_006130.1, "T-cell-specific surface glycoprotein CD28 isoform 1 precursor [*Homo sapiens*]," (Mar. 15, 2015).
GenBank Accession No. NP_008984.1, "160 antigen precursor [*Homo sapiens*]," (Mar. 15, 2015).
GenBank Accession No. NP_036224.1, "inducible T-cell costimulator precursor [*Homo sapiens*]," (May 30, 2016).
GenBank Accession No. NP_055081.1, "hematopoietic cell signal transducer isoform 1 precursor [*Homo sapiens*]," (Mar. 15, 2015).
GenBank Accession No. NP_068352.2, "leukocyte-associated immunoglobulin-like receptor 1 isoform b precursor [*Homo sapiens*]," (Aug. 28, 2016).
GenBank Accession No. NP_116171.3, "hepatitis a virus cellular receptor 2 precursor [*Homo sapiens*]," (Sep. 1, 2016).
GenBank Accession No. NP_776160.2, "T-cell immunoreceptor with Ig and ITIM domains precursor [*Homo sapiens*]," (Aug. 28, 2016).
GenBank Accession No. NP_861445.3, "B- and T-lymphocyte attenuator isoform 1 precursor [*Homo sapiens*]," (Sep. 1, 2016).
GenBank Accession No. NP_932170.1, "T-cell surface glycoprotein CD3 zeta chain isoform 1 precursor [*Homo sapiens*]," (Mar. 15, 2015).
GenBank Accession No. P10747.1, "T-cell-specific surface glycoprotein CD28," (Jul. 6, 2016).
GenBank Accession No. P41273.1, "Tumor necrosis factor ligand superfamily member 9," (Jul. 6, 2016).
GenBank Accession No. P43489.1, "Tumor necrosis factor receptor superfamily member 4," (Jul. 6, 2016).
Gersbach et al., "Targeted plasmid integration into the human genome by an engineered zinc-finger recombinase," *Nucl. Acids Res.*, 39:7868-7878 (2011).
Gierasch, "Signal sequences," *Biochem.*, 28:923-930 (1989).
Gilham et al., "Primary polyclonal human T lymphocytes targeted to carcino-embryonic antigens and neural cell adhesion molecule tumor antigens by CD3zeta-based chimeric immune receptors," *J Immunother.*, 25:139-151 (2002).
Gong et al., "Cancer patient T cells genetically targeted to prostate-specific membrane antigen specifically lyse prostate cancer cells and release cytokines in response to prostate-specific membrane antigen," *Neoplasia*, 1:123-127 (1999).
Greco et al., "Improving the safety of cell therapy with the TK-suicide gene," *Frontiers Pharmacol.*, 6:95 (2015).
Grupp et al., "Chimeric antigen receptor-modified T cells for acute lymphoid leukemia," *N. Engl. J. Med.*, 368(16):1509-1518 (2013).
Gubbels et al., "Mesothelin-MUC16 binding is a high affinity, N-glycan dependent interaction that facilitates peritoneal metastasis of ovarian tumors," *Mol. Cancer*, 5(1):50 (2006).

Guedan et al., "ICOS-based chimeric antigen receptors program bipolar TH17/TH1 cells," *Blood*, 124:1070-1080 (2014).
Gyobu et al., "Generation and targeting of human tumor-specific Tc1 and Th1 cells transduced with a lentivirus containing a chimeric immunoglobulin T-cell receptor," *Cancer Res.*, 64:1490-1495 (2004).
Gyorffy et al., "Combined treatment of a murine breast cancer model with type 5 adenovirus vectors expressing murine angiostatin and IL-12: a role for combined anti-angiogenesis and immunotherapy," *J Immunol.*, 166:6212-6217 (2001).
Hamid et al., "A prospective phase II trial exploring the association between tumor microenvironment biomarkers and clinical activity of ipilimumab in advanced melanoma," *J. Translational Med.*, 9(204) doi: 10.1186/1479-5876-9-204 (2011).
Haney et al., "Isolation of viable antigen-specific CD8+ T cells based on membrane-bound tumor necrosis factor (TNF)-α expression," *J. Immunol. Methods*, 369:33-41 (2011).
Hassan et al., "Localization of mesothelin in epithelial ovarian cancer," *Appl. Immunohistochem. Mol. Morphol.* 13:243-247 (2005).
Hassan et al., "Mesothelin is overexpressed in pancreaticobiliary adenocarcinomas but not in normal pancreas and chronic pancreatitis," *Am. J. Clin. Pathol.*, 124:838-845 (2005).
Hassan et al., "Mesothelin targeted cancer immunotherapy," *Eur. J. Cancer*, 44:46-53 (2008).
Hassan et al., "Phase I study of SS1P, a recombinant anti-mesothelin immunotoxin given as a bolus I.V. infusion to patients with mesothelin-expressing mesothelioma, ovarian, and pancreatic cancers," *Clin. Cancer Res.*, 13:5144-5149 (2007).
Haynes et al., "Fas-ligand-mediated lysis of erbB-2-expressing tumour cells by redirected cytotoxic T lymphocytes," *Cancer Immunol. Immunother.*, 47:278-286 (1999).
Haynes et al., "Redirecting mouse CTL against colon carcinoma: superior signaling efficacy of single-chain variable domain chimeras containing TCR-zeta vs Fc epsilon RI-gamma," *J Immunol.*, 166:182-187 (2001).
Haynes et al., "Rejection of syngeneic colon carcinoma by CTLs expressing single-chain antibody receptors codelivering CD28 costimulation," *J Immunol.*, 169:5780-5786 (2002).
Hegde et al., "Combinational targeting offsets antigen escape and enhances effector functions of adoptively transferred T cells in glioblastoma," *Mol. Ther.*, 21:2087-2101 (2013).
Hillerdal et al., "Systemic treatment with CAR-engineered T cells against PSCA delays subcutaneous tumor growth and prolongs survival of mice," *BMC Cancer*, 14:30 (2014).
Hirschhorn-Cymerman et al., "Induction of tumoricidal function in CD4+ T cells is associated with concomitant memory and terminally differentiated phenotype," *J Exp. Med.*, 209(11):2113-2126 (2012).
Ho et al., "Humoral immune response to mesothelin in mesothelioma and ovarian cancer patients," *Clin. Cancer Res.*, 11:3814-3820 (2005).
Hodi et al., "Improved survival with ipilimumab in patients with metastatic melanoma," *N. Engl. J Med.*, 363(8):711-723 (2010).
Hollyman et al., "Manufacturing validation of biologically functional T cells targeted to CD19 antigen for autologous adoptive cell therapy," *J. Immunother.*, 32:169-180 (2009).
Hombach et al., "A chimeric receptor that selectively targets membrane-bound carcinoembryonic antigen (mCEA) in the presence of soluble CEA," *Gene Ther.*, 6:300-304 (1999).
Hombach et al., "T cell activation by antibody-like immunoreceptors: the position of the binding epitope within the target molecule determines the efficiency of activation of redirected T cells," *J Immunol.*, 178(7):4650-4657 (2007).
Hombach et al., "T cell targeting of TAG72+ tumor cells by a chimeric receptor with antibody-like specificity for a carbohydrate epitope," *Gastroenterology*, 113:1163-1170 (1997).
Hong et al., "Diverse solid tumors expressing a restricted epitope of L1-CAM can be targeted by chimeric antigen receptor redirected T lymphocytes," *J. Immunother.*, 37:93-104 (2014).
Huang et al., "Genetically modified T cells targeting interleukin-11 receptor α-chain kill human osteosarcoma cells and induce the regression of established osteosarcoma lung metastases," *Cancer Res.*, 72:271-281 (2012).

(56) References Cited

OTHER PUBLICATIONS

Hudecek et al., "Receptor affinity and extracellular domain modifications affect tumor recognition by ROR1-specific chimeric antigen receptor T cells," *Clin. Cancer Res.*, 19:3153-3164 (2013).
Hughes et al. "Retroviral gene transfer to primitive normal and leukemic hematopoietic cells using clinically applicable procedures," *J. Clin. Invest.*, 89:1817-1824 (1992).
Huse et al., "Generation of a large combinatorial library of the immunoglobulin repertoire in phage lambda," *Science*, 246:1275-1281 (1989).
Huston et al., "Protein engineering of antibody binding sites: recovery of specific activity in an anti-digoxin single-chain Fv analogue produced in *Escherichia coli*," *Proc. Nat. Acad. Sci. USA*, 85:5879-5883 (1988).
Inami et al., "Secretion of N-ERC/mesothelin and expression of C-ERC/mesothelin in human pancreatic ductal carcinoma," *Oncol. Rep.*, 20:1375-1380 (2008).
International Search Report for International Application No. PCT/US2016/050128 dated Feb. 2, 2017.
International Search Report for International Application No. PCT/US2016/065578 dated May 3, 2017.
International Search Report for International Application No. PCT/US2017/049085 dated Jan. 11, 2018.
International Search Report for International Application No. PCT/US2018/021249 dated Aug. 10, 2018.
Ito et al., "ERC/mesothelin is expressed in human gastric cancer tissues and cell lines," *Oncol. Rep.*, 31:27-33 (2014).
James et al., "Antigen sensitivity of CD22-specific chimeric TCR is modulated by target epitope distance from the cell membrane," *J Immunol.*, 180(10):7028-7038 (2008).
James et al., "Mathematical modeling of chimeric TCR triggering predicts the magnitude of target lysis and its impairment by TCR downmodulation," *J Immunol.*, 184(8):4284-4294 (2010).
Jensen et al., "Design and implementation of adoptive therapy with chimeric antigen receptor-modified T cells," *Immunol. Rev.*, 257:127-133 (2014).
Ji et al., "An immune-active tumor microenvironment favors clinical response to ipilimumab," *Cancer Immunol. Immunother.*, 61(7):1019-1031 (2012).
John et al., "Anti-PD-1 antibody therapy potently enhances the eradication of established tumors by gene-modified T cells," *Clin. Cancer Res.*, 19(20):5636-5646 (2013).
Johnson et al., "Rational development and characterization of humanized anti-EGFR variant III chimeric antigen receptor T cells for glioblastoma," *Sci. Transl. Med.*, 7:275ra22 (2015).
Johnson, "Gene therapy for cystic fibrosis," *Chest*, 107:77S-83S (1995).
Jutz et al., "Assessment of costimulation and coinhibition in a triple parameter T cell reporter line: Simultaneous measurement of NF-κB, NFAT and AP-1.," *J Immunol. Methods*, 430:10-20. doi: 10.1016/j.jim.2016.01.007 (2016).
Kachala et al., "Mesothelin overexpression is a marker of tumor aggressiveness and is associated with reduced recurrence-free and overall survival in early-stage lung adenocarcinoma," Clin. Cancer Res., 20(4):1020-1028 (2014).
Kailayangiri et al., "The ganglioside antigen G(D2) is surface-expressed in Ewing sarcoma and allows for MHC-independent immune targeting," *Br. J Cancer*, 106:1123-1133 (2012).
Kaiser et al., "Towards a commercial process for the manufacture of genetically modified T cells for therapy," *Cancer Gene Therapy*, 22:72-78 (2015).
Kakarla et al., "Antitumor effects of chimeric receptor engineered human T cells directed to tumor stroma," *Mol. Ther.*, 21:1611-1620 (2013).
Kalos et al., "T cells with chimeric antigen receptors have potent antitumor effects and can establish memory in patients with advanced leukemia," *Sci. Transl. Med.*, 3(95):95ra73 (2011).
Kanagawa et al., "Tumor vessel-injuring ability improves antitumor effect of cytotoxic T lymphocytes in adoptive immunotherapy," *Cancer Gene Ther.*, 20:57-64 (2013).
Kandalaft et al., "A phase I clinical trial of adoptive transfer of folate receptor-alpha redirected autologous T cells for recurrent ovarian cancer," *J Transl. Med.*, 10:157 (2012).
Kaneko et al., "A binding domain on mesothelin for CA125/MUC16," *J. Biol. Chem.*, 284:3739-3749 (2009).
Kang et al., "Interleukin 12 gene therapy of cancer by peritumoral injection of transduced autologous fibroblasts: outcome of a phase I study," *Hum. Gene Ther.*, 12:671-684 (2001).
Kao et al., "Transcription factor T-bet represses expression of the inhibitory receptor PD-1 and sustains virus-specific CD8+ T cell responses during chronic infection," *Nat. Immunol.*, 12(7):663-671 (2011).
Katz et al., "Phase I Hepatic Immunotherapy for Metastases Study of Intra-Arterial Chimeric Antigen Receptor-Modified T-cell Therapy for CEA+ Liver Metastases," *Clin. Cancer Res.*, 21:3149-3159 (2015).
Kawamata et al., "C-ERC/mesothelin provokes lymphatic invasion of colorectal adenocarcinoma," *J Gastroenterol.*, 49:81-92 (2014).
Kawamata et al., "Intracellular localization of mesothelin predicts patient prognosis of extrahepatic bile duct cancer," *Int. J Oncol.*, 41:2109-2118 (2012).
Kelly et al., "Mesothelin-targeted agents in clinical trials and in preclinical development," *Mol. Cancer Ther.*, 11:517-525 (2012).
Kershaw et al., "A phase I study on adoptive immunotherapy using gene-modified T cells for ovarian cancer," *Clin. Cancer Res.*, 12:6106-6115 (2006).
Kershaw et al., "Gene-engineered T cells as a superior adjuvant therapy for metastatic cancer," *J Immunol.*, 173:2143-2150 (2004).
Kido et al., "Use of a retroviral vector with an internal opsin promoter to direct gene expression to retinal photoreceptor cells," *Curr. Eye Res.*, 15:833-844 (1996).
Kobayashi et al., "A chimeric antigen receptor for TRAIL-receptor 1 induces apoptosis in various types of tumor cells," *Biochem. Biophys. Res. Commun.* 453:798-803 (2014).
Koehler et al., "CD28 costimulation overcomes transforming growth factor-beta-mediated repression of proliferation of redirected human CD4+ and CD8+ T cells in an antitumor cell attack," *Cancer Res.*, 67(5):2265-2273 (2007).
Koneru et al., "IL-12 secreting tumor-targeted chimeric antigen receptor T cells eradicate ovarian tumors in vivo," *Oncoimmunology*, 4:e994446 (2015).
Kong et al., "Suppression of human glioma xenografts with second-generation IL13R-specific chimeric antigen receptor-modified T cells," *Clin. Cancer Res.*, 18:5949-5960 (2012).
Krause et al., "Antigen-dependent CD28 signaling selectively enhances survival and proliferation in genetically modified activated human primary T lymphocytes," *J Exp. Med.*, 188:619-626 (1998).
Krebs et al., "T cells redirected to interleukin-13Rα2 with interleukin-13 mutein—chimeric antigen receptors have anti-glioma activity but also recognize interleukin-13Rα1," Cytotherapy, 16:1121-1131 (2014).
Krishnamurthy et al., "Genetic Engineering of T Cells to Target HERV-K, an Ancient Retrovirus on Melanoma," *Clin. Cancer Res.*, 21:3241-3251 (2015).
Kushitani et al "Immunohistochemical marker panels for distinguishing between epithelioid mesothelioma and lung adenocarcinomam," *Pathol. Int.*, 57:190-199 (2007).
Lamers et al "Immune responses to transgene and retroviral vector in patients treated with ex vivo-engineered T cells," *Blood*, 117(1):72-82 (2011).
Lamers et al., "Treatment of metastatic renal cell carcinoma with CAIX CAR-engineered T cells: clinical evaluation and management of on-target toxicity," *Mol Ther.*, 21:904-912 (2013).
Lanitis et al., "Primary human ovarian epithelial cancer cells broadly express HER2 at immunologically-detectable levels," *PLoS One*, 7:e49829 (2012).
Lanitis et al., "Redirected antitumor activity of primary human lymphocytes transduced with a fully human anti-mesothelin chimeric receptor," *Mol. Ther.*, 20:633-643 (2012).
Latchman et al., "PD-L1-deficient mice show that PD-L1 on T cells, antigen-presenting cells, and host tissues negatively regulates T cells," *Proc. Natl. Acad. Sci. USA*, 101(29):10691-10696 (2004).

(56) References Cited

OTHER PUBLICATIONS

Latouche et al., "Induction of human cytotoxic T lymphocytes by artificial antigen-presenting cells," *Nat. Biotechnol.*, 18:405-409 (2000).
Lazovic et al., "Imaging immune response in vivo: cytolytic action of genetically altered T cells directed to glioblastoma multiforme" *Clin. Cancer Res.*, 14:3832-3839 (2008).
Le Gal La Salle et al., "An adenovirus vector for gene transfer into neurons and glia in the brain," *Science*, 259:988-990 (1993).
Le Mercier et al., "Beyond CTLA-4 and PD-1, the Generation Z of Negative Checkpoint Regulators," *Front. Immunol.*, 6:418 (2015).
Lenzi et al., "Phase I study of intraperitoneal recombinant human interleukin 12 in patients with Miillerian carcinoma, gastrointestinal primary malignancies, and mesothelioma," *Clin. Cancer Res.*, 8:3686-3695 (2002).
Lenzi et al., "Phase II study of intraperitoneal recombinant interleukin-12 (rhIL-12) in patients with peritoneal carcinomatosis (residual disease < 1 cm) associated with ovarian cancer or primary peritoneal carcinoma," *J Transl. Med.*, 5:66 (2007).
Li et al., "Genetically engineered T cells expressing a HER2-specific chimeric receptor mediate antigen-specific tumor regression," *Cancer Gene Ther.*, 15:382-392 (2008).
Li et al., "Mesothelin expression is associated with poor outcomes in breast cancer," *Breast Cancer Res. Treat.*, 147:675-684 (2014).
Li et al., "Mesothelin is a malignant factor and therapeutic vaccine target for pancreatic cancer," *Mol. Cancer Ther.*, 7(2):286-296 (2008).
Liebig et al., "Forced expression of deltaN-TCF-1B in colon cancer derived cell lines is accompanied by the induction of CEACAM5/6 and mesothelin," *Cancer Lett.*, 223:159-167 (2005).
Liu et al., "A Chimeric Switch-Receptor Targeting PD1 Augments the Efficacy of Second-Generation Cart Cells in Advanced Solid Tumors," *Cancer Res.*, 76:1578-1590 (2016).
Liu et al., "PD-1/PD-L1 expression on CD(4+) T cells and myeloid DCs correlates with the immune pathogenesis of atrial fibrillation," *J. Cell. Mol. Med.*, 19(6):1223-1233 (2015).
Lo et al., "Anti-GD3 chimeric sFv-CD28/T-cell receptor zeta designer T cells for treatment of metastatic melanoma and other neuroectodermal tumors," *Clin. Cancer Res.*, 16:2769-2780 (2010).
Long et al., "4-1BB costimulation ameliorates T cell exhaustion induced by tonic signaling of chimeric antigen receptors," *Nat. Med.*, 21(6):581-590 (2015).
Louis et al., "Antitumor activity and long-term fate of chimeric antigen receptor-positive T cells in patients with neuroblastoma," *Blood*, 118:6050-6056 (2011).
Ma et al., "Anti-prostate specific membrane antigen designer T cells for prostate cancer therapy," *Prostate*, 61:12-25 (2004).
Magnani et al., "Donor-derived CD19-targeted T cells in allogeneic transplants," *Curr. Opin. Hematol.*, 22(6):497-502 (2015).
Maher et al., "Human T-lymphocyte cytotoxicity and proliferation directed by a single chimeric TCRzeta /CD28 receptor," *Nat. Biotechnol.*, 20:70-75 (2002).
Mahvi et al., "Intratumoral injection of IL-12 plasmid DNA—results of a phase I/IB clinical trial," *Cancer Gene Ther.*, 14:717-723 (2007).
Maliar et al., "Redirected T cells that target pancreatic adenocarcinoma antigens eliminate tumors and metastases in mice," *Gastroenterology*, 143:1375-1384 (2012).
Markley et al., "IL-7 and IL-21 are superior to IL-2 and IL-15 in promoting human T cell-mediated rejection of systemic lymphoma in immunodeficient mice," *Blood*, 115(17):3508-3519 (2010).
Maus et al., "T cells expressing chimeric antigen receptors can cause anaphylaxis in humans," *Cancer Immunol. Res.*, 1(1):26-31 (2013).
McCoy et al., "Chromium-release assay for cell-mediated cytotoxicity of human leukemia and lymphoid tissue-culture cells," *Natl. Cancer Inst. Monogr.*, 37:59-67 (1973).
McGray et al "Immunotherapy-induced CD8+ T cells instigate immune suppression in the tumor," *Mol. Ther.*, 22(1):206-218 (2014).
McGuinness et al., "Anti-tumor activity of human T cells expressing the CC49-zeta chimeric immune receptor," *Hum Gene Ther.*, 10:165-173 (1999).
Memorial Sloan Kettering Cancer Center, "Malignant Pleural Disease Treated With Autologous T Cells Genetically Engineered to Target the Cancer-Cell Surface Antigen Mesothelin," ClinicalTrials.gov archive, pp. 1-10 (Apr. 12, 2018). Retrieved from the Internet: https://clinicaltrials.gov/ct2/show/NCT02414269, on Aug. 3, 2018.
Miao et al., "EGFRvIII-specific chimeric antigen receptor T cells migrate to and kill tumor deposits infiltrating the brain parenchyma in an invasive xenograft model of glioblastoma," *PLoS One*, 9:e94281 (2014).
Miettinen et al., "Expression of calretinin, thrombomodulin, keratin 5, and mesothelin in lung carcinomas of different types: an immunohistochemical analysis of 596 tumors in comparison with epithelioid mesotheliomas of the pleura," *Am. J Surg. Pathol.*, 27:150-158 (2003).
Miller et al., "Generation of helper-free amphotropic retroviruses that transduce a dominant-acting, methotrexate-resistant dihydrofolate reductase gene," *Mol. Cell. Biol.*, 5:431-437 (1985).
Miller et al., "Improved Retroviral Vectors for Gene Transfer and Expression," *Biotechniques*, 7:980-990 (1989).
Miller et al., "Redesign of retrovirus packaging cell lines to avoid recombination leading to helper virus production," *Mol. Cell. Biol.*, 6:2895-2902 (1986).
Miller, "Retrovirus packaging cells," *Hum. Gene Ther.*, 1(1):5-14 (1990).
Miller et al., "CD19-Targeted CAR T Cells: A New Tool in the Fight against B Cell Malignancies," *Oncol. Res. Treat.*, 38:683-690 (2015).
Miyoshi et al., "Stable and efficient gene transfer into the retina using an HIV-based lentiviral vector," *Proc. Natl. Acad. Sci. U.S.A.*, 94:10319-10323 (1997).
Moen, "Directions in gene therapy," *Blood Cells*, 17:407-416 (1991).
Montes et al., "Optimum in vitro expansion of human antigen-specific CD8 T cells for adoptive transfer therapy," *Clin. Exp. Immunol.* 142:292-302 (2005).
Moon et al., "Blockade of Programmed Death 1 Augments the Ability of Human T Cells Engineered to Target NY-ESO-1 to Control Tumor Growth after Adoptive Transfer," *Clin. Cancer Res.*, 22(2):436-447 (2016).
Moon et al., "Expression of a functional CCR2 receptor enhances tumor localization and tumor eradication by retargeted human T cells expressing a mesothelin-specific chimeric antibody receptor," *Clin. Cancer Res.*, 17:4719-4730 (2011).
Moon et al., "Multifactorial T-cell hypofunction that is reversible can limit the efficacy of chimeric antigen receptor-transduced human T cells in solid tumors," *Clin. Cancer Res.*, 20(16):4262-4273 (2014).
Morgan et al., "Cancer regression in patients after transfer of genetically engineered lymphocytes," *Science*, 314:126-129 (2006).
Morgan et al., "Recognition of glioma stem cells by genetically modified T cells targeting EGFRvIII and development of adoptive cell therapy for glioma," *Hum. Gene Ther.*, 23:1043-1053 (2012).
Morgenroth et al., "Targeting of tumor cells expressing the prostate stem cell antigen (PSCA) using genetically engineered T-cells," *Prostate*, 67:1121-1131 (2007).
Moritz et al., "Cytotoxic T lymphocytes with a grafted recognition specificity for ERBB2-expressing tumor cells," *Proc. Natl. Acad. Sci. U.S.A.*, 91:4318-4322 (1994).
Movassagh et al., "Retrovirus-mediated gene transfer into T cells: 95% transduction efficiency without further in vitro selection," *Hum. Gene Ther.*, 11:1189-1200 (2000).
Mueller et al., "High antigen levels are the cause of T cell exhaustion during chronic viral infection," *Proc. Natl. Acad. Sci. U.S.A.*, 106(21):8623-8628 (2009).
Naldini et al., "In Vivo Gene Delivery and Stable Transduction of Nondividing Cells by a Lentiviral Vector," *Science*, 272:263-267 (1996).
Nanni et al., "Combined allogeneic tumor cell vaccination and systemic interleukin 12 prevents mammary carcinogenesis in HER-2/neu transgenic mice," *J. Exp. Med.*, 194:1195-1205 (2001).

(56) References Cited

OTHER PUBLICATIONS

National Cancer Institute, "CAR T Cell Receptor Immunotherapy Targeting Mesothelin for Patients With Metastatic Cancer," ClinicalTrials.gov archive, pp. 1-12 (Aug. 3, 2018). Retrieved from the Internet: https://clinicaltrials.gov/ct2/show/NCT01583686, on Aug. 3, 2018.

Neeson et al., "Ex vivo culture of chimeric antigen receptor T cells generates functional CD8+ T cells with effector and central memory-like phenotype" *Gene Ther.*, 17:1105-1116 (2010).

Nesbeth et al., "CD4+ T cells elicit host immune responses to MHC class II-negative ovarian cancer through CCL5 secretion and CD40-mediated licensing of dendritic cells," *J. Immunol.*, 184(10):5654-5662 (2010).

Nolan et al., "Bypassing immunization: optimized design of "designer T cells" against carcinoembryonic antigen (CEA)-expressing tumors, and lack of suppression by soluble CEA," *Clin Cancer Res.*, 5:3928-3941 (1999).

Nomura et al., "Mesothelin expression is a prognostic factor in cholangiocellular carcinoma," *Int. Surg.*, 98:164-169 (2013).

Obulhasim et al., "Mesothelin gene expression and promoter methylation/hypomethylation in gynecological tumors," *Eur. J Gynaecol. Oncol.*, 31:63-71 (2010).

Ohno et al., "Expression of miR-17-92 enhances anti-tumor activity of T-cells transduced with the anti-EGFRvIII chimeric antigen receptor in mice bearing human GBM xenografts," *J Immunother. Cancer*, 1:21 (2013).

Ohno et al., "Retrovirally engineered T-cell-based immunotherapy targeting type III variant epidermal growth factor receptor, a glioma-associated antigen," *Cancer Sci.*, 101:2518-2524 (2010).

Ordonez et al., "Diagnostic utility of immunohistochemistry in distinguishing between epithelioid pleural mesotheliomas and breast carcinomas: a comparative study," *Hum. Pathol.*, 45:1529-1540 (2014).

Ordonez, "Application of mesothelin immunostaining in tumor diagnosis," *Am. J Surg. Pathol.*, 27:1418-1428 (2003).

Ordonez, "The diagnostic utility of immunohistochemistry in distinguishing between epithelioid mesotheliomas and squamous carcinomas of the lung: a comparative study," *Mod. Pathol.*, 19:417-428 (2006).

Ordonez, "The diagnostic utility of immunohistochemistry in distinguishing between mesothelioma and renal cell carcinoma: a comparative study," *Hum. Pathol.*, 35:697-710 (2004).

Ordonez, "The immunohistochemical diagnosis of mesothelioma: a comparative study of epithelioid mesothelioma and lung adenocarcinoma," *Am. J Surg. Pathol.*, 27:1031-1051 (2003).

Ordonez, "Value of mesothelin immunostaining in the diagnosis of mesothelioma," *Mod. Pathol.*, 16:192-197 (2003).

Palumbo et al., "Molecular targets and targeted therapies for malignant mesothelioma," *Curr. Med. Chem.*, 15:855-867 (2008).

Pan et al., "Expression of calretinin and other mesothelioma-related markers in thymic carcinoma and thymoma," *Hum. Pathol.*, 34:1155-1162 (2003).

Panelli et al., "A tumor-infiltrating lymphocyte from a melanoma metastasis with decreased expression of melanoma differentiation antigens recognizes MAGE-12," *J Immunol.*, 164:4382-4392 (2000).

Panelli et al., "Expansion of tumor-T cell pairs from fine needle aspirates of melanoma metastases," *J. Immunol.*, 164:495-504 (2000).

Papa et al., "Clinical Evaluation of ErbB-Targeted CAR T-Cells, Following Intracavity Delivery in Patients with ErbB-Expressing Solid Tumors," *Methods Mol. Biol.*, 1317:365-382 (2015).

Papanicolaou et al., "Rapid expansion of cytomegalovirus-specific cytotoxic T lymphocytes by artificial antigen-presenting cells expressing a single HLA allele," *Blood*, 102:2498-2505 (2003).

Papapetrou et al., "Stoichiometric and temporal requirements of Oct4, Sox2, Klf4, and c-Myc expression for efficient human iPSC induction and differentiation," *Proc. Natl. Acad. Sci. U.S.A.*, 106(31):12759-12764 (2009).

Pardoll, "The blockade of immune checkpoints in cancer immunotherapy," *Nat. Rev. Cancer*, 12(4):252-264 (2012).

Parente-Pereira et al., "Use of retroviral-mediated gene transfer to deliver and test function of chimeric antigen receptors in human T-cells," *J. Biol. Methods*, 1(2):e7 (2014).

Parida et al., "T-Cell Therapy: Options for Infectious Diseases," *Clin. Infect. Dis.*, 61(Suppl 3):S217-S224 (2015).

Parinyanitikul et al., "Mesothelin expression and survival outcomes in triple receptor negative breast cancer," *Clin. Breast Cancer*, 13(5): doi:10.1016/j.clbc.2013.05.001 (2013).

Park et al., "Adoptive transfer of chimeric antigen receptor re-directed cytolytic T lymphocyte clones in patients with neuroblastoma," *Mol. Ther.*, 15:825-833 (2007).

Park et al., "Soluble mesothelin-related protein in an asbestos-exposed population: the dust diseases board cohort study," *Am. J. Respir. Crit. Care Med.*, 178:832-837 (2008).

Parker et al., "Expansion and characterization of T cells transduced with a chimeric receptor against ovarian cancer," *Hum. Gene Ther.*, 11:2377-2387 (2000).

Pass et al., "Soluble mesothelin-related peptide level elevation in mesothelioma serum and pleural effusions," *Ann. Thorac. Surg.*, 85:265-272 (2008).

Patel et al., "T-cell killing of heterogenous tumor or viral targets with bispecific chimeric immune receptors," *Cancer Gene Ther.* 7:1127-1134 (2000).

Petrausch et al., "Re-directed T cells for the treatment of fibroblast activation protein (FAP)-positive malignant pleural mesothelioma (FAPME-1)," *BMC Cancer*, 12:615 (2012).

Piccirillo et al., "CD4(+)CD25(+) regulatory T cells can mediate suppressor function in the absence of transforming growth factor beta1 production and responsiveness," *J. Exp. Med.*, 196(2):237-245 (2002).

Pinthus et al "Immuno-gene therapy of established prostate tumors using chimeric receptor-redirected human lymphocytes," *Cancer Res.*, 63:2470-2476 (2003).

Pollok et al., "Costimulation of transduced T lymphocytes via T cell receptor-CD3 complex and CD28 leads to increased transcription of integrated retrovirus," *Hum. Gene Ther.*, 10:2221-2236 (1999).

Prosser et al., "Tumor PD-L1 co-stimulates primary human CD8(+) cytotoxic T cells modified to express a PD1:CD28 chimeric receptor," *Mol. Immunol.*, 51(3-4):263-272 (2012).

Pu et al., "Utility of WT-1, p63, MOC31, mesothelin, and cytokeratin (K903 and CK5/6) immunostains in differentiating adenocarcinoma, squamous cell carcinoma, and malignant mesothelioma in effusions," *Diagn. Cytopathol.*, 36:20-25 (2008).

Pule et al., "Virus-specific T cells engineered to coexpress tumor-specific receptors: persistence and antitumor activity in individuals with neuroblastoma," *Nat. Med.*, 14:1264-1270 (2008).

Quinn et al., "T cell activation modulates retrovirus-mediated gene expression," *Hum. Gene Ther.*, 9:1457-1467 (1998).

Rainusso et al "Immunotherapy targeting HER2 with genetically modified T cells eliminates tumor-initiating cells in osteosarcoma," *Cancer Gene Ther.*, 19:212-217 (2012).

Relander et al., "Gene transfer to repopulating human CD34+ cells using amphotropic-, GALV-, or RD114-pseudotyped HIV-1-based vectors from stable producer," *Mol. Therap.*, 11:452-459 (2005).

Rettig et al., "Transduction and selection of human T cells with novel CD34/thymidine kinase chimeric suicide genes for the treatment of graft-versus-host disease," *Mol. Ther.*, 8:29-41 (2003).

Riese et al., "Enhanced effector responses in activated CD8+ T cells deficient in diacylglycerol kinases," *Cancer Res.*, 73:3566-3577 (2013).

Riviere et al., "Effects of retroviral vector design on expression of human adenosine deaminase in murine bone marrow transplant recipients engrafted with genetically modified cells," *Proc. Natl. Acad. Sci. USA*, 92:6733-6737 (1995).

Riviere et al., "Novel strategies for cancer therapy: the potential of genetically modified T lymphocytes," *Curr. Hematol. Rep.*, 3:290-297 (2004).

Rizk et al., "Tissue and serum mesothelin are potential markers of neoplastic progression in Barrett's associated esophageal adenocarcinoma," *Cancer Epidemiol. Biomarkers Prev.*, 21(3):482-486 (2012).

(56) References Cited

OTHER PUBLICATIONS

Rizvi et al., "Cancer immunology. Mutational landscape determines sensitivity to PD-1 blockade in non-small cell lung cancer," *Science*, 348(6230):124-128 (2015).
Robbins et al., "Tumor regression in patients with metastatic synovial cell sarcoma and melanoma using genetically engineered lymphocytes reactive with NY-ESO-1," *J. Clin. Oncol.*, 29:917-924 (2011).
Robinson et al., "Soluble mesothelin-related protein—a blood test for mesothelioma," *Lung Cancer*, 49 Suppl 1:S109-S111 (2005).
Rodriguez Portal et al., "Serum levels of soluble mesothelin-related peptides in malignant and nonmalignant asbestos-related pleural disease: relation with past asbestos exposure," *Cancer Epidemiol. Biomarkers Prev.*, 18(2):646-650 (2009).
Roe et al., "Mesothelin-related predictive and prognostic factors in malignant mesothelioma: a nested case-control study," *Lung Cancer*, 61:235-243 (2008).
Rosen et al., "Potential markers that complement expression of CA125 in epithelial ovarian cancer," *Gynecol. Oncol.* 99:267-277 (2005).
Rosenberg et al., "Gene transfer into humans—immunotherapy of patients with advanced melanoma, using tumor-infiltrating lymphocytes modified by retroviral gene transduction," *N. Engl. J. Med.*, 323:570-578 (1990).
Rossig et al., "Targeting of G(D2)-positive tumor cells by human T lymphocytes engineered to express chimeric T-cell receptor genes," *Int. J Cancer*, 94:228-236 (2001).
Sabel et al., "Intratumoral delivery of encapsulated IL-12, IL-18 and TNF-alpha in a model of metastatic breast cancer," *Breast Cancer Res. Treat.*, 122:325-336 (2010).
Sadelain et al., "Targeting tumours with genetically enhanced T lymphocytes," *Nat. Rev. Cancer.*, 3(1):35-45 (2003).
Sadelain et al., "The basic principles of chimeric antigen receptor design," *Cancer Discov.*, 3(4):388-398 (2013).
Sadelain et al., "The promise and potential pitfalls of chimeric antigen receptors," *Curr. Opin. Immunol.*, 21(2):215-223 (2009).
Sampson et al., "EGFRvIII mCAR-modified T-cell therapy cures mice with established intracerebral glioma and generates host immunity against tumor-antigen loss," *Clin. Cancer Res.*, 20:972-984 (2014).
Sanchez et al., "Combining T-cell immunotherapy and anti-androgen therapy for prostate cancer," *Prostate Cancer Prostatic Dis.*, 16:123-131 (2013).
Sautto et al., "Chimeric antigen receptor (CAR)-engineered T cells redirected against hepatitis C virus (HCV) E2 glycoprotein," *Gut*, 65(3):512-523 (2015).
Scales et al., "An antimesothelin-monomethyl auristatin e conjugate with potent antitumor activity in ovarian, pancreatic, and mesothelioma models," *Mol. Cancer Ther.*, 13:2630-2640 (2014).
Schietinger et al., "Rescued tolerant CD8 T cells are preprogrammed to reestablish the tolerant state," *Science*, 335(6069):723-727 (2012).
Schirrmann et al., "Human natural killer cell line modified with a chimeric immunoglobulin T-cell receptor gene leads to tumor growth inhibition in vivo," *Cancer Gene Ther.*, 9:390-398 (2002).
Schmidt et al., "Eradication of melanomas by targeted elimination of a minor subset of tumor cells," *Proc. Natl. Acad. Sci. U.S.A.*, 108:2474-2479 (2011).
Scholler et al., "Decade-Long Safety and Function of Retroviral-Modified Chimeric Antigen Receptor T-cells," *Sci. Transl. Med.*, 4:132ra53 (2012).
Schuberth et al., "Treatment of malignant pleural mesothelioma by fibroblast activation protein-specific re-directed T cells," *J. Transl. Med.*, 11:187 (2013).
Segawa et al., "MESOMARK kit detects C-ERC/mesothelin, but not SMRP with C-terminus," *Biochem. Biophys. Res. Commun.*, 369:915-918 (2008).
Serfling et al., "NFAT in lymphocytes: a factor for all events?," *Sci. STKE*, 398:pe42 (2007).
Servais et al., "An in vivo platform for tumor biomarker assessment," *PLoS One*, 6(10):e26722 (2011).
Servais et al., *Current Protocols in Pharmacology*, Enna ed., John Wiley & Sons, Chapter 14, Unit14 21 (2011).
Servais et al., "Mesothelin overexpression promotes mesothelioma cell invasion and MMP-9 secretion in an orthotopic mouse model and in epithelioid pleural mesothelioma patients," *Clin. Cancer Res.*, 18(9):2478-2489 (2012).
Seung et al., "PD-1 blockade in chronically HIV-1-infected humanized mice suppresses viral loads," *PLoS ONE*, 8(10):e77780 (2013).
Sharifzadeh et al., "Genetically engineered T cells bearing chimeric nanoconstructed receptors harboring TAG-72-specific camelid single domain antibodies as targeting agents," *Cancer Lett.*, 334:237-244 (2013).
Sharp, "Gene Therapy," *Lancet*, 337:1277-1278 (1991).
Sharpe et al., "Genetically modified T cells in cancer therapy: opportunities and challenges," *Dis. Model Mech.*, 8(4):337-350 (2015).
Shen et al., "Chimeric antigen receptor containing ICOS signaling domain mediates specific and efficient antitumor effect of T cells against EGFRvIII expressing glioma," *J Hematol. Oncol.*, 6:33 (2013).
Sheppard, "Dominant negative mutants: tools for the study of protein function in vitro and in vivo," *Am. J. Respir. Cell Mol. Biol.*, 11:1-6 (1994).
Shibaguchi et al., "A fully human chimeric immune receptor for retargeting T-cells to CEA-expressing tumor cells," *Anticancer Res.*, 26:4067-4072 (2006).
Shin et al., "Positive conversion of negative signaling of CTLA4 potentiates antitumor efficacy of adoptive T-cell therapy in murine tumor models," *Blood*, 119(24):5678-5687 (2012).
Shin et al., "Enhanced Anti-tumor Reactivity of Cytotoxic T Lymphocytes Expressing PD-1 Decoy," *Immune Netw.*, 16(2):134-139 (2016).
Shirasu et al., "Molecular characterization of a fully human chimeric T-cell antigen receptor for tumor-associated antigen EpCAM.," *J Biomed. Biotechnol.*, 2012:ID853879 (2012).
Singh et al., "Nature of tumor control by permanently and transiently modified GD2 chimeric antigen receptor T cells in xenograft models of neuroblastoma," *Cancer Immunol. Res.*, 2:1059-1070 (2014).
Song et al., Chimeric NKG2D CAR-expressing T cell-mediated attack of human ovarian cancer is enhanced by histone deacetylase inhibition *Hum. Gene Ther.*, 24:295-305 (2013).
Song et al., "Eomesodermin is required for antitumor immunity mediated by 4-1BB-agonist immunotherapy," *Oncoimmunology*, 3(1):e27680 (2014).
Song et al., "In vivo persistence, tumor localization, and antitumor activity of CAR-engineered T cells is enhanced by costimulatory signaling through CD137 (4-1BB)," *Cancer Res.*, 71:4617-4627 (2011).
Song et al., "A fully human chimeric antigen receptor with potent activity against cancer cells but reduced risk for off-tumor toxicity," *Oncotarget*, 6(25):21533-21546 (2015).
Sontheimer, "The Bacterial Origins of the CRISPR Genome-Editing Revolution," *Hum. Gene Ther.*, 26(7):413-424 (2015).
Spear et al., "Collaboration of chimeric antigen receptor (CAR)-expressing T cells and host T cells for optimal elimination of established ovarian tumors," *Oncoimmunology*, 2(4):e23564 (2013).
Spranger et al., "Up-regulation of PD-L1, IDO, and T(regs) in the melanoma tumor microenvironment is driven by CD8(+) T cells," *Sci. Transl. Med.*, 5(200):200ra116 (2013).
Stancovski et al., "Targeting of T lymphocytes to Neu/HER2-expressing cells using chimeric single chain Fv receptors," *J Immunol.*, 151:6577-6582 (1993).
Stastny et al., "Medulloblastomas expressing IL13Ralpha2 are targets for IL13-zetakine+ cytolytic T cells," *J Pediatr. Hematol. Oncol.*, 29:669-677 (2007).
Stephan et al., "T cell-encoded CD80 and 4-1BBL induce auto- and transcostimulation, resulting in potent tumor rejection," *Nat. Med.*, 13:1440-1449 (2007).
Strome et al., "B7-H1 blockade augments adoptive T-cell immunotherapy for squamous cell carcinoma," *Cancer Res.*, 63(19):6501-6505 (2003).

(56) References Cited

OTHER PUBLICATIONS

Sun et al., "Construction and evaluation of a novel humanized HER2-specific chimeric receptor," *Breast Cancer Res.*, 16:R61 (2014).
Swierczynski et al., "Analysis of novel tumor markers in pancreatic and biliary carcinomas using tissue microarrays," *Hum. Pathol.*, 35:357-366 (2004).
Szymczak et al., "Development of 2A peptide-based strategies in the design of multicistronic vectors," *Expert Opin. Biol. Therapy*, 5(5):627-638 (2005).
Tajima et al., "ERC/mesothelin as a marker for chemotherapeutic response in patients with mesothelioma," *Anticancer Res.*, 28:3933-3936 (2008).
Talay et al., "B7-H1 (PD-L1) on T cells is required for T-cell-mediated conditioning of dendritic cell maturation," *Proc. Natl. Acad. Sci. USA*, 106(8):2741-2746 (2009).
Tan et al., "Mesothelin (MSLN) promoter is hypomethylated in malignant mesothelioma, but its expression is not associated with methylation status of the promoter," *Hum. Pathol.*,41:1330-1338 (2010).
Tang et al., "T cells expressing a LMP1-specific chimeric antigen receptor mediate antitumor effects against LMP1-positive nasopharyngeal carcinoma cells in vitro and in vivo," *J Biomed. Res.*, 28:468-475 (2014).
Tchou et al., "Mesothelin, a novel immunotherapy target for triple negative breast cancer," *Breast Cancer Res. Treat.*, 133:799-804 (2012).
Thomas et al., "Mesothelin-specific CD8(+) T cell responses provide evidence of in vivo cross-priming by antigen-presenting cells in vaccinated pancreatic cancer patients," *J. Exp. Med.*, 200:297-306 (2004).
Tolstoshev et al., "Gene expression using retroviral vectors," *Current Opin. Biotechnol.*, 1:55-61 (1990).
Topalian et al., "Safety, activity, and immune correlates of anti-Pd-1 antibody in cancer," *N. Engl. J. Med.*, 366(26):2443-2454 (2012).
Tozbikian et al., "Mesothelin expression in triple negative breast carcinomas correlates significantly with basal-like phenotype, distant metastases and decreased survival," *PLoS One*, 9(12):e114900 (2014).
Uehara et al., "Mesothelin promotes anchorage-independent growth and prevents anoikis via extracellular signal-regulated kinase signaling pathway in human breast cancer cells," *Mol. Cancer Res.*, 6:186-193 (2008).
University of Pennsylvania, "Autologous Redirected RNA Meso-CIR T Cells," ClinicalTrials.gov archive, pp. 1-7 (Sep. 19, 2017). Retrieved from the Internet: https://clinicaltrials.gov/ct2/show/NCT01355965, on Aug. 3, 2018.
University of Pennsylvania, "CART-meso in Mesothelin Expressing Cancers," ClinicalTrials.gov archive, pp. 1-7 (Nov. 9, 2017). Retrieved from the Internet: https://clinicaltrials.gov/ct2/show/NCT02159716, on Aug. 6, 2018.
Van Den Heuvel et al., "Non-invasive diagnosis of pleural malignancies: the role of tumour markers," *Lung Cancer*, 59:350-354 (2008).
Van Lent et al., "Functional human antigen-specific T cells produced in vitro using retroviral T cell receptor transfer into hematopoietic progenitors," *J. Immunol.*, 179:4959-4968 (2007).
Vasileva et al., "Genome-editing tools for stem cell biology," *Cell Death Dis.*, 6:e1831. (2015).
Vezys et al., "4-1BB signaling synergizes with programmed death ligand 1 blockade to augment CD8 T cell responses during chronic viral infection," *J Immunol.*, 187:1634-1642 (2011).
Voest et al., "Inhibition of angiogenesis in vivo by interleukin 12," *J Natl. Cancer. Inst.*, 87:581-586 (1995).
Von Heijne, "Signal sequences. The limits of variation," *J. Mol. Biol.*, 184(1):99-105 (1985).
Wang et al., "Clinicopathological significance of mesothelin expression in invasive breast cancer," *J Int. Med. Res.*, 40:909-916 (2012).

Wang et al., "Generation of Potent T-cell Immunotherapy for Cancer Using DAP12-Based, Multichain, Chimeric Immunoreceptors," *Cancer Immunol. Res.*, 3:815-826 (2015).
Wang et al., "Genetically targeted T cells eradicate established breast cancer in syngeneic mice," *Clin. Cancer Res.*, 15:943-950 (2009).
Wang et al., "Mesothelin promotes invasion and metastasis in breast cancer cells," *J. Int. Med. Res.*, 40:2109-2116 (2012).
Wang et al., "Quantitative analysis of clinically relevant mutations occurring in lymphoid cells harboring gamma-retrovirus-encoded hsvtk suicide genes," *Gene Therapy*, 15:1454-1459 (2008).
Wang et al., "Overcoming intrinsic inhibitory pathways to augment the antineoplastic activity of adoptively transferred T cells: Retuning your CAR before hitting a rocky road," *Oncoimmunology*, 2(11):e26492 (2013).
Wang et al., "Specificity redirection by CAR with human VEGFR-1 affinity endows T lymphocytes with tumor-killing ability and anti-angiogenic potency," *Gene Ther.*, 20:970-978 (2013).
Wang et al., "Targeting fibroblast activation protein in tumor stroma with chimeric antigen receptor T cells can inhibit tumor growth and augment host immunity without severe toxicity," *Cancer Immunol. Res.*, 2:154-166 (2014).
Ward et al., "Binding activities of a repertoire of single immunoglobulin variable domains secreted from *Escherichia coli*," *Nature*, 341:544-546 (1989).
Watanabe et al., "Target antigen density governs the efficacy of anti-CD2O-CD28-CD3 ζ chimeric antigen receptor-modified effector CD8+ T cells," *J Immunol.*, 194(3):911-920 (2015).
Wei et al., "Strength of PD-1 signaling differentially affects T-cell effector functions," *Proc. Natl. Acad. Sci. U.S.A.*, 110(27):E2480-E2489 (2013).
Wesa et al., "Polarized type-1 dendritic cells (DC1) producing high levels of IL-12 family members rescue patient TH1-type antimelanoma CD4+ T cell responses in vitro," *J Immunother.*, 30, 75-82 (2007).
Westwood et al., "Adoptive transfer of T cells modified with a humanized chimeric receptor gene inhibits growth of Lewis-Y-expressing tumors in mice," *Proc. Natl. Acad. Sci. U.S.A.*, 102:19051-19056 (2005).
Westwood et al., "The Lewis-Y carbohydrate antigen is expressed by many human tumors and can serve as a target for genetically redirected T cells despite the presence of soluble antigen in serum," *J Immunother.*, 32:292-301 (2009).
Wieser et al., "Signaling activity of transforming growth factor beta type II receptors lacking specific domains in the cytoplasmic region," *Mol. Cell. Biol.*, 13:7239-7247 (1993).
Wilkie et al., "Dual targeting of ErbB2 and MUC1 in breast cancer using chimeric antigen receptors engineered to provide complementary signaling," *J Clin. Immunol.*, 32:1059-1070 (2012).
Wilkie et al., "Retargeting of human T cells to tumor-associated MUC1: the evolution of a chimeric antigen receptor," *J Immunol.*, 180:4901-4909 (2008).
Willemsen et al., "A phage display selected fab fragment with MHC class I-restricted specificity for MAGE-A1 allows for retargeting of primary human T lymphocytes," *Gene Ther.*, 8:1601-1608 (2001).
Willemsen et al., "T cell retargeting with MHC class I-restricted antibodies: the CD28 costimulatory domain enhances antigen-specific cytotoxicity and cytokine production," *J Immunol.*, 174:7853-7858 (2005).
Winter et al., "Humanized antibodies," *Immunol. Today*, 14:243-246 (1993).
Wolchok et al., "Nivolumab plus ipilimumab in advanced melanoma," *N. Engl. J. Med.*, 369(2):122-133 (2013).
Wolfl et al., "Antigen-specific activation and cytokine-facilitated expansion of naive, human CD8+ T cells," *Nat. Protocols*, 9:950-966 (2014).
Written Opinion for International Application No. PCT/US2016/050128 dated Feb. 2, 2017.
Written Opinion for International Application No. PCT/US2016/065578 dated May 3, 2017.
Written Opinion for International Application No. PCT/US2017/049085 dated Jan. 11, 2018.
Written Opinion for International Application No. PCT/US2018/021249 dated Aug. 10, 2018.

(56) References Cited

OTHER PUBLICATIONS

Wu et al., "B7H6-Specific Bispecific T Cell Engagers Lead to Tumor Elimination and Host Antitumor Immunity," *J Immunol.*, 194:5305-5311 (2015).

Wu et al., "B7H6-specific chimeric antigen receptors lead to tumor elimination and host antitumor immunity," *Gene Ther.*, 22:675-684 (2015).

Wu et al., "DNAM-1-based chimeric antigen receptors enhance T cell effector function and exhibit in vivo efficacy against melanoma," *Cancer Immunol. Immunother.*, 64:409-418 (2015).

Wu et al., "Heterogeneity of breast cancer metastases: comparison of therapeutic target expression and promoter methylation between primary tumors and their multifocal metastases," *Clin. Cancer Res.*, 14:1938-1946 (2008).

Wu et al., "Immunotherapies: the blockade of inhibitory signals," *Int. J. Biol. Sci.*, 8:1420-1430.

Xu et al., "Correction of the enzyme deficiency in hematopoietic cells of Gaucher patients using a clinically acceptable retroviral supernatant transduction protocol," *Exp. Hemat.*, 22:223-230 (1994).

Yen et al., "Diffuse mesothelin expression correlates with prolonged patient survival in ovarian serous carcinoma," *Clin. Cancer Res.*, 12:827-831 (2006).

Yokokawa et al., "Identification of novel human CTL epitopes and their agonist epitopes of mesothelin," *Clin. Cancer Res.*, 11:6342-6351 (2005).

Yu et al., "Mesothelin as a potential therapeutic target in human cholangiocarcinoma," *J Cancer*, 1:141-149 (2010).

Yun et al., "Targeting of T lymphocytes to melanoma cells through chimeric anti-GD3 immunoglobulin T-cell receptors," *Neoplasia*, 2:449-459 (2000).

Yvon et al "Immunotherapy of metastatic melanoma using genetically engineered GD2-specific T cells," *Clin. Cancer Res.*, 15:5852-5860 (2009).

Zervos et al., "Malignant mesothelioma 2008," *Curr. Opin. Pulm. Med.*, 14:303-309 (2008).

Zhang et al., "An NKp30-based chimeric antigen receptor promotes T cell effector functions and antitumor efficacy in vivo," *J Immunol.*, 189:2290-2299 (2012).

Zhang et al., "Anti-melanoma activity of T cells redirected with a TCR-like chimeric antigen receptor," *Sci. Rep.*, 4:3571 (2014).

Zhang et al., "Inhibition of TGF-$\beta$ signaling in genetically engineered tumor antigen-reactive T cells significantly enhances tumor treatment efficacy," *Gene Ther.*, 20(5):575-580 (2013).

Zhang et al., "Retargeting NK-92 for anti-melanoma activity by a TCR-like single-domain antibody," *Immunol. Cell Biol.*, 91:615-624 (2013).

Zhao et al., "herceptin-based chimeric antigen receptor with modified signaling domains leads to enhanced survival of transduced T lymphocytes and antitumor activity," *J. Immunol.*, 183:5563-5574 (2009).

Zhao et al., "Multiple injections of electroporated autologous T cells expressing a chimeric antigen receptor mediate regression of human disseminated tumor," *Cancer Res.*, 70:9053-9061 (2010).

Zhong et al., "Chimeric antigen receptors combining 4-1BB and CD28 signaling domains augment PI3kinase/AKT/Bcl-XL activation and CD8+ T cell-mediated tumor eradication," *Molecular Therapy*, 18(2):413-420 (2010).

U.S. Appl. No. 16/329,142, filed Aug. 29, 2017, Adusumilli.

U.S. Appl. No. 62/126,804, filed Mar. 2, 2015; Modified Cell and Uses Thereof, Wu et al., 32 pp.

Certified English translation of U.S. Appl. No. 62/126,804, certified Feb. 11, 2020, 24 pp.

Definition of "truncate." The American Heritage® Stedman's Medical Dictionary, Copyright © 2002 by Houghton Mifflin Company, 1 p.

Gorelik and Flavell, 2000, "Abrogation of TGFbeta signaling in T cells leads to spontaneous T cell differentiation and autoimmune disease", *Immunity*, 12(2): 171-181.

Liu et al., Mar. 15, 2016, "A chimeric switch-receptor targeting PD1 augments the efficacy of second generation CAR T-Cells in advanced solid tumors," *Cancer Res.* 76(6): 1578-1590.

\* cited by examiner

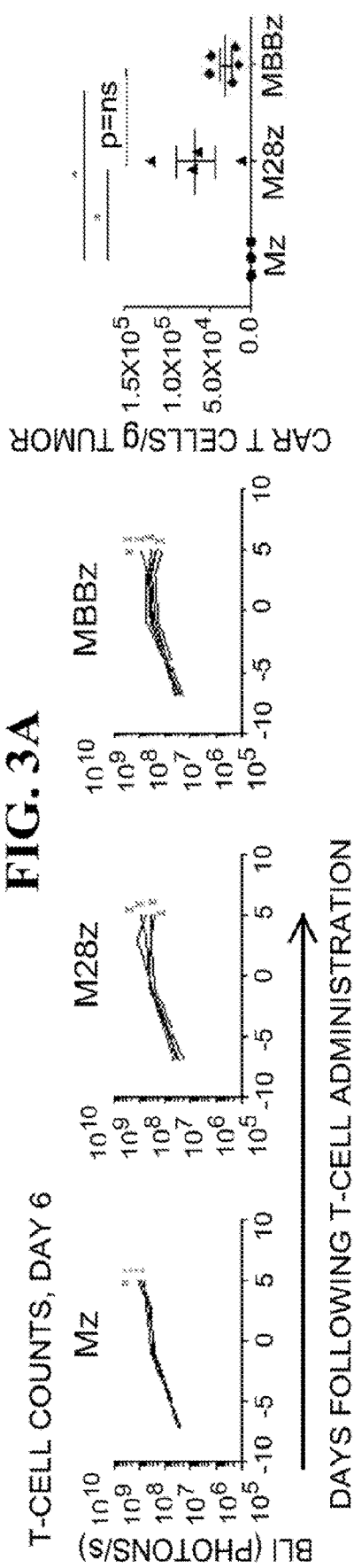
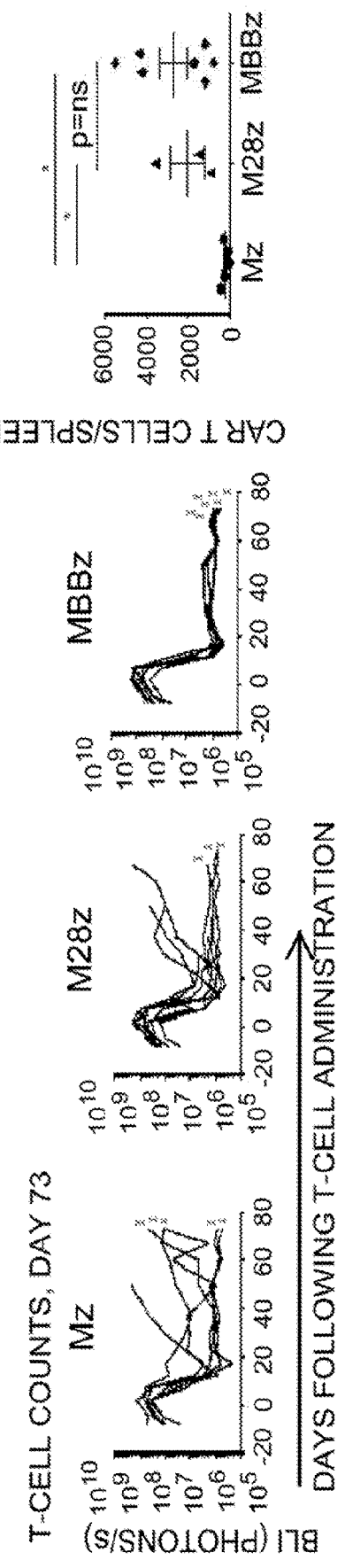
FIG. 3A
FIG. 3B

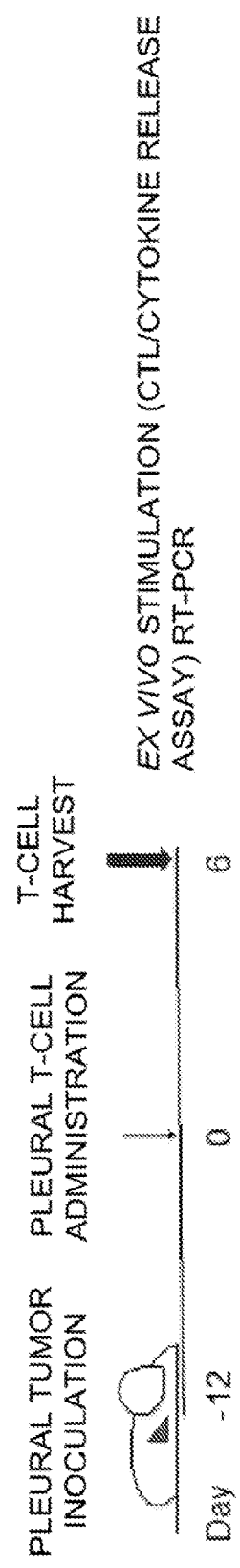
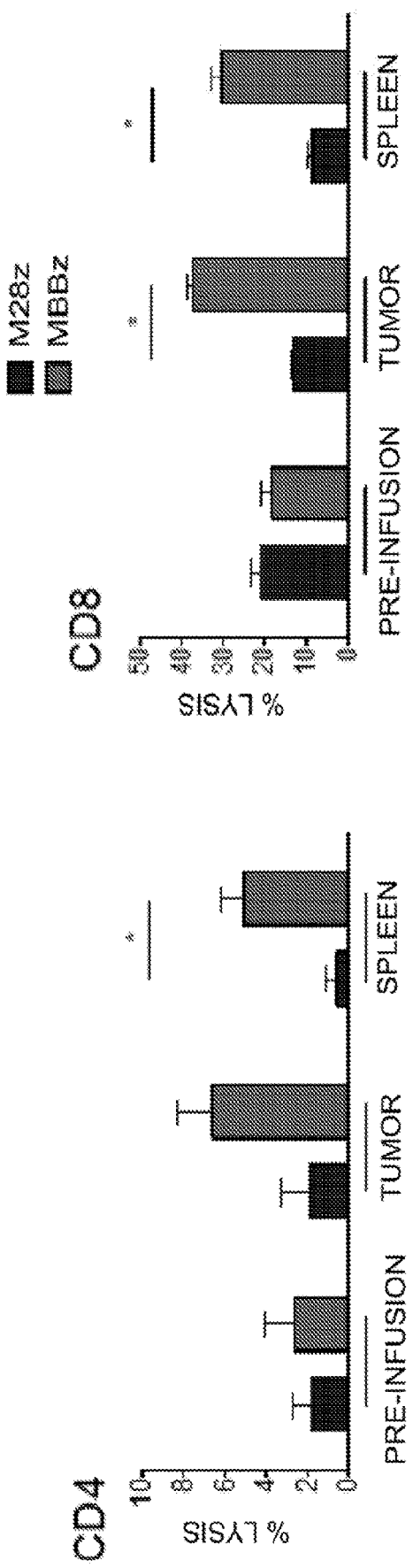
FIG. 4A
FIG. 4B

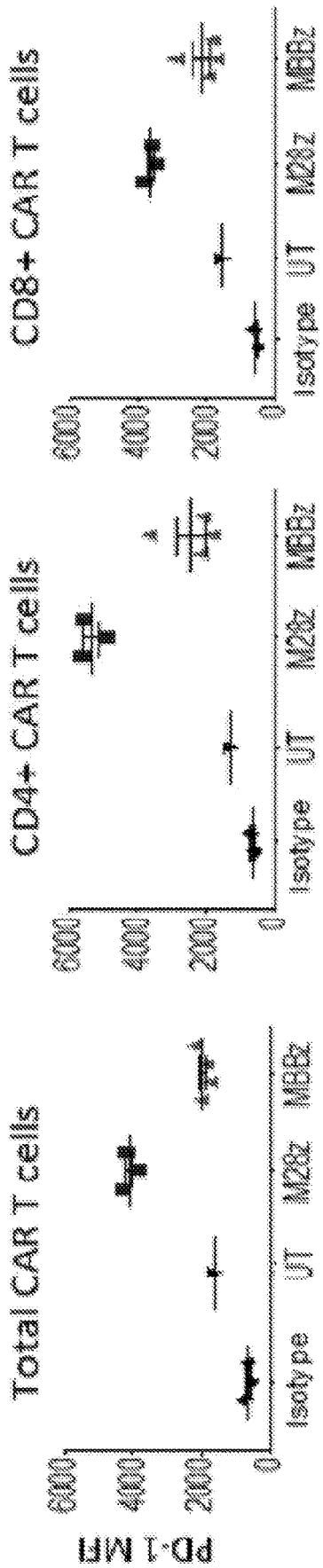
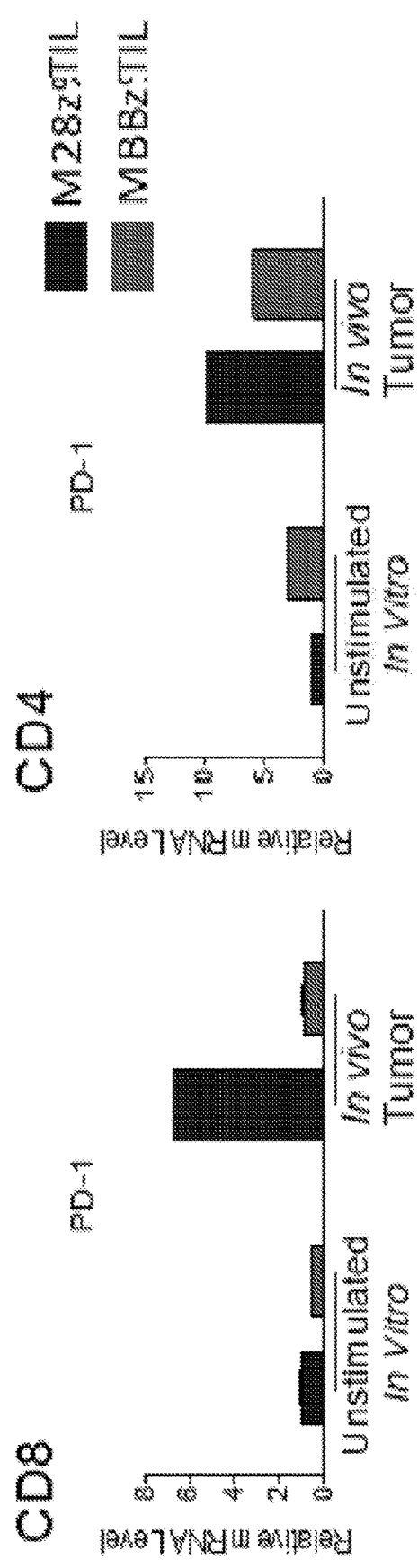
FIG. 6B
FIG. 6C

Day 43 Following M28z

*In vivo*

*In vivo*

*In vitro*

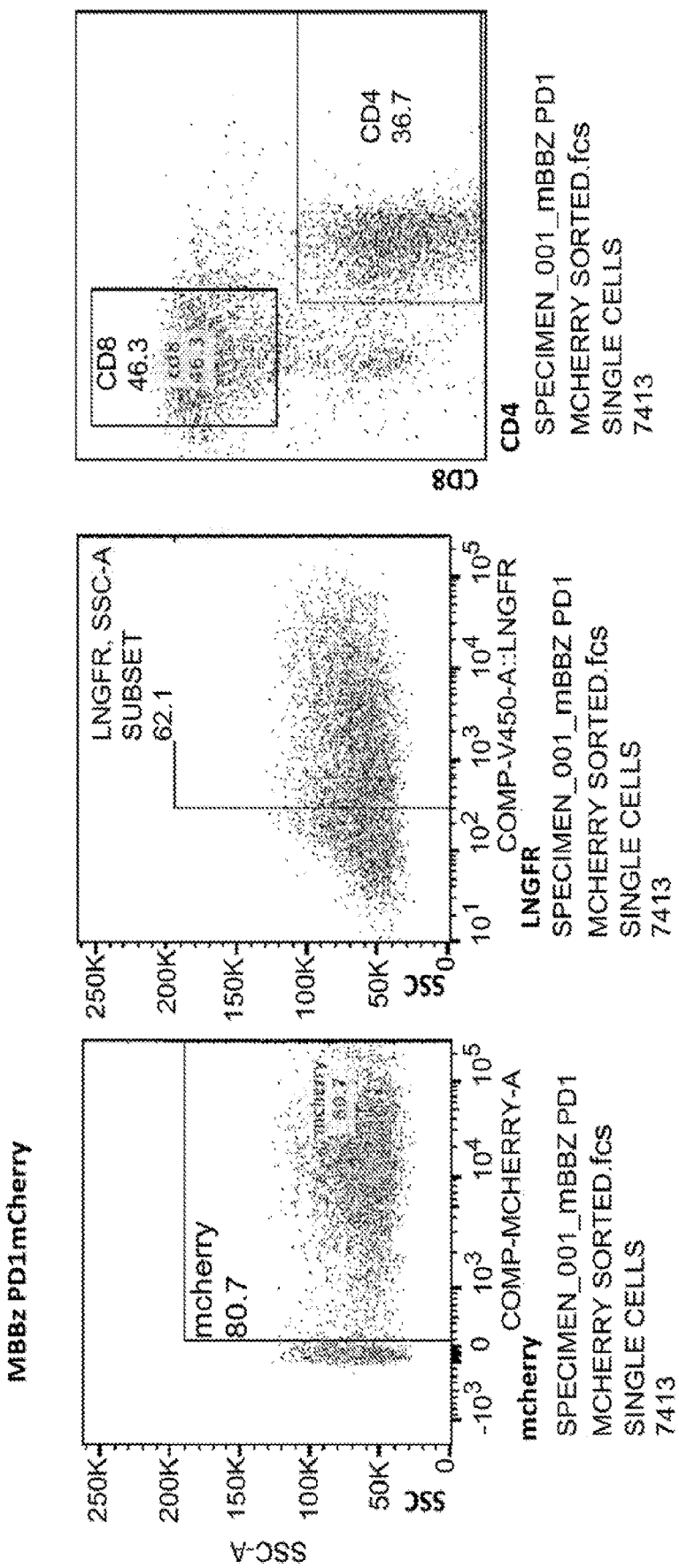

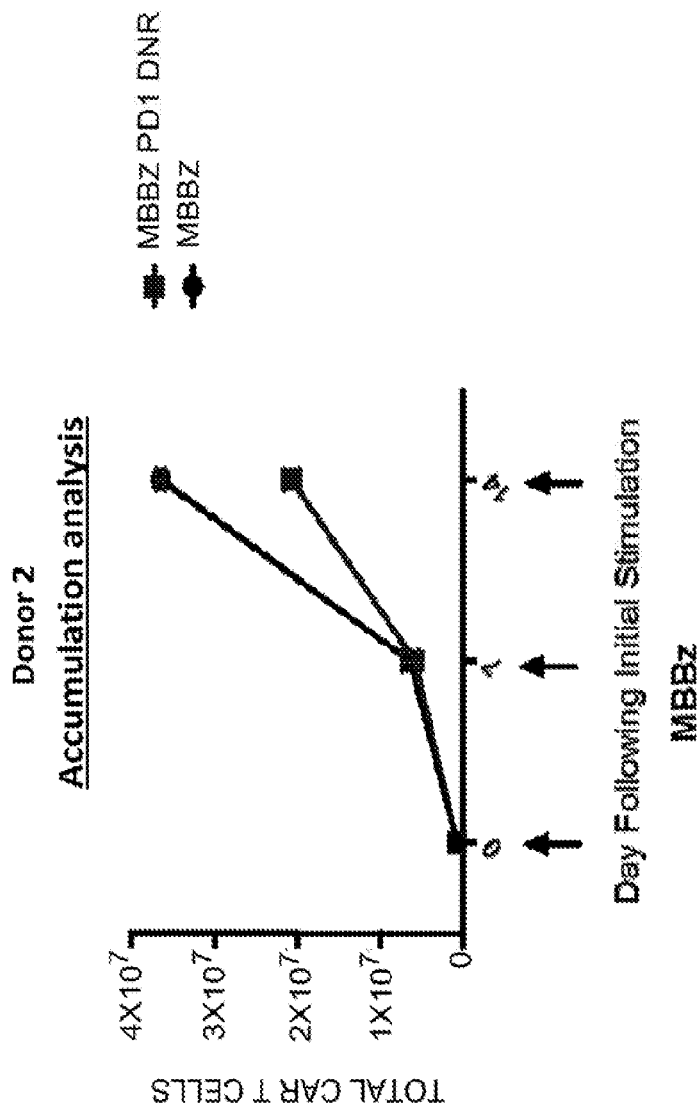
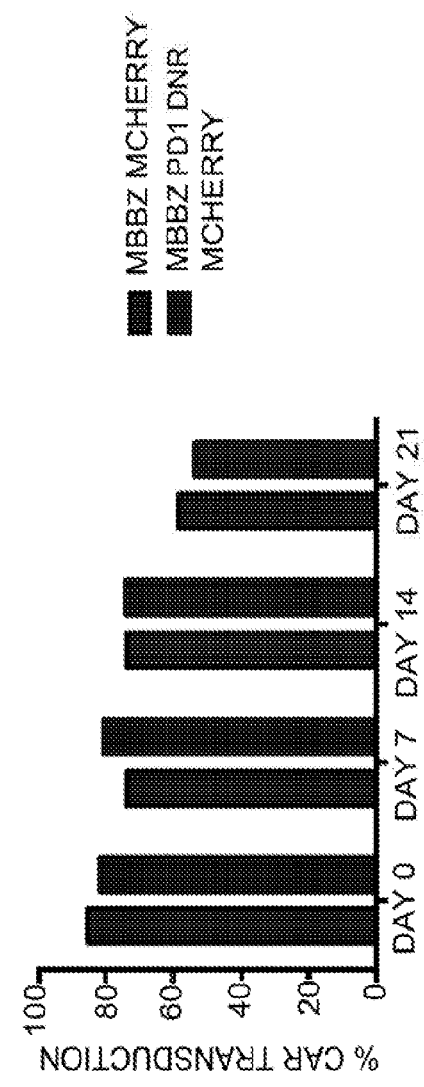
FIG. 17A
FIG. 17B

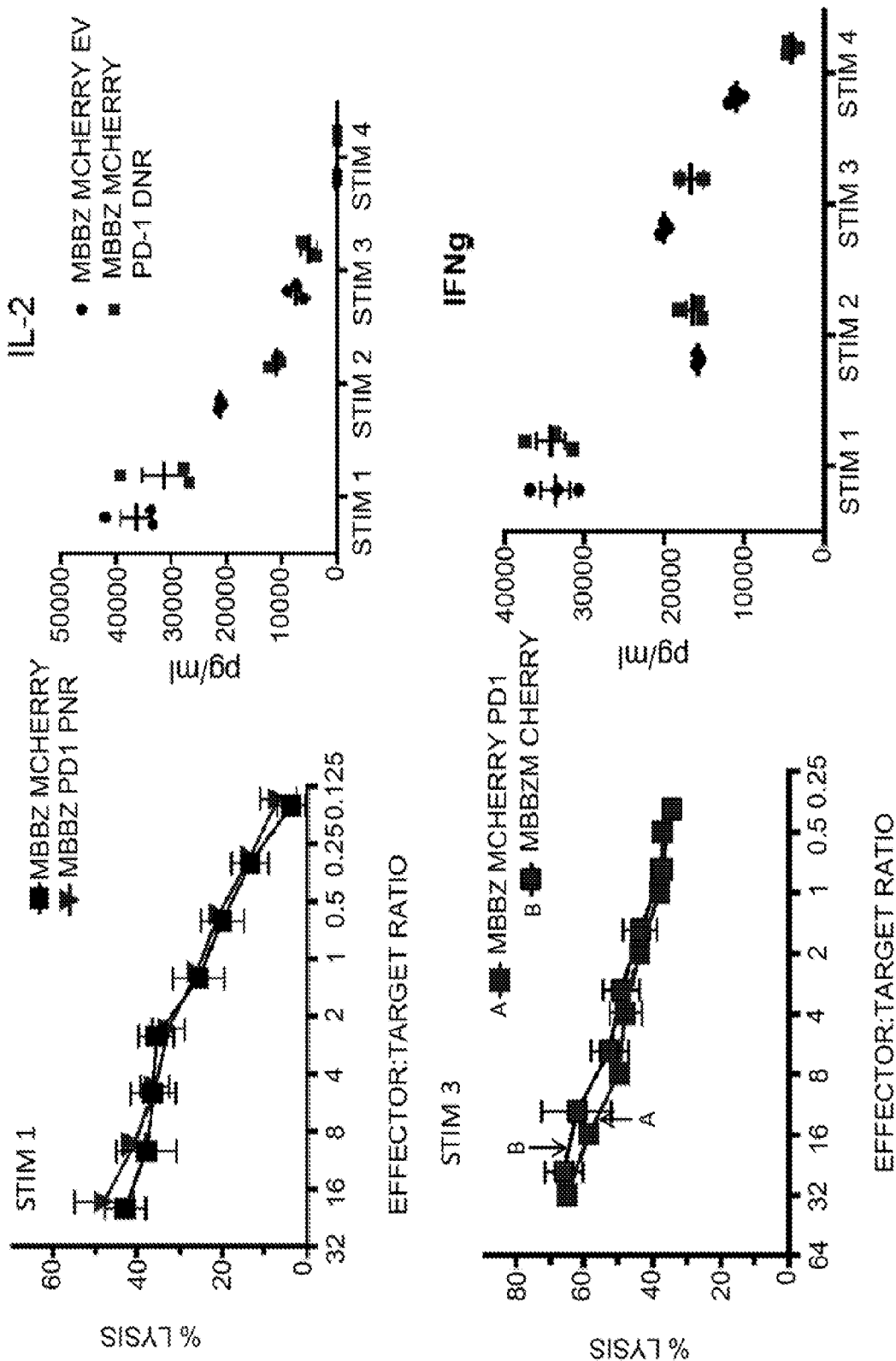

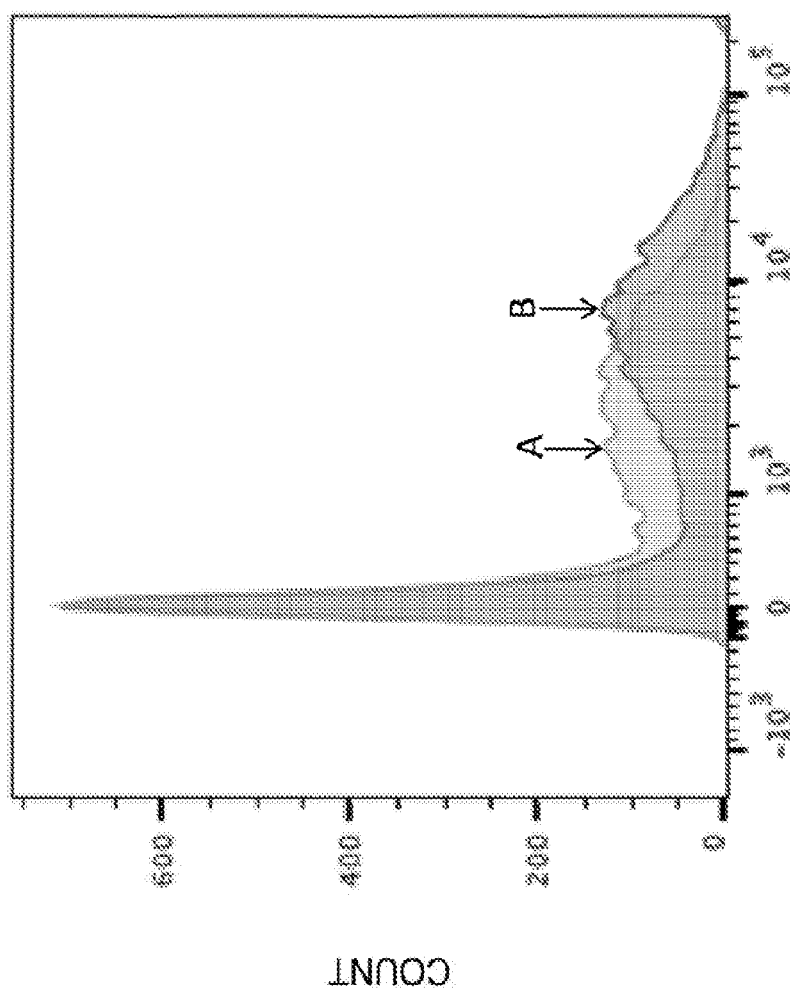

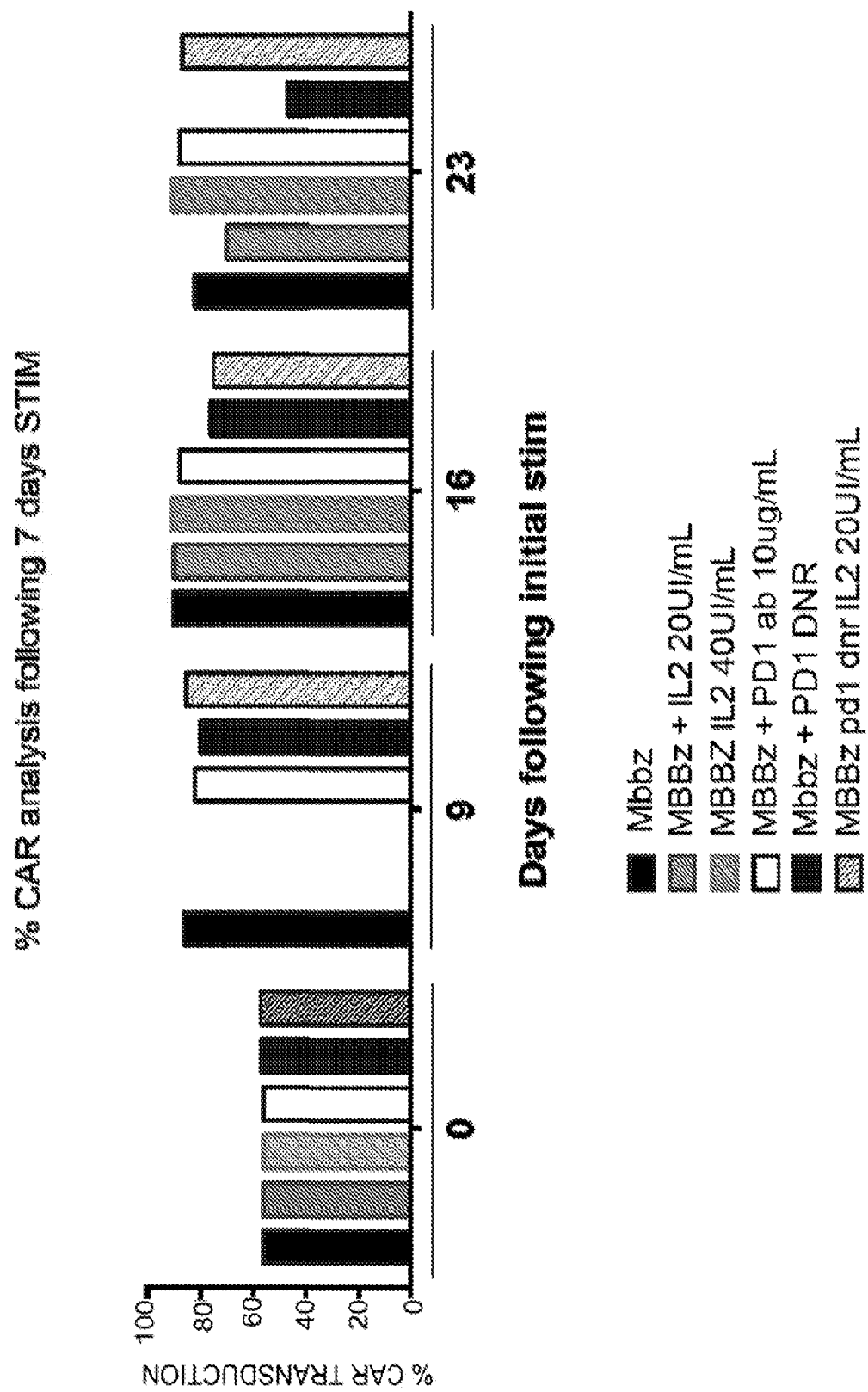

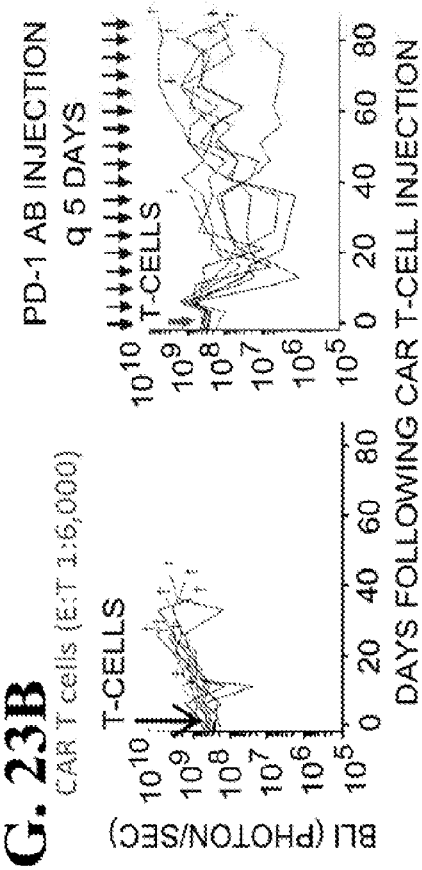
FIG. 23A
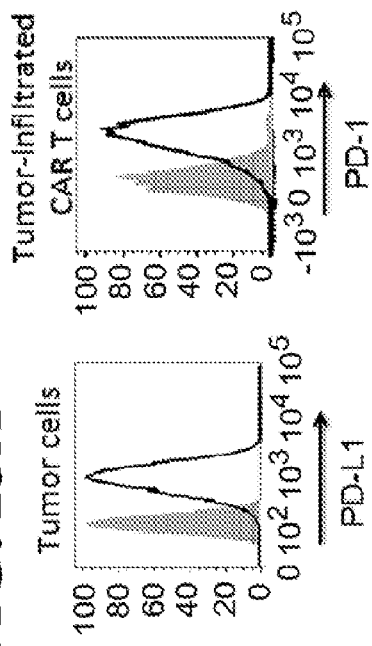
FIG. 23C
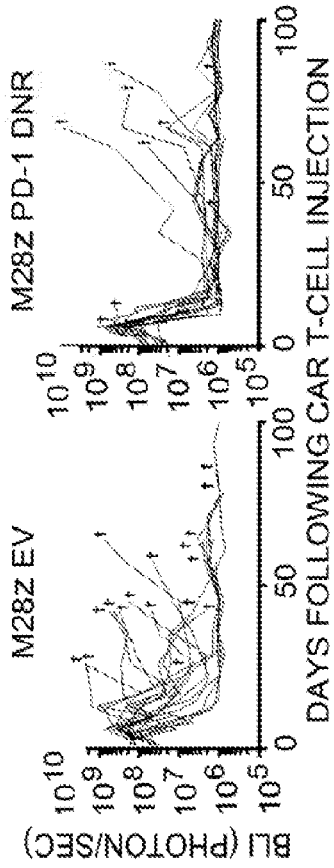
FIG. 23B
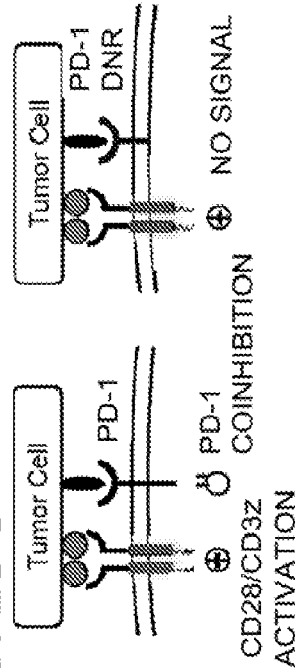
FIG. 23D
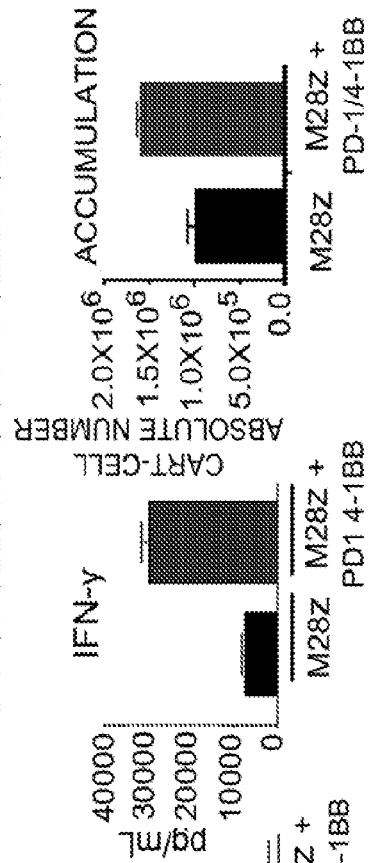
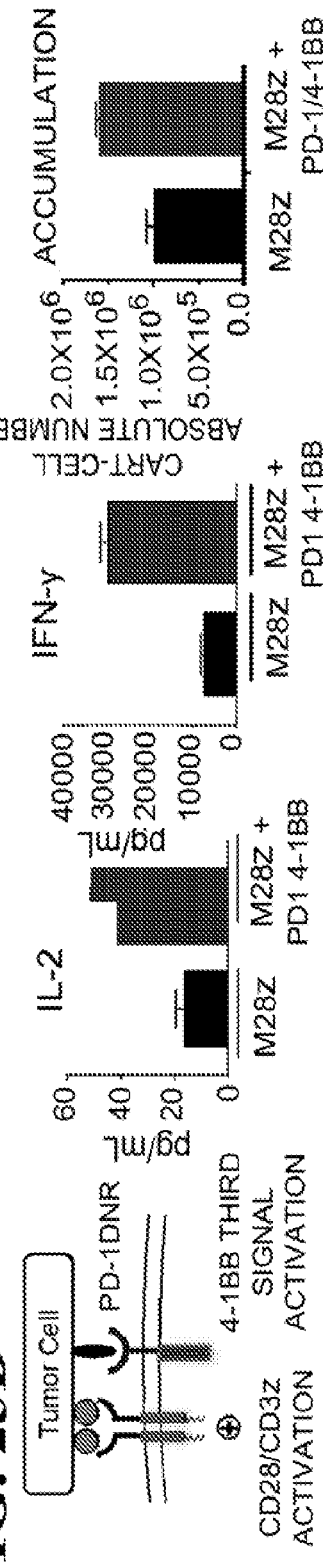

SEQUENCE LISTING

```
<160> NUMBER OF SEQ ID NOS: 48

<210> SEQ ID NO 1
<211> LENGTH: 164
<212> TYPE: PRT
<213> ORGANISM: Homo sapiens

<400> SEQUENCE: 1

Met Lys Trp Lys Ala Leu Phe Thr Ala Ala Ile Leu Gln Ala Gln Leu
1               5                   10                  15

Pro Ile Thr Glu Ala Gln Ser Phe Gly Leu Leu Asp Pro Lys Leu Cys
            20                  25                  30

Tyr Leu Leu Asp Gly Ile Leu Phe Ile Tyr Gly Val Ile Leu Thr Ala
        35                  40                  45

Leu Phe Leu Arg Val Lys Phe Ser Arg Ser Ala Asp Ala Pro Ala Tyr
    50                  55                  60

Gln Gln Gly Gln Asn Gln Leu Tyr Asn Glu Leu Asn Leu Gly Arg Arg
65                  70                  75                  80

Glu Glu Tyr Asp Val Leu Asp Lys Arg Arg Gly Arg Asp Pro Glu Met
                85                  90                  95

Gly Gly Lys Pro Gln Arg Arg Lys Asn Pro Gln Glu Gly Leu Tyr Asn
            100                 105                 110
```

```
Glu Leu Gln Lys Asp Lys Met Ala Glu Ala Tyr Ser Glu Ile Gly Met
            115                 120                 125

Lys Gly Glu Arg Arg Gly Lys Gly His Asp Gly Leu Tyr Gln Gly
            130                 135                 140

Leu Ser Thr Ala Thr Lys Asp Thr Tyr Asp Ala Leu His Met Gln Ala
145                 150                 155                 160

Leu Pro Pro Arg

<210> SEQ ID NO 2
<211> LENGTH: 339
<212> TYPE: DNA
<213> ORGANISM: Homo sapiens

<400> SEQUENCE: 2
agagtgaagt tcagcaggag cgcagacgcc cccgcgtacc agcagggcca gaaccagctc      60
tataacgagc tcaatctagg acgaagagag gagtacgatg ttttggacaa gagacgtggc     120
cgggaccctg atggggggg aaagccgaga aggaagaacc ctcaggaagg cctgtacaat     180
gaactgcaga aagataagat ggcggaggcc tacagtgaga ttgggatgaa aggcgagcgc     240
cggaggggca aggggcacga tggcctttac cagggtctca gtacagccac caaggacacc     300
tacgacgccc ttcacatgca ggccctgccc cctcgctaa                            339

<210> SEQ ID NO 3
<211> LENGTH: 220
<212> TYPE: PRT
<213> ORGANISM: Homo sapiens

<400> SEQUENCE: 3

Met Leu Arg Leu Leu Ala Leu Asn Leu Phe Pro Ser Ile Gln Val
1               5                   10                  15

Thr Gly Asn Lys Ile Leu Val Lys Gln Ser Pro Met Leu Val Ala Tyr
            20                  25                  30

Asp Asn Ala Val Asn Leu Ser Cys Lys Tyr Ser Tyr Asn Leu Phe Ser
            35                  40                  45

Arg Glu Phe Arg Ala Ser Leu His Lys Gly Leu Asp Ser Ala Val Glu
50                  55                  60

Val Cys Val Val Tyr Gly Asn Tyr Ser Gln Gln Leu Gln Val Tyr Ser
65                  70                  75                  80

Lys Thr Gly Phe Asn Cys Asp Gly Lys Leu Gly Asn Glu Ser Val Thr
            85                  90                  95

Phe Tyr Leu Gln Asn Leu Tyr Val Asn Gln Thr Asp Ile Tyr Phe Cys
            100                 105                 110

Lys Ile Glu Val Met Tyr Pro Pro Pro Tyr Leu Asp Asn Glu Lys Ser
            115                 120                 125

Asn Gly Thr Ile Ile His Val Lys Gly Lys His Leu Cys Pro Ser Pro
130                 135                 140

Leu Phe Pro Gly Pro Ser Lys Pro Phe Trp Val Leu Val Val Val Gly
145                 150                 155                 160

Gly Val Leu Ala Cys Tyr Ser Leu Leu Val Thr Val Ala Phe Ile Ile
            165                 170                 175

Phe Trp Val Arg Ser Lys Arg Ser Arg Leu Leu His Ser Asp Tyr Met
            180                 185                 190

Asn Met Thr Pro Arg Arg Pro Gly Pro Thr Arg Lys His Tyr Gln Pro
            195                 200                 205
```

Tyr Ala Pro Pro Arg Asp Phe Ala Ala Tyr Arg Ser
    210                 215                 220

<210> SEQ ID NO 4
<211> LENGTH: 321
<212> TYPE: DNA
<213> ORGANISM: Homo sapiens

<400> SEQUENCE: 4
attgaagtta tgtatcctcc tccttaccta gacaatgaga agagcaatgg aaccattatc      60
catgtgaaag ggaaacacct ttgtccaagt cccctatttc ccggaccttc taagcccttt     120
tgggtgctgg tggtggttgg tggagtcctg gcttgctata gcttgctagt aacagtggcc     180
tttattattt tctgggtgag gagtaagagg agcaggctcc tgcacagtga ctacatgaac     240
atgactcccc gccgcccggg gcccacccgc aagcattacc agccctatgc cccaccacgc     300
gacttcgcag cctatcgctc c                                               321

<210> SEQ ID NO 5
<211> LENGTH: 255
<212> TYPE: PRT
<213> ORGANISM: Homo sapiens

<400> SEQUENCE: 5

Met Gly Asn Ser Cys Tyr Asn Ile Val Ala Thr Leu Leu Leu Val Leu
1               5                   10                  15

Asn Phe Glu Arg Thr Arg Ser Leu Gln Asp Pro Cys Ser Asn Cys Pro
            20                  25                  30

Ala Gly Thr Phe Cys Asp Asn Asn Arg Asn Gln Ile Cys Ser Pro Cys
        35                  40                  45

Pro Pro Asn Ser Phe Ser Ser Ala Gly Gly Gln Arg Thr Cys Asp Ile
    50                  55                  60

Cys Arg Gln Cys Lys Gly Val Phe Arg Thr Arg Lys Glu Cys Ser Ser
65                  70                  75                  80

Thr Ser Asn Ala Glu Cys Asp Cys Thr Pro Gly Phe His Cys Leu Gly
                85                  90                  95

Ala Gly Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
        115                 120                 125

Lys Arg Gly Ile Cys Arg Pro Trp Thr Asn Cys Ser Leu Asp Gly Lys
    130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu
            180                 185                 190

Ala Leu Thr Ser Thr Ala Leu Leu Phe Leu Leu Phe Phe Leu Thr Leu
        195                 200                 205

Arg Phe Ser Val Val Lys Arg Gly Arg Lys Lys Leu Leu Tyr Ile Phe
    210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu
                245                 250                 255

<210> SEQ ID NO 6
<211> LENGTH: 277
<212> TYPE: PRT
<213> ORGANISM: Homo sapiens

<400> SEQUENCE: 6

Met Cys Val Gly Ala Arg Arg Leu Gly Arg Gly Pro Cys Ala Ala Leu
1               5                   10                  15

Leu Leu Leu Gly Leu Gly Leu Ser Thr Val Thr Gly Leu His Cys Val
            20                  25                  30

Gly Asp Thr Tyr Pro Ser Asn Asp Arg Cys Cys His Glu Cys Arg Pro
        35                  40                  45

Gly Asn Gly Met Val Ser Arg Cys Ser Arg Ser Gln Asn Thr Val Cys
    50                  55                  60

Arg Pro Cys Gly Pro Gly Phe Tyr Asn Asp Val Val Ser Ser Lys Pro
65                  70                  75                  80

Cys Lys Pro Cys Thr Trp Cys Asn Leu Arg Ser Gly Ser Glu Arg Lys
                85                  90                  95

Gln Leu Cys Thr Ala Thr Gln Asp Thr Val Cys Arg Cys Arg Ala Gly
            100                 105                 110

Thr Gln Pro Leu Asp Ser Tyr Lys Pro Gly Val Asp Cys Ala Pro Cys
        115                 120                 125

Pro Pro Gly His Phe Ser Pro Gly Asp Asn Gln Ala Cys Lys Pro Trp
    130                 135                 140

Thr Asn Cys Thr Leu Ala Gly Lys His Thr Leu Gln Pro Ala Ser Asn
145                 150                 155                 160

Ser Ser Asp Ala Ile Cys Glu Asp Arg Asp Pro Pro Ala Thr Gln Pro
                165                 170                 175

Gln Glu Thr Gln Gly Pro Pro Ala Arg Pro Ile Thr Val Gln Pro Thr
            180                 185                 190

Glu Ala Trp Pro Arg Thr Ser Gln Gly Pro Ser Thr Arg Pro Val Glu
        195                 200                 205

Val Pro Gly Gly Arg Ala Val Ala Ala Ile Leu Gly Leu Gly Leu Val
    210                 215                 220

Leu Gly Leu Leu Gly Pro Leu Ala Ile Leu Leu Ala Leu Tyr Leu Leu
225                 230                 235                 240

Arg Arg Asp Gln Arg Leu Pro Pro Asp Ala His Lys Pro Pro Gly Gly
                245                 250                 255

Gly Ser Phe Arg Thr Pro Ile Gln Glu Glu Gln Ala Asp Ala His Ser
            260                 265                 270

Thr Leu Ala Lys Ile
        275

<210> SEQ ID NO 7
<211> LENGTH: 199
<212> TYPE: PRT
<213> ORGANISM: Homo sapiens

<400> SEQUENCE: 7

Met Lys Ser Gly Leu Trp Tyr Phe Phe Leu Phe Cys Leu Arg Ile Lys
1               5                   10                  15

Val Leu Thr Gly Glu Ile Asn Gly Ser Ala Asn Tyr Glu Met Phe Ile
            20                  25                  30

Phe His Asn Gly Gly Val Gln Ile Leu Cys Lys Tyr Pro Asp Ile Val
        35                  40                  45

```
Gln Gln Phe Lys Met Gln Leu Leu Lys Gly Gly Gln Ile Leu Cys Asp
        50                  55                  60
Leu Thr Lys Thr Lys Gly Ser Gly Asn Thr Val Ser Ile Lys Ser Leu
 65                  70                  75                  80
Lys Phe Cys His Ser Gln Leu Ser Asn Asn Ser Val Ser Phe Phe Leu
                 85                  90                  95
Tyr Asn Leu Asp His Ser His Ala Asn Tyr Tyr Phe Cys Asn Leu Ser
                100                 105                 110
Ile Phe Asp Pro Pro Pro Phe Lys Val Thr Leu Thr Gly Gly Tyr Leu
            115                 120                 125
His Ile Tyr Glu Ser Gln Leu Cys Cys Gln Leu Lys Phe Trp Leu Pro
        130                 135                 140
Ile Gly Cys Ala Ala Phe Val Val Cys Ile Leu Gly Cys Ile Leu
145                 150                 155                 160
Ile Cys Trp Leu Thr Lys Lys Lys Tyr Ser Ser Ser Val His Asp Pro
                165                 170                 175
Asn Gly Glu Tyr Met Phe Met Arg Ala Val Asn Thr Ala Lys Lys Ser
                180                 185                 190
Arg Leu Thr Asp Val Thr Leu
            195

<210> SEQ ID NO 8
<211> LENGTH: 93
<212> TYPE: PRT
<213> ORGANISM: Homo sapiens

<400> SEQUENCE: 8

Met Ile His Leu Gly His Ile Leu Phe Leu Leu Leu Pro Val Ala
 1               5                  10                  15
Ala Ala Gln Thr Thr Pro Gly Glu Arg Ser Ser Leu Pro Ala Phe Tyr
                20                  25                  30
Pro Gly Thr Ser Gly Ser Cys Ser Gly Cys Gly Ser Leu Ser Leu Pro
            35                  40                  45
Leu Leu Ala Gly Leu Val Ala Ala Asp Ala Val Ala Ser Leu Leu Ile
        50                  55                  60
Val Gly Ala Val Phe Leu Cys Ala Arg Pro Arg Arg Ser Pro Ala Gln
 65                  70                  75                  80
Glu Asp Gly Lys Val Tyr Ile Asn Met Pro Gly Arg Gly
                85                  90

<210> SEQ ID NO 9
<211> LENGTH: 21
<212> TYPE: PRT
<213> ORGANISM: Homo sapiens

<400> SEQUENCE: 9

Met Ala Leu Pro Val Thr Ala Leu Leu Leu Pro Leu Ala Leu Leu Leu
 1               5                  10                  15
His Ala Ala Arg Pro
            20

<210> SEQ ID NO 10
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 10

Gly Gly Gly Gly Ser Gly Gly Gly Ser Gly Gly Gly Ser
1               5                   10                  15

<210> SEQ ID NO 11
<211> LENGTH: 235
<212> TYPE: PRT
<213> ORGANISM: Homo sapiens

<400> SEQUENCE: 11

Met Ala Leu Pro Val Thr Ala Leu Leu Leu Pro Leu Ala Leu Leu Leu
1               5                   10                  15

His Ala Ala Arg Pro Ser Gln Phe Arg Val Ser Pro Leu Asp Arg Thr
                20                  25                  30

Trp Asn Leu Gly Glu Thr Val Glu Leu Lys Cys Gln Val Leu Leu Ser
            35                  40                  45

Asn Pro Thr Ser Gly Cys Ser Trp Leu Phe Gln Pro Arg Gly Ala Ala
        50                  55                  60

Ala Ser Pro Thr Phe Leu Leu Tyr Leu Ser Gln Asn Lys Pro Lys Ala
65                  70                  75                  80

Ala Glu Gly Leu Asp Thr Gln Arg Phe Ser Gly Lys Arg Leu Gly Asp
                85                  90                  95

Thr Phe Val Leu Thr Leu Ser Asp Phe Arg Arg Glu Asn Glu Gly Tyr
                100                 105                 110

Tyr Phe Cys Ser Ala Leu Ser Asn Ser Ile Met Tyr Phe Ser His Phe
            115                 120                 125

Val Pro Val Phe Leu Pro Ala Lys Pro Thr Thr Thr Pro Ala Pro Arg
130                 135                 140

Pro Pro Thr Pro Ala Pro Thr Ile Ala Ser Gln Pro Leu Ser Leu Arg
145                 150                 155                 160

Pro Glu Ala Cys Arg Pro Ala Ala Gly Gly Ala Val His Thr Arg Gly
                165                 170                 175

Leu Asp Phe Ala Cys Asp Ile Tyr Ile Trp Ala Pro Leu Ala Gly Thr
            180                 185                 190

Cys Gly Val Leu Leu Leu Ser Leu Val Ile Thr Leu Tyr Cys Asn His
        195                 200                 205

Arg Asn Arg Arg Arg Val Cys Lys Cys Pro Arg Pro Val Val Lys Ser
210                 215                 220

Gly Asp Lys Pro Ser Leu Ser Ala Arg Tyr Val
225                 230                 235

<210> SEQ ID NO 12
<211> LENGTH: 458
<212> TYPE: PRT
<213> ORGANISM: Homo sapiens

<400> SEQUENCE: 12

Met Asn Arg Gly Val Pro Phe Arg His Leu Leu Leu Val Leu Gln Leu
1               5                   10                  15

Ala Leu Leu Pro Ala Ala Thr Gln Gly Lys Lys Val Val Leu Gly Lys
                20                  25                  30

Lys Gly Asp Thr Val Glu Leu Thr Cys Thr Ala Ser Gln Lys Lys Ser
            35                  40                  45

Ile Gln Phe His Trp Lys Asn Ser Asn Gln Ile Lys Ile Leu Gly Asn
        50                  55                  60

Gln Gly Ser Phe Leu Thr Lys Gly Pro Ser Lys Leu Asn Asp Arg Ala
```

```
                65                  70                  75                  80
Asp Ser Arg Arg Ser Leu Trp Asp Gln Gly Asn Phe Pro Leu Ile Ile
                    85                  90                  95

Lys Asn Leu Lys Ile Glu Asp Ser Asp Thr Tyr Ile Cys Glu Val Glu
                100                 105                 110

Asp Gln Lys Glu Glu Val Gln Leu Leu Val Phe Gly Leu Thr Ala Asn
            115                 120                 125

Ser Asp Thr His Leu Leu Gln Gly Gln Ser Leu Thr Leu Thr Leu Glu
        130                 135                 140

Ser Pro Pro Gly Ser Ser Pro Ser Val Gln Cys Arg Ser Pro Arg Gly
145                 150                 155                 160

Lys Asn Ile Gln Gly Gly Lys Thr Leu Ser Val Ser Gln Leu Glu Leu
                165                 170                 175

Gln Asp Ser Gly Thr Trp Thr Cys Thr Val Leu Gln Asn Gln Lys Lys
            180                 185                 190

Val Glu Phe Lys Ile Asp Ile Val Val Leu Ala Phe Gln Lys Ala Ser
        195                 200                 205

Ser Ile Val Tyr Lys Lys Glu Gly Glu Gln Val Glu Phe Ser Phe Pro
    210                 215                 220

Leu Ala Phe Thr Val Glu Lys Leu Thr Gly Ser Gly Glu Leu Trp Trp
225                 230                 235                 240

Gln Ala Glu Arg Ala Ser Ser Ser Lys Ser Trp Ile Thr Phe Asp Leu
                245                 250                 255

Lys Asn Lys Glu Val Ser Val Lys Arg Val Thr Gln Asp Pro Lys Leu
            260                 265                 270

Gln Met Gly Lys Lys Leu Pro Leu His Leu Thr Leu Pro Gln Ala Leu
        275                 280                 285

Pro Gln Tyr Ala Gly Ser Gly Asn Leu Thr Leu Ala Leu Glu Ala Lys
    290                 295                 300

Thr Gly Lys Leu His Gln Glu Val Asn Leu Val Val Met Arg Ala Thr
305                 310                 315                 320

Gln Leu Gln Lys Asn Leu Thr Cys Glu Val Trp Gly Pro Thr Ser Pro
                325                 330                 335

Lys Leu Met Leu Ser Leu Lys Leu Glu Asn Lys Glu Ala Lys Val Ser
            340                 345                 350

Lys Arg Glu Lys Ala Val Trp Val Leu Asn Pro Glu Ala Gly Met Trp
        355                 360                 365

Gln Cys Leu Leu Ser Asp Ser Gly Gln Val Leu Leu Glu Ser Asn Ile
    370                 375                 380

Lys Val Leu Pro Thr Trp Ser Thr Pro Val Gln Pro Met Ala Leu Ile
385                 390                 395                 400

Val Leu Gly Gly Val Ala Gly Leu Leu Leu Phe Ile Gly Leu Gly Ile
                405                 410                 415

Phe Phe Cys Val Arg Cys Arg His Arg Arg Arg Gln Ala Glu Arg Met
            420                 425                 430

Ser Gln Ile Lys Arg Leu Leu Ser Glu Lys Lys Thr Cys Gln Cys Pro
        435                 440                 445

His Arg Phe Gln Lys Thr Cys Ser Pro Ile
    450                 455

<210> SEQ ID NO 13
<211> LENGTH: 622
<212> TYPE: PRT
<213> ORGANISM: Homo sapiens
```

<400> SEQUENCE: 13

```
Met Ala Leu Pro Thr Ala Arg Pro Leu Leu Gly Ser Cys Gly Thr Pro
1               5                   10                  15

Ala Leu Gly Ser Leu Leu Phe Leu Leu Phe Ser Leu Gly Trp Val Gln
            20                  25                  30

Pro Ser Arg Thr Leu Ala Gly Glu Thr Gly Gln Glu Ala Ala Pro Leu
        35                  40                  45

Asp Gly Val Leu Ala Asn Pro Asn Ile Ser Ser Leu Ser Pro Arg
    50                  55                  60

Gln Leu Leu Gly Phe Pro Cys Ala Glu Val Ser Gly Leu Ser Thr Glu
65                  70                  75                  80

Arg Val Arg Glu Leu Ala Val Ala Leu Ala Gln Lys Asn Val Lys Leu
                85                  90                  95

Ser Thr Glu Gln Leu Arg Cys Leu Ala His Arg Leu Ser Glu Pro Pro
            100                 105                 110

Glu Asp Leu Asp Ala Leu Pro Leu Asp Leu Leu Leu Phe Leu Asn Pro
        115                 120                 125

Asp Ala Phe Ser Gly Pro Gln Ala Cys Thr His Phe Phe Ser Arg Ile
    130                 135                 140

Thr Lys Ala Asn Val Asp Leu Leu Pro Arg Gly Ala Pro Glu Arg Gln
145                 150                 155                 160

Arg Leu Leu Pro Ala Ala Leu Ala Cys Trp Gly Val Arg Gly Ser Leu
                165                 170                 175

Leu Ser Glu Ala Asp Val Arg Ala Leu Gly Gly Leu Ala Cys Asp Leu
            180                 185                 190

Pro Gly Arg Phe Val Ala Glu Ser Ala Glu Val Leu Leu Pro Arg Leu
        195                 200                 205

Val Ser Cys Pro Gly Pro Leu Asp Gln Asp Gln Gln Glu Ala Ala Arg
    210                 215                 220

Ala Ala Leu Gln Gly Gly Gly Pro Pro Tyr Gly Pro Pro Ser Thr Trp
225                 230                 235                 240

Ser Val Ser Thr Met Asp Ala Leu Arg Gly Leu Leu Pro Val Leu Gly
                245                 250                 255

Gln Pro Ile Ile Arg Ser Ile Pro Gln Gly Ile Val Ala Ala Trp Arg
            260                 265                 270

Gln Arg Ser Ser Arg Asp Pro Ser Trp Arg Gln Pro Glu Arg Thr Ile
        275                 280                 285

Leu Arg Pro Arg Phe Arg Arg Glu Val Glu Lys Thr Ala Cys Pro Ser
    290                 295                 300

Gly Lys Lys Ala Arg Glu Ile Asp Glu Ser Leu Ile Phe Tyr Lys Lys
305                 310                 315                 320

Trp Glu Leu Glu Ala Cys Val Asp Ala Ala Leu Leu Ala Thr Gln Met
                325                 330                 335

Asp Arg Val Asn Ala Ile Pro Phe Thr Tyr Glu Gln Leu Asp Val Leu
            340                 345                 350

Lys His Lys Leu Asp Glu Leu Tyr Pro Gln Gly Tyr Pro Glu Ser Val
        355                 360                 365

Ile Gln His Leu Gly Tyr Leu Phe Leu Lys Met Ser Pro Glu Asp Ile
    370                 375                 380

Arg Lys Trp Asn Val Thr Ser Leu Glu Thr Leu Lys Ala Leu Leu Glu
385                 390                 395                 400

Val Asn Lys Gly His Glu Met Ser Pro Gln Val Ala Thr Leu Ile Asp
```

```
            405                 410                 415
Arg Phe Val Lys Gly Arg Gly Gln Leu Asp Lys Asp Thr Leu Asp Thr
        420                 425                 430

Leu Thr Ala Phe Tyr Pro Gly Tyr Leu Cys Ser Leu Ser Pro Glu Glu
        435                 440                 445

Leu Ser Ser Val Pro Pro Ser Ser Ile Trp Ala Val Arg Pro Gln Asp
    450                 455                 460

Leu Asp Thr Cys Asp Pro Arg Gln Leu Asp Val Leu Tyr Pro Lys Ala
465                 470                 475                 480

Arg Leu Ala Phe Gln Asn Met Asn Gly Ser Glu Tyr Phe Val Lys Ile
                485                 490                 495

Gln Ser Phe Leu Gly Gly Ala Pro Thr Glu Asp Leu Lys Ala Leu Ser
            500                 505                 510

Gln Gln Asn Val Ser Met Asp Leu Ala Thr Phe Met Lys Leu Arg Thr
        515                 520                 525

Asp Ala Val Leu Pro Leu Thr Val Ala Glu Val Gln Lys Leu Leu Gly
    530                 535                 540

Pro His Val Glu Gly Leu Lys Ala Glu Glu Arg His Arg Pro Val Arg
545                 550                 555                 560

Asp Trp Ile Leu Arg Gln Arg Gln Asp Asp Leu Asp Thr Leu Gly Leu
                565                 570                 575

Gly Leu Gln Gly Gly Ile Pro Asn Gly Tyr Leu Val Leu Asp Leu Ser
            580                 585                 590

Val Gln Glu Ala Leu Ser Gly Thr Pro Cys Leu Leu Gly Pro Gly Pro
        595                 600                 605

Val Leu Thr Val Leu Ala Leu Leu Ala Ser Thr Leu Ala
    610                 615                 620

<210> SEQ ID NO 14
<211> LENGTH: 230
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Ser Tyr Tyr Trp Ser Trp Ile Arg Gln Pro Pro Gly Lys Gly Leu Glu
        35                  40                  45

Trp Ile Gly Tyr Ile Tyr Tyr Ser Gly Ser Thr Asn Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Gly Lys Asn Gly Ala Phe Asp Ile Trp Gly Gln Gly
            100                 105                 110

Thr Met Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140
```

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr Ser Gly Gln Ala Gly
225                 230

<210> SEQ ID NO 15
<211> LENGTH: 693
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15
caggtgcagc tgcaggagtc cggcccagga ctggtgaagc cttcggagac cctgtccctc      60
acctgcactg tctctggtgg ctccgtcagc agtggtagtt actactggag ctggatccgg     120
cagcccccag ggaagggact ggagtggatt gggtatatct attacagtgg gagcaccaac     180
tacaacccct ccctcaagag tcgagtcacc atatcagtag acacgtccaa gaaccagttc     240
tccctgaagc tgagctctgt gaccgctgcg gacacggccg tgtattactg tgcgagagag     300
gggaagaatg gggcttttga tatctggggc caagggacaa tggtcaccgt ctcttcagcc     360
tccaccaagg gcccatcggt cttccccctg gcaccctcct ccaagagcac ctctgggggc     420
acagcggccc tgggctgcct ggtcaaggac tacttccccg aaccggtgac ggtgtcgtgg     480
aactcaggcg ccctgaccag cggcgtgcac accttcccgg ctgtcctaca gtcctcagga     540
ctctactccc tcagcagcgt ggtgaccgtg ccctccagca gcttgggcac ccagacctac     600
atctgcaacg tgaatcacaa gcccagcaac accaaggtgg acaagaaagt tgagcccaaa     660
tcttgtgaca aaactagtgg ccaggccggc cac                                  693

<210> SEQ ID NO 16
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Gly Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 17
<211> LENGTH: 640
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17
gacatccaga tgacccagtc tccatcctcc ctgtctgcat ctgtaggaga cagagtcacc     60
atcacttgcc gggcaagtca gagcattagc agctatttaa attggtatca gcagaaacca    120
gggaaagccc ctaagctcct gatctatgct gcatccagtt tgcaaagtgg ggtcccatca    180
gggttcagtg gcagtggatc tgggacagat ttcactctca ccatcagcag tctgcaacct    240
gaagattttg caacttacta ctgtcaacag agttacagta ccccgctcac tttcggcgga    300
gggaccaagg tggagatcaa acgaactgtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctact gcctcagcag cacctgacg    540 ctgagcaaag cagactacga gaaacacaaa ctctacgcct gcgaagtcac ccatcagggc    600
ctgagctcgc ccgtcacaaa gagcttcaac aggggagagt                          640

<210> SEQ ID NO 18
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Arg His Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

```
Tyr Ala Ala Ser Ser Leu Gln Ser Gly Val Pro Ser Gly Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Leu
                 85                  90                  95

Thr Phe Gly Gly Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
                210

<210> SEQ ID NO 19
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Gln Val Gln Leu Gln Glu Ser Gly Pro Gly Leu Val Lys Pro Ser Glu
 1               5                  10                  15

Thr Leu Ser Leu Thr Cys Thr Val Ser Gly Gly Ser Val Ser Ser Gly
                 20                  25                  30

Ser Tyr Tyr Trp Ser Trp Ile Arg Gln Pro Pro Gly Lys Gly Leu Glu
             35                  40                  45

Trp Ile Gly Tyr Ile Tyr Tyr Ser Gly Ser Thr Asn Tyr Asn Pro Ser
 50                  55                  60

Leu Lys Ser Arg Val Thr Ile Ser Val Asp Thr Ser Lys Asn Gln Phe
65                   70                  75                  80

Ser Leu Lys Leu Ser Ser Val Thr Ala Ala Asp Thr Ala Val Tyr Tyr
                 85                  90                  95

Cys Ala Arg Glu Gly Lys Asn Gly Ala Phe Asp Ile Trp Gly Gln Gly
                100                 105                 110

Thr Met Val Thr Val Ser Ser Ser
            115                 120

<210> SEQ ID NO 20
<211> LENGTH: 262
<212> TYPE: PRT
<213> ORGANISM: Homo sapiens

<400> SEQUENCE: 20

Gln Val Gln Leu Gln Glu Ser Gly Pro Gly Leu Val Lys Pro Ser Glu
 1               5                  10                  15
```

```
Thr Leu Ser Leu Thr Cys Thr Val Ser Gly Gly Ser Val Ser Ser Gly
             20                  25                  30

Ser Tyr Tyr Trp Ser Trp Ile Arg Gln Pro Pro Gly Lys Gly Leu Glu
         35                  40                  45

Trp Ile Gly Tyr Ile Tyr Tyr Ser Gly Ser Thr Asn Tyr Asn Pro Ser
 50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
             85                  90                  95

Cys Ala Arg Glu Gly Lys Asn Gly Ala Phe Asp Ile Trp Gly Gln Gly
            100                 105                 110

Thr Met Val Thr Val Ser Ser Gly Gly Gly Gly Ser Gly Gly Gly Gly
            115                 120                 125

Gly Ser Gly Gly Gly Gly Ser Arg His Gln Met Thr Gln Ser Pro Ser
    130                 135                 140

Ser Leu Ser Ala Ser Val Gly Asp Arg Val Thr Ile Thr Cys Arg Ala
145                 150                 155                 160

Ser Gln Ser Ile Ser Ser Tyr Leu Asn Trp Tyr Gln Gln Lys Pro Gly
                165                 170                 175

Lys Ala Pro Lys Leu Leu Ile Tyr Ala Ala Ser Ser Leu Gln Ser Gly
            180                 185                 190

Val Pro Ser Arg Phe Ser Gly Ser Gly Ser Gly Thr Asp Phe Thr Leu
        195                 200                 205

Thr Ile Ser Ser Leu Gln Pro Glu Asp Phe Ala Thr Tyr Tyr Cys Gln
    210                 215                 220

Gln Ser Tyr Ser Thr Pro Leu Thr Phe Gly Gly Gly Thr Lys Val Glu
225                 230                 235                 240

Ile Lys Gly Gln Ala Gly His His His His His Gly Asp Tyr Lys
                245                 250                 255

Asp Asp Asp Asp Lys Gly
            260

<210> SEQ ID NO 21
<211> LENGTH: 801
<212> TYPE: DNA
<213> ORGANISM: Homo sapiens

<400> SEQUENCE: 21
atggccttac cagtgaccgc cttgctcctg ccgctggcct tgctgctcca cgccgccagg      60
ccgcaggtgc agctgcagga gtccggccca ggactggtga agccttcgga gaccctgtcc     120
ctcacctgca ctgtctctgg tggctccgtc agcagtggta gttactactg gagctggatc     180
cggcagcccc cagggaaggg actggagtgg attgggtata tctattacag tgggagcacc     240
aactacaacc cctccctcaa gagtcgagtc accatatcag tagacacgtc caagaaccag     300
ttctccctga agctgagctc tgtgaccgct gcggacacgg ccgtgtatta ctgtgcgaga     360
gaggggaaga atggggcttt tgatatctgg ggccaaggga caatggtcac cgtctcttca     420
ggtggaggcg gttcaggcgg aggtggctct ggcggtggcg gatcacgaca tcagatgacc     480
cagtctccat cctccctgtc tgcatctgta ggagacagag tcaccatcac ttgccgggca     540
agtcagagca ttagcagcta tttaaattgg tatcagcaga aaccagggaa agcccctaag     600
ctcctgatct atgctgcatc cagtttgcaa agtggggtcc catcaaggtt cagtggcagt     660
```

| | |
|---|---:|
| ggatctggga cagatttcac tctcaccatc agcagtctgc aacctgaaga ttttgcaact | 720 |
| tactactgtc aacagagtta cagtacccccg ctcactttcg gcggagggac caaggtggag | 780 |
| atcaaacgga ctgcggccgc a | 801 |

<210> SEQ ID NO 22
<211> LENGTH: 801
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 22

| | |
|---|---:|
| atggcgctgc cggtgaccgc gctgctgctg ccgctggcgc tgctgctgca tgcggcgcgc | 60 |
| ccgcaggtgc agctgcagga aagcggcccg ggcctggtga aaccgagcga aaccctgagc | 120 |
| ctgacctgca ccgtgagcgg cggcagcgtg agcagcggca gctattattg gagctggatt | 180 |
| cgccagccgc cgggcaaagg cctggaatgg attggctata tttattatag cggcagcacc | 240 |
| aactataacc cgagcctgaa aagccgcgtg accattagcg tggataccag caaaaaccag | 300 |
| tttagcctga aactgagcag cgtgaccgcg gcggataccg cggtgtatta ttgcgcgcgc | 360 |
| gaaggcaaaa acggcgcgtt tgatatttgg ggccagggca ccatggtgac cgtgagcagc | 420 |
| ggcggcggcg gcagcggcgg cggcggcagc ggcggcggcg gcagccgcca tcagatgacc | 480 |
| cagagcccga gcagcctgag cgcgagcgtg ggcgatcgcg tgaccattac ctgccgcgcg | 540 |
| agccagagca ttagcagcta tctgaactgg tatcagcaga aaccgggcaa agcgccgaaa | 600 |
| ctgctgattt atgcggcgag cagcctgcag agcggcgtgc cgagccgctt tagcggcagc | 660 |
| ggcagcggca ccgattttac cctgaccatt agcagcctgc agccggaaga ttttgcgacc | 720 |
| tattattgcc agcagagcta tagcacccccg ctgacctttg gcggcggcac caaagtggaa | 780 |
| attaaacgca ccgcggcggc g | 801 |

<210> SEQ ID NO 23
<211> LENGTH: 801
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 23

| | |
|---|---:|
| atggccctcc cggtaacggc tctgctgctt ccactcgcac tgctcttgca tgctgccaga | 60 |
| ccacaggtcc agctgcagga gagtgggcct ggactggtta agccgagtga cacttttcc | 120 |
| ttgacgtgca ctgtgagcgg gggaagtgtg tcctcaggta gttattactg gtcctggatt | 180 |
| cgccagccac caggaaaggg actggagtgg ataggttata tctattattc tggcagcact | 240 |
| aattacaatc cttctctcaa aagtagggtg acaatttcag tggatacttc caaaaatcag | 300 |
| tttagtctga agctcagctc tgtgacagct gctgatactg cagtttacta ctgcgccagg | 360 |
| gaggggaaga atggcgcctt cgatatttgg ggacagggca ctatggtgac tgtatcaagc | 420 |
| ggaggcggtg gcagcggcgg gggagggagt ggaggcggcg gtctcgaca tcagatgaca | 480 |
| cagagcccat catcacttag cgccagcgtt ggcgaccggg ttacgataac atgcagggct | 540 |
| tcccaatcta tcagttctta tctgaactgg tatcagcaga accaggtaa ggccccaag | 600 |
| ctgctcatct acgcagcctc atccctgcag agcggcgtcc ctagtcgatt ttccggtagt | 660 |
| gggtcaggga cagattttac cctgactatc agttcactgc agcccgagga cttcgcgaca | 720 |

```
tactattgcc aacagtccta tagtacaccc ttgacatttg gcggcgggac taaagtagaa      780
attaaacgca ccgcggccgc a                                                801
```

<210> SEQ ID NO 24
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

```
Gly Gly Ser Val Ser Ser Gly Ser Tyr Tyr
1               5                   10
```

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

```
Ile Tyr Tyr Ser Gly Ser Thr
1               5
```

<210> SEQ ID NO 26
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

```
Ala Arg Glu Gly Lys Asn Gly Ala Phe Asp Ile Trp
1               5                   10
```

<210> SEQ ID NO 27
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

```
Gln Ser Ile Ser Ser Tyr
1               5
```

<210> SEQ ID NO 28
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

```
Ala Ala Ser Ser
1
```

<210> SEQ ID NO 29
<211> LENGTH: 10
<212> TYPE: PRT

<213> ORGANISM: Artificial Sequence
<220> FEATURE:
<223> OTHER INFORMATION: Description of Artificial Sequence: Synthetic peptide

<400> SEQUENCE: 29

Gln Gln Ser Tyr Ser Thr Pro Leu Thr Phe
1               5                   10

<210> SEQ ID NO 30
<211> LENGTH: 21
<212> TYPE: PRT
<213> ORGANISM: Homo sapiens

<400> SEQUENCE: 30

Met Ala Leu Pro Val Thr Ala Leu Leu Leu Pro Leu Ala Leu Leu Leu
1               5                   10                  15

His Ala Ala Arg Pro
            20

<210> SEQ ID NO 31
<211> LENGTH: 21
<212> TYPE: PRT
<213> ORGANISM: Homo sapiens

<400> SEQUENCE: 31

Met Ala Leu Pro Val Thr Ala Leu Leu Leu Pro Leu Ala Leu Leu Leu
1               5                   10                  15

His Ala Ala Arg Pro
            20

<210> SEQ ID NO 32
<211> LENGTH: 21
<212> TYPE: PRT
<213> ORGANISM: Homo sapiens

<400> SEQUENCE: 32

Met Ala Leu Pro Val Thr Ala Leu Leu Leu Pro Leu Ala Leu Leu Leu
1               5                   10                  15

His Ala Ala Arg Pro
            20

<210> SEQ ID NO 33
<211> LENGTH: 288
<212> TYPE: PRT
<213> ORGANISM: Homo sapiens

<400> SEQUENCE: 33

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
                20                  25                  30

Asn Pro Pro Thr Phe Ser Pro Ala Leu Leu Val Val Thr Glu Gly Asp
            35                  40                  45

Asn Ala Thr Phe Thr Cys Ser Phe Ser Asn Thr Ser Glu Ser Phe Val
        50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg

```
            100                 105                 110
Ala Arg Arg Asn Asp Ser Gly Thr Tyr Leu Cys Gly Ala Ile Ser Leu
            115                 120                 125

Ala Pro Lys Ala Gln Ile Lys Glu Ser Leu Arg Ala Glu Leu Arg Val
        130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
        195                 200                 205

Leu Lys Glu Asp Pro Ser Ala Val Pro Val Phe Ser Val Asp Tyr Gly
            210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
        275                 280                 285

<210> SEQ ID NO 34
<211> LENGTH: 223
<212> TYPE: PRT
<213> ORGANISM: Homo sapiens

<400> SEQUENCE: 34

Met Ala Cys Leu Gly Phe Gln Arg His Lys Ala Gln Leu Asn Leu Ala
1               5                   10                  15

Thr Arg Thr Trp Pro Cys Thr Leu Leu Phe Phe Leu Leu Phe Ile Pro
            20                  25                  30

Val Phe Cys Lys Ala Met His Val Ala Gln Pro Ala Val Val Leu Ala
        35                  40                  45

Ser Ser Arg Gly Ile Ala Ser Phe Val Cys Glu Tyr Ala Ser Pro Gly
    50                  55                  60

Lys Ala Thr Glu Val Arg Val Thr Val Leu Arg Gln Ala Asp Ser Gln
65                  70                  75                  80

Val Thr Glu Val Cys Ala Ala Thr Tyr Met Met Gly Asn Glu Leu Thr
                85                  90                  95

Phe Leu Asp Asp Ser Ile Cys Thr Gly Thr Ser Ser Gly Asn Gln Val
            100                 105                 110

Asn Leu Thr Ile Gln Gly Leu Arg Ala Met Asp Thr Gly Leu Tyr Ile
        115                 120                 125

Cys Lys Val Glu Leu Met Tyr Pro Pro Pro Tyr Tyr Leu Gly Ile Gly
    130                 135                 140

Asn Gly Thr Gln Ile Tyr Val Ile Asp Pro Glu Pro Cys Pro Asp Ser
145                 150                 155                 160

Asp Phe Leu Leu Trp Ile Leu Ala Ala Val Ser Ser Gly Leu Phe Phe
                165                 170                 175

Tyr Ser Phe Leu Leu Thr Ala Val Ser Leu Ser Lys Met Leu Lys Lys
            180                 185                 190
```

```
Arg Ser Pro Leu Thr Thr Gly Val Tyr Val Lys Met Pro Thr Glu
        195                 200                 205

Pro Glu Cys Glu Lys Gln Phe Gln Pro Tyr Phe Ile Pro Ile Asn
    210                 215                 220
```

<210> SEQ ID NO 35
<211> LENGTH: 289
<212> TYPE: PRT
<213> ORGANISM: Homo sapiens

<400> SEQUENCE: 35

```
Met Lys Thr Leu Pro Ala Met Leu Gly Thr Gly Lys Leu Phe Trp Val
1               5                   10                  15

Phe Phe Leu Ile Pro Tyr Leu Asp Ile Trp Asn Ile His Gly Lys Glu
                20                  25                  30

Ser Cys Asp Val Gln Leu Tyr Ile Lys Arg Gln Ser Glu His Ser Ile
            35                  40                  45

Leu Ala Gly Asp Pro Phe Glu Leu Glu Cys Pro Val Lys Tyr Cys Ala
        50                  55                  60

Asn Arg Pro His Val Thr Trp Cys Lys Leu Asn Gly Thr Thr Cys Val
65                  70                  75                  80

Lys Leu Glu Asp Arg Gln Thr Ser Trp Lys Glu Lys Asn Ile Ser
                85                  90                  95

Phe Phe Ile Leu His Phe Glu Pro Val Leu Pro Asn Asp Asn Gly Ser
                100                 105                 110

Tyr Arg Cys Ser Ala Asn Phe Gln Ser Asn Leu Ile Glu Ser His Ser
            115                 120                 125

Thr Thr Leu Tyr Val Thr Asp Val Lys Ser Ala Ser Glu Arg Pro Ser
        130                 135                 140

Lys Asp Glu Met Ala Ser Arg Pro Trp Leu Leu Tyr Ser Leu Leu Pro
145                 150                 155                 160

Leu Gly Gly Leu Pro Leu Leu Ile Thr Thr Cys Phe Cys Leu Phe Cys
                165                 170                 175

Cys Leu Arg Arg His Gln Gly Lys Gln Asn Glu Leu Ser Asp Thr Ala
            180                 185                 190

Gly Arg Glu Ile Asn Leu Val Asp Ala His Leu Lys Ser Glu Gln Thr
        195                 200                 205

Glu Ala Ser Thr Arg Gln Asn Ser Gln Val Leu Leu Ser Glu Thr Gly
    210                 215                 220

Ile Tyr Asp Asn Asp Pro Asp Leu Cys Phe Arg Met Gln Glu Gly Ser
225                 230                 235                 240

Glu Val Tyr Ser Asn Pro Cys Leu Glu Glu Asn Lys Pro Gly Ile Val
                245                 250                 255

Tyr Ala Ser Leu Asn His Ser Val Ile Gly Pro Asn Ser Arg Leu Ala
            260                 265                 270

Arg Asn Val Lys Glu Ala Pro Thr Glu Tyr Ala Ser Ile Cys Val Arg
        275                 280                 285

Ser
```

<210> SEQ ID NO 36
<211> LENGTH: 301
<212> TYPE: PRT
<213> ORGANISM: Homo sapiens

<400> SEQUENCE: 36

```
Met Phe Ser His Leu Pro Phe Asp Cys Val Leu Leu Leu Leu Leu
```

-continued

```
             1               5                  10                 15
            Leu Leu Thr Arg Ser Ser Glu Val Glu Tyr Arg Ala Glu Val Gly Gln
                           20                  25                 30

Asn Ala Tyr Leu Pro Cys Phe Tyr Thr Pro Ala Ala Pro Gly Asn Leu
                           35                  40                 45

Val Pro Val Cys Trp Gly Lys Gly Ala Cys Pro Val Phe Glu Cys Gly
                50                      55                 60

Asn Val Val Leu Arg Thr Asp Glu Arg Asp Val Asn Tyr Trp Thr Ser
            65                      70                 75                 80

Arg Tyr Trp Leu Asn Gly Asp Phe Arg Lys Gly Asp Val Ser Leu Thr
                                85                 90                 95

Ile Glu Asn Val Thr Leu Ala Asp Ser Gly Ile Tyr Cys Cys Arg Ile
                           100                 105                110

Gln Ile Pro Gly Ile Met Asn Asp Glu Lys Phe Asn Leu Lys Leu Val
                           115                 120                125

Ile Lys Pro Ala Lys Val Thr Pro Ala Pro Thr Arg Gln Arg Asp Phe
                      130                 135                140

Thr Ala Ala Phe Pro Arg Met Leu Thr Thr Arg Gly His Gly Pro Ala
            145                     150                 155                160

Glu Thr Gln Thr Leu Gly Ser Leu Pro Asp Ile Asn Leu Thr Gln Ile
                                165                 170                175

Ser Thr Leu Ala Asn Glu Leu Arg Asp Ser Arg Leu Ala Asn Asp Leu
                           180                 185                190

Arg Asp Ser Gly Ala Thr Ile Arg Ile Gly Ile Tyr Ile Gly Ala Gly
                      195                 200                205

Ile Cys Ala Gly Leu Ala Leu Ala Leu Ile Phe Gly Ala Leu Ile Phe
                      210                 215                220

Lys Trp Tyr Ser His Ser Lys Glu Lys Ile Gln Asn Leu Ser Leu Ile
            225                     230                 235                240

Ser Leu Ala Asn Leu Pro Pro Ser Gly Leu Ala Asn Ala Val Ala Glu
                           245                 250                255

Gly Ile Arg Ser Glu Glu Asn Ile Tyr Thr Ile Glu Glu Asn Val Tyr
                           260                 265                270

Glu Val Glu Glu Pro Asn Glu Tyr Tyr Cys Tyr Val Ser Ser Arg Gln
                      275                 280                285

Gln Pro Ser Gln Pro Leu Gly Cys Arg Phe Ala Met Pro
                      290                 295                300

<210> SEQ ID NO 37
<211> LENGTH: 525
<212> TYPE: PRT
<213> ORGANISM: Homo sapiens

<400> SEQUENCE: 37

Met Trp Glu Ala Gln Phe Leu Gly Leu Leu Phe Leu Gln Pro Leu Trp
            1               5                  10                 15

Val Ala Pro Val Lys Pro Leu Gln Pro Gly Ala Glu Val Pro Val Val
                           20                  25                 30

Trp Ala Gln Glu Gly Ala Pro Ala Gln Leu Pro Cys Ser Pro Thr Ile
                           35                  40                 45

Pro Leu Gln Asp Leu Ser Leu Leu Arg Arg Ala Gly Val Thr Trp Gln
                      50                  55                 60

His Gln Pro Asp Ser Gly Pro Pro Ala Ala Ala Pro Gly His Pro Leu
            65                      70                 75                 80
```

```
Ala Pro Gly Pro His Pro Ala Ala Pro Ser Trp Gly Pro Arg Pro
            85                  90                  95

Arg Arg Tyr Thr Val Leu Ser Val Gly Pro Gly Leu Arg Ser Gly
        100                 105                 110

Arg Leu Pro Leu Gln Pro Arg Val Gln Leu Asp Glu Arg Gly Arg Gln
        115                 120                 125

Arg Gly Asp Phe Ser Leu Trp Leu Arg Pro Ala Arg Arg Ala Asp Ala
130                 135                 140

Gly Glu Tyr Arg Ala Ala Val His Leu Arg Asp Arg Ala Leu Ser Cys
145                 150                 155                 160

Arg Leu Arg Leu Arg Leu Gly Gln Ala Ser Met Thr Ala Ser Pro Pro
                165                 170                 175

Gly Ser Leu Arg Ala Ser Asp Trp Val Ile Leu Asn Cys Ser Phe Ser
            180                 185                 190

Arg Pro Asp Arg Pro Ala Ser Val His Trp Phe Arg Asn Arg Gly Gln
            195                 200                 205

Gly Arg Val Pro Val Arg Glu Ser Pro His His Leu Ala Glu Ser
210                 215                 220

Phe Leu Phe Leu Pro Gln Val Ser Pro Met Asp Ser Gly Pro Trp Gly
225                 230                 235                 240

Cys Ile Leu Thr Tyr Arg Asp Gly Phe Asn Val Ser Ile Met Tyr Asn
                245                 250                 255

Leu Thr Val Leu Gly Leu Glu Pro Pro Thr Pro Leu Thr Val Tyr Ala
            260                 265                 270

Gly Ala Gly Ser Arg Val Gly Leu Pro Cys Arg Leu Pro Ala Gly Val
            275                 280                 285

Gly Thr Arg Ser Phe Leu Thr Ala Lys Trp Thr Pro Pro Gly Gly Gly
290                 295                 300

Pro Asp Leu Leu Val Thr Gly Asp Asn Gly Asp Phe Thr Leu Arg Leu
305                 310                 315                 320

Glu Asp Val Ser Gln Ala Gln Ala Gly Thr Tyr Thr Cys His Ile His
                325                 330                 335

Leu Gln Glu Gln Gln Leu Asn Ala Thr Val Thr Leu Ala Ile Ile Thr
            340                 345                 350

Val Thr Pro Lys Ser Phe Gly Ser Pro Gly Ser Leu Gly Lys Leu Leu
            355                 360                 365

Cys Glu Val Thr Pro Val Ser Gly Gln Glu Arg Phe Val Trp Ser Ser
        370                 375                 380

Leu Asp Thr Pro Ser Gln Arg Ser Phe Ser Gly Pro Trp Leu Glu Ala
385                 390                 395                 400

Gln Glu Ala Gln Leu Leu Ser Gln Pro Trp Gln Cys Gln Leu Tyr Gln
                405                 410                 415

Gly Glu Arg Leu Leu Gly Ala Ala Val Tyr Phe Thr Glu Leu Ser Ser
            420                 425                 430

Pro Gly Ala Gln Arg Ser Gly Arg Ala Pro Gly Ala Leu Pro Ala Gly
            435                 440                 445

His Leu Leu Leu Phe Leu Ile Leu Gly Val Leu Ser Leu Leu Leu Leu
450                 455                 460

Val Thr Gly Ala Phe Gly Phe His Leu Trp Arg Arg Gln Trp Arg Pro
465                 470                 475                 480

Arg Arg Phe Ser Ala Leu Glu Gln Gly Ile His Pro Pro Gln Ala Gln
                485                 490                 495

Ser Lys Ile Glu Glu Leu Glu Gln Glu Pro Glu Pro Glu Pro Glu Pro
```

```
                500                 505                 510
Glu Pro Glu Pro Glu Pro Glu Pro Glu Pro Glu Gln Leu
        515                 520                 525

<210> SEQ ID NO 38
<211> LENGTH: 244
<212> TYPE: PRT
<213> ORGANISM: Homo sapiens

<400> SEQUENCE: 38

Met Arg Trp Cys Leu Leu Ile Trp Ala Gln Gly Leu Arg Gln Ala
1               5                   10                  15

Pro Leu Ala Ser Gly Met Met Thr Gly Thr Ile Glu Thr Gly Asn
            20                  25                  30

Ile Ser Ala Glu Lys Gly Gly Ser Ile Ile Leu Gln Cys His Leu Ser
                35                  40                  45

Ser Thr Thr Ala Gln Val Thr Gln Val Asn Trp Glu Gln Gln Asp Gln
    50                  55                  60

Leu Leu Ala Ile Cys Asn Ala Asp Leu Gly Trp His Ile Ser Pro Ser
65                  70                  75                  80

Phe Lys Asp Arg Val Ala Pro Gly Pro Gly Leu Gly Leu Thr Leu Gln
                85                  90                  95

Ser Leu Thr Val Asn Asp Thr Gly Glu Tyr Phe Cys Ile Tyr His Thr
            100                 105                 110

Tyr Pro Asp Gly Thr Tyr Thr Gly Arg Ile Phe Leu Glu Val Leu Glu
            115                 120                 125

Ser Ser Val Ala Glu His Gly Ala Arg Phe Gln Ile Pro Leu Leu Gly
        130                 135                 140

Ala Met Ala Ala Thr Leu Val Val Ile Cys Thr Ala Val Ile Val Val
145                 150                 155                 160

Val Ala Leu Thr Arg Lys Lys Lys Ala Leu Arg Ile His Ser Val Glu
                165                 170                 175

Gly Asp Leu Arg Arg Lys Ser Ala Gly Gln Glu Glu Trp Ser Pro Ser
            180                 185                 190

Ala Pro Ser Pro Pro Gly Ser Cys Val Gln Ala Glu Ala Ala Pro Ala
            195                 200                 205

Gly Leu Cys Gly Glu Gln Arg Gly Glu Asp Cys Ala Glu Leu His Asp
        210                 215                 220

Tyr Phe Asn Val Leu Ser Tyr Arg Ser Leu Gly Asn Cys Ser Phe Phe
225                 230                 235                 240

Thr Glu Thr Gly

<210> SEQ ID NO 39
<211> LENGTH: 287
<212> TYPE: PRT
<213> ORGANISM: Homo sapiens

<400> SEQUENCE: 39

Met Ser Pro His Pro Thr Ala Leu Leu Gly Leu Val Leu Cys Leu Ala
1               5                   10                  15

Gln Thr Ile His Thr Gln Glu Glu Asp Leu Pro Arg Pro Ser Ile Ser
            20                  25                  30

Ala Glu Pro Gly Thr Val Ile Pro Leu Gly Ser His Val Thr Phe Val
            35                  40                  45

Cys Arg Gly Pro Val Gly Val Gln Thr Phe Arg Leu Glu Arg Asp Ser
        50                  55                  60
```

Arg Ser Thr Tyr Asn Asp Thr Glu Asp Val Ser Gln Ala Ser Pro Ser
65                  70                  75                  80

Glu Ser Glu Ala Arg Phe Arg Ile Asp Ser Val Arg Glu Gly Asn Ala
                85                  90                  95

Gly Leu Tyr Arg Cys Ile Tyr Tyr Lys Pro Pro Lys Trp Ser Glu Gln
            100                 105                 110

Ser Asp Tyr Leu Glu Leu Leu Val Lys Glu Ser Ser Gly Gly Pro Asp
                115                 120                 125

Ser Pro Asp Thr Glu Pro Gly Ser Ser Ala Gly Pro Thr Gln Arg Pro
130                 135                 140

Ser Asp Asn Ser His Asn Glu His Ala Pro Ala Ser Gln Gly Leu Lys
145                 150                 155                 160

Ala Glu His Leu Tyr Ile Leu Ile Gly Val Ser Val Val Phe Leu Phe
                165                 170                 175

Cys Leu Leu Leu Leu Val Leu Phe Cys Leu His Arg Gln Asn Gln Ile
                180                 185                 190

Lys Gln Gly Pro Pro Arg Ser Lys Asp Glu Glu Gln Lys Pro Gln Gln
                195                 200                 205

Arg Pro Asp Leu Ala Val Asp Val Leu Glu Arg Thr Ala Asp Lys Ala
210                 215                 220

Thr Val Asn Gly Leu Pro Glu Lys Asp Arg Glu Thr Asp Thr Ser Ala
225                 230                 235                 240

Leu Ala Ala Gly Ser Ser Gln Glu Val Thr Tyr Ala Gln Leu Asp His
                245                 250                 255

Trp Ala Leu Thr Gln Arg Thr Ala Arg Ala Val Ser Pro Gln Ser Thr
                260                 265                 270

Lys Pro Met Ala Glu Ser Ile Thr Tyr Ala Ala Val Ala Arg His
                275                 280                 285

<210> SEQ ID NO 40
<211> LENGTH: 370
<212> TYPE: PRT
<213> ORGANISM: Homo sapiens

<400> SEQUENCE: 40

Met Leu Gly Gln Val Val Thr Leu Ile Leu Leu Leu Leu Lys Val
1               5                   10                  15

Tyr Gln Gly Lys Gly Cys Gln Gly Ser Ala Asp His Val Val Ser Ile
                20                  25                  30

Ser Gly Val Pro Leu Gln Leu Gln Pro Asn Ser Ile Gln Thr Lys Val
            35                  40                  45

Asp Ser Ile Ala Trp Lys Lys Leu Leu Pro Ser Gln Asn Gly Phe His
    50                  55                  60

His Ile Leu Lys Trp Glu Asn Gly Ser Leu Pro Ser Asn Thr Ser Asn
65                  70                  75                  80

Asp Arg Phe Ser Phe Ile Val Lys Asn Leu Ser Leu Leu Ile Lys Ala
                85                  90                  95

Ala Gln Gln Gln Asp Ser Gly Leu Tyr Cys Leu Glu Val Thr Ser Ile
            100                 105                 110

Ser Gly Lys Val Gln Thr Ala Thr Phe Gln Val Phe Val Phe Glu Ser
            115                 120                 125

Leu Leu Pro Asp Lys Val Glu Lys Pro Arg Leu Gln Gly Gln Gly Lys
130                 135                 140

Ile Leu Asp Arg Gly Arg Cys Gln Val Ala Leu Ser Cys Leu Val Ser

```
                    145                 150                 155                 160
Arg Asp Gly Asn Val Ser Tyr Ala Trp Tyr Arg Gly Ser Lys Leu Ile
                165                 170                 175

Gln Thr Ala Gly Asn Leu Thr Tyr Leu Asp Glu Val Asp Ile Asn
                180                 185                 190

Gly Thr His Thr Tyr Thr Cys Asn Val Ser Asn Pro Val Ser Trp Glu
                195                 200                 205

Ser His Thr Leu Asn Leu Thr Gln Asp Cys Gln Asn Ala His Gln Glu
                210                 215                 220

Phe Arg Phe Trp Pro Phe Leu Val Ile Ile Val Ile Leu Ser Ala Leu
225                 230                 235                 240

Phe Leu Gly Thr Leu Ala Cys Phe Cys Val Trp Arg Arg Lys Arg Lys
                245                 250                 255

Glu Lys Gln Ser Glu Thr Ser Pro Lys Glu Phe Leu Thr Ile Tyr Glu
                260                 265                 270

Asp Val Lys Asp Leu Lys Thr Arg Arg Asn His Glu Gln Glu Gln Thr
                275                 280                 285

Phe Pro Gly Gly Gly Ser Thr Ile Tyr Ser Met Ile Gln Ser Gln Ser
                290                 295                 300

Ser Ala Pro Thr Ser Gln Glu Pro Ala Tyr Thr Leu Tyr Ser Leu Ile
305                 310                 315                 320

Gln Pro Ser Arg Lys Ser Gly Ser Arg Lys Arg Asn His Ser Pro Ser
                325                 330                 335

Phe Asn Ser Thr Ile Tyr Glu Val Ile Gly Lys Ser Gln Pro Lys Ala
                340                 345                 350

Gln Asn Pro Ala Arg Leu Ser Arg Lys Glu Leu Glu Asn Phe Asp Val
                355                 360                 365

Tyr Ser
    370

<210> SEQ ID NO 41
<211> LENGTH: 181
<212> TYPE: PRT
<213> ORGANISM: Homo sapiens

<400> SEQUENCE: 41

Met Leu Leu Glu Pro Gly Arg Gly Cys Cys Ala Leu Ala Ile Leu Leu
1               5                   10                  15

Ala Ile Val Asp Ile Gln Ser Gly Gly Cys Ile Asn Ile Thr Ser Ser
                20                  25                  30

Ala Ser Gln Glu Gly Thr Arg Leu Asn Leu Ile Cys Thr Val Trp His
                35                  40                  45

Lys Lys Glu Glu Ala Glu Gly Phe Val Val Phe Leu Cys Lys Asp Arg
                50                  55                  60

Ser Gly Asp Cys Ser Pro Glu Thr Ser Leu Lys Gln Leu Arg Leu Lys
65                  70                  75                  80

Arg Asp Pro Gly Ile Asp Gly Val Gly Glu Ile Ser Ser Gln Leu Met
                85                  90                  95

Phe Thr Ile Ser Gln Val Thr Pro Leu His Ser Gly Thr Tyr Gln Cys
                100                 105                 110

Cys Ala Arg Ser Gln Lys Ser Gly Ile Arg Leu Gln Gly His Phe Phe
                115                 120                 125

Ser Ile Leu Phe Thr Glu Thr Gly Asn Tyr Thr Val Thr Gly Leu Lys
                130                 135                 140
```

```
Gln Arg Gln His Leu Glu Phe Ser His Asn Glu Gly Thr Leu Ser Ser
145                 150                 155                 160

Gly Phe Leu Gln Glu Lys Val Trp Val Met Leu Val Thr Ser Leu Val
                165                 170                 175

Ala Leu Gln Ala Leu
            180

<210> SEQ ID NO 42
<211> LENGTH: 592
<212> TYPE: PRT
<213> ORGANISM: Homo sapiens

<400> SEQUENCE: 42

Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Asp
                20                  25                  30

Val Glu Met Glu Ala Gln Lys Asp Glu Ile Ile Cys Pro Ser Cys Asn
            35                  40                  45

Arg Thr Ala His Pro Leu Arg His Ile Asn Asn Asp Met Ile Val Thr
    50                  55                  60

Asp Asn Asn Gly Ala Val Lys Phe Pro Gln Leu Cys Lys Phe Cys Asp
65                  70                  75                  80

Val Arg Phe Ser Thr Cys Asp Asn Gln Lys Ser Cys Met Ser Asn Cys
                85                  90                  95

Ser Ile Thr Ser Ile Cys Glu Lys Pro Gln Glu Val Cys Val Ala Val
                100                 105                 110

Trp Arg Lys Asn Asp Glu Asn Ile Thr Leu Glu Thr Val Cys His Asp
            115                 120                 125

Pro Lys Leu Pro Tyr His Asp Phe Ile Leu Glu Asp Ala Ala Ser Pro
    130                 135                 140

Lys Cys Ile Met Lys Glu Lys Lys Pro Gly Glu Thr Phe Phe Met
145                 150                 155                 160

Cys Ser Cys Ser Ser Asp Glu Cys Asn Asp Asn Ile Ile Phe Ser Glu
                165                 170                 175

Glu Tyr Asn Thr Ser Asn Pro Asp Leu Leu Leu Val Ile Phe Gln Val
                180                 185                 190

Thr Gly Ile Ser Leu Leu Pro Pro Leu Gly Val Ala Ile Ser Val Ile
            195                 200                 205

Ile Ile Phe Tyr Cys Tyr Arg Val Asn Arg Gln Gln Lys Leu Ser Ser
    210                 215                 220

Thr Trp Glu Thr Gly Lys Thr Arg Lys Leu Met Glu Phe Ser Glu His
225                 230                 235                 240

Cys Ala Ile Ile Leu Glu Asp Asp Arg Ser Asp Ile Ser Ser Thr Cys
                245                 250                 255

Ala Asn Asn Ile Asn His Asn Thr Glu Leu Leu Pro Ile Glu Leu Asp
                260                 265                 270

Thr Leu Val Gly Lys Gly Arg Phe Ala Glu Val Tyr Lys Ala Lys Leu
            275                 280                 285

Lys Gln Asn Thr Ser Glu Gln Phe Glu Thr Val Ala Val Lys Ile Phe
    290                 295                 300

Pro Tyr Glu Glu Tyr Ala Ser Trp Lys Thr Glu Lys Asp Ile Phe Ser
305                 310                 315                 320

Asp Ile Asn Leu Lys His Glu Asn Ile Leu Gln Phe Leu Thr Ala Glu
                325                 330                 335
```

Glu Arg Lys Thr Glu Leu Gly Lys Gln Tyr Trp Leu Ile Thr Ala Phe
            340                 345                 350

His Ala Lys Gly Asn Leu Gln Glu Tyr Leu Thr Arg His Val Ile Ser
        355                 360                 365

Trp Glu Asp Leu Arg Lys Leu Gly Ser Ser Leu Ala Arg Gly Ile Ala
    370                 375                 380

His Leu His Ser Asp His Thr Pro Cys Gly Arg Pro Lys Met Pro Ile
385                 390                 395                 400

Val His Arg Asp Leu Lys Ser Ser Asn Ile Leu Val Lys Asn Asp Leu
                405                 410                 415

Thr Cys Cys Leu Cys Asp Phe Gly Leu Ser Leu Arg Leu Asp Pro Thr
            420                 425                 430

Leu Ser Val Asp Asp Leu Ala Asn Ser Gly Gln Val Gly Thr Ala Arg
        435                 440                 445

Tyr Met Ala Pro Glu Val Leu Glu Ser Arg Met Asn Leu Glu Asn Val
    450                 455                 460

Glu Ser Phe Lys Gln Thr Asp Val Tyr Ser Met Ala Leu Val Leu Trp
465                 470                 475                 480

Glu Met Thr Ser Arg Cys Asn Ala Val Gly Glu Val Lys Asp Tyr Glu
                485                 490                 495

Pro Pro Phe Gly Ser Lys Val Arg Glu His Pro Cys Val Glu Ser Met
            500                 505                 510

Lys Asp Asn Val Leu Arg Asp Arg Gly Arg Pro Glu Ile Pro Ser Phe
        515                 520                 525

Trp Leu Asn His Gln Gly Ile Gln Met Val Cys Glu Thr Leu Thr Glu
    530                 535                 540

Cys Trp Asp His Asp Pro Glu Ala Arg Leu Thr Ala Gln Cys Val Ala
545                 550                 555                 560

Glu Arg Phe Ser Glu Leu Glu His Leu Asp Arg Leu Ser Gly Arg Ser
                565                 570                 575

Cys Ser Glu Glu Lys Ile Pro Glu Asp Gly Ser Leu Asn Thr Thr Lys
            580                 585                 590

<210> SEQ ID NO 43
<211> LENGTH: 244
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg

```
                    100                 105                 110
Ala Arg Arg Asn Asp Ser Gly Thr Tyr Leu Cys Gly Ala Ile Ser Leu
            115                 120                 125

Ala Pro Lys Ala Gln Ile Lys Glu Ser Leu Arg Ala Glu Leu Arg Val
        130                 135                 140

Thr Glu Arg Arg Ala Glu Val Pro Thr Ala His Pro Ser Pro Ser Pro
145                 150                 155                 160

Arg Pro Ala Gly Gln Ala Ala Pro Thr Thr Pro Ala Pro Arg
                165                 170                 175

Pro Pro Thr Pro Ala Pro Thr Ile Ala Ser Gln Pro Leu Ser Leu Arg
                180                 185                 190

Pro Glu Ala Cys Arg Pro Ala Ala Gly Gly Ala Val His Thr Arg Gly
            195                 200                 205

Leu Asp Phe Ala Cys Asp Ile Tyr Ile Trp Ala Pro Leu Ala Gly Thr
        210                 215                 220

Cys Gly Val Leu Leu Leu Ser Leu Val Ile Thr Leu Tyr Cys Asn His
225                 230                 235                 240

Arg Arg Ile Gln

<210> SEQ ID NO 44
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gly Ser Gly Ala Thr Asn Phe Ser Leu Leu Lys Gln Ala Gly Asp Val
1               5                   10                  15

Glu Glu Asn Pro Gly Pro Met
            20

<210> SEQ ID NO 45
<211> LENGTH: 236
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Met Val Ser Lys Gly Glu Glu Asp Asn Met Ala Ile Ile Lys Glu Phe
1               5                   10                  15

Met Arg Phe Lys Val His Met Glu Gly Ser Val Asn Gly His Glu Phe
            20                  25                  30

Glu Ile Glu Gly Glu Gly Glu Gly Arg Pro Tyr Glu Gly Thr Gln Thr
        35                  40                  45

Ala Lys Leu Lys Val Thr Lys Gly Gly Pro Leu Pro Phe Ala Trp Asp
    50                  55                  60

Ile Leu Ser Pro Gln Phe Met Tyr Gly Ser Lys Ala Tyr Val Lys His
65                  70                  75                  80

Pro Ala Asp Ile Pro Asp Tyr Leu Lys Leu Ser Phe Pro Glu Gly Phe
                85                  90                  95

Lys Trp Glu Arg Val Met Asn Phe Glu Asp Gly Gly Val Val Thr Val
            100                 105                 110

Thr Gln Asp Ser Ser Leu Gln Asp Gly Glu Phe Ile Tyr Lys Val Lys
        115                 120                 125
```

```
Leu Arg Gly Thr Asn Phe Pro Ser Asp Gly Pro Val Met Gln Lys Lys
            130                 135                 140

Thr Met Gly Trp Glu Ala Ser Ser Glu Arg Met Tyr Pro Glu Asp Gly
145                 150                 155                 160

Ala Leu Lys Gly Glu Ile Lys Gln Arg Leu Lys Leu Lys Asp Gly Gly
                165                 170                 175

His Tyr Asp Ala Glu Val Lys Thr Thr Tyr Lys Ala Lys Lys Pro Val
            180                 185                 190

Gln Leu Pro Gly Ala Tyr Asn Val Asn Ile Lys Leu Asp Ile Thr Ser
        195                 200                 205

His Asn Glu Asp Tyr Thr Ile Val Glu Gln Tyr Glu Arg Ala Glu Gly
    210                 215                 220

Arg His Ser Thr Gly Gly Met Asp Glu Leu Tyr Lys
225                 230                 235

<210> SEQ ID NO 46
<211> LENGTH: 502
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Ala Ala Ala Pro Thr Thr Pro Ala Pro Arg
                165                 170                 175

Pro Pro Thr Pro Ala Pro Thr Ile Ala Ser Gln Pro Leu Ser Leu Arg
            180                 185                 190

Pro Glu Ala Cys Arg Pro Ala Ala Gly Gly Ala Val His Thr Arg Gly
        195                 200                 205

Leu Asp Phe Ala Cys Asp Ile Tyr Ile Trp Ala Pro Leu Ala Gly Thr
    210                 215                 220

Cys Gly Val Leu Leu Leu Ser Leu Val Ile Thr Leu Tyr Cys Asn His
225                 230                 235                 240

Arg Arg Ile Gln Gly Ser Gly Ala Thr Asn Phe Ser Leu Leu Lys Gln
```

```
            245                 250                 255
Ala Gly Asp Val Glu Glu Asn Pro Gly Pro Met Val Ser Lys Gly Glu
            260                 265                 270

Glu Asp Asn Met Ala Ile Ile Lys Glu Phe Met Arg Phe Lys Val His
            275                 280                 285

Met Glu Gly Ser Val Asn Gly His Glu Phe Glu Ile Glu Gly Glu Gly
            290                 295                 300

Glu Gly Arg Pro Tyr Glu Gly Thr Gln Thr Ala Lys Leu Lys Val Thr
305                 310                 315                 320

Lys Gly Gly Pro Leu Pro Phe Ala Trp Asp Ile Leu Ser Pro Gln Phe
                325                 330                 335

Met Tyr Gly Ser Lys Ala Tyr Val Lys His Pro Ala Asp Ile Pro Asp
            340                 345                 350

Tyr Leu Lys Leu Ser Phe Pro Glu Gly Phe Lys Trp Glu Arg Val Met
            355                 360                 365

Asn Phe Glu Asp Gly Gly Val Val Thr Val Thr Gln Asp Ser Ser Leu
370                 375                 380

Gln Asp Gly Glu Phe Ile Tyr Lys Val Lys Leu Arg Gly Thr Asn Phe
385                 390                 395                 400

Pro Ser Asp Gly Pro Val Met Gln Lys Lys Thr Met Gly Trp Glu Ala
                405                 410                 415

Ser Ser Glu Arg Met Tyr Pro Glu Asp Gly Ala Leu Lys Gly Glu Ile
            420                 425                 430

Lys Gln Arg Leu Lys Leu Lys Asp Gly Gly His Tyr Asp Ala Glu Val
            435                 440                 445

Lys Thr Thr Tyr Lys Ala Lys Lys Pro Val Gln Leu Pro Gly Ala Tyr
            450                 455                 460

Asn Val Asn Ile Lys Leu Asp Ile Thr Ser His Asn Glu Asp Tyr Thr
465                 470                 475                 480

Ile Val Glu Gln Tyr Glu Arg Ala Glu Gly Arg His Ser Thr Gly Gly
                485                 490                 495

Met Asp Glu Leu Tyr Lys
            500

<210> SEQ ID NO 47
<211> LENGTH: 1726
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 47
accggtggta cctcaccctt accgagtcgg cgacacagtg tgggtccgcc gacaccagac      60
taagaaccta gaacctcgct ggaaaggacc ttacacagtc ctgctgacca cccccaccgc     120
cctcaaagta gacggcatcg cagcttggat acacgccgcc cacgtgaagg ctgccgaccc     180 cggggggtgga ccatcctcta gactggccac catgcagatc ccacaggcgc cctggccagt     240
cgtctgggcg gtgctacaac tgggctggcg gccaggatgg ttcttagact ccccagacag     300
gccctggaac ccccccacct tctccccagc cctgctcgtg gtgaccgaag ggacaacgc      360 caccttcacc tgcagcttct ccaacacatc ggagagcttc gtgctaaact ggtaccgcat     420
gagccccagc aaccagacgg acaagctggc cgctttcccc gaggaccgca gccagcccgg     480
ccaggactgc cgcttccgtg tcacacaact gcccaacggg cgtgacttcc acatgagcgt     540
```

```
ggtcagggcc cggcgcaatg acagcggcac ctacctctgt ggggccatct ccctggcccc    600
caaggcgcag atcaaagaga gcctgcgggc agagctcagg gtgacagaga gaagggcaga    660
agtgcccaca gcccacccca gcccctcacc caggccagcc ggccaggcgg ccgcacccac    720
cacgacgcca gcgccgcgac caccaacccc ggcgcccacg atcgcgtcgc agccctgtc     780 cctgcgccca gaggcgtgcc ggccagcggc gggggcgca gtgcacacga gggggctgga     840
cttcgcctgt gatatctaca tctgggcgcc cctggccggg acttgtgggg tccttctcct    900
gtcactggtt atcacccttt actgcaacca caggcggatc caaggatctg gagcaacaaa    960
cttctcacta ctcaaacaag caggtgacgt ggaggagaat cccggcccca tggtgagcaa   1020
gggcgaggag gataacatgg ccatcatcaa ggagttcatg cgcttcaagg tgcacatgga   1080
gggctccgtg aacggccacg agttcgagat cgagggcgag ggcgagggcc gcccctacga   1140
gggcacccag accgccaagc tgaaggtgac caagggtggc cccctgccct cgcctggga    1200 catcctgtcc cctcagttca tgtacggctc caaggcctac gtgaagcacc ccgccgacat   1260
ccccgactac ttgaagctgt ccttcccga gggcttcaag tgggagcgcg tgatgaactt    1320
cgaggacggc ggcgtggtga ccgtgaccca ggactcctcc ctgcaggacg gcgagttcat   1380
ctacaaggtg aagctgcgcg gcaccaactt ccctccgac ggccccgtaa tgcagaagaa    1440
gaccatgggc tgggaggcct cctccgagcg gatgtacccc gaggacggcg ccctgaaggg   1500
cgagatcaag cagaggctga agctgaagga cggcggccac tacgacgctg aggtcaagac   1560
cacctacaag gccaagaagc ccgtgcagct gcccggcgcc tacaacgtca acatcaagtt   1620
ggacatcacc tcccacaacg aggactacac catcgtggaa cagtacgaac gcgccgaggg   1680
ccgccactcc accggcggca tggacgagct gtacaagtaa ctcgag                  1726
```

<210> SEQ ID NO 48
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Ser Gly Gly Gly Ser
1               5

IMMUNE CELL COMPOSITIONS AND METHODS OF USE

1. CROSS-REFERENCE TO RELATED APPLICATIONS

This application is a national stage application of International Patent Application No. PCT/US2016/050128, filed Sep. 2, 2016, which claims the benefit of U.S. Provisional application No. 62/214,809, filed Sep. 4, 2015, which is incorporated by reference herein in its entirety.

GOVERNMENT RIGHTS STATEMENT

This invention was made with government support under grant numbers W81WH-11-1-0783 and W81WH-12-1-0230, awarded by the U.S. Department of Defense. The government has certain rights in the invention.

REFERENCE TO SEQUENCE LISTING SUBMITTED ELECTRONICALLY

This application incorporates by reference a Sequence Listing with this application as an ASCII text file entitled "13542-020-228_SL.TXT" created on Aug. 30, 2016 and having a size of 81,752 bytes.

2. FIELD

The present invention relates generally to cancer treatment, and more specifically to immunotherapy for cancer treatment.

3. BACKGROUND

Recent years have provided tremendous advancements in the treatment of cancer. Among these advancement are the use of immunotherapy, where a cancer patient's immune response is harnessed to treat cancer. Such immunotherapy treatment methods include the use of cell-based immunotherapy, where cells of the immune system are utilized for therapeutic treatment. Immune system cells such as T cells and other immune cells can be modified to target tumor antigens.

In response to immune attack, solid tumors upregulate PD-L1 in response to immune attack, which in turn binds PD-1 receptor expressed on T cells, resulting in T-cell inhibition (see Pardoll, *Nat. Rev. Cancer* 12(4):252-64 (2012)). Upregulation of PD-L1 on T cells and antigen presenting cells (APCs) was described as well, resulting in inhibition of activated T cells (Talay et al., *Proc. Natl. Acad. Sci. USA* 106(8):2741-2746 (2009); Latchman et al., *Proc. Natl. Acad. Sci. USA* 101(29):10691-10696 (2004); Liu et al., *J. Cell. Mol. Med.* 19(6):1223-1233 (2015)). PD-1/PD-L1 checkpoint blockade therapy counteracts this inhibition, thereby leading to activated T cells. Various strategies to inhibit the immune checkpoint blockade mediated by PD-1 have been described, including the use of PD-1 or PDL-1 antibodies (Burga et al., *Cancer Immunol. Immunother.* 64(7):817-829 (2015); Moon et al., *Clin. Cancer Res.* 20(16):4262-4273 (2014); John et al., *Clin. Cancer Res.* 19(20):5636-5646 (2013)), RNA interference (Borkner et al., *Cancer Immunol. Immunother.* 59(8):1173-1183 (2010)), and co-stimulatory molecules (Prosser et al., *Mol. Immunol.* 51(3-4):263-272 (2012); Ankri et al., *J. Immunol.* 191(8):4121-4129 (2013)).

Chimeric antigen receptors (CARs) are synthetic receptors that retarget T cells to tumor surface antigens (Sadelain et al., *Nat. Rev. Cancer.* 3(1):35-45 (2003); Sadelain et al., *Cancer Discovery* 3(4):388-398 (2013)). Chimeric antigen receptors (CARs) are engineered receptors that provide both antigen binding and immune cell activation functions. CARs can be used to graft the specificity of an antibody, such as a monoclonal antibody, onto an immune cell such as a T cell. First-generation receptors link an antibody-derived tumor-binding element, such as an scFv, that is responsible for antigen recognition to either CD3zeta or Fc receptor signaling domains, which trigger T-cell activation. The advent of second-generation CARs, which combine activating and costimulatory signaling domains, has led to encouraging results in patients with chemorefractory B-cell malignancies (Brentjens et al., *Science Translational Medicine* 5(177):177ra38 (2013); Brentjens et al., *Blood* 118(18):4817-4828 (2011); Davila et al., *Science Translational Medicine* 6(224):224ra25 (2014); Grupp et al., *N. Engl. J. Med.* 368(16):1509-1518 (2013); Kalos et al., *Science Translational Medicine* 3(95):95ra73 (2011)). The translation of this clinical success to solid tumors requires overcoming additional obstacles, including achieving sufficient T-cell infiltration into tumors and resisting tumor immune escape. The extracellular antigen-binding domain of a CAR is usually derived from a monoclonal antibody (mAb) or from receptors or their ligands. Antigen recognition is therefore not MHC-restricted (Riviere et al., *Curr. Hematol. Rep.* 3:290-297 (2004); Stephan et al., *Nat. Med.* 13:1440-1449 (2007)) and is therefore applicable to any patient expressing the target cancer antigen using the corresponding CAR. Antigen binding by the CARs triggers phosphorylation of immunoreceptor tyrosine-based activation motifs (ITAMs) in the intracellular domain, initiating a signaling cascade required for cytolysis induction, cytokine secretion, and proliferation. Because MHC restriction of antigen recognition is bypassed, the function of CAR-targeted T cells is not affected by HLA downregulation or defects in the antigen-processing machinery.

To overcome the limitations of tumor infiltration and delayed activation observed with systemic T-cell administration, the merits of regional administration of mesothelin-specific CART cells in a clinically relevant model of pleural mesothelioma was recently demonstrated (Adusumilli et al., *Science Translational Medicine* 6(261):261ra151 (2014)). Mesothelin (MSLN) is a tumor-associated cell-surface antigen, which was selected on the basis of its overexpression in several cancers and observations of its association with tumor aggressiveness and decreased survival in mesothelioma, lung and breast cancer patients (Argani et al., *Clin. Cancer Res.* 7(12):3862-3868 (2001); Frierson et al., *Hum. Pathol.* 34(6):605-609 (2003); Gubbels et al., *Mol. Cancer* 5(1):50 (2006); Kachala et al., *Clin. Cancer Res.* 20(4):1020-1028 (2014); Li et al., *Mol. Cancer Ther.* 7(2):286-296 (2008); Rizk et al., *Cancer Epidemiol Biomarkers Prev.* 21(3):482-486 (2012); Servais et al., *Clin. Cancer Res.* 18(9):2478-2489 (2012); Tozbikian et al., *PLoS One* 9(12):e114900 (2014)). Regional administration of MSLN-targeted CAR T cells eradicates primary tumor and establishes long-term systemic immunosurveillance at 30-fold lower doses than intravenous administration (Adusumilli et al., *Science Translational Medicine* 6(261):261ra151 (2014)). These results are encouraging for the treatment of solid malignancies and have led to the initiation of a phase I clinical trial of intrapleural administration of mesothelin-targeted CAR T cells (ClinicalTrials.gov record NCT02414269).

To eliminate tumor cells, T cells must sustain cytolytic and proliferative function first in the absence of costimulatory ligands on tumor cells and elude the eventual inhibitory signals in the tumor microenvironment upon repeated antigen encounter. The success of second generation CAR T cells has been attributed to the enhanced T-cell persistence observed with costimulatory signaling domains, such as CD28 and 4-1BB. However, T cells naturally undergo activation-induced upregulation of coinhibitory pathways, which may limit the antitumor immune response. PD-1, CTLA-4, and other coinhibitory receptors are upregulated in T cells following antigen encounter, while tumor cells augment the expression of coinhibitory ligands following exposure to T-cell-secreted Th1 cytokines (McGray et al., *Mol. Ther.* 22(1):206-218 (2014); Spranger et al., *Science Translational Medicine* 5(200):200ra116 (2013); Moon et al., *Clin. Cancer Res.* 20(16):4262-4273 (2014)). The success of antibody therapy targeting immune checkpoints such as PD-1 and CTLA-4 underscores the therapeutic potential of immunotherapies that aim to counteract immune inhibition (Hodi et al., *N. Engl. J. Med.* 363(8):711-723 (2010); Wolchok et al., *N. Engl. J. Med.* 369(2):122-133 (2013); Topalian et al., *N. Engl. J. Med.* 366(26):2443-2454 (2012)). However, success with antibody therapies require the presence of infiltrating T cells and a relatively high mutation burden (Ji et al., *Cancer Immunol. Immunother.* 61(7):1019-1031 (2012); Rizvi et al., *Science* 348(6230):124-128 (2015); Hamid et al., *J. Translational Med.;* 9(204) doi: 10.1186/1479-5876-9-204 (2011)). Adoptive transfer of tumor-targeted T cells can therefore fill the void in patients with less immunogenic or "noninflamed" tumors (Nesbeth et al., *J. Immunol.* 184(10):5654-5662 (2010); Spear et al., *Oncoimmunology* 2(4):e23564 (2013)). As adoptively transferred T cells are themselves susceptible to immuno inhibition, strategies to counteract immuno inhibition using antibodies have been described (John et al., *Clin. Cancer Res.* 19(20):5636-5646 (2013); Strome et al., *Cancer Res.* 63(19):6501-6505 (2003)).

While immunotherapy methods have provided new modalities for cancer treatment, including antibody therapies and cell-based therapies using immune cells such as T cells, limitations have been found for the effectiveness of such treatments. Malignant cells adapt to generate an immunosuppressive microenvironment that protects the cells from immune recognition and elimination. This tumor microenvironment poses a challenge to methods of treatment involving stimulation of an immune response, including immunotherapy methods such as targeted T cell therapies. Solid tumors can be restricted within anatomical compartments such that access of therapeutic immune cells to the tumors is limited. In addition, an immunosuppressive microenvironment must be overcome so that the immunotherapy is effective. The successful elimination of solid tumors or other cancers thus requires effective tumor infiltration and overcoming tumor-induced or cancer cell-induced immunosuppression.

Thus, there exists a need for therapies to provide improved treatment of cancer that overcome microenvironments associated with malignant cells or tumors that inhibit effective immunotherapies. The present invention satisfies this need and provides related advantages as well.

4. SUMMARY OF INVENTION

The present invention relates to cells that are immune cells or precursor cells thereof, which recombinantly express a chimeric antigen receptor (CAR), and a dominant negative form of an inhibitor of a cell-mediated immune response.

In one aspect, provided herein is a cell that is an immune cell or precursor cell thereof, which cell recombinantly expresses (a) a chimeric antigen receptor (CAR), and (b) a dominant negative form of an inhibitor of a cell-mediated immune response of the immune cell, wherein the CAR binds to a cancer antigen. In certain embodiments, the immune cell is a T cell. In certain embodiments, the precursor cell is a hematopoietic stem or hematopoietic progenitor cell. In a specific embodiment, the immune cell is a cytotoxic T lymphocyte (CTL). In another embodiment, the cell is a T cell. In another embodiment, the cell is a Natural Killer (NK) cell.

In certain embodiments of a cell of the invention, the inhibitor of a cell-mediated immune response is an immune checkpoint inhibitor. In certain embodiments, the immune checkpoint inhibitor is selected from the group consisting of programmed death 1 (PD-1), cytotoxic T lymphocyte antigen-4 (CTLA-4), B- and T-lymphocyte attenuator (BTLA), T cell immunoglobulin mucin-3 (TIM-3), lymphocyte-activation protein 3 (LAG-3), T cell immunoreceptor with Ig and ITIM domains (TIGIT), leukocyte-associated immunoglobulin-like receptor 1 (LAIR1), natural killer cell receptor 2B4 (2B4), and CD160. In a particular embodiment, the immune checkpoint inhibitor is PD-1. In another embodiment, the inhibitor of a cell-mediated immune response is transforming growth factor β (TGF-β) receptor.

In certain embodiments of cells of the invention, the cancer antigen is selected from the group consisting of mesothelin, prostate specific membrane antigen (PSMA), prostate stem cell antigen (PCSA), carbonic anhydrase IX (CAIX), carcinoembryonic antigen (CEA), CD5, CD7, CD10, CD19, CD20, CD22, CD30, CD33, CD34, CD38, CD41, CD44, CD49f, CD56, CD74, CD123, CD133, CD138, epithelial glycoprotein2 (EGP 2), epithelial glycoprotein-40 (EGP-40), epithelial cell adhesion molecule (Ep-CAM), folate-binding protein (FBP), fetal acetylcholine receptor (AChR), folate receptor-α and β (FRα and β), Ganglioside G2 (GD2), Ganglioside G3 (GD3), human Epidermal Growth Factor Receptor 2 (HER-2/ERB2), Epidermal Growth Factor Receptor vIII (EGFRvIII), ERB3, ERB4, human telomerase reverse transcriptase (hTERT), Interleukin-13 receptor subunit alpha-2 (IL-13Rα2), κ-light chain, kinase insert domain receptor (KDR), Lewis A (CA19.9), Lewis Y (LeY), L1 cell adhesion molecule (L1CAM), melanoma-associated antigen 1 (melanoma antigen family A1, MAGE-A1), Mucin 16 (Muc-16), Mucin 1 (Muc-1), NKG2D ligands, cancer-testis antigen NY-ESO-1, oncofetal antigen (h5T4), tumor-associated glycoprotein 72 (TAG-72), vascular endothelial growth factor R2 (VEGF-R2), Wilms tumor protein (WT-1), type 1 tyrosine-protein kinase transmembrane receptor (ROR1), B7-H3 (CD276), B7-H6 (Nkp30), Chondroitin sulfate proteoglycan-4 (CSPG4), DNAX Accessory Molecule (DNAM-1), Ephrin type A Receptor 2 (EpHA2), Fibroblast Associated Protein (FAP), Gp100/HLA-A2, Glypican 3 (GPC3), HA-1H, HERK-V, IL-11Rα, Latent Membrane Protein 1 (LMP1), Neural cell-adhesion molecule (N-CAM/CD56), and Trail Receptor (TRAIL R). In a particular embodiment, the cancer antigen is mesothelin. In a particular embodiment, the cancer antigen is mesothelin and the inhibitor of a cell-mediated immune response is PD-1. In certain embodiments of the invention, the cell further recombinantly expresses a suicide gene. In a specific embodiment, the suicide gene comprises inducible Caspase 9.

In another aspect, provided herein are pharmaceutical compositions comprising a therapeutically effective amount of a cell of the invention that is an immune cell or precursor cell thereof, which cell recombinantly expresses (a) a chimeric antigen receptor (CAR), and (b) a dominant negative form of an inhibitor of a cell-mediated immune response of the immune cell, wherein the CAR binds to a cancer antigen; and a pharmaceutically acceptable carrier.

In yet another aspect, provided herein are polypeptides comprising (a) at least a portion of an extracellular domain of an immune checkpoint inhibitor, said portion comprising the ligand binding region, and (b) a transmembrane domain; wherein the polypeptide is a dominant negative form of the immune checkpoint inhibitor. In certain embodiments, the transmembrane domain is derived from a polypeptide other than the immune checkpoint inhibitor. In certain embodiments, the polypeptide lacks the intracellular domain of the polypeptide.

In certain embodiments of a polypeptide of the invention, the immune checkpoint inhibitor is a receptor selected from the group consisting of programmed death 1 (PD-1), cytotoxic T lymphocyte antigen-4 (CTLA-4), B- and T-lymphocyte attenuator (BTLA), T cell immunoglobulin mucin-3 (TIM-3), lymphocyte-activation protein 3 (LAG-3), T cell immunoreceptor with Ig and ITIM domains (TIGIT), leukocyte-associated immunoglobulin-like receptor 1 (LAIR1), natural killer cell receptor 2B4 (2B4), and CD160. In a specific embodiment, the immune checkpoint inhibitor is PD-1.

In certain embodiments of a polypeptide of the invention, the transmembrane domain is of a cell surface polypeptide of a T cell. In specific embodiments, the transmembrane domain is of a cell surface polypeptide selected from the group consisting of CD3, CD4, CD8, CD28, 4-1BB, OX40, ICOS, CTLA-4, LAG3, 2B4 and BTLA. In specific embodiments, the transmembrane domain is of the cell surface polypeptide is CD8 or CD28. In specific embodiments of a polypeptide of the invention, the amino acid sequence of the polypeptide consists of the extracellular domain of PD-1 fused to the transmembrane and hinge domains of CD8.

In another aspect, provided herein are nucleic acids encoding the polypeptides of the invention encoding a dominant negative form of an immune checkpoint inhibitor, wherein the dominant negative form is a polypeptide comprising (a) at least a portion of an extracellular domain of an immune checkpoint inhibitor, said portion comprising the ligand binding region, and (b) a transmembrane domain; wherein the polypeptide is a dominant negative form of the immune checkpoint inhibitor. In still another aspect, provided herein are vectors comprising the nucleic acid. In yet another aspect, provided herein are cells comprising the polypeptide of the invention encoding a dominant negative form of an immune checkpoint inhibitor, described above. In another aspect, provided herein are cells comprising the nucleic acid of the invention, described above. In another embodiment, provided herein are cells comprising a vector, which comprises a nucleic acid of the invention, described above.

In another aspect, provided herein are T cells that recognize and are sensitized to a cancer antigen, which T cells recombinantly express a dominant negative form of an inhibitor of a T cell-mediated immune response. In certain embodiments of T cells of the invention, the inhibitor of a T cell-mediated immune response is an immune checkpoint inhibitor. In a particular embodiment, the immune checkpoint inhibitor is selected from the group consisting of programmed death 1 (PD-1), cytotoxic T lymphocyte antigen-4 (CTLA-4), B- and T-lymphocyte attenuator (BTLA), T cell immunoglobulin mucin-3 (TIM-3), lymphocyte-activation protein 3 (LAG-3), T cell immunoreceptor with Ig and ITIM domains (TIGIT), leukocyte-associated immunoglobulin-like receptor 1 (LAIR1), natural killer cell receptor 2B4 (2B4), and CD160. In a specific embodiment, the immune checkpoint inhibitor is PD-1. In another embodiment, the inhibitor of a cell-mediated immune response is transforming growth factor β (TGF-β) receptor.

In certain embodiments of T cells of the invention, the cancer antigen is selected from the group consisting of mesothelin, prostate specific membrane antigen (PSMA), prostate stem cell antigen (PCSA), carbonic anhydrase IX (CAIX), carcinoembryonic antigen (CEA), CD5, CD7, CD10, CD19, CD20, CD22, CD30, CD33, CD34, CD38, CD41, CD44, CD49f, CD56, CD74, CD123, CD133, CD138, epithelial glycoprotein2 (EGP 2), epithelial glycoprotein-40 (EGP-40), epithelial cell adhesion molecule (Ep-CAM), folate-binding protein (FBP), fetal acetylcholine receptor (AChR), folate receptor-α and β (FRα and β), Ganglioside G2 (GD2), Ganglioside G3 (GD3), human Epidermal Growth Factor Receptor 2 (HER-2/ERB2), Epidermal Growth Factor Receptor vIII (EGFRvIII), ERB3, ERB4, human telomerase reverse transcriptase (hTERT), Interleukin-13 receptor subunit alpha-2 (IL-13Rα2), κ-light chain, kinase insert domain receptor (KDR), Lewis A (CA19.9), Lewis Y (LeY), L1 cell adhesion molecule (L1CAM), melanoma-associated antigen 1 (melanoma antigen family A1, MAGE-A1), Mucin 16 (Muc-16), Mucin 1 (Muc-1), NKG2D ligands, cancer-testis antigen NY-ESO-1, oncofetal antigen (h5T4), tumor-associated glycoprotein 72 (TAG-72), vascular endothelial growth factor R2 (VEGF-R2), Wilms tumor protein (WT-1), type 1 tyrosine-protein kinase transmembrane receptor (ROR1), B7-H3 (CD276), B7-H6 (Nkp30), Chondroitin sulfate proteoglycan-4 (CSPG4), DNAX Accessory Molecule (DNAM-1), Ephrin type A Receptor 2 (EpHA2), Fibroblast Associated Protein (FAP), Gp100/HLA-A2, Glypican 3 (GPC3), HA-1H, HERK-V, IL-11Rα, Latent Membrane Protein 1 (LMP1), Neural cell-adhesion molecule (N-CAM/CD56), and Trail Receptor (TRAIL R). In a particular embodiment, the cancer antigen is mesothelin. In another particular embodiment, the cancer antigen is mesothelin and the inhibitor of a cell-mediated immune response is PD-1.

In certain embodiments of T cells of the invention, the T cell further recombinantly expresses a suicide gene. In a particular embodiment, the suicide gene comprises inducible Caspase 9.

In still another aspect, provided herein is a pharmaceutical composition comprising a therapeutically effective amount of the T cells described above that recognize and are sensitized to a cancer antigen and which recombinantly express a dominant negative form of an inhibitor of a T cell-mediated immune response; and a pharmaceutically acceptable carrier.

In another aspect, provided herein are methods of treating a cancer in a subject in need thereof, comprising administering to the subject a therapeutically effective amount of a cell that is an immune cell or precursor cell thereof, which cell recombinantly expresses (a) a chimeric antigen receptor (CAR), and (b) a dominant negative form of an inhibitor of a cell-mediated immune response of the immune cell, wherein the CAR binds to a cancer antigen, described above.

In another aspect, provided herein are methods of treating a cancer in a subject in need thereof, comprising administering to the subject a pharmaceutical composition comprising a cell that is an immune cell or precursor cell thereof, which cell recombinantly expresses (a) a chimeric antigen receptor (CAR), and (b) a dominant negative form of an inhibitor of a cell-mediated immune response of the immune cell, wherein the cancer antigen is an antigen of the cancer. In another aspect, provided herein are methods of treating a cancer in a subject in need thereof, comprising administering to the subject a pharmaceutical composition comprising T cells that recognize and are sensitized to a cancer antigen and which recombinantly express a dominant negative form of an inhibitor of a T cell-mediated immune response, wherein the CAR binds to a cancer antigen.

In another aspect, provided herein are methods of treating a cancer in a subject in need thereof, comprising administering to the subject a therapeutically effective amount of T cells that recognize and are sensitized to a cancer antigen and which recombinantly express a dominant negative form of an inhibitor of a T cell-mediated immune response, wherein the cancer antigen is an antigen of the cancer.

In certain aspects of methods of the invention, the cancer is selected from the group consisting of mesothelioma, lung cancer, pancreatic cancer, ovarian cancer, breast cancer, colon cancer, pleural tumor, glioblastoma, esophageal cancer, gastric cancer, and synovial sarcoma. In certain aspects of methods of the invention, the administering is by intrapleural administration, intravenous administration, subcutaneous administration, intranodal administration, intratumoral administration, intrathecal administration, intraperitoneal administration, intracranial administration, or direct administration to the thymus.

In certain aspects of methods of the invention, the cancer antigen is mesothelin, and the cancer is selected from the group consisting of mesothelioma, lung cancer, and breast cancer. In specific embodiments of methods of the invention, the subject has malignant pleural disease. In specific embodiments of methods of the invention, the cells are administered intrapleurally. In certain aspects of methods of the invention, the subject has a tumor. In certain aspects of methods of the invention, tumor growth is inhibited.

In certain aspects of methods of the invention, the cell is administered in a dose in the range of $10^4$ to $10^{10}$ cells per kilogram of body weight. In specific embodiments, the dose is in the range of $3 \times 10^5$ to $3 \times 10^6$ cells per kilogram of body weight.

In certain aspects of methods of the invention, the subject is a human. In specific aspects, a cell of the invention that is an immune cell or precursor cell thereof, is derived from a human, which cell recombinantly expresses (a) a chimeric antigen receptor (CAR), and (b) a dominant negative form of an inhibitor of a cell-mediated immune response of the immune cell, wherein the CAR binds to a cancer antigen. In specific aspects, T cells of the invention that recognize and are sensitized to a cancer antigen, which T cells recombinantly express a dominant negative form of an inhibitor of a T cell-mediated immune response, are T cells derived from a human. In specific aspects of methods of the invention, the cells used in the methods to treat a human subject are derived from a human.

In certain aspects of methods of the invention, the CAR comprises a co-stimulatory signaling domain. In certain embodiments, the co-stimulatory signaling domain is the intracellular signaling domain of 4-1BB. In certain embodiments, the method of the invention further comprises administering a cytokine to the subject. In certain embodiments, the cytokine is IL-2 or GM-CSF. In a particular embodiment the cytokine is IL-2.

In certain aspects of methods of the invention, the method further comprises administering an immune cell recombinantly expressing the chimeric antigen receptor (CAR) and a switch receptor, wherein the switch receptor comprises (i) at least the extracellular ligand binding domain of an immune checkpoint inhibitor, (ii) a transmembrane domain, and (iii) a co-stimulatory signaling domain. In certain embodiments, the co-stimulatory signaling domain of the switch receptor is different from the co-stimulatory signaling domain of the CAR. In certain embodiments, the co-stimulatory signaling domain of the CAR is the intracellular signaling domain of CD28. In a specific embodiment, the co-stimulatory signaling domain of the switch receptor is the intracellular signaling domain of 4-1BB.

5. DESCRIPTION OF THE DRAWINGS

Figure 1B:
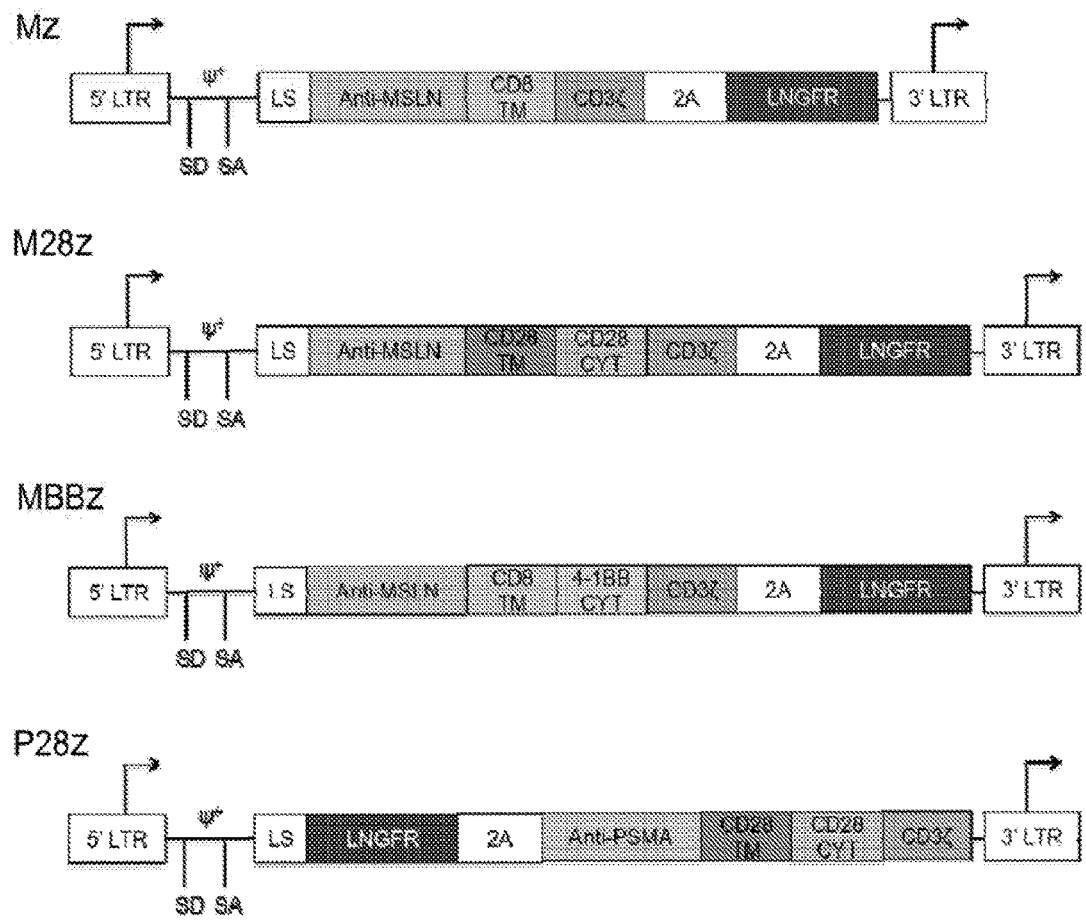
Figure 1C:
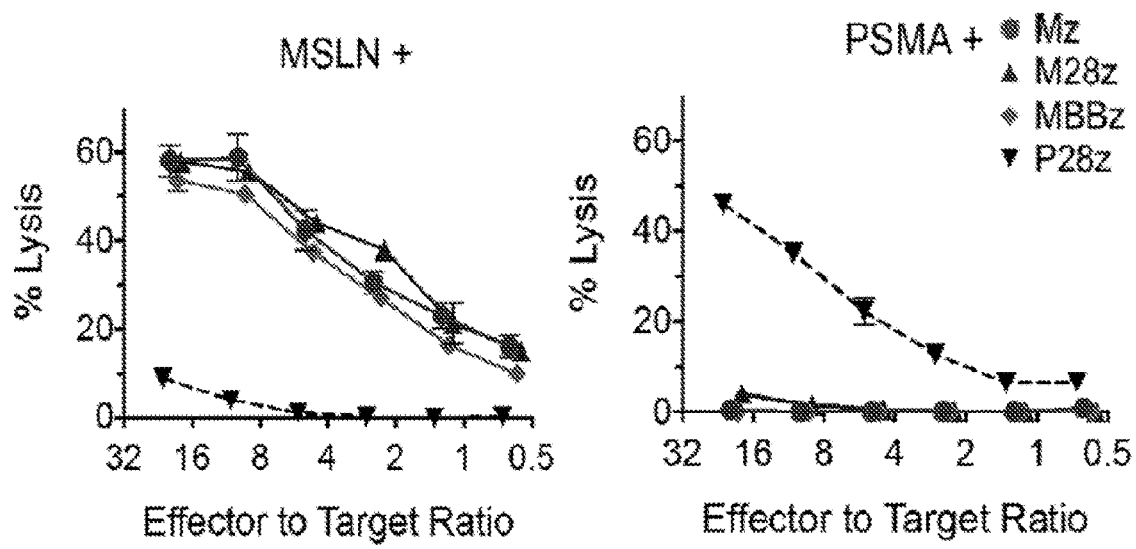
Figure 1D:
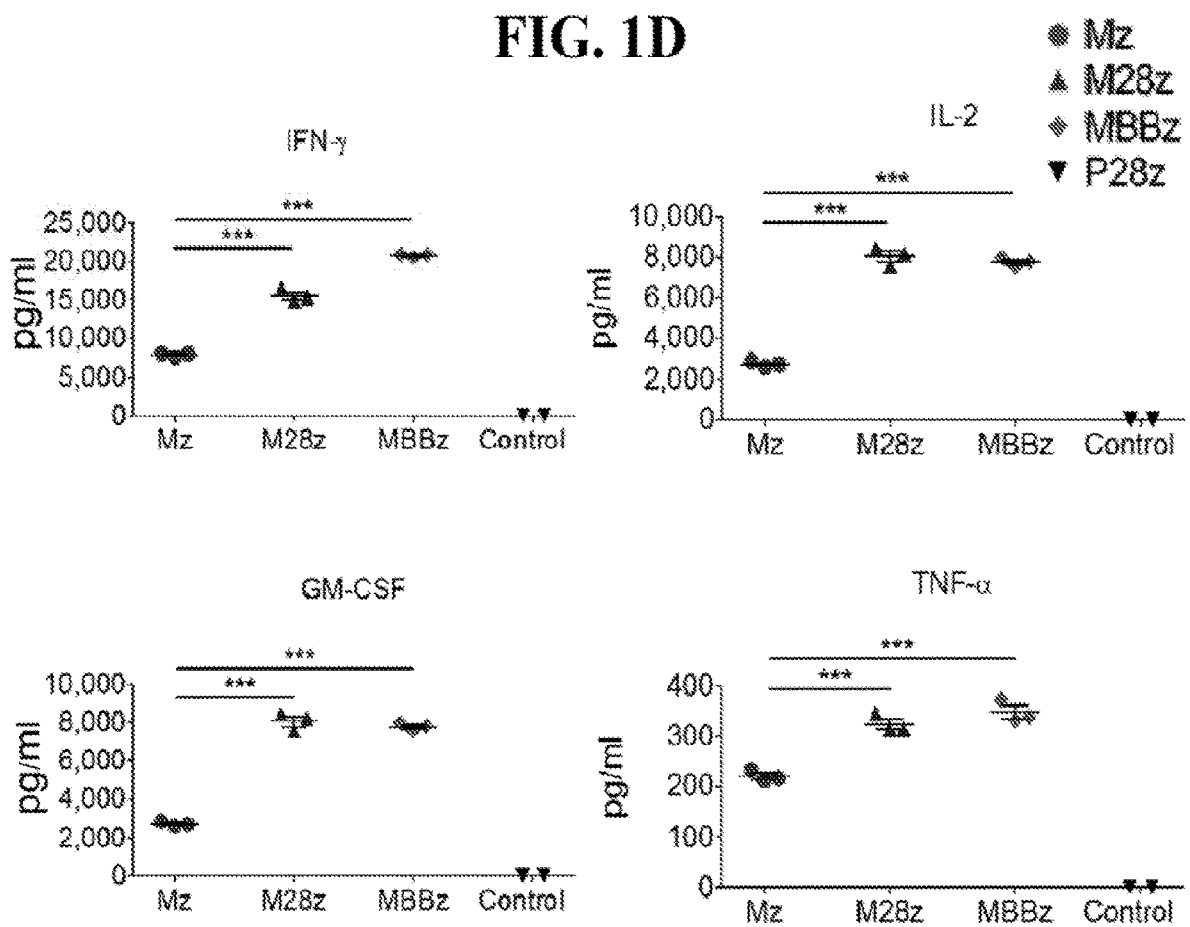
Figure 1E:
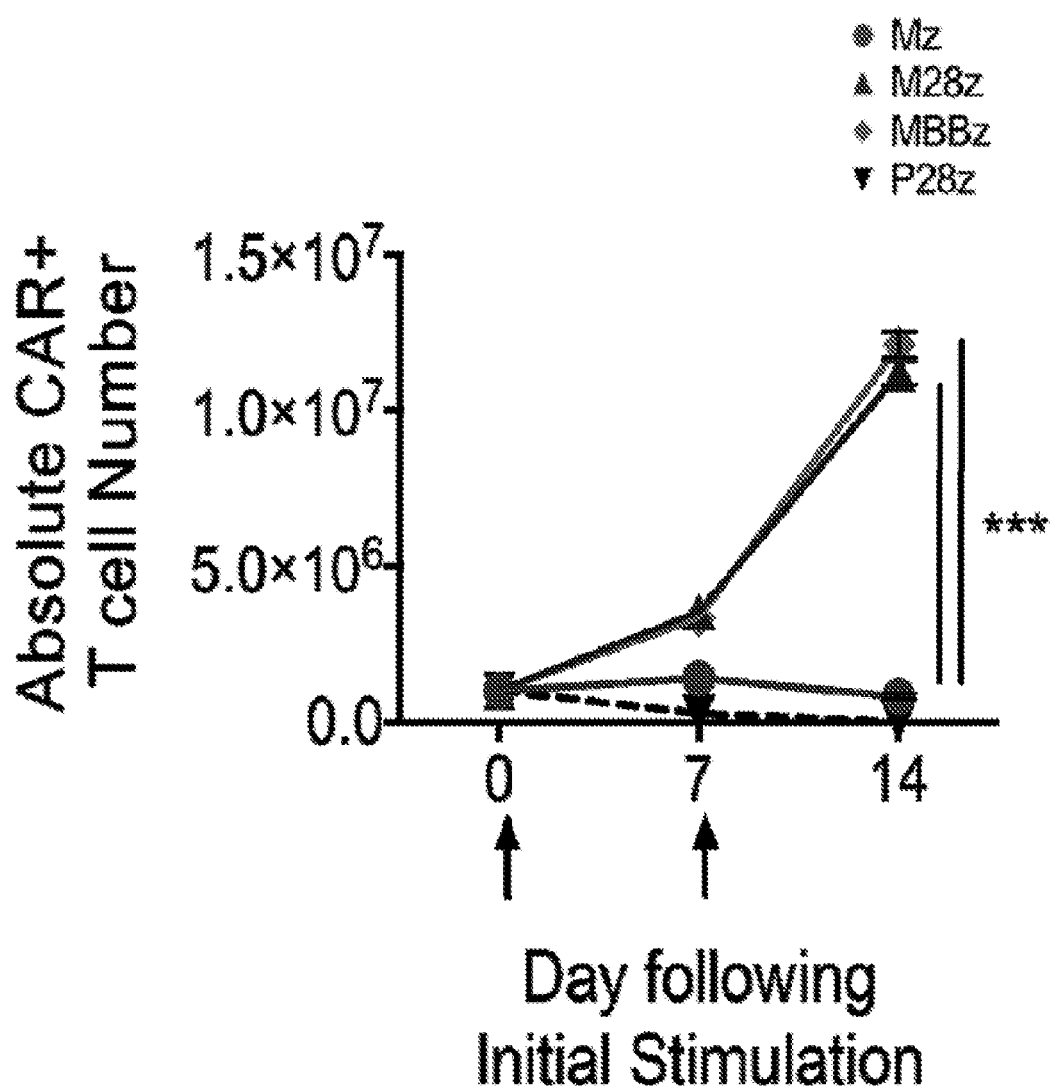

FIGS. 1A-1E show that chimeric antigen receptors (CARs) with CD28 or 4-1BB costimulation exhibit equivalent effector cytokine secretion and proliferation in vitro upon initial antigen stimulation. FIG. 1A. First- and second-generation CARs. FIG. 1B. Mesothelin (MSLN)-targeted CARs contain the CD3ζ endodomain either alone (Mz, first-generation CAR) or in combination with the CD28 (M28z) or 4-1BB (MBBz) costimulatory domain (second-generation CAR). A prostate-specific membrane antigen (PSMA)-directed CAR with CD28 costimulation (P28z) as well as PSMA-expressing targets (PSMA+) are included in experiments as negative controls. CYT, cytoplasmic domain; LS, leader sequence; LTR, long terminal repeat; SA, splice acceptor; SD, splice donor; TM, transmembrane. FIGS. 1C-1E. Antigen-specific effector functions of CAR-transduced T cells. FIG. 1C. Lysis of MSLN-expressing targets (MSLN+), but not PSMA+ targets, as measured by chromium-release assays. FIG. 1D. 4-1BB and CD28 costimulations enhance cytokine secretion, as assessed by Luminex assay, after coculture of CAR T cells with MSLN+ cells. FIG. 1E. M28z and MBBz CARs facilitate robust T-cell accumulation after stimulation with MSLN+ cells. Data represent the mean±SEM (FIGS. 1C, 1E) of three replicates or are plotted as individual points (FIG. 1D). ***$P<0.001$, comparing costimulated CAR T cells (M28z or MBBz) with the first-generation receptor (Mz), by Student's t test; significance was determined using the Bonferroni correction for multiple comparisons.

Figure 2A:
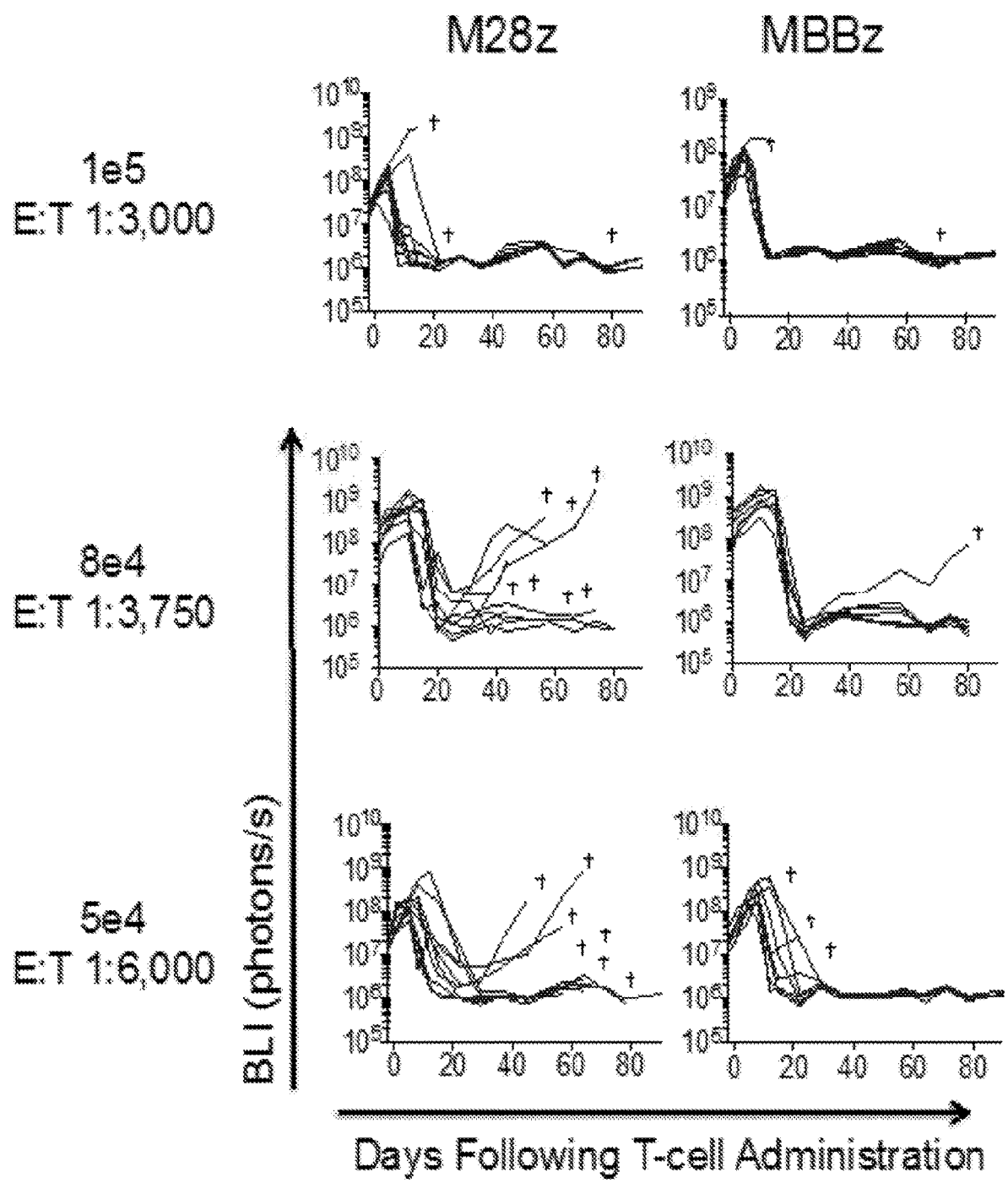
Figure 2B:
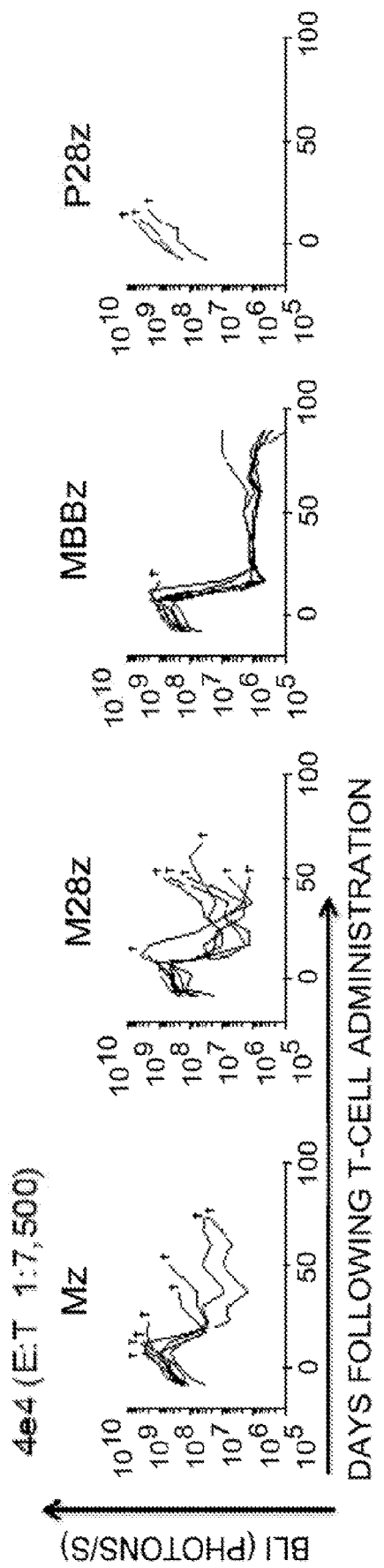
Figure 2C:
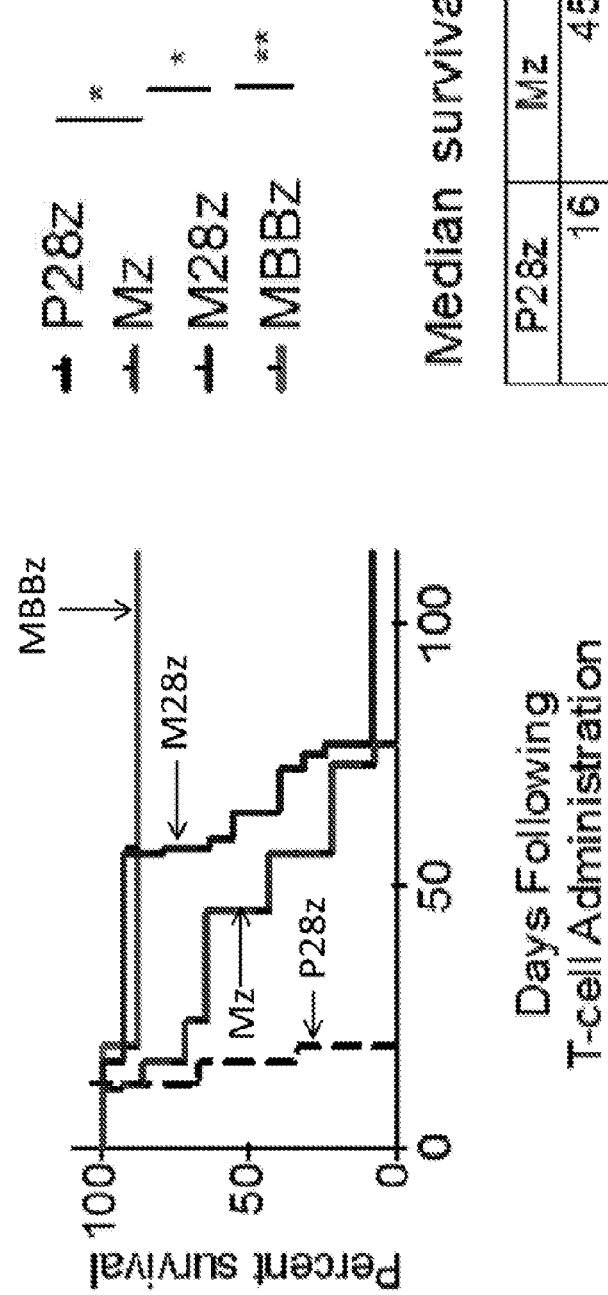

FIGS. 2A-2C show that mice treated with M28z and MBBz CAR T cells demonstrate tumor eradication at a higher dose whereas treatment with lower doses results in higher rate of tumor relapse with M28z. FIG. 2A. In vivo bioluminescence imaging (BLI) was used to monitor tumor burden (firefly luciferase+ MSLN+) in NOD/SCID/$\gamma_c^{null}$ mice. Mice with established pleural tumor were treated with a single dose of 1e5 (effector to target (E:T) ratio 1:3,000), 8e4 (E:T1:3,750), or 5e4 (E:T 1:6,000) M28z or MBBz CAR T cells. The (✝) symbol indicates the death of a mouse. Two similar experiments with the same donor are combined for the illustration. FIG. 2B. Mice were treated with 4e4 CAR T cells (E:T 1:7,500). The first generation Mz CAR and negative control P28z are included. FIG. 2C. Kaplan-Meier survival analysis comparing the in vivo efficacy of intrapleural administration of 4e4 Mz (n=13, second curve from left), M28z (n=15, third curve from left), MBBz (n=8, curve across top), and P28z (n=3, first curve from left) CAR T cells. Median survival in days following T-cell administration (P28z, 16; Mz, 45; M28z, 64; MBBz, not reached). The survival curve was analyzed using the log-rank test. *$P<0.05$; **$P<0.01$.

Figure 3C:
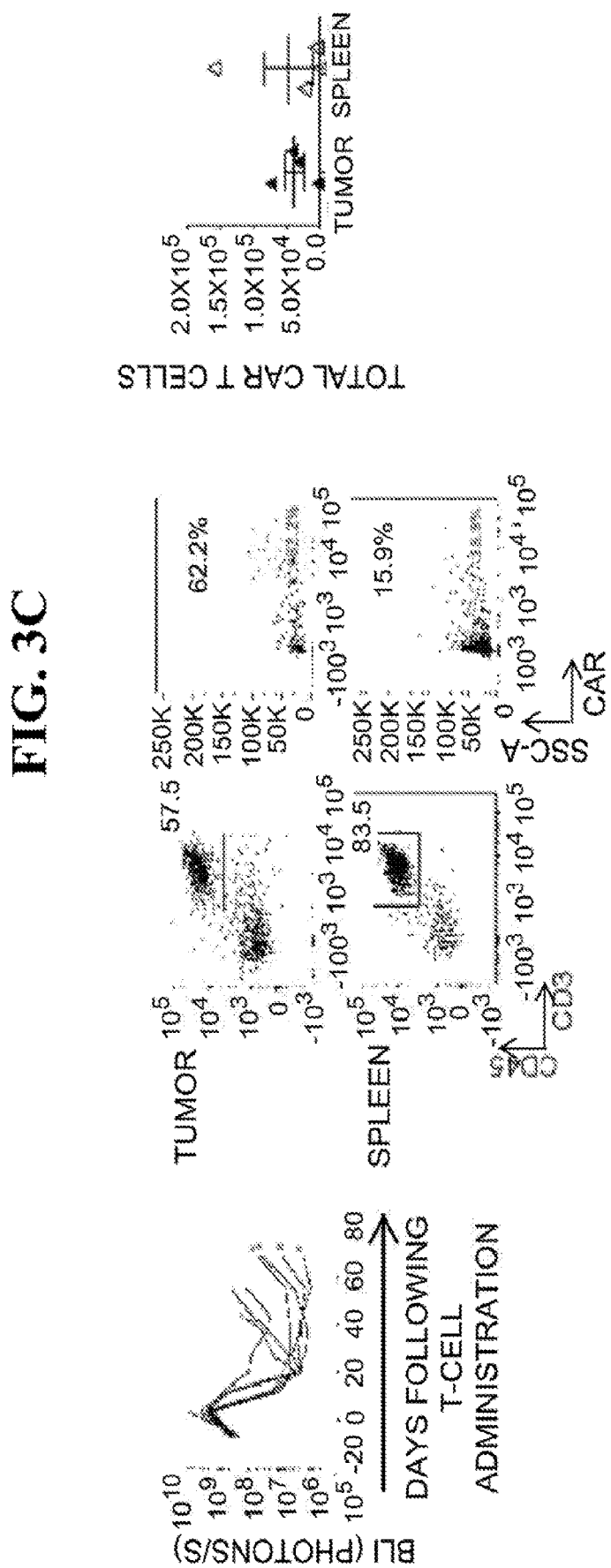

FIGS. 3A-3C show that M28z- and MBBz-treated mice demonstrate similar early and long-term CAR T-cell accumulation, and M28z-treated mice with progressing tumors contain persisting CAR T cells. FIG. 3A. CD28 and 4-1BB costimulation enhance intratumoral CAR T-cell accumulation to equal extents. The left panels show the results of tumor BLI after after administration of a single dose of $8e^4$ CAR T cells. After 6 days, T cells were harvested from the tumor; x denotes mice whose T-cell counts are represented as data points. The right panel shows absolute CAR T cells per gram of tumor tissue (*P<0.05). Student's t tests were performed and statistical significance was determined using the Bonferroni correction for multiple comparisons. FIG. 3B. CD28 and 4-1BB costimulation enhance CAR T-cell persistence, as measured in the spleen, to equal extents. Absolute CAR T cells per spleen are shown 73 days after intrapleural administration of CAR T cells ($8e^4$). The left panels show the results of tumor BLI; x denotes mice whose T-cell counts are represented as data points (*P<0.05). Student's t tests were performed and statistical significance was determined using the Bonferroni correction for multiple comparisons. FIG. 3C. Mice treated with a low dose of M28z T cells ($4e^4$) display tumor recurrence with persisting CAR T cells in the spleen and tumor. The left panel shows the results of tumor BLI. Spleen and tumor from mice denoted by an x were harvested and used for FACs analysis (middle panel) and T-cell quantification (right panel).

Figure 4C:
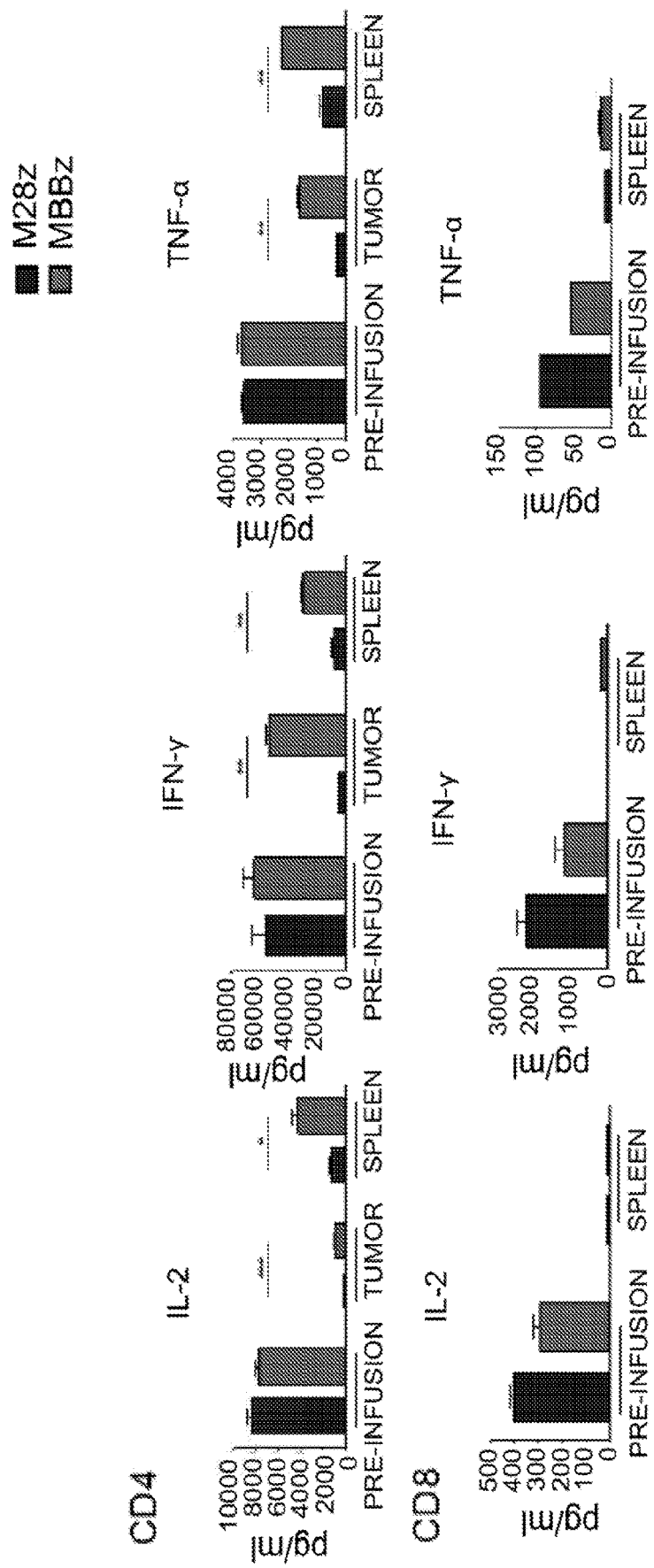
Figure 4D:
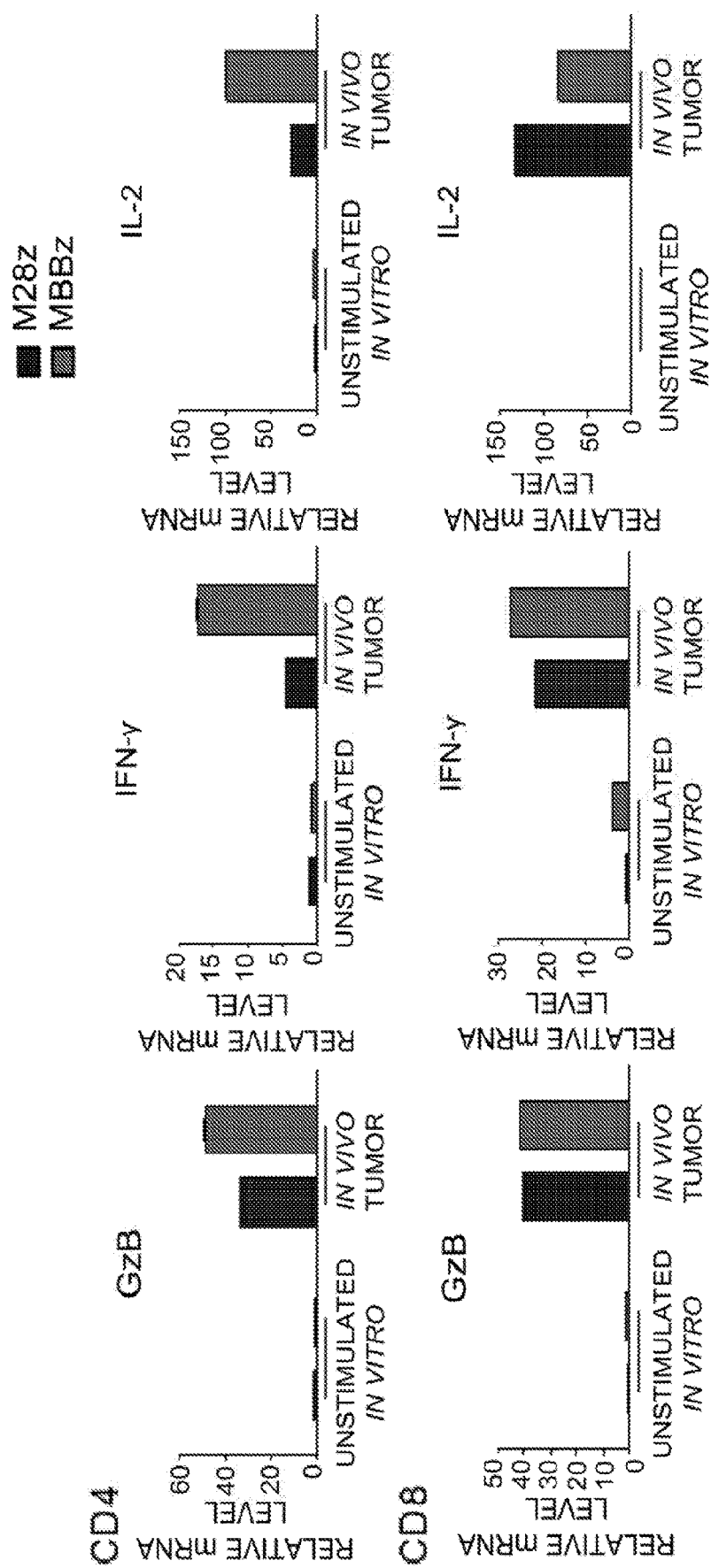

FIGS. 4A-4D show that CAR T cells become exhausted following in vivo antigen exposure, although MBBz CAR T cells preferentially retain effector cytokine secretion and cytotoxicity. FIG. 4A. Six days after intrapleural administration of CAR T cells, M28z and MBBz CAR T cells were isolated from the tumor and spleen and subjected to ex vivo antigen stimulation. FIG. 4B. Chromium-release assay upon ex vivo stimulation demonstrates a decrease in M28z but persistent MBBz cytolytic function (E:T ratio 1:5). FIG. 4C. Cytokine secretion measurements demonstrate decreases in effector cytokine secretion by CAR T cells, although MBBz CAR T cells are better able to retain secretion. FIG. 4D. RT-PCR measurements of GzB, IFN-γ, and IL-2 expression by harvested CAR T cells correlate well with protein level measurements. Data represent the fold-change relative to the mRNA expression of unstimulated M28z CAR T cell in vitro. Data represent the mean±SEM of three individual wells per condition. Student's t tests were performed, and statistical significance was determined using the Bonferroni correction for multiple comparisons (*P<0.05; P<0.01; *P<0.001). Results are reproduced in two separate cohorts of mice used for each of the two experiments. In each of FIGS. 4B-4D, each pair of bar graphs show, from left to right, M28z, MBBZ.

Figure 5A:
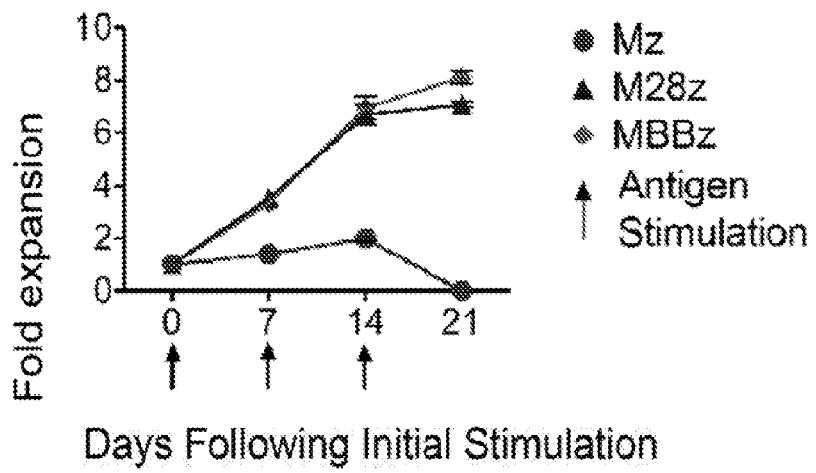
Figure 5B:
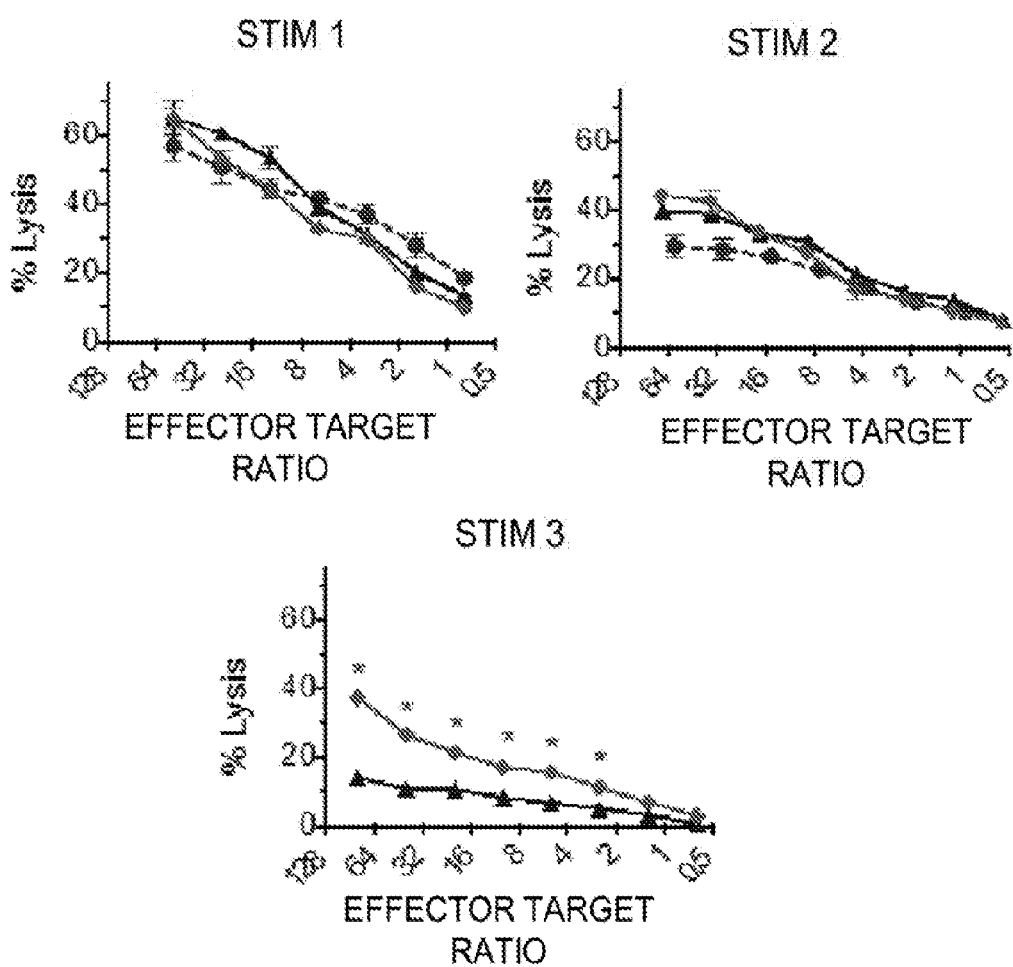
Figure 5C:
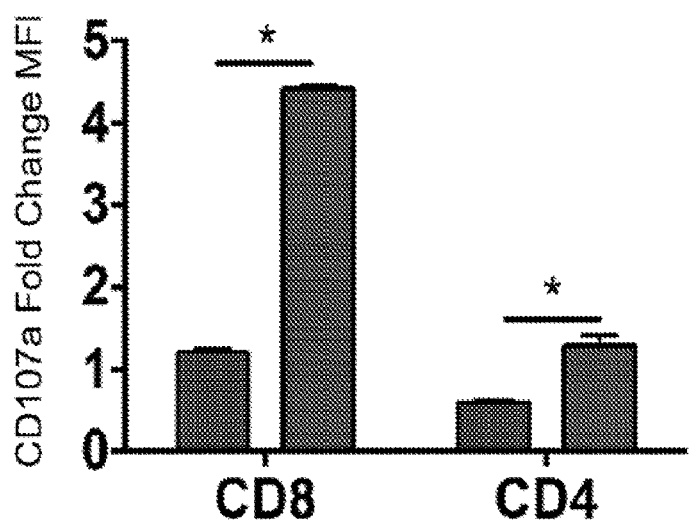
Figure 5D:
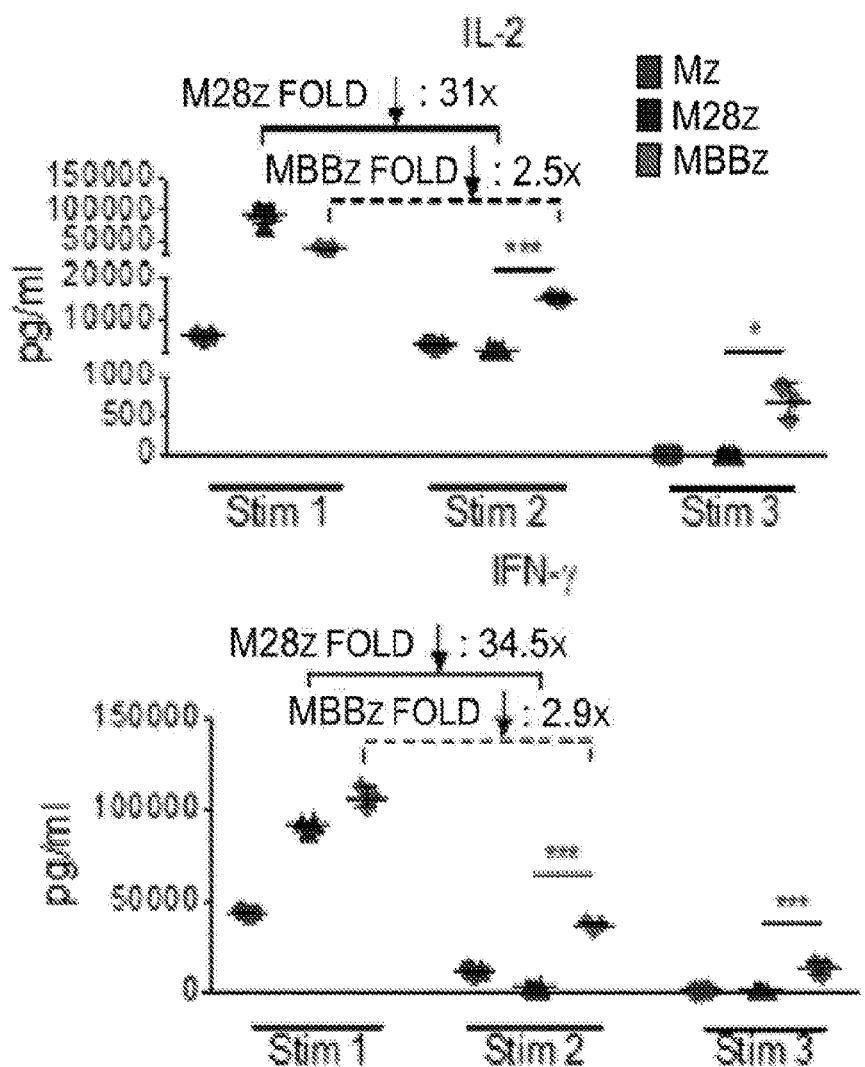
Figure 5E:
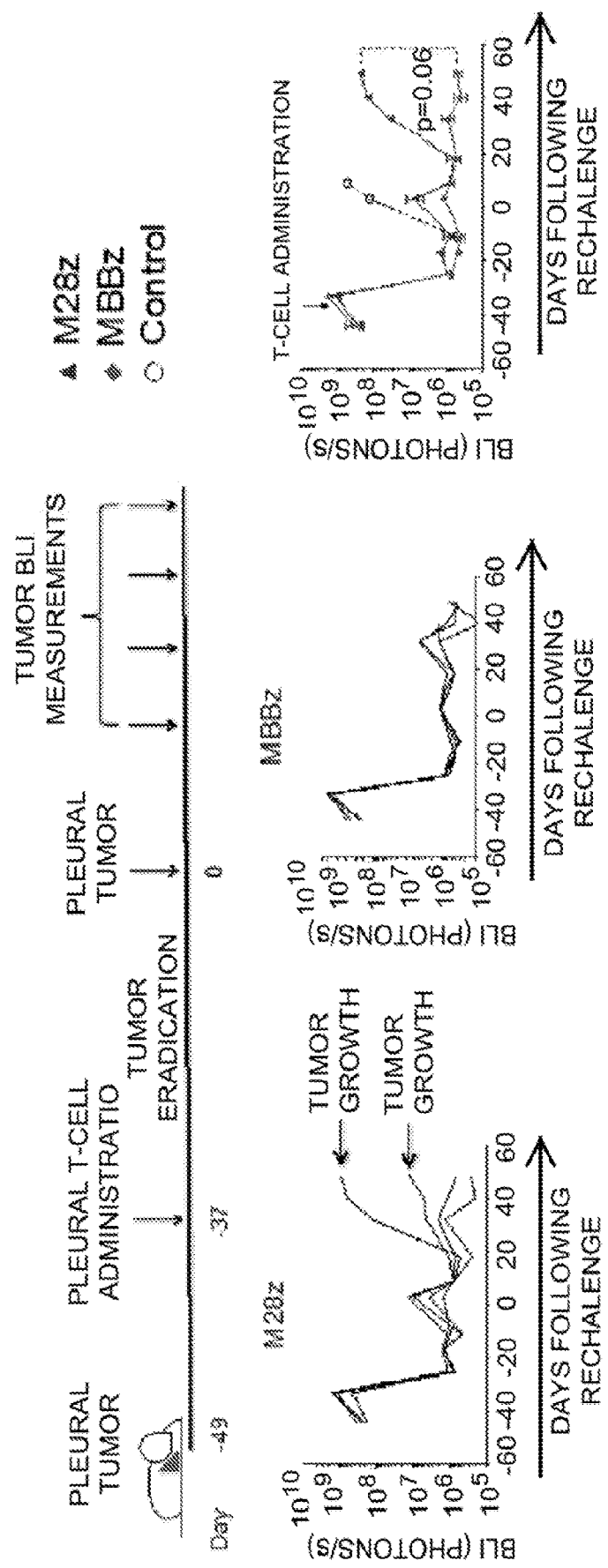

FIGS. 5A-5E show that CAR T cells become exhausted upon repeated antigen stimulation in vitro, although MBBz CAR T cells preferentially retain effector cytokine secretion and cytotoxicity in vitro and upon tumor rechallenge in vivo. FIG. 5A. Both M28z and MBBz CAR T cells retain proliferative capacity in vitro upon repeated antigen stimulation. T cells were also tested for cytotoxicity by chromium-release assay and for cytokine secretion by Luminex assay (FIGS. 5B-5D). FIG. 5B. CAR T cells demonstrate equal killing at the first stimulation (left) and loss of cytolytic function upon repeated antigen stimulation, although MBBz CAR T cells are better able to retain cytolytic function as measured by chromium-release assay (circles, MZ; triangles, M28z; diamonds, MBBz). FIG. 5C. Cytotoxic granule release as measured by CD107a expression (shown at the third stimulation) correlates with chromium release assay (FIG. 5B). Data represent the mean±SD (triplicates) of the fold-change relative to the CD107a MFI of unstimulated CAR T cells (each pair of bar graphs shows, from left to right, M28z, MBBz). FIG. 5D. Cytokine secretion measurements similarly demonstrate loss of CAR T-cell effector function upon repeated antigen encounter; again, MBBz CAR T cells are better able to preserve their function (each set of symbols above "Stim 1," "Stim 2" and "Stim 3" are, from left to right, Mz, M28z, MBBz). FIG. 5E. Although equally persistent, MBBz CAR T cells demonstrate superior functional persistence. Twenty-eight days after pleural tumor eradication (following a single dose of $1e^5$ CAR T cells), $1e^6$ MSLN+ tumor cells were injected into the pleural cavity (tumor rechallenge). MBBz CAR T cells prevented tumor growth in all mice, whereas tumor growth and death were observed in 2 of 4 mice initially treated with M28z CAR T cells. Student's t tests were performed and statistical significance was determined using the Bonferroni correction (*P<0.05; ***P<0.001). Data represent the mean±SEM of three replicates or are plotted as individual points.

Figure 6A:
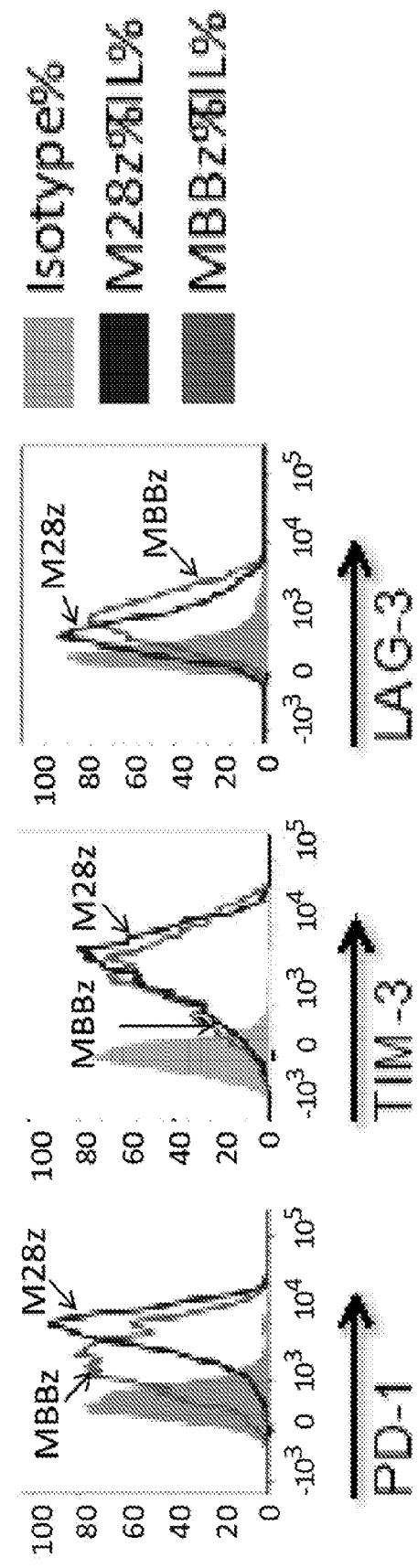
Figure 6D:
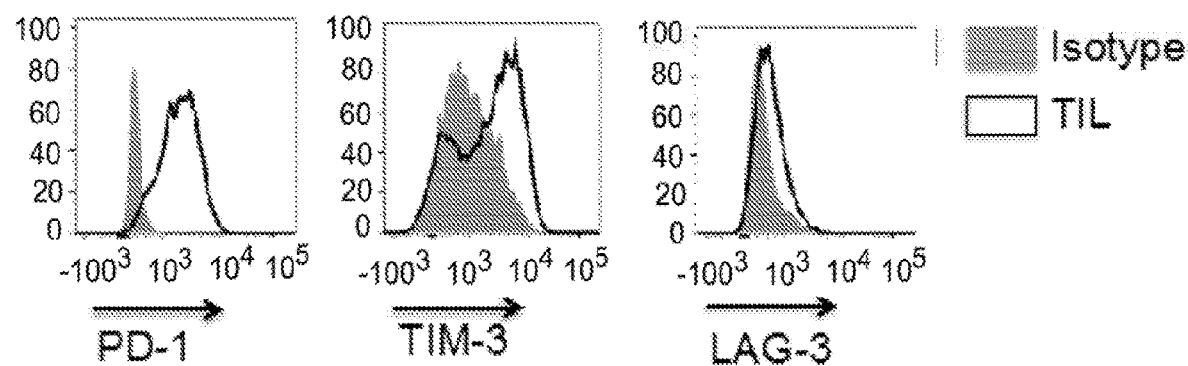
Figure 6E:
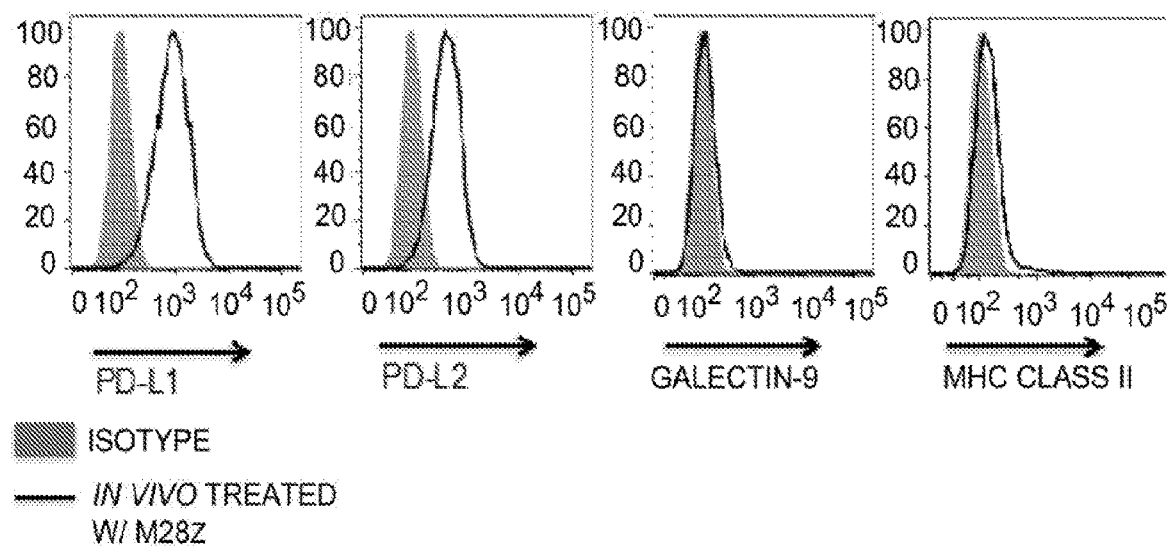
Figure 6F:
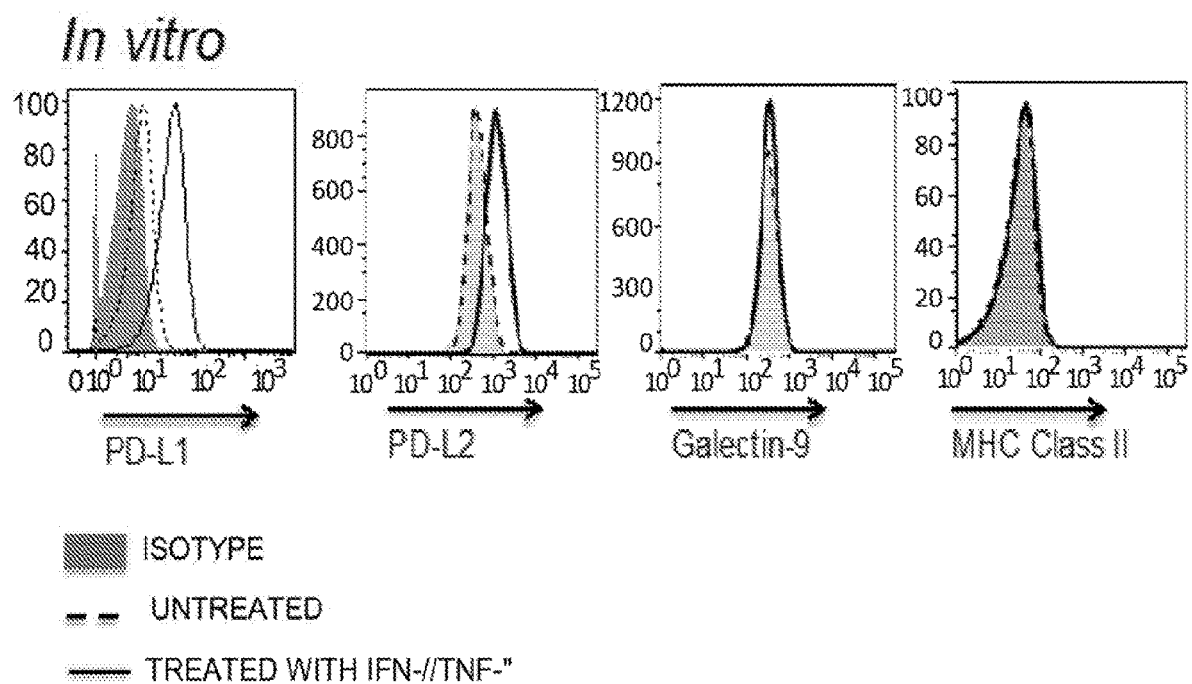

FIGS. 6A-6F show that PD-1 receptor and its ligands are upregulated in vivo (FIGS. 6A-6D, harvested T cells; FIGS. 6E-6F, tumor cells). FIG. 6A. Tumor-infiltrating M28z and MBBz CAR T cells express inhibitory receptors 6 days after their administration, but MBBz CART cells express lower levels of PD-1. FIG. 6B. Mean fluorescence intensity (MFI) of PD-1 receptor expression of tumor-infiltrating CAR T cells (TIL) 6 days after intrapleural administration. FIG. 6C. Relative expression of PD-1 mRNA in CD4 and CD8 subsets of tumor-infiltrating CAR T cells 6 days after intrapleural administration. Data are represented in fold-change relative to the PD-1 mRNA expression of unstimulated M28z T cells (for each pair of bar graphs, M28z, left, MBBz, right). FIG. 6D. Tumor-infiltrating M28z CAR T cells isolated from progressing tumors express inhibitory receptors PD-1, Tim-3, and Lag-3. FIG. 6E. Single-cell tumor suspensions harvested from mice treated with M28z CAR T cells express high levels of PD-1 binding ligands. FIG. 6F. In vitro cultured mesothelioma tumor cells express the ligands (PD-L1, PD-L2) for the PD-1 receptor, and expression is further upregulated following incubation for 24 h with IFN-γ and TNF-α.

Figure 7A:
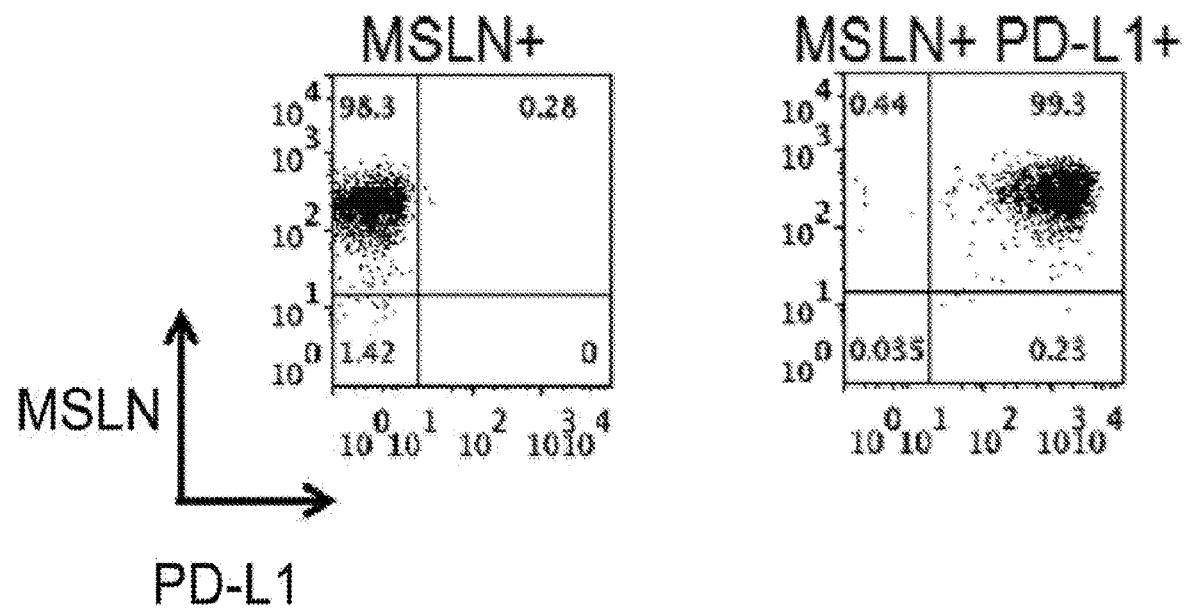
Figure 7B:
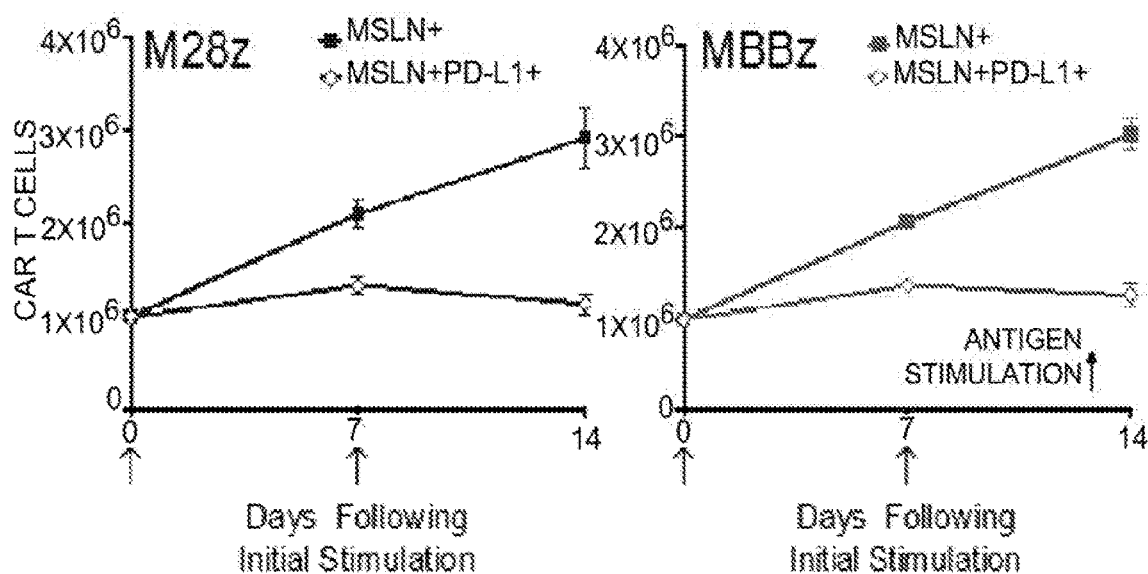
Figure 7C:
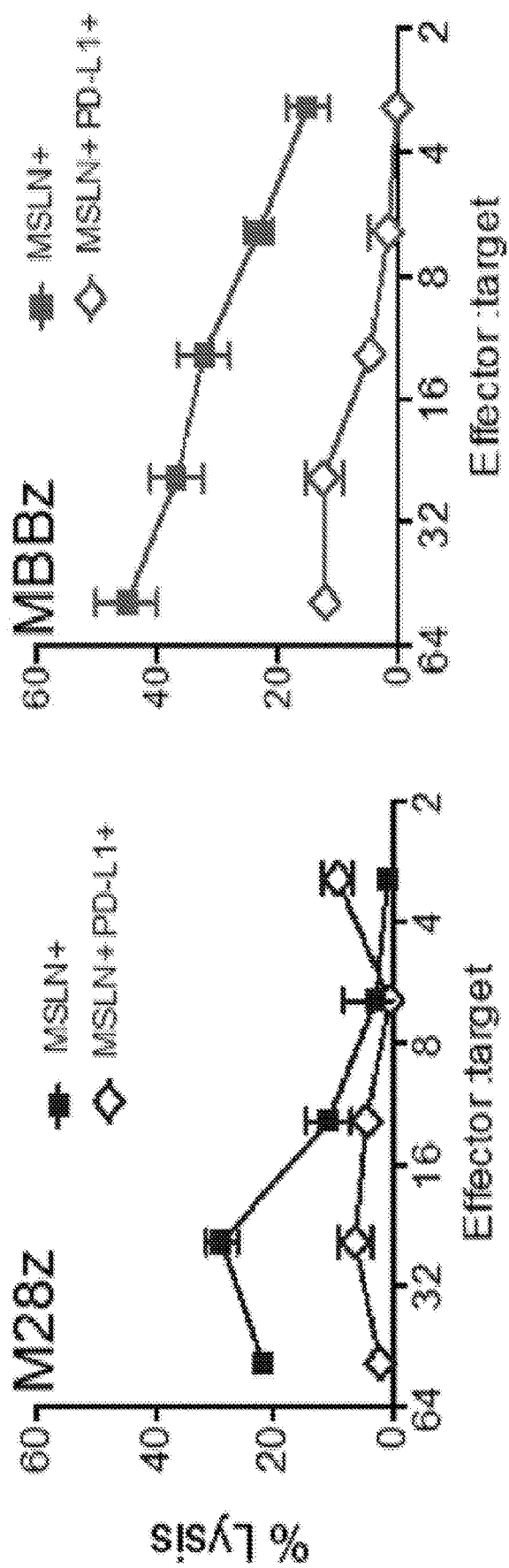
Figure 7D:
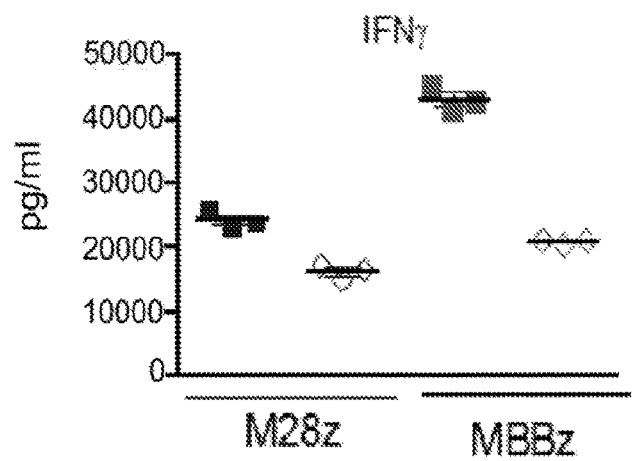
Figure 7D:
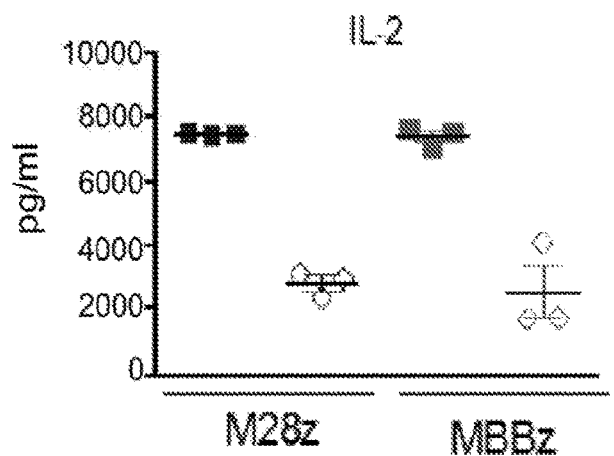
Figure 7D:
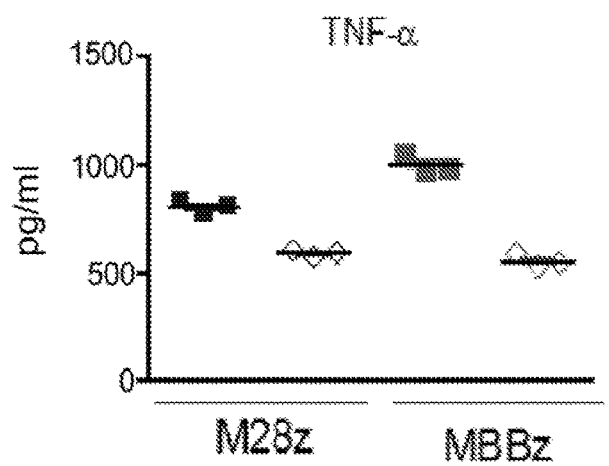

FIGS. 7A-7D show that PD-L1 inhibits CAR T-cell effector function. FIG. 7A. 3T3 fibroblasts were transduced to either express mesothelin alone (MSLN+, left) or coexpress MSLN in addition to PD-L1 (MSLN+ PD-L1+, right). FIGS. 7B-7D. M28z and MBBz CAR T-cell effector functions were assessed after stimulation with 3T3 MSLN+ or MSLN+ PD-L1+ targets. PD-L1 inhibits M28z and MBBz CAR T-cell accumulation upon repeated antigen stimulation (FIG. 7B), cytolytic function following two stimulations with MSLN+ PD-L1+ tumor cells (FIG. 7C), and Th1 effector cytokine secretion upon the first stimulation (FIG. 7D). Data represent the mean±SEM of three replicates or are plotted as individual points.

Figure 8A:
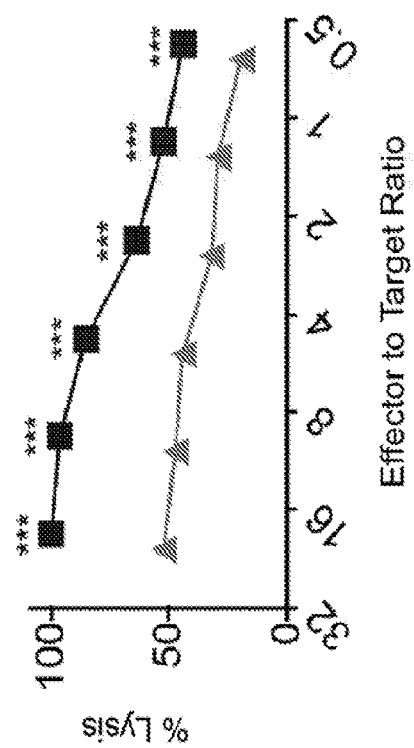
Figure 8B:
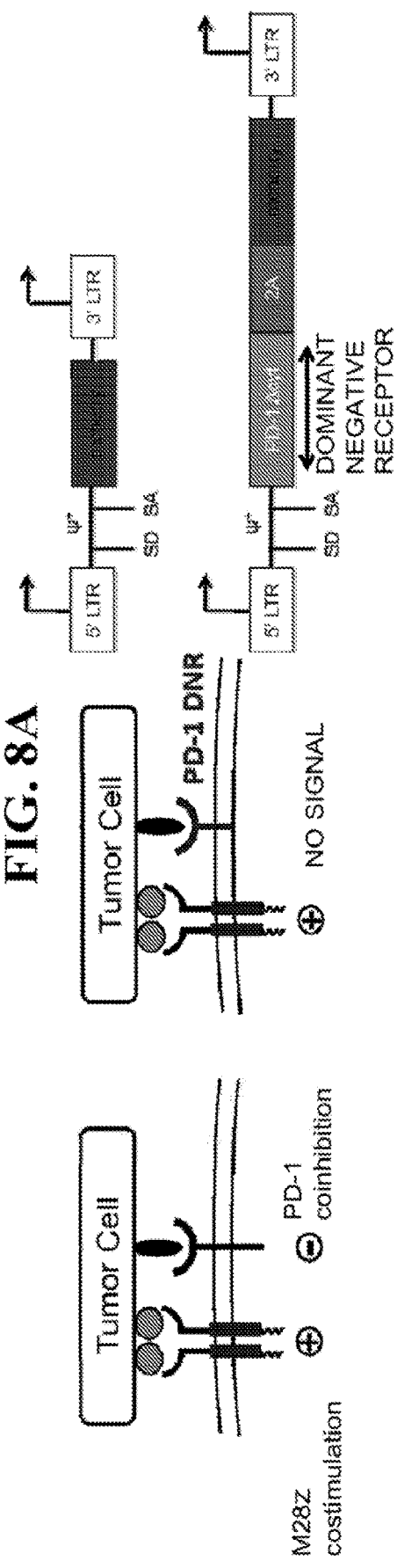
Figure 8C:
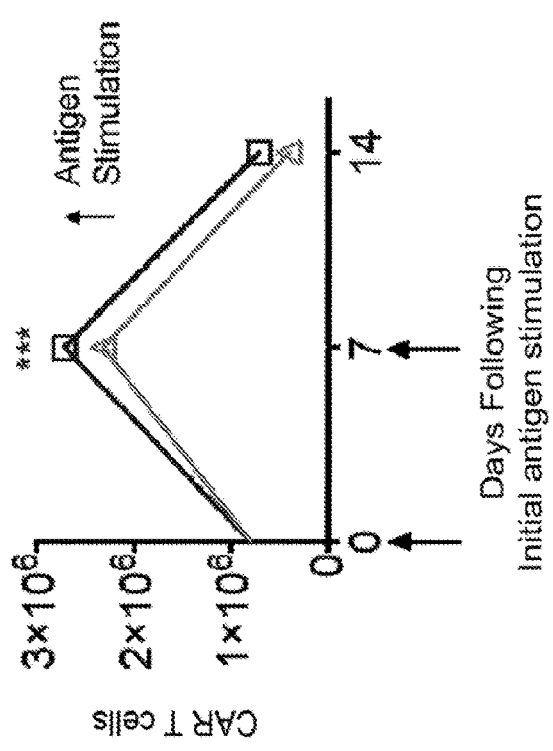
Figure 8D:
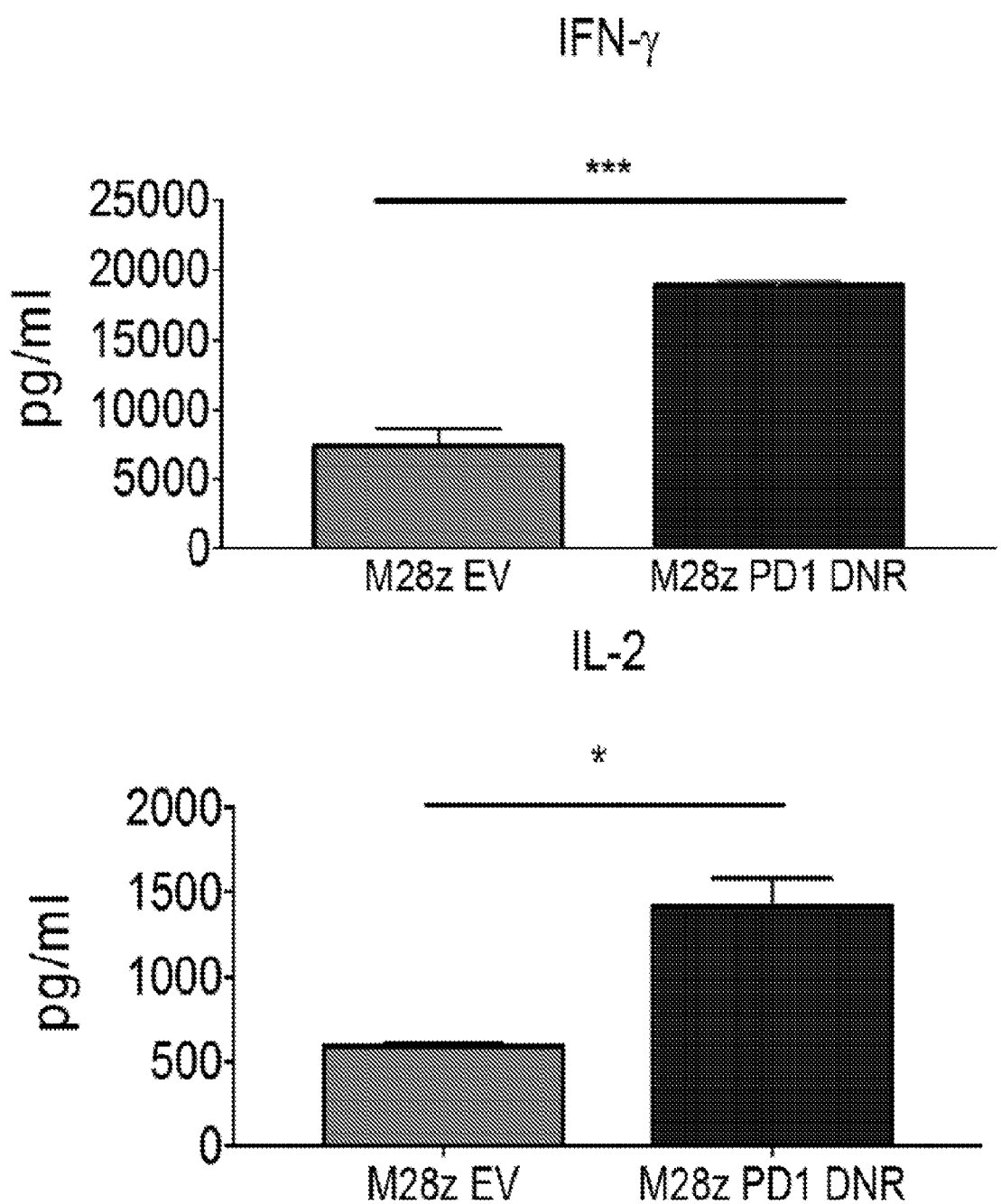
Figure 8E:
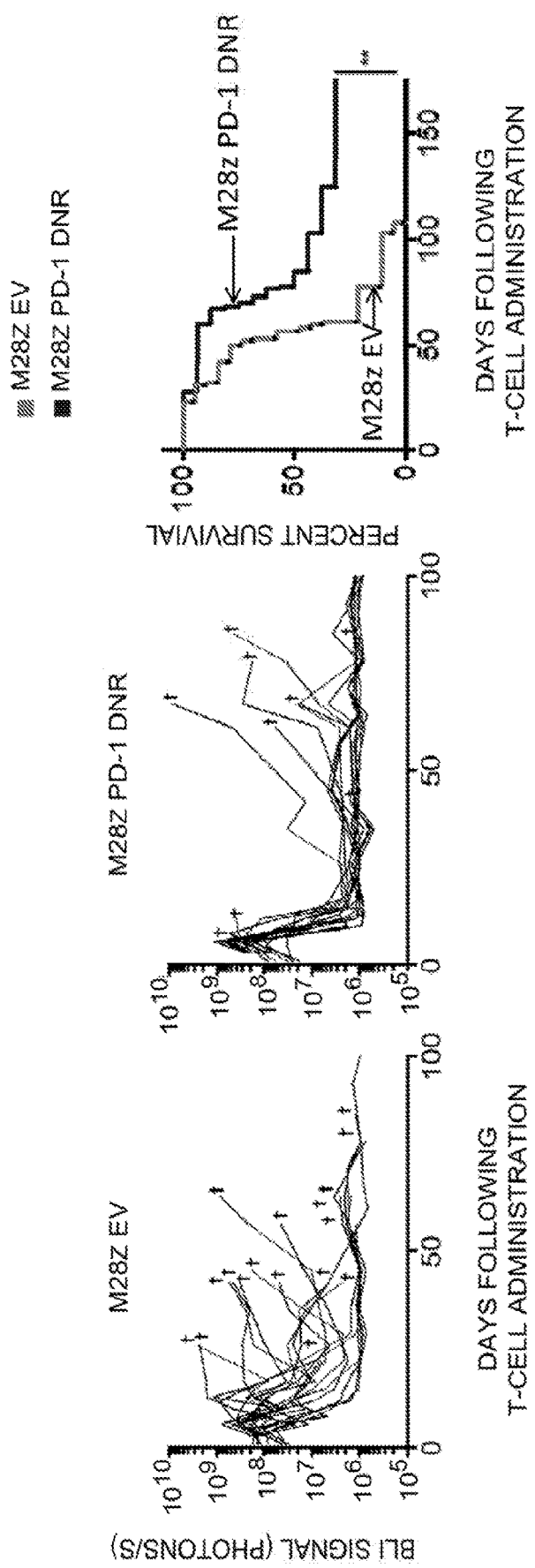

FIGS. 8A-8E show that cotransduction of a PD-1 dominant negative receptor (PD-1 DNR) rescues M28z CAR T cells from PD-1 Ligand-mediated inhibition in vitro and in vivo. FIG. 8A. (Left) Schematic representations of CD28-costimulated T cells binding tumor ligand via the endogenous PD-1 receptor (transmitting a coinhibitory signal) or a cotransduced PD-1 DNR lacking an inhibitory signaling domain. (Right) For in vitro and in vivo experiments, M28z CAR T cells were cotransduced with either empty vector (EV; SFG-mCherry) or PD-1 DNR (SFG-2A-PD-1 DNR). CAR T cells sorted for mCherry expression were then incubated for 24 h with MSLN+ tumor cells that had been treated with IFN-γ and TNF-α to upregulate PD-1 ligands. M28z PD-1 DNR CAR T cells demonstrated a small but statistically significant enhancement in accumulation upon repeated antigen stimulation (FIG. 8B; triangles, M28z EV; squares, M28z PD-1 DNR), an enhanced cytolytic function, as measured by chromium release assay upon the 3rd stimulation with MSLN+ PD-L1+ tumor cells (FIG. 8C; triangles, M28z EV; squares, M28z PD-1 DNR), and an increased expression of Th1 supernatant cytokines upon initial stimulation (FIG. 8D). Student's t tests were performed, and statistical significance was determined using the Bonferroni correction for multiple comparisons (*P<0.05; P<0.01; *P<0.001). Data represent the mean±SEM of triplicates or are plotted as individual points. FIG. 8E. Tumor BLI (left) and Kaplan-Meier survival analysis (right) comparing the in vivo efficacy of a single dose of 5e4 M28z EV (n=19) or M28z PD-1 DNR (n=16) pleurally administrated. Data shown are a combination of two independent experiments. The (✝) symbol indicates death. Median survival is shown in days. The survival curve was analyzed using the log-rank test (P=0.001). The log-rank test for each independent experiment was significant to the P<0.05 level; two experiments are combined for illustration. A cohort of the mice (M28z PD-1 DNR) in this experiment survived beyond 450 days in spite of repeated tumor rechallenge, demonstrating the "functional persistence" of CAR T cells transduced with PD-1 DNR.

Figure 9:
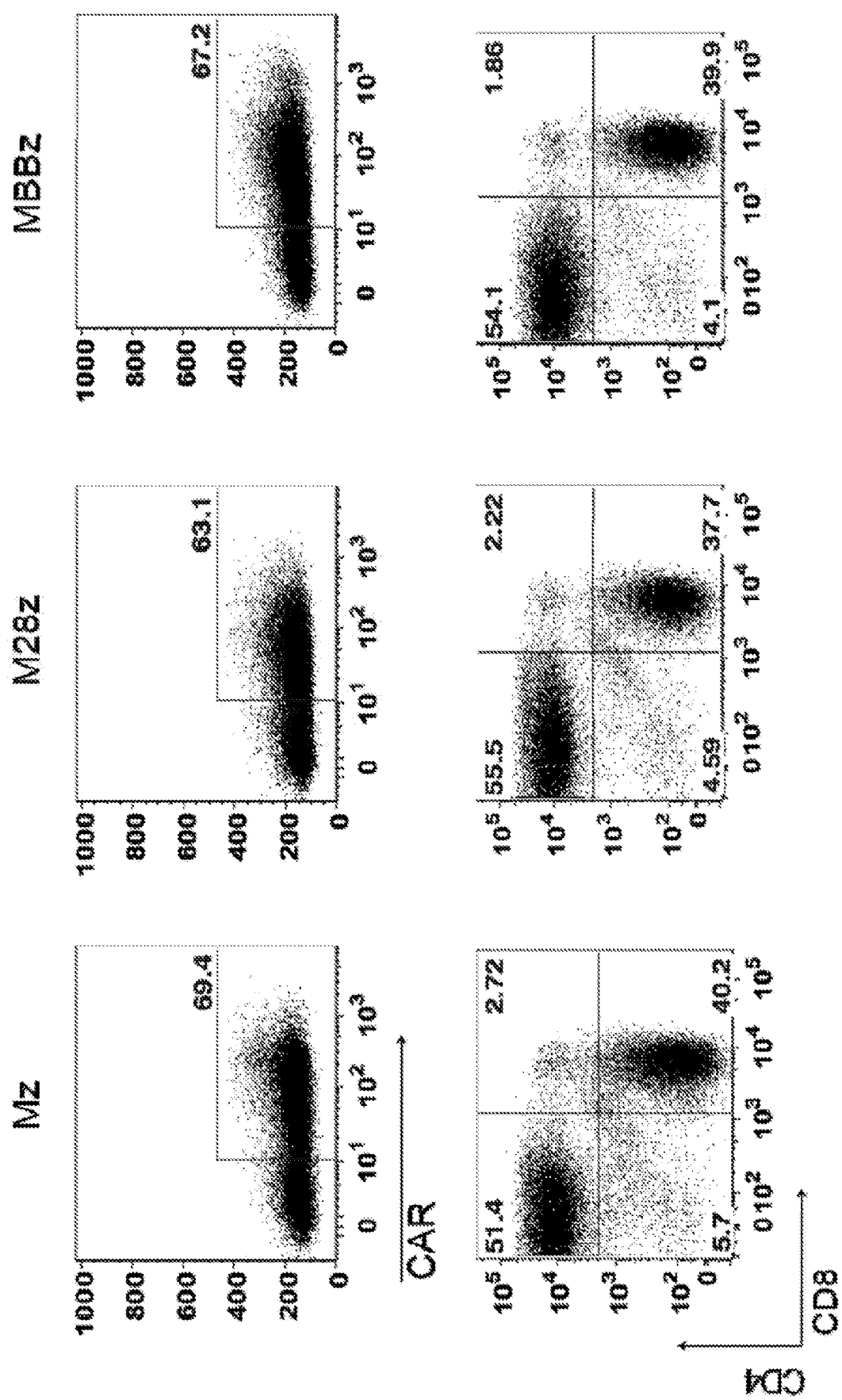

FIG. 9 shows efficient retroviral transduction of human T cells to express Mz, M28z, and MBBz CARs. (Top) Shown is representative FACS analysis 4 days after gene transfer. Fluorescence minus one staining was used to set positive gates after a live/dead stain excluded nonviable cells. All experiments used T cells with 50% to 70% CAR transduction efficiency; transduction percentages between T-cell groups were within 5% of each other. (Bottom) Both CD4+ and CD8+ T-cell subsets were efficiently transduced. CD4+ and CD8+ percentages after gating for CAR T cells are shown.

Figure 10:
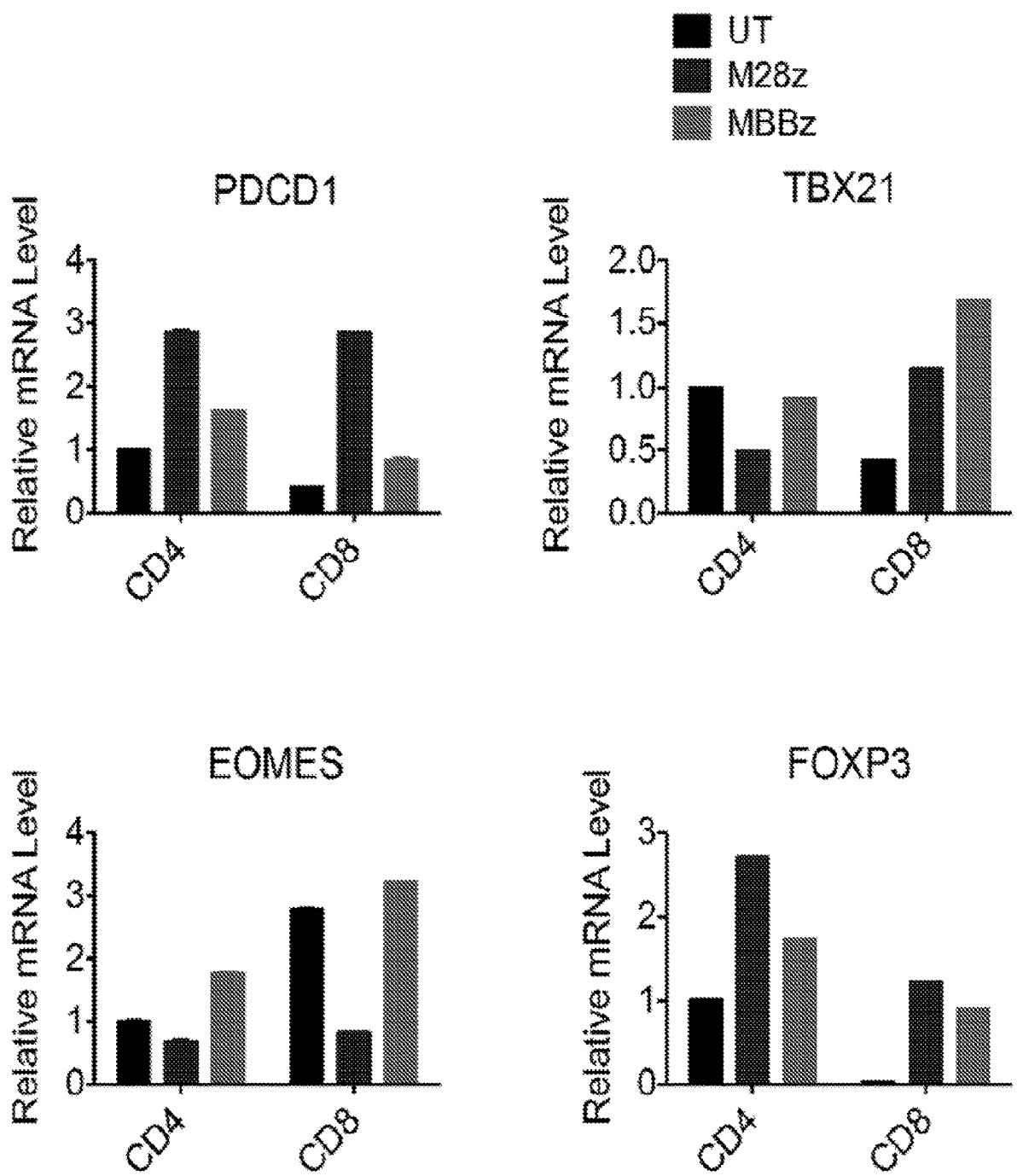

FIG. 10 shows that MBBz CAR T cells express a less exhausted, more potent phenotype compared to M28z CAR T cells. 4-1BB- and CD28-costimulated T cells were expanded with repeated antigen stimulation, and mRNA was extracted and subjected to RT-PCR analysis 20 h after the third stimulation. Data are represented in fold change relative to the mRNA expression of CD4+ unstransduced T cells. MBBz CAR T cells express higher levels of EOMES (Eomesodermin) and TBX21 (T-bet), and lower levels of PDCD1 (PD-1) and FOXP3 (Foxp3). All comparisons were significant at P<0.001. Results were similar in 3 separate experiments using different donors. Each group of bar graphs shows, left to right, UT (untransduced T cells used as a control), M28z, MBBz.

Figure 11:
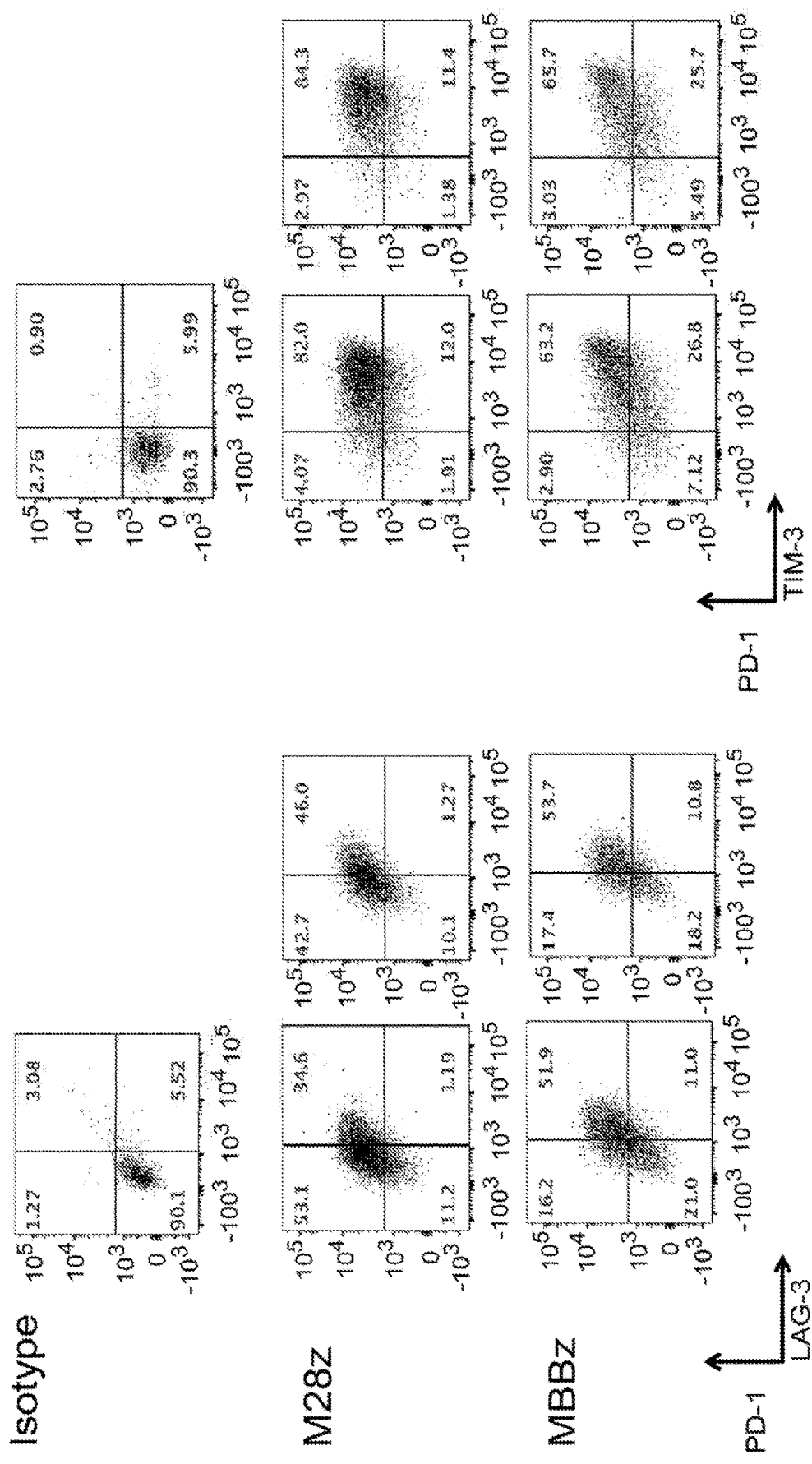

FIG. 11 shows M28z and MBBz CAR T cells coexpress PD-1 along with other inhibitory receptors. Tumor-infiltrating M28z and MBBz CAR T cells were harvested 6 days following intrapleural administration to pleural tumor bearing mice. Cells were costained with antibodies for PD-1 and for either LAG-3 (left) or TIM-3 (right) and analyzed by flow cytometry. Isotype staining controls (top) were used to establish positive gates.

Figure 12A:
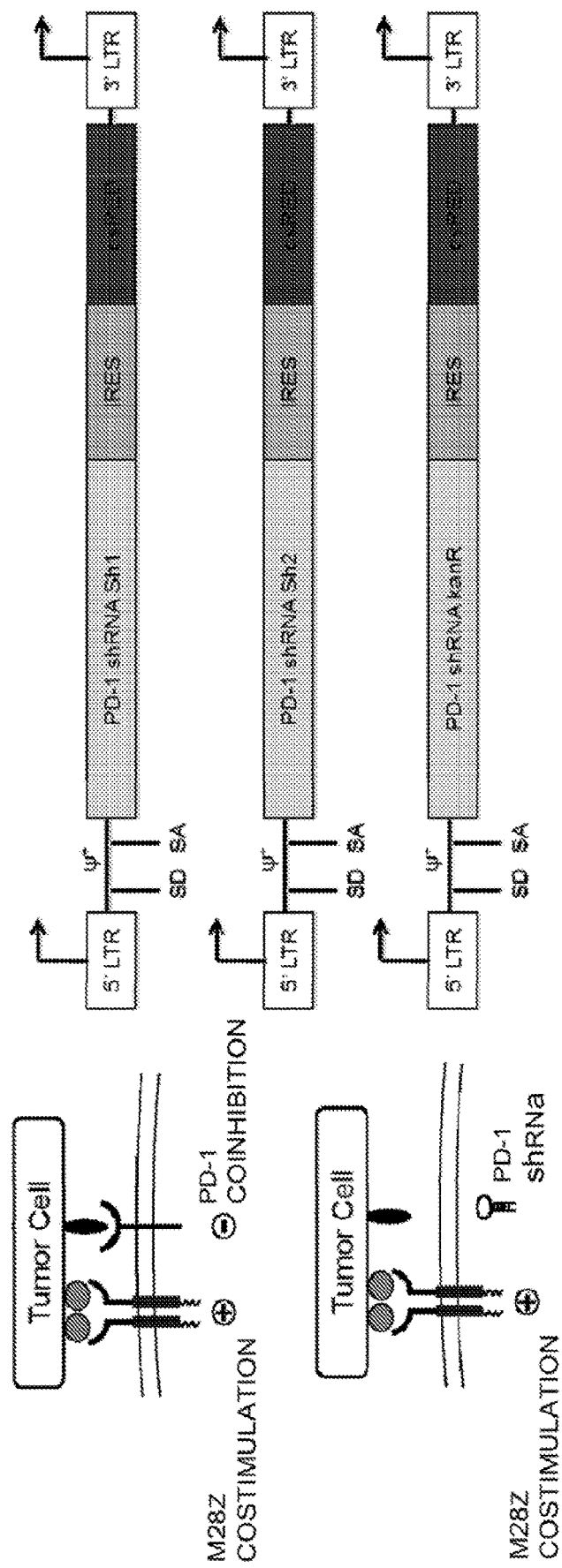
Figure 12B:
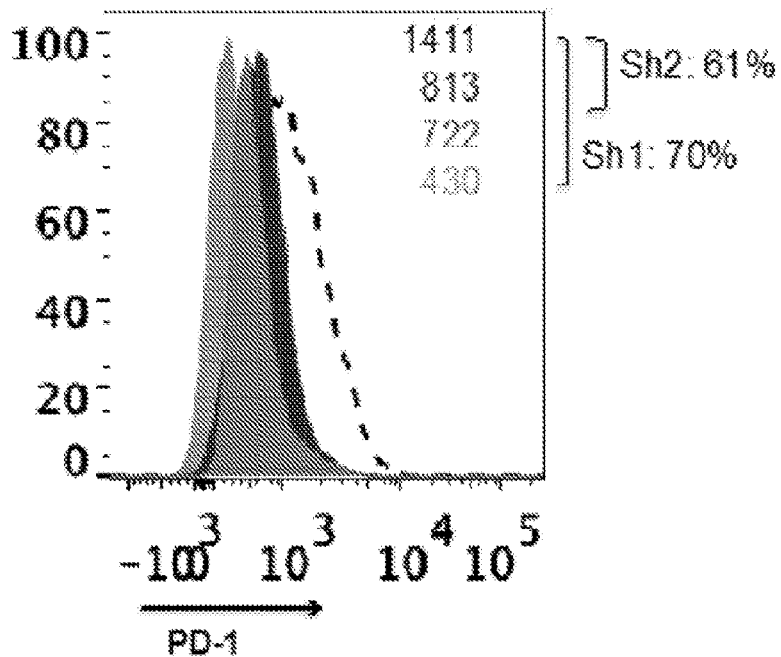
Figure 12C:
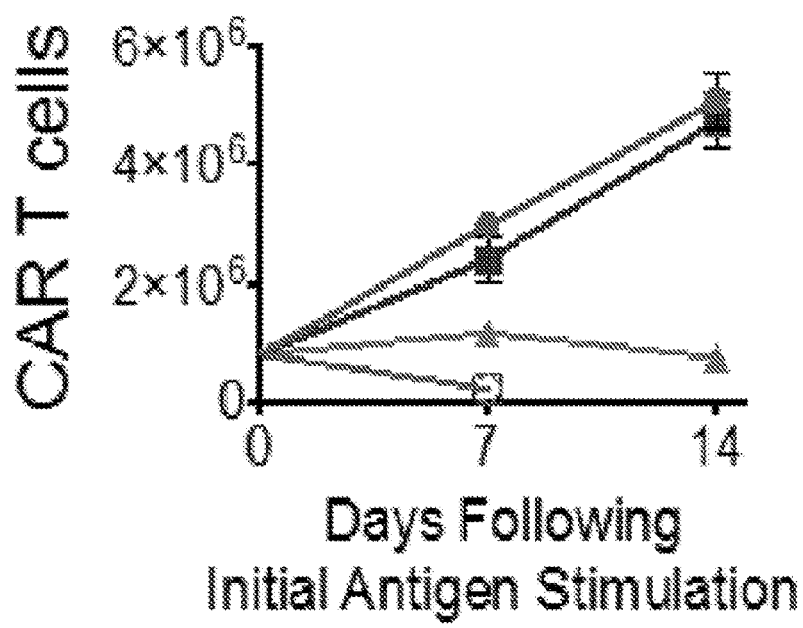
Figure 12D:
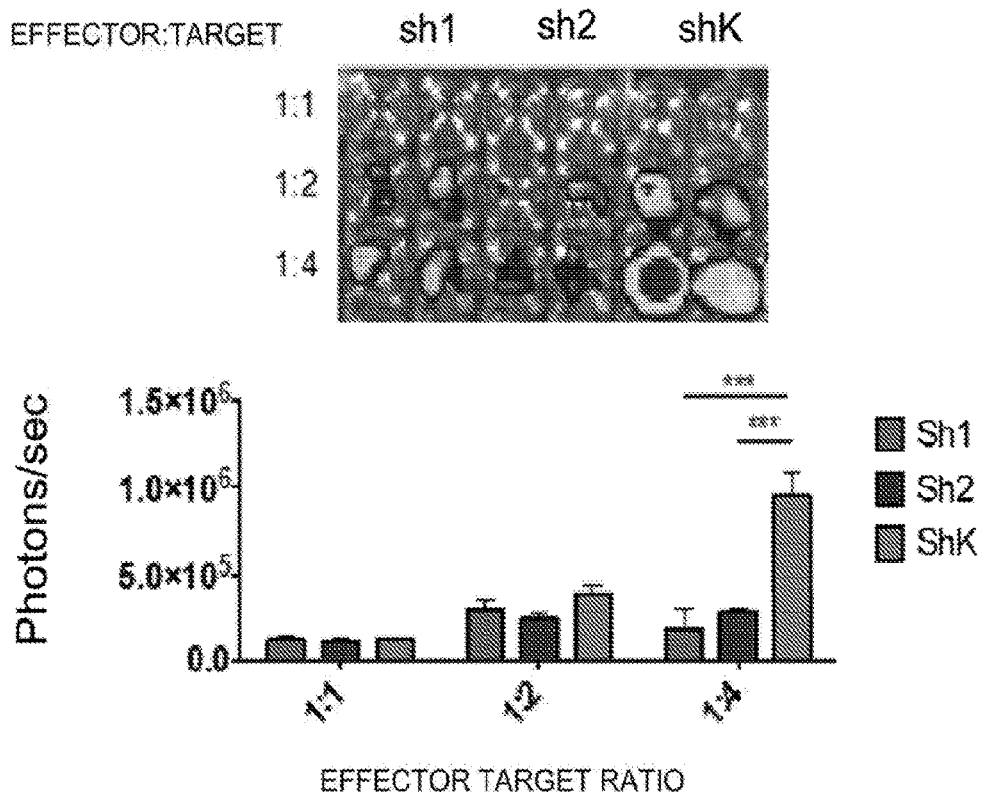
Figure 12E:
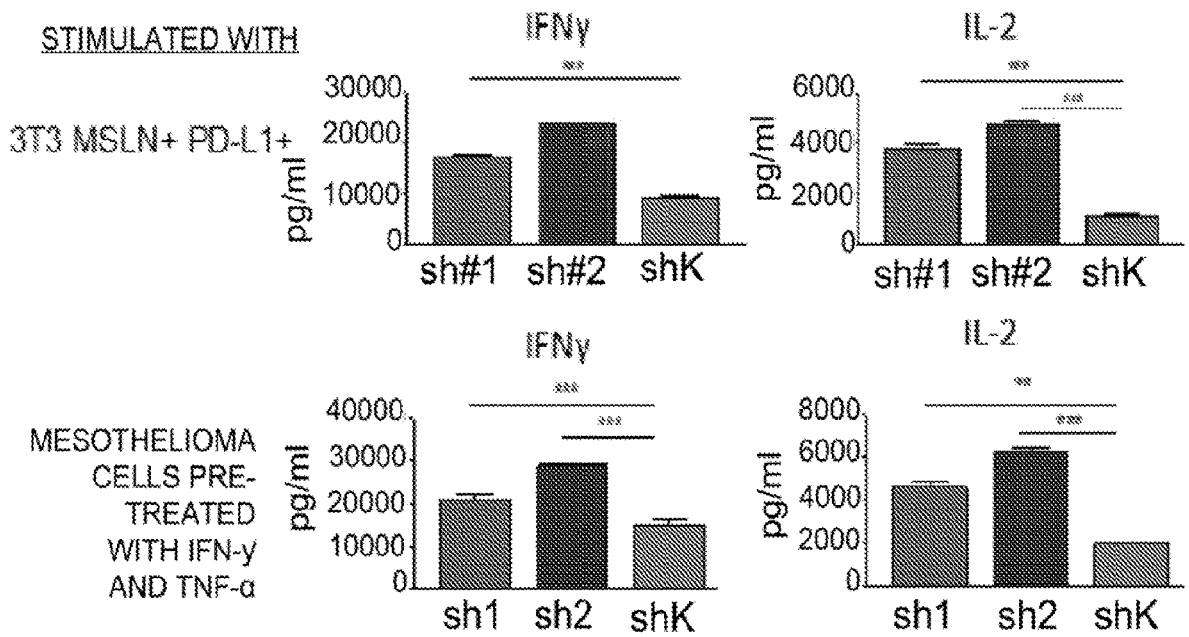

FIGS. 12A-12E show that cotransduction of PD-1 receptor-targeting shRNAs rescues M28z CAR T cells from PD-L1/PD-1-mediated inhibition in vitro. FIG. 12A. (Left) Schematic representation of CD28-costimulated T cells binding tumor-expressed PD-L1 via endogenous PD-1 receptor, with or without coexpression of PD-1-targeting shRNA. (Right) All experiments included M28z CAR T cells cotransduced with one of two PD-1-targeting shRNAs (sh1 or sh2 coexpressing a dsRED reporter) or with an shRNA targeting a bacterial sequence (KanR). FIG. 12B. Compared with KanR-transduced cells, M28z CAR T cells cotransduced with PD-1-targeting shRNAs demonstrated a 60% to 70% knockdown in PD-1 receptor protein expression upon stimulation with phytohemagglutinin (graphs left to right correspond to 430, 722, 813 and 1411). Cells were incubated with either 3T3 fibroblasts overexpressing PD-L1 (3T3 MSLN+ PD-L1+) or mesothelioma tumor cells that had been treated with IFN-γ and TNF-α in order to upregulate PD-L1 and PD-L2. M28z PD1 shRNA CAR T cells demonstrate enhanced accumulation upon repeated antigen stimulation (FIG. 12C), enhanced cytolytic function at low effector to target ratios, as measured by luciferase activity of remaining live tumor cells (FIG. 12D; each group of bar grafts, from left to right, Sh1, Sh2, ShK), and increased Th1 cytokine secretion (FIG. 12E; each group of bar grafts, from left to right, Sh1, Sh2, ShK) (P<0.01; *P<0.001). Student's t tests were performed and statistical significance was determined using the Bonferroni correction for multiple comparisons. Data represent the mean±SEM of three replicates.

Figure 13A:
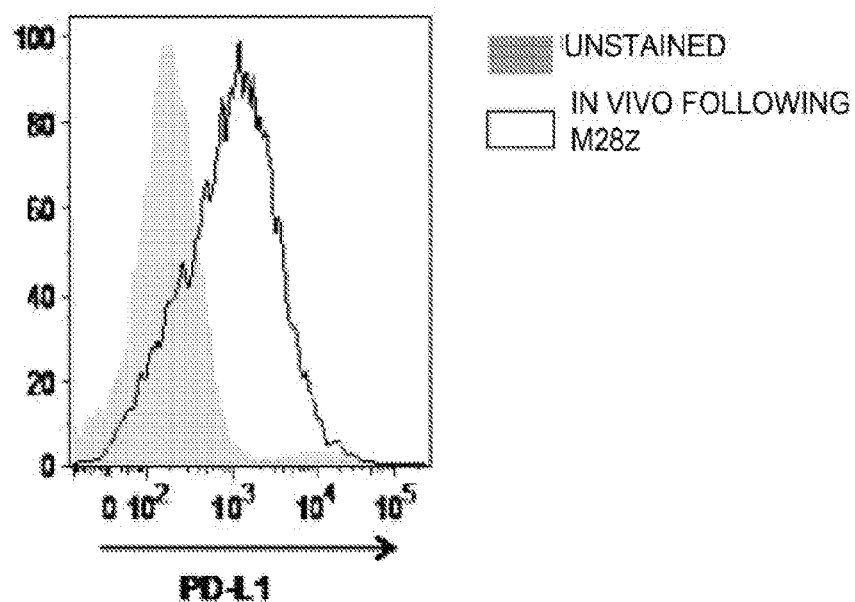
Figure 13B:
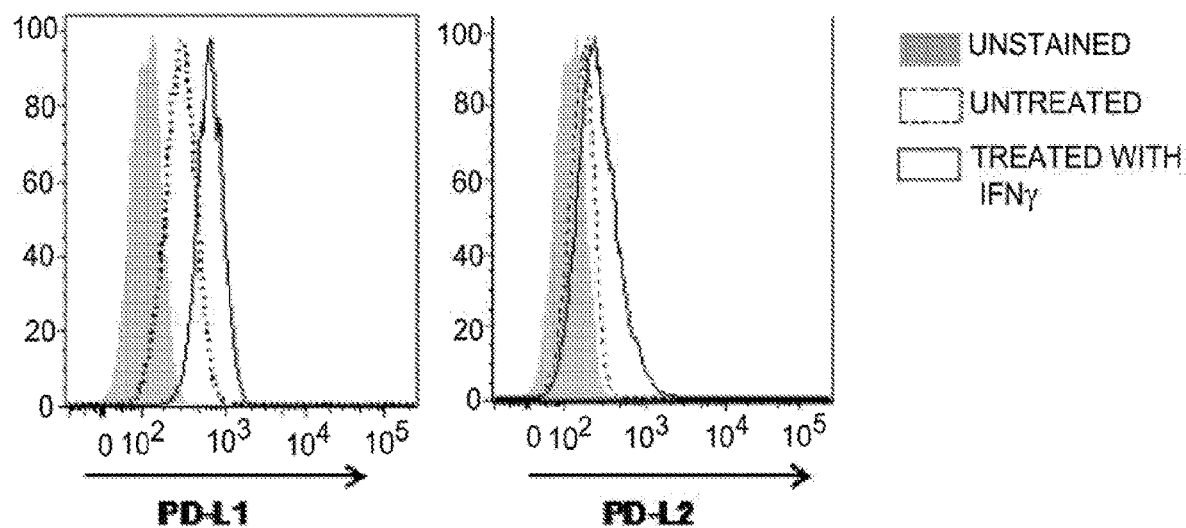
Figure 13C:
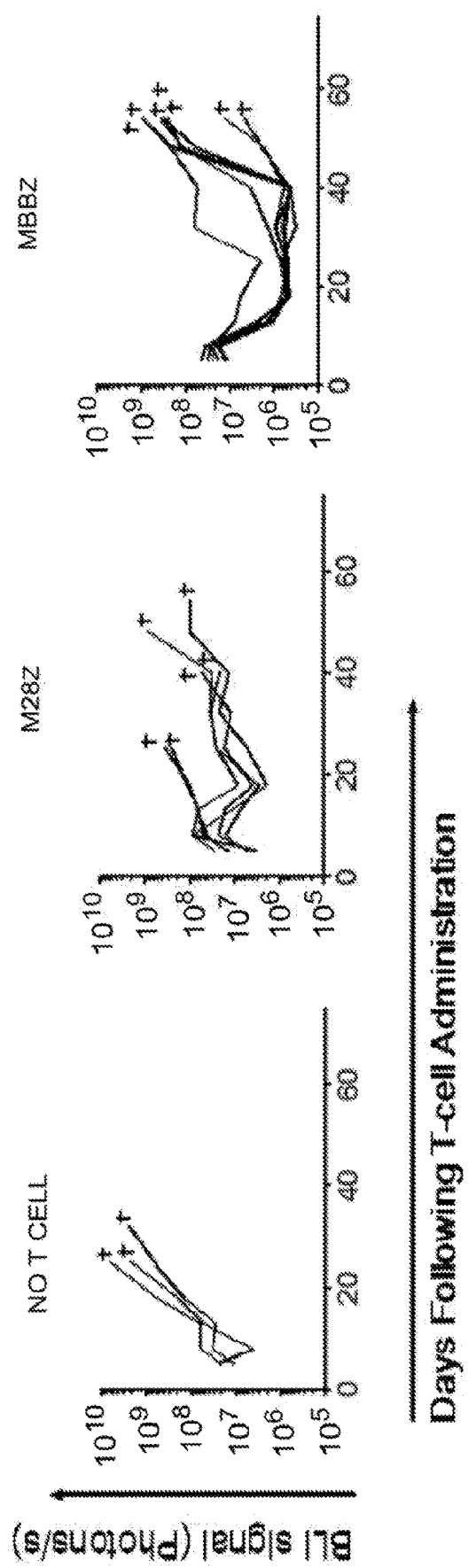
Figure 13D:
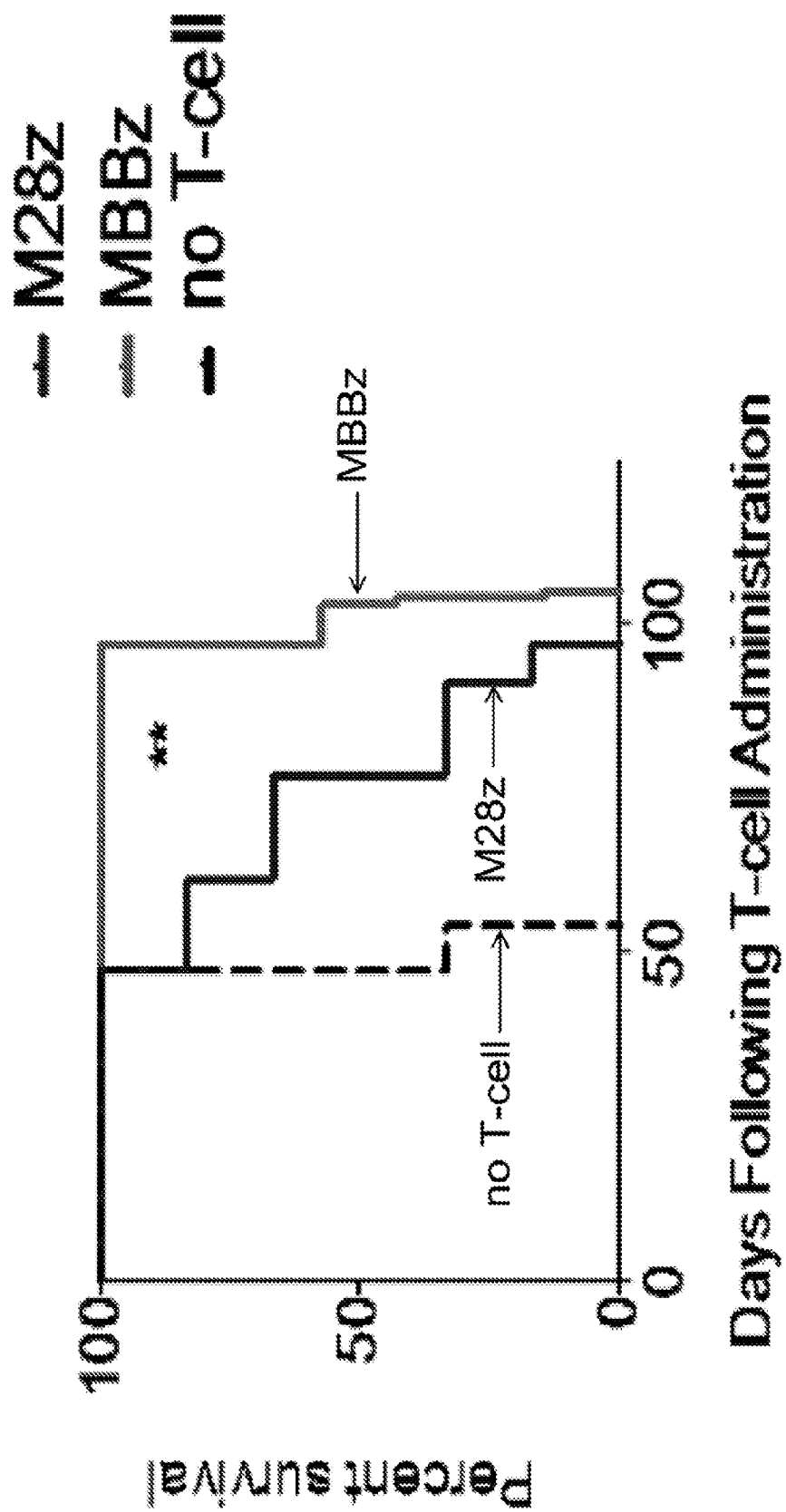

FIGS. 13A-13D show that MBBz CAR T cells prolong tumor-free survival in a mouse model of metastatic lung cancer that includes expression of PD-1 receptor and complementary ligands. FIG. 13A. Single-cell tumor suspensions (A549 lung cancer cells) harvested from mice treated with M28z CART cells express high levels of PD-L1. FIG. 13B. In vitro cultured lung cancer cells express the ligands (PD-L1, PD-L2) for PD-1 receptor, and expression is further upregulated following incubation for 24 h with IFN-γ. FIG. 13C. In vivo, BLI was used to monitor tumor burden (firefly luciferase+ MSLN+) in NOD/SCID/$\gamma_c^{null}$ mice. Mice with established lung tumor were treated with $5 \times 10^4$ MBBz or M28z CAR T cells or no T cells. FIG. 13D. Kaplan-Meier survival analysis comparing in vivo efficacy of intrapleurally administered M28z (n=6, middle graph) or MBBz (n=7, right graph) CAR T cells or no T cells (n=3, left graph). The survival curve was analyzed using the log-rank test. **P<0.01.

Figure 14A:
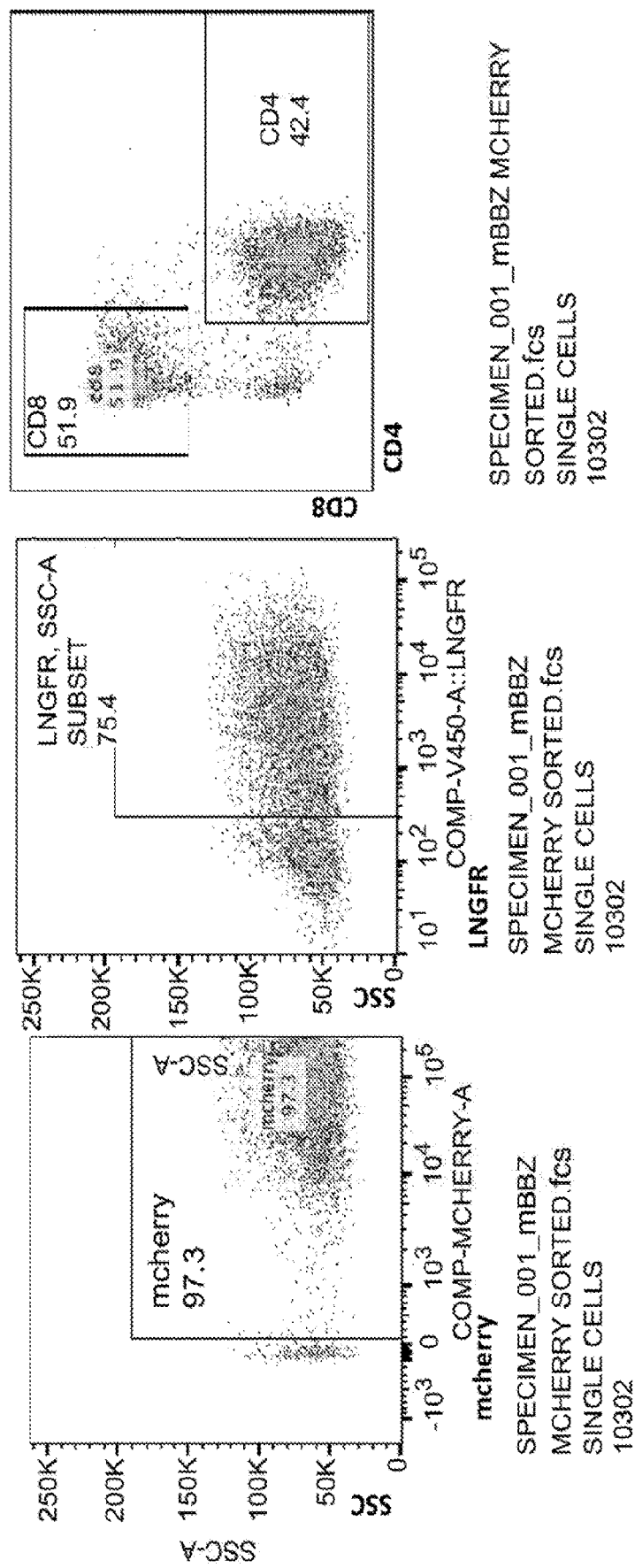
Figure 14C:
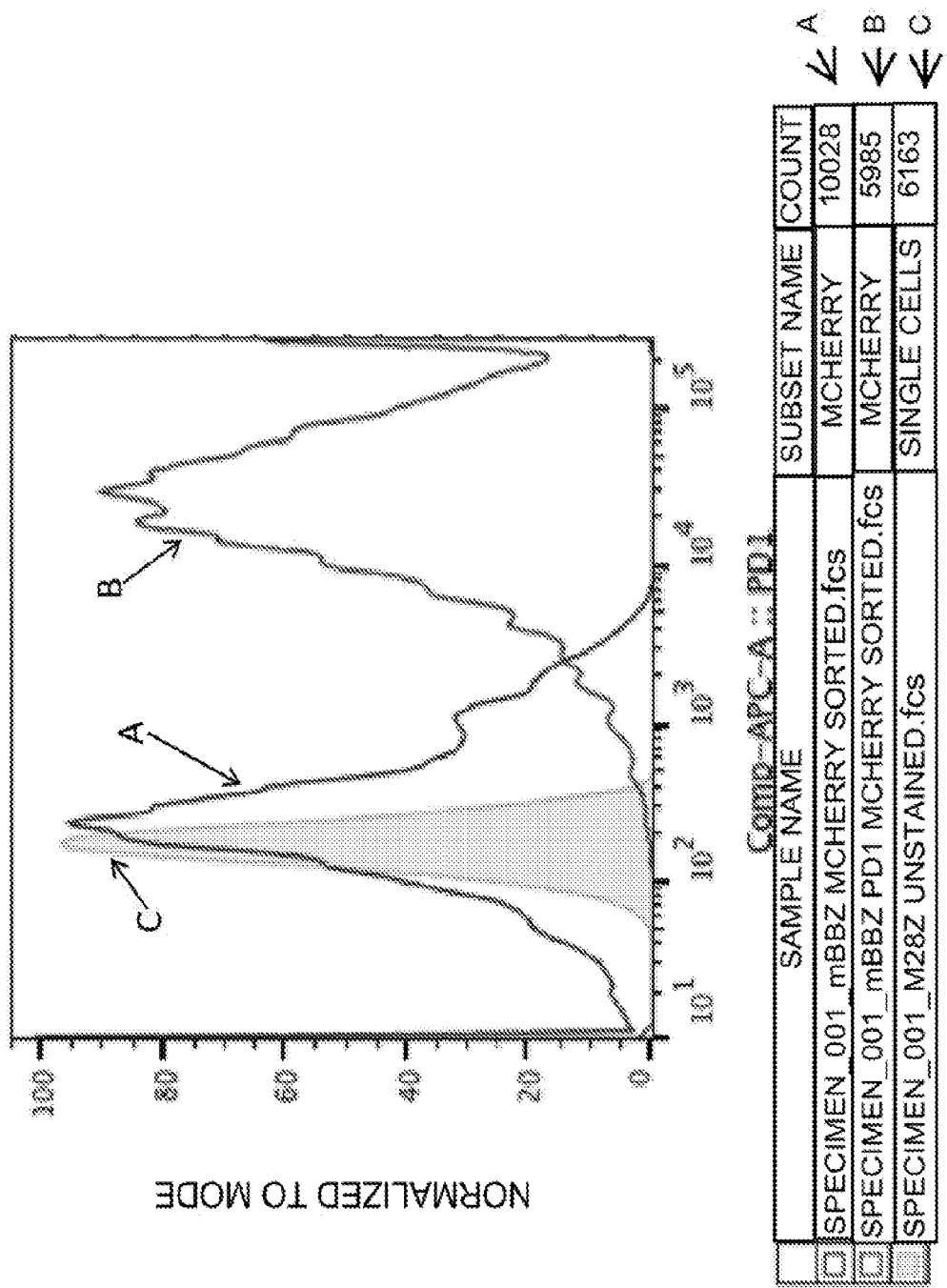

FIGS. 14A-14C show the results of PD1 DNR transduction into T cells transduced to express the MBBz CAR. From donor 1, human T cells were isolated and transduced with MBBz or MBBzPD1DNR CAR constructs, both with a mcherry marker to identify CAR transduced T cells. FIGS. 14A and 14B show FACS analysis of the transduced cells; FIG. 14A, MBBz mcherry; FIG. 14B, MBBz PD1 mcherry. Staining with PD-1 antibody shows the expression of PD1 DNR in transduced T cells (FIG. 14C). FIG. 14C, A, MBBz mcherry sorted cells; B, MBBz PD1 mcherry sorted cells; C, M28z unstained.

Figure 15A:
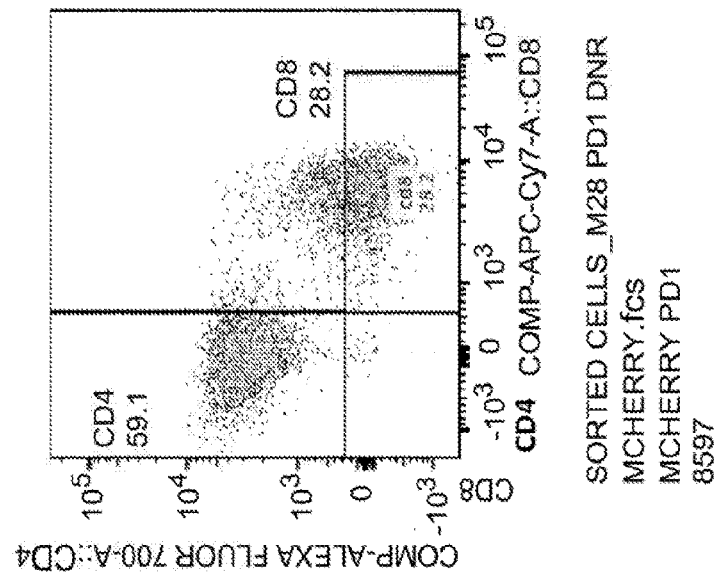
Figure 15A:
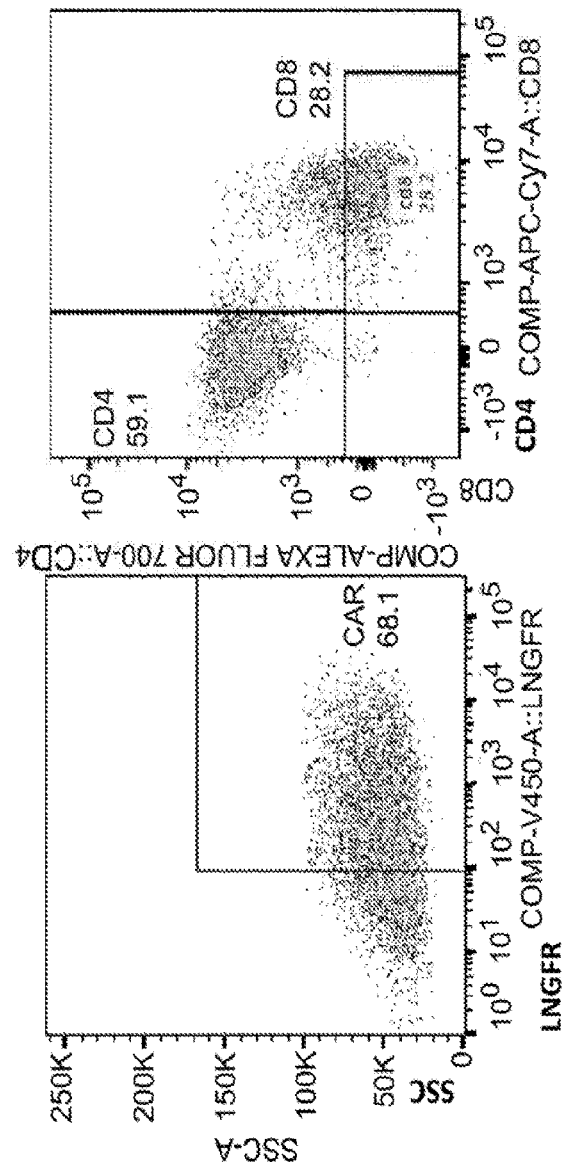
Figure 15A:
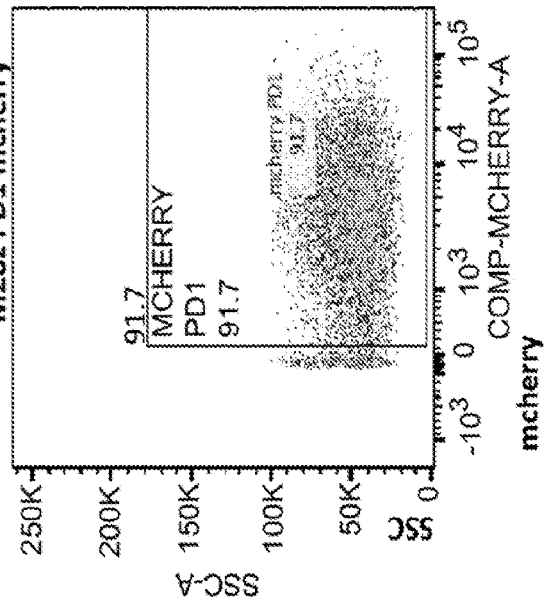
Figure 15B:
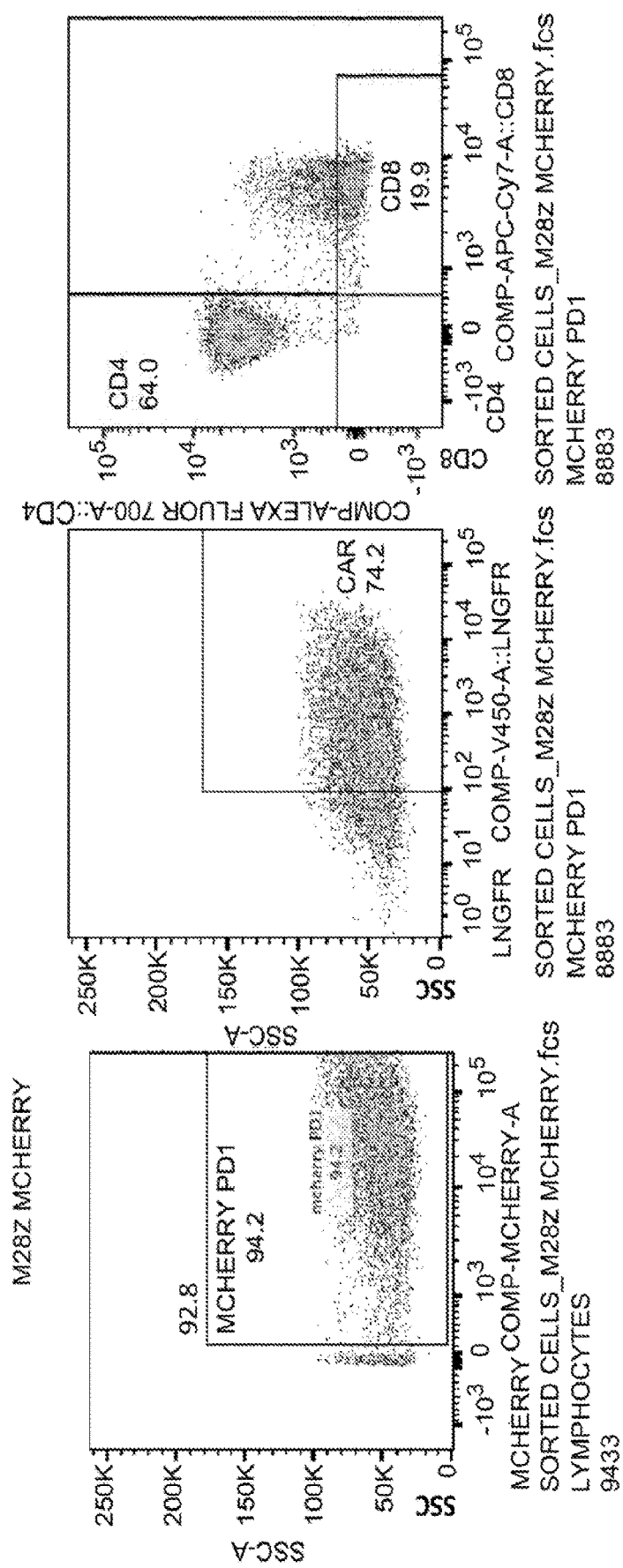
Figure 15C:
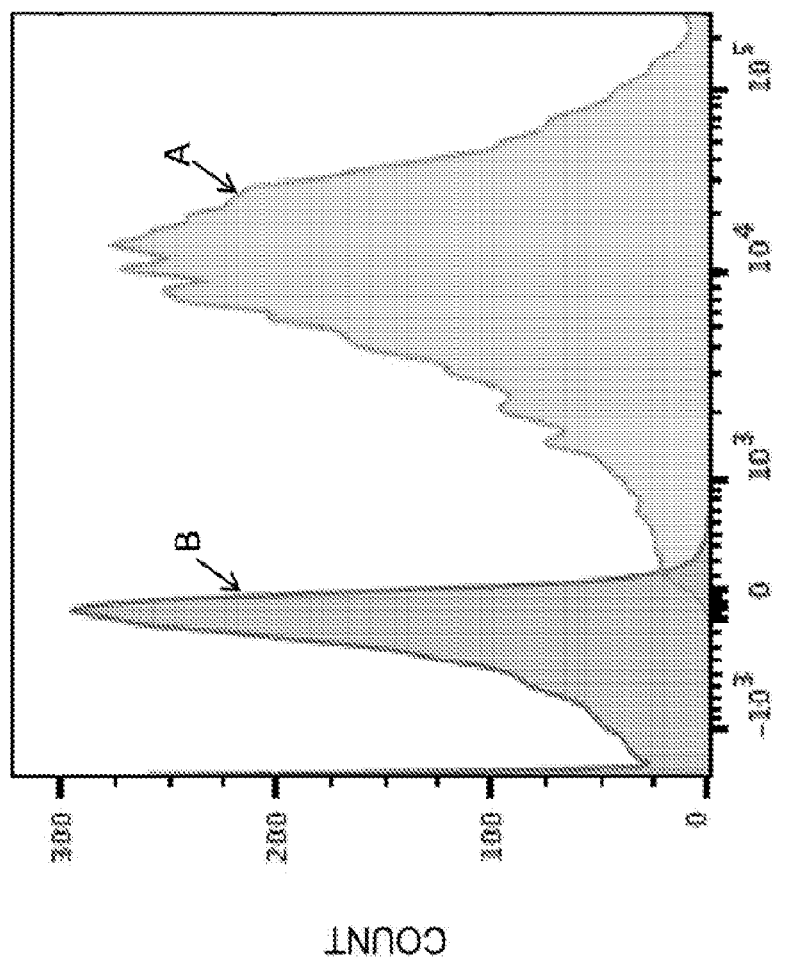

FIGS. 15A-15C show the results of PD1 DNR transduction into T cells transduced to express the M28z CAR. From donor 2, human T cells were isolated and transduced with M28z or M28zPD1DNR CAR constructs, both with a mcherry marker to identify CAR transduced T cells. FIGS. 15A and 15B show FACS analysis of the transduced cells; FIG. 15A, M28z PD1 mcherry; FIG. 15B, M28z mcherry. Staining with PD-1 antibody shows the expression of PD1 DNR in transduced T cells (FIG. 15C). FIG. 15C, A, M28z PD1 DNR mcherry sorted cells; B, M28z mcherry sorted cells.

Figure 16A:
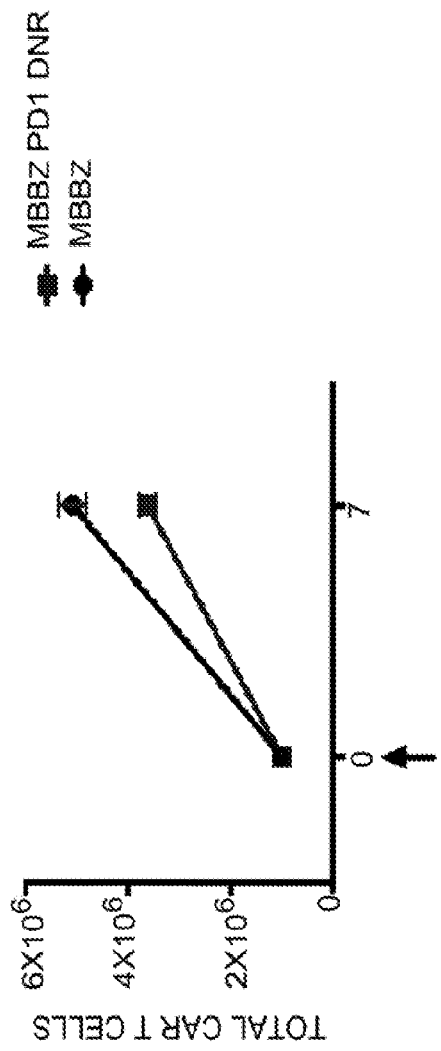
Figure 16B:
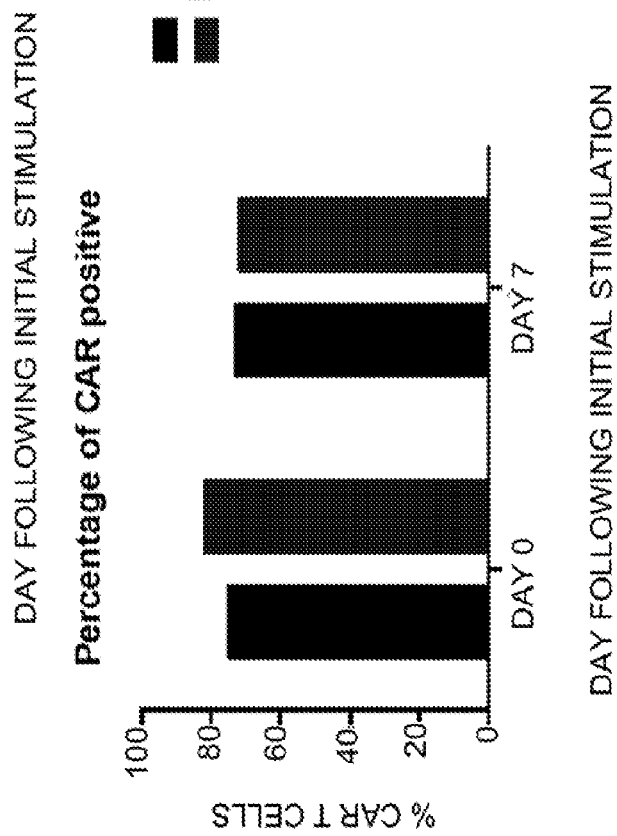
Figure 16D:
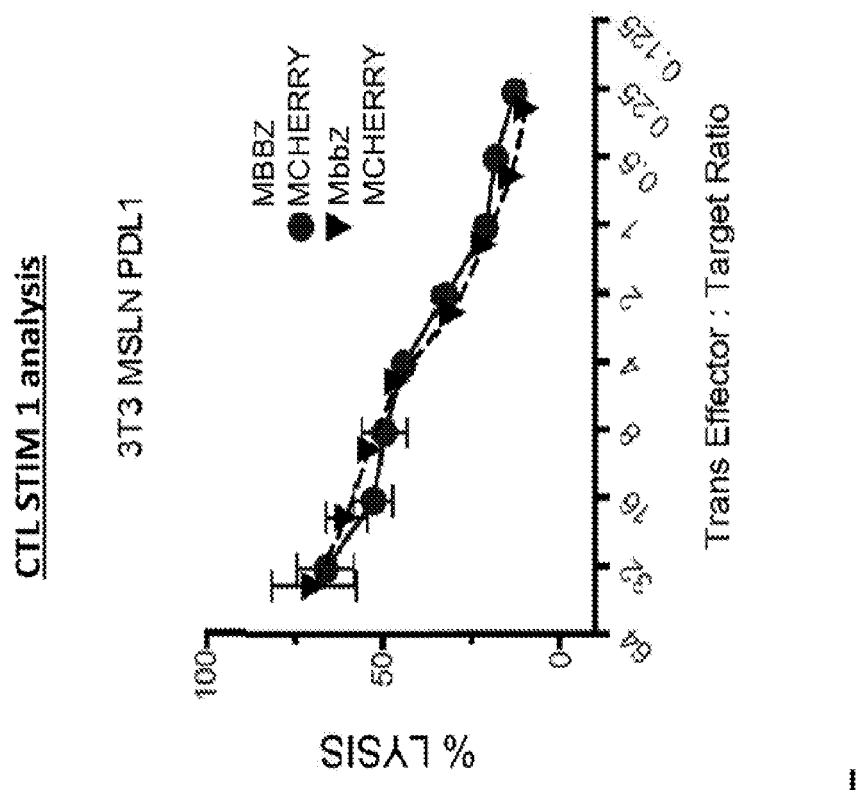
Figure 16C:
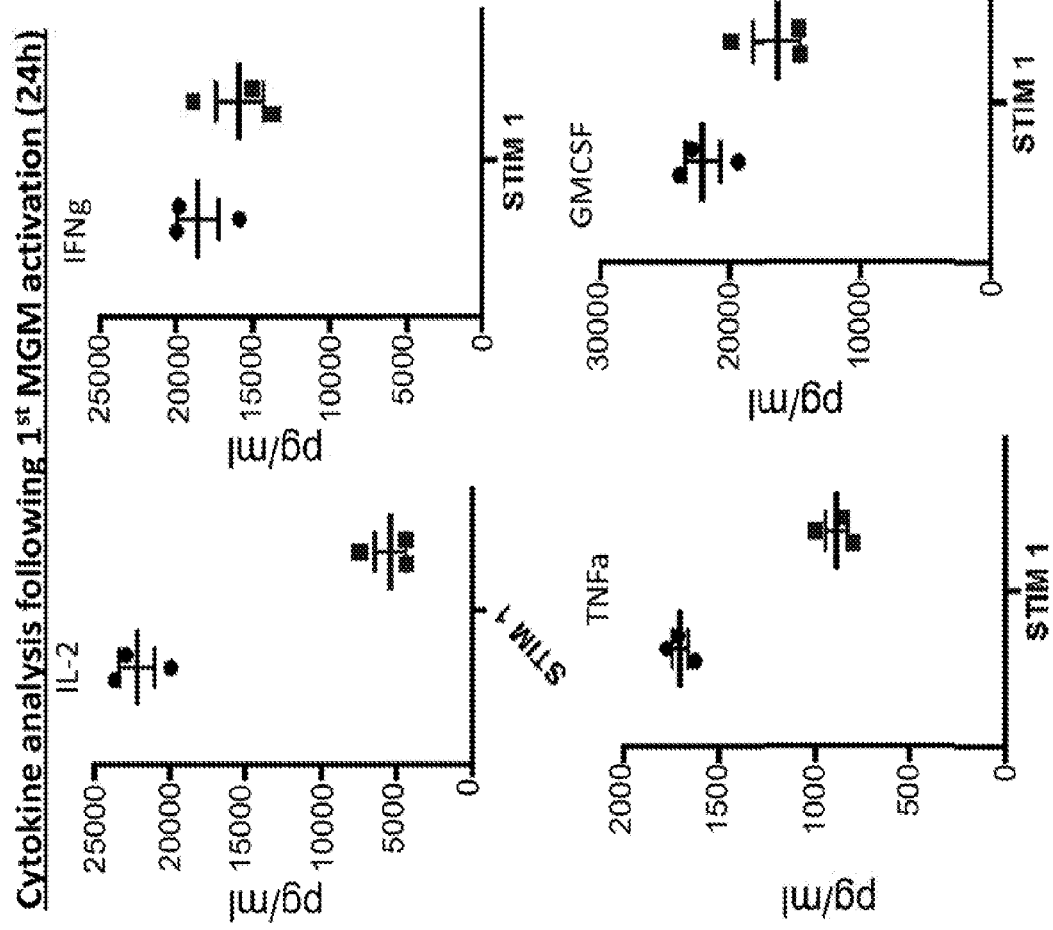

FIGS. 16A-16D show the efficacy of cells transduced with MBBz versus MBBz PD1 DNR CAR constructs in vitro. In human T cells isolated from donor 1, both MBBz and MBBz PD1DNR transduced cells were exposed to antigen-expressing (mesothelin) targets and analyzed for T-cell accumulation, cytokine secretion and cytotoxicity. FIG. 16A shows accumulation analysis of cells transduced with MBBz PD1 DNR versus MBBz. FIG. 16B shows the percentage of CAR positive cells. FIG. 16B, MBBz mcherry, left bar; MBBzPD1 DNR mcherry, right bar, at day 0 and day 7, respectively. FIG. 16C shows cytokine analysis (IL-2, IFN-γ, TNF-α and GM-CSF) following the first MGM (mesothelin expressing cells) activation. FIG. 16C, MBBz, circles (left in respective graphs), MBBz PD1 DNR, squares (right in respective graphs). FIG. 16D shows lysis of antigen-expressing (mesothelin) cells.

FIGS. 17A-17D show the efficacy of cells transduced with MBBz versus MBBz PD1 DNR CAR constructs in vitro. In human T cells isolated from donor 2, both MBBz and MBBz PD1DNR transduced cells were exposed to antigen-expressing (mesothelin) targets and analyzed for T-cell accumulation, cytokine secretion and cytotoxicity. In this experiment, cytotoxicity was measured repeatedly after repeated antigen exposure. FIG. 17A shows accumulation analysis of MBBz and MBBz PD1 DNR transduced cells. FIG. 17B shows the percentage of CAR transduction. FIG. 17B, MBBz mcherry left bar; MBBz PD1 DNR cherry, right bar. FIG. 17C shows lysis of antigen-expressing (mesothelin) cells after a first and third stimulation with MGM (mesothelin expressing cells). FIG. 17D shows cytokine analysis for IL-2 and IFN-γ in cells transduced with MBBz or MBBz PD-1 DNR. FIG. 17D, MBBz mcherry, left (circles), MBBz mcherry PD-1, right (squares) at each stimulation (STIM), respectively.

Figure 18A:
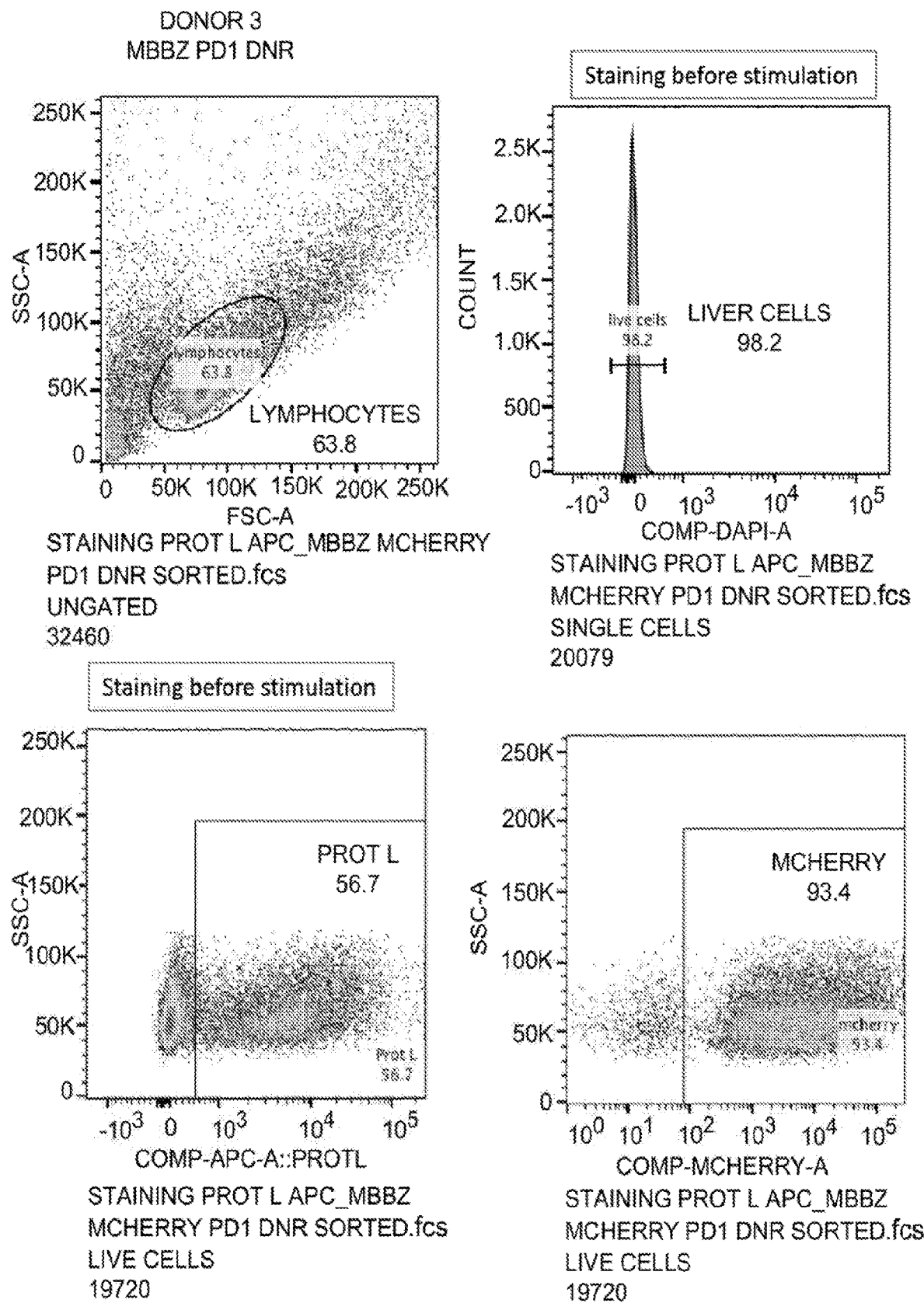
Figure 18B:
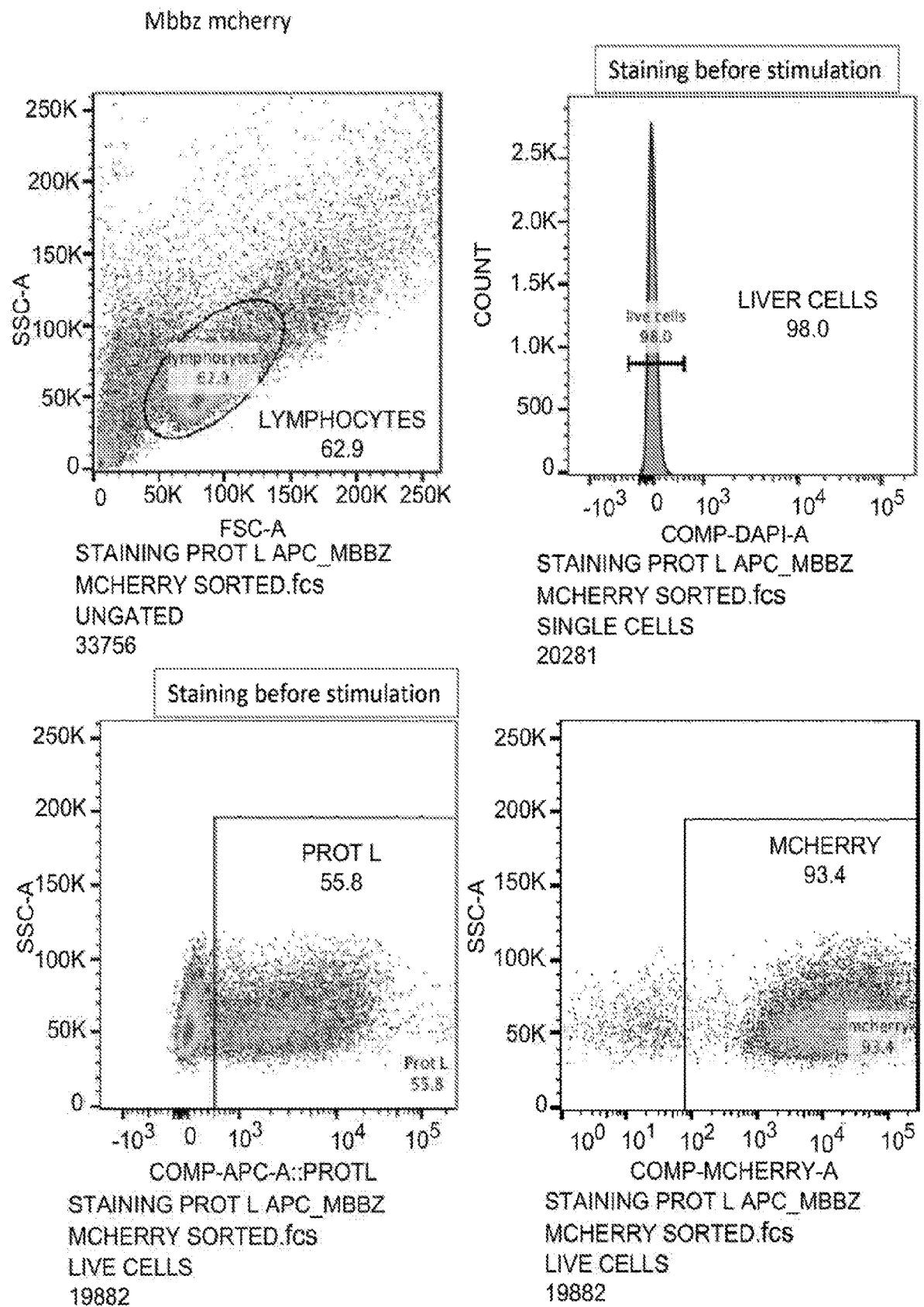

FIGS. 18A-18C show the results of PD1 DNR transduction into T cells transduced to express the MBBz CAR. From donor 3, human T cells were isolated and transduced with MBBz or MBBzPD1DNR CAR constructs, both with a mcherry marker to identify CAR transduced T cells. FIGS. 18A and 18B show FACS analysis of cells transduced with MBBz PD1 DNR or MBBz. Staining was performed before and after stimulation. Staining with PD-1 antibody shows the expression of PD1 DNR in transduced T cells (FIG. 18C). FIG. 18C, A, MBBz mcherry sorted cells; B, MBBz mcherry PD1 DNR sorted cells.

Figure 19C:
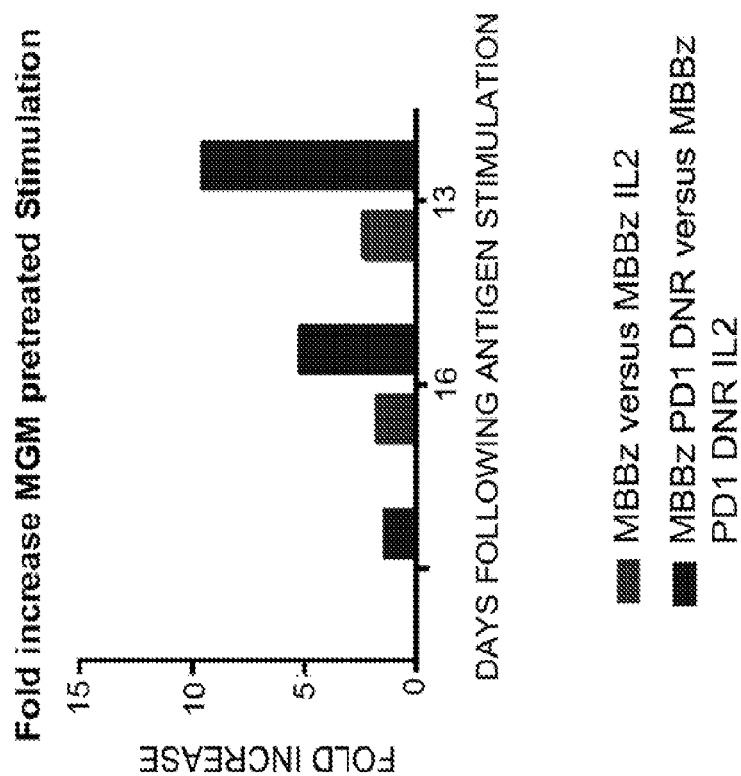
Figure 19B:
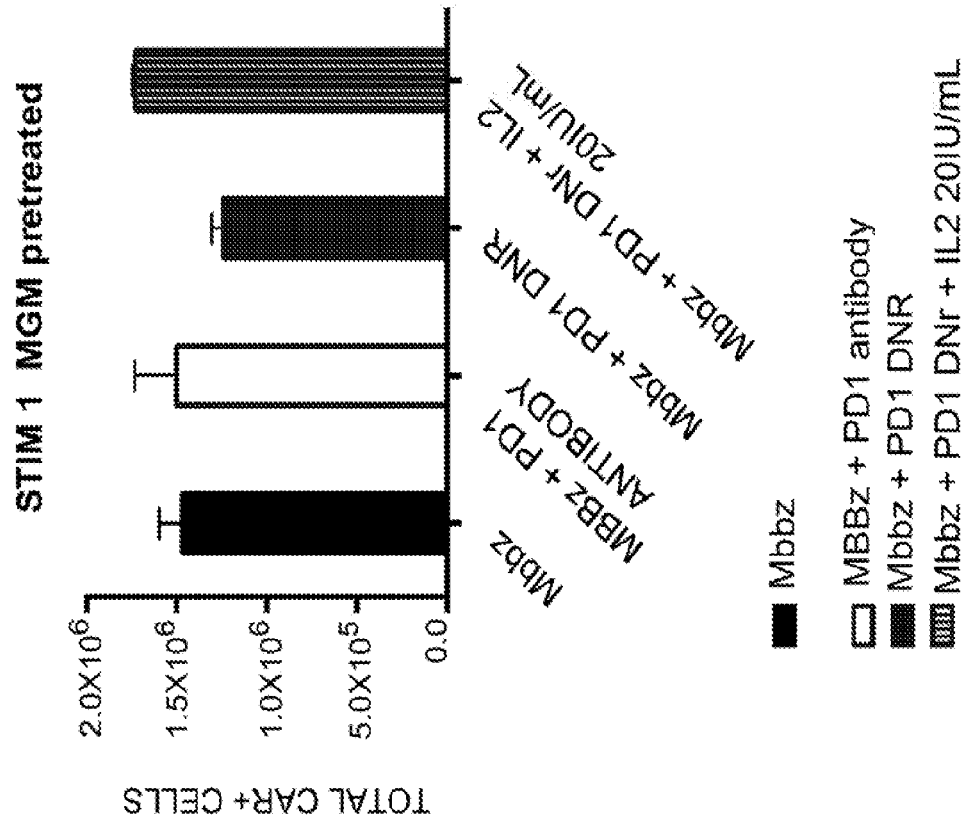

FIGS. 19A-19C show the results of PD1 DNR transduction into T cells transduced to express the MBBz CAR. MBBz or MBBzPD1DNR CAR T cell accumulation was tested with or without IL-2 in the media. FIG. 19A shows percentage of CAR transduction at 0, 9, 16 and 23 days following initial stimulation. FIG. 19A, bars left to right: MBBz; MBBz+IL-2 20 UI/mL; MBBz+IL-2 40 UI/mL; MBBz+PD1 antibody (Ab) 10 µg/mL; MBBz+PD1 DNR; MBBz PD1 DNR+IL-2 20 UI/mL, on respective days 0, 9, 16 and 23 following initial stimulation. FIG. 19B shows total CAR positive cells at stimulus 1, MGM (mesothelin expressing cells) pretreated. FIG. 19B, bars left to right: MBBz; MBBz+PD1 antibody; MBBz+PD1 DNR; MBBz+PD1 DNR+IL-2 20 IU/mL.

FIG. 19C shows the fold increase of MBBz transduced cells versus MBBz transduced cells treated with IL-2, and MBBz PD1 DNR transduced cells versus MBBz PD1 DNR transduced cells treated with IL-2. FIG. 19C, respective sets of bars, left, MBBz versus MBBz+IL2; right MBBz PD1 DNR versus MBBz PD1 DNR IL2.

Figure 20A:
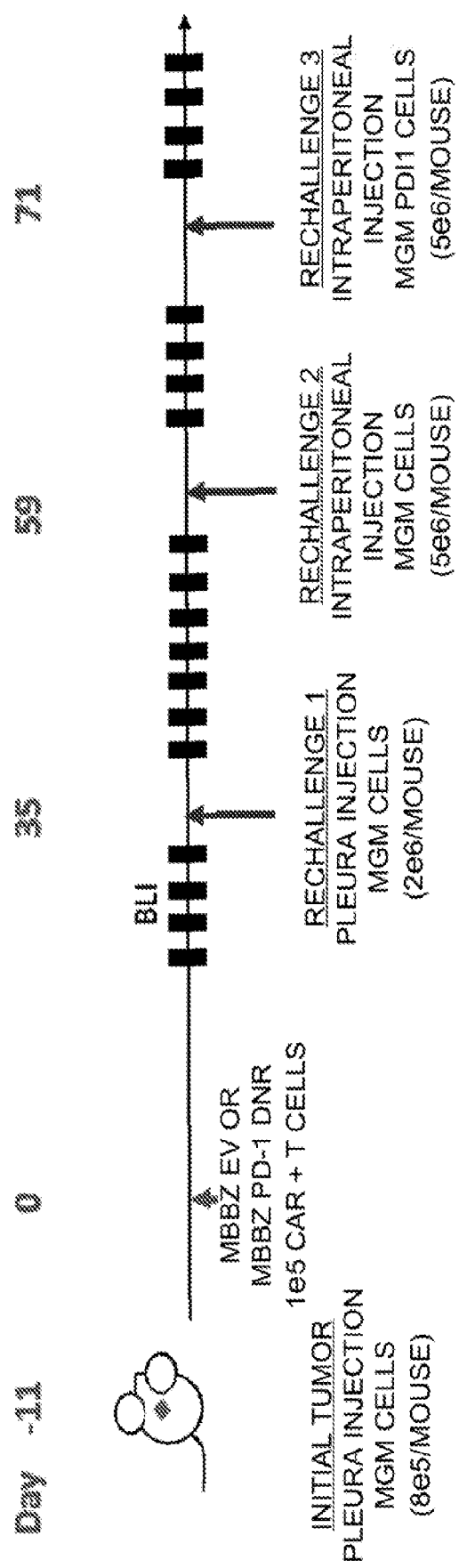
Figure 20B:
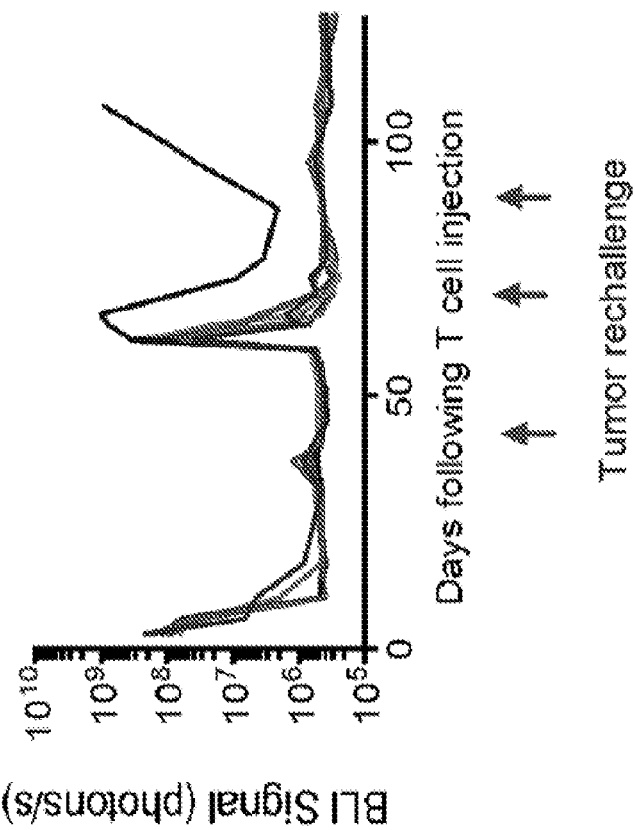
Figure 20C:
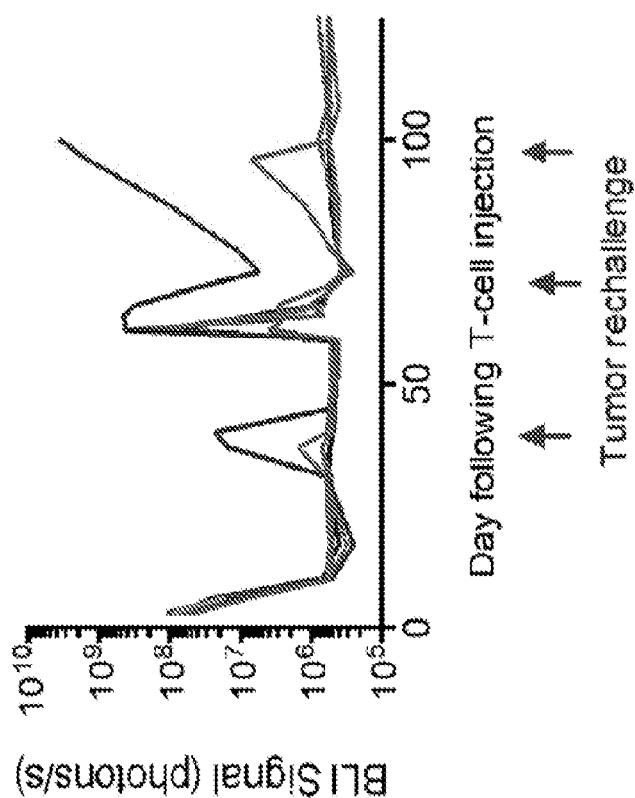
Figure 20D:
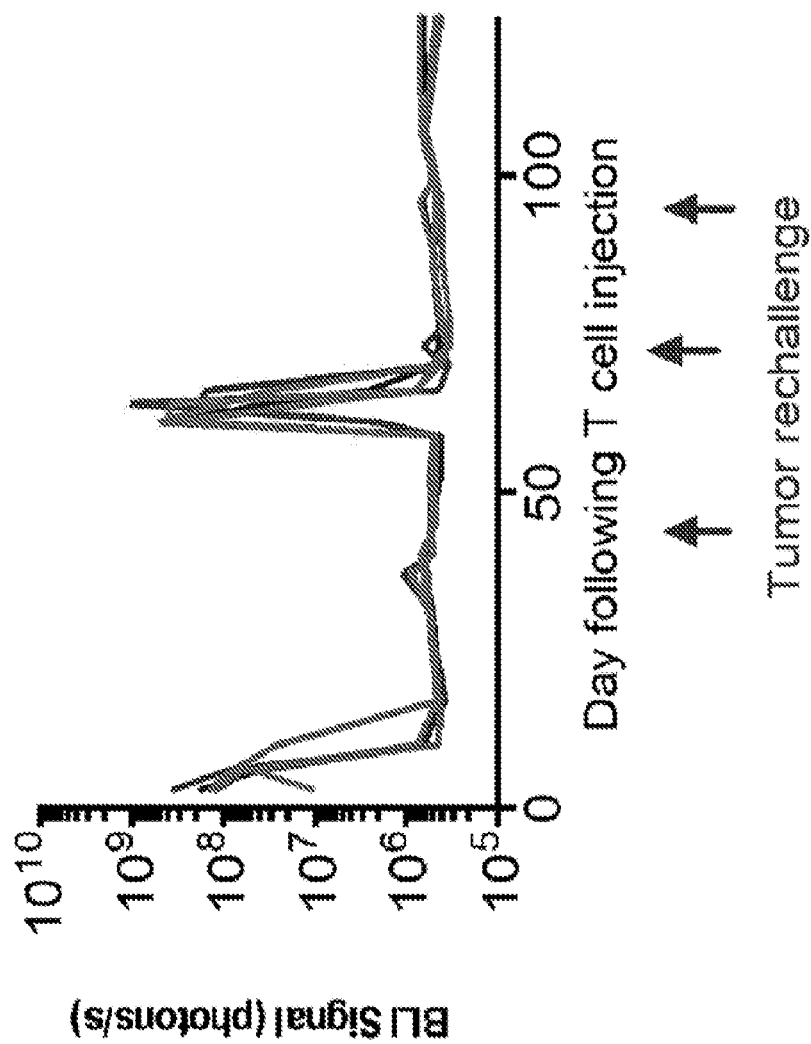

FIGS. 20A-20D show the efficacy of cells transduced with MBBz and MBBz PD1 DNR CAR constructs in vivo. Mice with established pleurla tumor were treated with a single dose of T cells expressing MBBz or MBBzPD1DNR CAR. Following tumor eradication, mice were rechallenged with either pleural or peritoneal tumor (FIG. 20A), and CAR T-cell functional persistence was assessed by tumor regression and eradication by bioluminescence imaging (BLI). As shown in FIG. 20B-20D, three groups of mice (each group represented in a separate graph) were treated with a single low dose of MBBz, MBBz PD1 DNR or MBBz+PD1 blocking antibody. Each line in the graph indicates one mouse.

Figure 21:
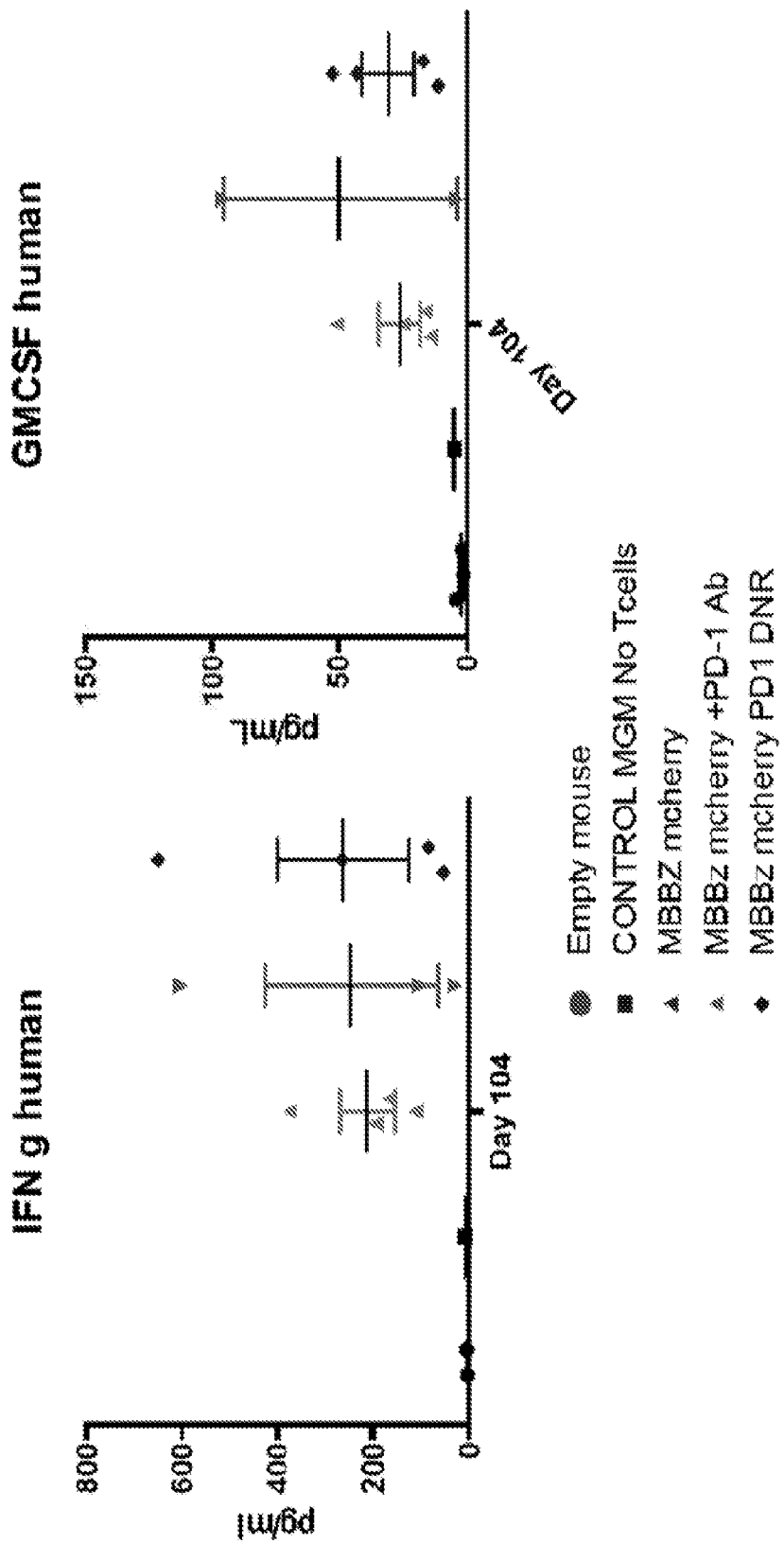

FIG. 21 shows analysis of cytokines in mouse serum following re challenge at day 100. The functional persistence of both MBBz and MBBz PD1 DNR transduced CAR T cells was shown by detection of human cytokines (IFN-γ and GM-CSF) in mouse serum. The graphs show from left to right, circle (empty mouse)—mice with no tumor and no treatment; square (control MGM no T cells)—mice with tumor, no treatment; triangle (MBBz mcherry)—mice with tumor treated with MBBz CAR T cells; triangle (MBBz mcherry+PD-1 Ab)—mice with tumor treated with MBBz+PD1 blocking antibody; diamond (MBBz mcherry PD1 DNR)—mice with tumor treated with MBBz PD1 DNR CAR T cells.

Figure 22:
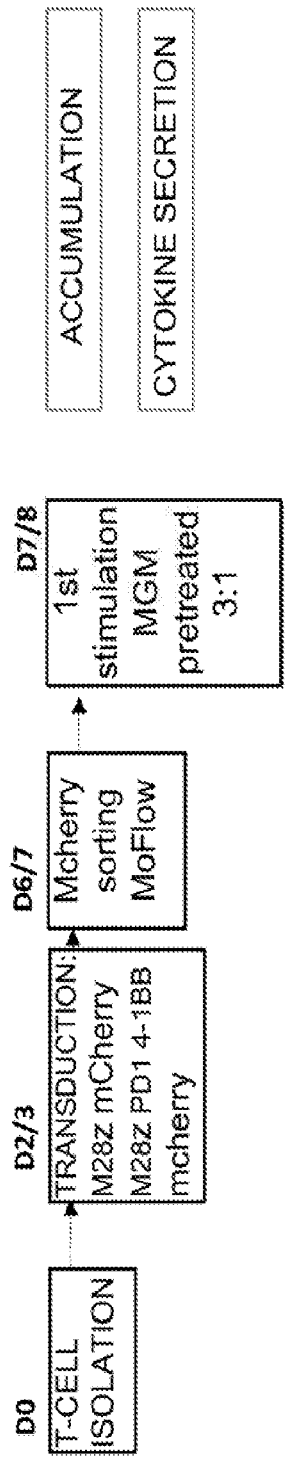
Figure 22:
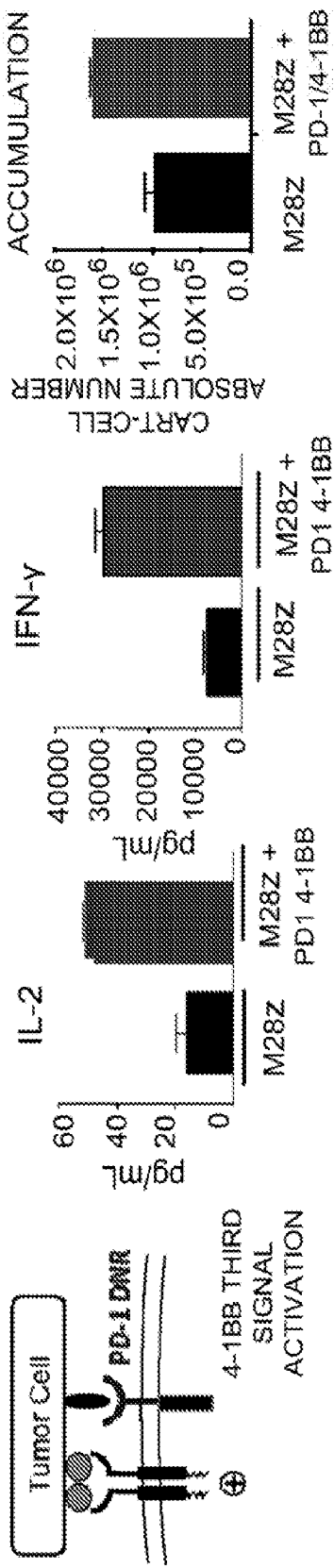

FIG. 22 shows effect of expressing a switch receptor in CART cells. To rescue the PD-1/PD-L1 mediated inhibition, a PD-1 4-1BB (a switch receptor) construct was cotransduced into T cells expressing M28z CAR, and a third stimulation was induced following PD-L1 engagement. Human T cells were transduced with M28z or M28z PD1 4-1BB CAR, both with a mcherry marker, and were flow sorted and tested for cytokine secretion (IL-2 and IFN-γ) and T-cell accumulation.

FIGS. 23A-23D show the effect of conversion of tumor-mediated PD-L1 inhibition into CAR T cell costimulation to potentiate thoracic cancer. FIG. 23A shows tumor harvest analysis, showing PD-1 and PD-L1 upregulation on CAR T cells and tumor cells. FIG. 23B shows that the addition of PD-1 blocking potentiates CAR T cell therapy in vivo, but its efficacy requires multiple injections. FIG. 23C shows a schematic of a CAR and PD-1 coinhibition versus a CAR coexpressed with a PD-1 DNR (left). FIG. 23C also shows that a single dose of M28z T cells coexpressing PD1-DNR restores effector functions, enhances tumor burden control, and prolongs median survival (two graphs on right). FIG. 23D shows a schematic of a CAR co-expressed with a switch receptor (left). FIG. 23D also shows that converting PD-L1 inhibition into a positive costimulatory signal by a PD-1/4-1BB construct cotransduced into M28z CAR T cells enhanced cytokine secretion and T cell accumulation (IL-2, IFN-γ and accumulation shown in graphs left to right).

6. DETAILED DESCRIPTION OF THE INVENTION

The present invention relates to compositions and methods for treating cancer. It is known that malignant cells adapt to generate an immunosuppressive microenvironment to protect the cells from immune recognition and elimination. The immunosuppressive microenvironment provides a mechanism for cancer cells and/or tumors to inhibit the effects of a patient's immune system to avoid tumor growth inhibition or elimination. This tumor microenvironment poses a challenge to methods of treatment involving stimulation of an immune response, including immunotherapy methods such as targeted T cell therapies. The present invention is based on the discovery that the effectiveness of cell-based immunotherapy methods can be enhanced by modifying the cells used in immunotherapy to express certain proteins that overcome the immunosuppressive microenvironment. As described herein, immunotherapy cells can be genetically engineered to intrinsically express proteins that are dominant negative mutants and that inhibit blockades that limit the anticancer effect of the immune cells used in immunotherapy. By inhibiting the blockade, immune cells are permitted to provide a more effective immune response against the cancer.

In one aspect, provided herein are cells that are immune cells, or precursor cells thereof, that recombinantly express (a) a chimeric antigen receptor (CAR), and (b) a dominant negative form of an inhibitor of a cell-mediated immune response of the immune cell, wherein the CAR binds to a cancer antigen. Also provided are pharmaceutical compositions comprising a therapeutically effective amount of the cells; and a pharmaceutically acceptable carrier. Additionally provided are polypeptides encoding dominant negative forms of an immune checkpoint inhibitor, for example, containing (a) at least a portion of an extracellular domain of an immune checkpoint inhibitor, said portion comprising the ligand binding region, and (b) a transmembrane domain, wherein the polypeptide is a dominant negative form of the immune checkpoint inhibitor, which polypeptide can optionally be purified. Also provided are T cells that recognize and are sensitized to a cancer antigen, wherein the T cells recombinantly express a dominant negative form of an inhibitor of a T cell-mediated immune response. Further provided are nucleic acids encoding the dominant negative forms of an immune checkpoint inhibitor, as well as vectors encoding the nucleic acids. In another aspect, provided herein are methods of treating a cancer in a subject in need thereof, comprising administering to the subject a therapeutically effective amount of the cells, described above, that recombinantly expresses a CAR and a dominant negative form of an inhibitor of a cell-mediated immune response, wherein the cancer antigen is an antigen of the cancer. Additionally provided are methods of treating a cancer in a subject in need thereof, comprising administering to the subject a pharmaceutical composition comprising a therapeutically effective amount of the cells, described above, and a pharmaceutically acceptable carrier, wherein the cancer antigen is an antigen of the cancer. Further provided are methods of treating a cancer in a subject in need thereof, comprising administering to the subject a therapeutically effective amount of a T cell that recognizes and is sensitized to a cancer antigen, where the T cells recombinantly express a dominant negative form of an inhibitor of a T cell-mediated immune response, wherein the cancer antigen is an antigen of the cancer.

6.1 Cells

In one embodiment, the invention provides cells that are immune cells, or precursor cells thereof, that recombinantly express (i) a CAR that binds to a cancer antigen and (ii) a dominant negative form (hereinafter "DN form") of an inhibitor of a cell-mediated immune response, preferably of the immune cell. The recombinant cells can be used to enhance or provide an immune response against a target such as a cancer antigen. Preferably, the cells are derived from a human (are of human origin prior to being made recombinant) (and human-derived cells are particularly preferred for administration to a human in the methods of treatment of the invention).

The immune cells of the invention can be cells of the lymphoid lineage. Non-limiting examples of cells of the lymphoid lineage that can be used as immune cells include T cells and Natural Killer (NK) cells. T cells express the T cell receptor (TCR), with most cells expressing α and β chains and a smaller population expressing γ and δ chains. T cells useful as immune cells of the invention can be CD4+ or CD8+ and can include, but are not limited to, T helper cells (CD4+), cytotoxic T cells (also referred to as cytotoxic T lymphocytes, CTL; CD8+ T cells), and memory T cells, including central memory T cells, stem-cell-like memory T cells (or stem-like memory T cells), and effector memory T cells, for example, $T_{EM}$ cells and $T_{EMRA}$ (CD45RA+) cells, natural killer T cells, mucosal associated invariant T cells (MAIT), and γδ T cells. Other exemplary immune cells include, but are not limited to, macrophages, antigen presenting cells (APCs) such as dendritic cells, or any immune cell that expresses an inhibitor of a cell-mediated immune response, for example, an immune checkpoint inhibitor pathway receptor, e.g., PD-1 (in such instance expression of the DN form in the cell inhibits the inhibitor of the cell-mediated immune response to promote sustained activation of the cell). Precursor cells of immune cells that can be used according to the invention, which recombinantly express a CAR and a DN form, as described above, are, by way of example, hematopoietic stem and/or progenitor cells. Hematopoietic stem and/or progenitor cells can be derived from bone marrow, umbilical cord blood, adult peripheral blood after cytokine mobilization, and the like, by methods known in the art, and then are genetically engineered to recombinantly express a CAR and DN form. Particularly useful precursor cells are those that can differentiate into the lymphoid lineage, for example, hematopoietic stem cells or progenitor cells of the lymphoid lineage.

Immune cells and precursor cells thereof can be isolated by methods well known in the art, including commercially available isolation methods (see, for example, Rowland-Jones et al., *Lymphocytes: A Practical Approach*, Oxford University Press, New York (1999)). Sources for the immune cells or precursor cells thereof include, but are not limited to, peripheral blood, umbilical cord blood, bone marrow, or other sources of hematopoietic cells. Various techniques can be employed to separate the cells to isolate or enrich for desired immune cells. For instance, negative selection methods can be used to remove cells that are not the desired immune cells. Additionally, positive selection methods can be used to isolate or enrich for desired immune cells or precursor cells thereof, or a combination of positive and negative selection methods can be employed. Monoclonal antibodies (MAbs) are particularly useful for identifying markers associated with particular cell lineages and/or stages of differentiation for both positive and negative selections. If a particular type of cell is to be isolated, for example, a particular type of T cell, various cell surface markers or combinations of markers, including but not limited to, CD3, CD4, CD8, CD34 (for hematopoietic stem and progenitor cells) and the like, can be used to separate the cells, as is well known in the art (see Kearse, *T Cell Protocols: Development and Activation*, Humana Press, Totowa N.J. (2000); De Libero, *T Cell Protocols*, Vol. 514 of *Methods in Molecular Biology*, Humana Press, Totowa N.J. (2009)).

Procedures for separation of cells include, but are not limited to, density gradient centrifugation, coupling to particles that modify cell density, magnetic separation with antibody-coated magnetic beads, affinity chromatography; cytotoxic agents joined to or used in conjunction with a monoclonal antibody (mAb), including, but not limited to, complement and cytotoxins, and panning with an antibody attached to a solid matrix, for example, a plate or chip, elutriation, flow cytometry, or any other convenient technique (see, for example, Recktenwald et al., *Cell Separation Methods and Applications*, Marcel Dekker, Inc., New York (1998)).

The immune cells or precursor cells thereof can be autologous or non-autologous to the subject to which they are administered in the methods of treatment of the invention. Autologous cells are isolated from the subject to which the engineered cells recombinantly expressing a CAR and DN form are to be administered. Optionally, the cells can be obtained by leukapheresis, where leukocytes are selectively removed from withdrawn blood, made recombinant, and then retransfused into the donor. Alternatively, allogeneic cells from a non-autologous donor that is not the subject can be used. In the case of a non-autologous donor, the cells are typed and matched for human leukocyte antigen (HLA) to determine an appropriate level of compatibility, as is well known in the art. For both autologous and and non-autologous cells, the cells can optionally be cryopreserved until ready to be used for genetic manipulation and/or administration to a subject using methods well known in the art.

Various methods for isolating immune cells that can be used for recombinant expression of a CAR have been described previously, and can be used, including but not limited to, using peripheral donor lymphocytes (Sadelain et al., *Nat. Rev. Cancer* 3:35-45 (2003); Morgan et al., *Science* 314:126-129 (2006), using lymphocyte cultures derived from tumor infiltrating lymphocytes (TILs) in tumor biopsies (Panelli et al., *J Immunol.* 164:495-504 (2000); Panelli et al., *J. Immunol.* 164:4382-4392 (2000)), and using selectively in vitro-expanded antigen-specific peripheral blood leukocytes employing artificial antigen-presenting cells (AAPCs) or dendritic cells (Dupont et al., *Cancer Res.* 65:5417-5427 (2005); Papanicolaou et al., *Blood* 102:2498-2505 (2003)). In the case of using stem cells, the cells can be isolated by methods well known in the art (see, for example, Klug et al., *Hematopoietic Stem Cell Protocols*, Humana Press, New Jersey (2002); Freshney et al., *Culture of Human Stem Cells*, John Wiley & Sons (2007)).

In a second embodiment, the invention provides T cells that recognize and are sensitized to a cancer antigen, and also which recombinantly express a DN form of an inhibitor of a T cell-mediated immune response. Such T cells can but need not express a CAR that binds to a cancer antigen, since the cells already are cancer antigen-specific so that their immune response (for example, cytotoxicity) is stimulated specifically by such cancer antigen (generally in the form of a cell expressing the cancer antigen on its cell surface). Such T cells that recognize and are sensitized to a cancer antigen can be obtained by known methods, by way of example, in vitro sensitization methods using naive T cells (see, for example, Wolfl et al., *Nat. Protocols* 9:950-966 (2014)) or hematopoietic progenitor cells (see van Lent et al., *J. Immunol.* 179:4959-4968 (2007)); or obtained from a subject that has been exposed to and is mounting an immune response against the cancer antigen. Methods for isolating an antigen-specific T cell from a subject are well known in the art. Such methods include, but are not limited to, a cytokine capture system or cytokine secretion assay, which is based on the secretion of cytokines from antigen stimulated T cells that can be used to identify and isolate antigen-specific, and expansion of cells in vitro (see Assenmacher et al., *Cytometric Cytokine Secretion Assay, in Analyzing T Cell Responses: How to Analyze Cellular Immune Responses Against Tumor Associated Antigens*, Nagorsen et al., eds., Chapter 10, pp. 183-195, Springer, The Netherlands (2005); Haney et al., *J. Immunol. Methods* 369:33-41 (2011); Bunos et al., Vox *Sanguinis* DOI: 10.1111/vox.12291 (2015); Montes et al., *Clin. Exp. Immunol.* 142:292-302 (2005); Adusumilli et al., *Sci Transl Med.* 6:261ra151 (2014)). Such cytokines include, but are not limited to interferon-γ and tumor necrosis factor-α. The antigen-specific T cells can be isolated using well known techniques as described above for isolating immune cells, which include, but are not limited to, flow cytometry, magnetic beads, panning on a solid phase, and so forth. Antigen-specific T cell isolation techniques are also commercially available, which can be used or adapted for clinical applications (see, for example, Miltenyi Biotec, Cambridge, Mass.; Proimmune, Oxford, UK; and the like).

In a specific embodiment, isolated immune cells and precursor cells are genetically engineered ex vivo for recombinant expression of a DN form and a CAR. In a specific embodiment, isolated T cells are genetically engineered ex vivo for recombinant expression of a DN form. The cells can be genetically engineered for recombinant expression by methods well known in the art.

In an embodiment where cancer antigen sensitized T cells that recombinantly express a DN form are used, and wherein such cells are obtained by in vitro sensitization, the sensitization can occur before or after the T cells are genetically engineered to recombinantly express a DN form. In an embodiment where the sensitized T cells are isolated from in vivo sources, it will be self-evident that genetic engineering occurs of the already-sensitized T cells.

The immune cells or precursor cells thereof can be subjected to conditions that favor maintenance or expansion of the immune cells or precursor cells thereof (see Kearse, *T Cell Protocols: Development and Activation*, Humana Press, Totowa N.J. (2000); De Libero, *T Cell Protocols*, Vol. 514 of *Methods in Molecular Biology*, Humana Press, Totowa N. J. (2009); Parente-Pereira et al., *J. Biol. Methods* 1(2) e7 (doi 10.14440/jbm.2014.30) (2014); Movassagh et al., *Hum. Gene Ther.* 11:1189-1200 (2000); Rettig et al., *Mol. Ther.* 8:29-41 (2003); Agarwal et al., *J. Virol.* 72:3720-3728 (1998); Pollok et al., *Hum. Gene Ther.* 10:2221-2236 (1999); Quinn et al., *Hum. Gene Ther.* 9:1457-1467 (1998); see also commercially available methods such as Dynabeads™ human T cell activator products, Thermo Fisher Scientific, Waltham, Mass.)). The immune cells or precursor cells thereof, or cancer antigen sensitized T cells, can optionally be expanded prior to or after ex vivo genetic engineering. Expansion of the cells is particularly useful to increase the number of cells for administration to a subject. Such methods for expansion of immune cells are well known in the art (see Kaiser et al., *Cancer Gene Therapy* 22:72-78 (2015); Wolfl et al., *Nat. Protocols* 9:950-966 (2014)). Furthermore, the cells can optionally be cryopreserved after isolation and/or genetic engineering, and/or expansion of genetically engineered cells (see Kaiser et al., supra, 2015)). Methods for cyropreserving cells are well known in the art (see, for example, Freshney, *Culture of Animal Cells: A Manual of Basic Techniques*, 4th ed., Wiley-Liss, New York (2000); Harrison and Rae, *General Techniques of Cell Culture*, Cambridge University Press (1997)).

With respect to generating cells recombinantly expressing a DN form or a CAR and DN form, one or more nucleic acids encoding the DN form or the CAR and DN form is introduced into the immune cell or precursor cell thereof using a suitable expression vector. The immune cells (for example, T cells) or precursor cells thereof are preferably transduced with one or more nucleic acids encoding a DN form, or a CAR and DN form. In the case of expressing both a CAR and DN form, the CAR and DN form encoding nucleic acids can be on separate vectors or on the same vector, as desired. For example, a polynucleotide encoding a CAR or DN form of the invention can be cloned into a suitable vector, such as a retroviral vector, and introduced into the immune cell using well known molecular biology techniques (see Ausubel et al., *Current Protocols in Molecular Biology*, John Wiley and Sons, Baltimore, Md. (1999)).

Any vector suitable for expression in a cell of the invention, particularly a human immune cell or a precursor cell thereof, can be employed. The vectors contain suitable expression elements such as promoters that provide for expression of the encoded nucleic acids in the immune cell. In the case of a retroviral vector, cells can optionally be activated to increase transduction efficiency (see Parente-Pereira et al., *J. Biol. Methods* 1(2) e7 (doi 10.14440/jbm.2014.30) (2014); Movassagh et al., *Hum. Gene Ther.* 11:1189-1200 (2000); Rettig et al., *Mol. Ther.* 8:29-41 (2003); Agarwal et al., *J. Virol.* 72:3720-3728 (1998); Pollok et al., *Hum. Gene Ther.* 10:2221-2236 (1998); Quinn et al., *Hum. Gene Ther.* 9:1457-1467 (1998); see also commercially available methods such as Dynabeads™ human T cell activator products, Thermo Fisher Scientific, Waltham, Mass.).

In one embodiment, the vector is a retroviral vector, for example, a gamma retroviral or lentiviral vector, which is employed for the introduction of a CAR or DN form into the immune cell or precursor cell thereof. For genetic modification of the cells to express a CAR and/or DN form, a retroviral vector is generally employed for transduction. However, it is understood that any suitable viral vector or non-viral delivery system can be used. Combinations of a retroviral vector and an appropriate packaging line are also suitable, where the capsid proteins will be functional for infecting human cells. Various amphotropic virus-producing cell lines are known, including, but not limited to, PA12 (Miller et al., *Mol. Cell. Biol.* 5:431-437 (1985)); PA317 (Miller et al., *Mol. Cell. Biol.* 6:2895-2902(1986)); and CRIP (Danos et al., *Proc. Natl. Acad. Sci. USA* 85:6460-6464 (1988)). Non-amphotropic particles are suitable too, for example, particles pseudotyped with VSVG, RD114 or GALV envelope and any other known in the art (Relander et al., *Mol. Therap.* 11:452-459 (2005)). Possible methods of transduction also include direct co-culture of the cells with producer cells (for example, Bregni et al., *Blood* 80:1418-1422 (1992)), or culturing with viral supernatant alone or concentrated vector stocks with or without appropriate growth factors and polycations (see, for example, Xu et al., *Exp. Hemat.* 22:223-230 (1994); Hughes, et al. *J. Clin. Invest.* 89:1817-1824 (1992)).

Generally, the chosen vector exhibits high efficiency of infection and stable integration and expression (see, for example, Cayouette et al., *Human Gene Therapy* 8:423-430 (1997); Kido et al., *Current Eye Research* 15:833-844 (1996); Bloomer et al., *J. Virol.* 71:6641-6649 (1997); Naldini et al., *Science* 272:263 267 (1996); and Miyoshi et al., *Proc. Natl. Acad. Sci. U.S.A.* 94:10319-10323 (1997)). Other viral vectors that can be used include, for example, adenoviral, lentiviral, and adeno-associated viral vectors, vaccinia virus, a bovine papilloma virus derived vector, or a herpes virus, such as Epstein-Barr Virus (see, for example, Miller, *Hum. Gene Ther.* 1(1):5-14 (1990); Friedman, *Science* 244:1275-1281 (1989); Eglitis et al., *BioTechniques* 6:608-614 (1988); Tolstoshev et al., *Current Opin. Biotechnol.* 1:55-61 (1990); Sharp, *Lancet* 337:1277-1278 (1991); Cornetta et al., *Prog. Nucleic Acid Res. Mol. Biol.* 36:311-322 (1989); Anderson, *Science* 226:401-409 (1984); Moen, *Blood Cells* 17:407-416 (1991); Miller et al., *Biotechnology* 7:980-990 (1989); Le Gal La Salle et al., *Science* 259:988-990 (1993); and Johnson, *Chest* 107:77S-83S (1995)). Retroviral vectors are particularly well developed and have been used in clinical settings (Rosenberg et al., *N. Engl. J. Med.* 323:370 (1990); Anderson et al., U.S. Pat. No. 5,399,346).

Particularly useful vectors for expressing a CAR and/or DN form of the invention include vectors that have been used in human gene therapy. In one non-limiting embodiment, a vector is a retroviral vector. The use of retroviral vectors for expression in T cells or other immune cells, including engineered CAR T cells, has been described (see Scholler et al., *Sci. Transl. Med.* 4:132-153 (2012; Parente-Pereira et al., *J. Biol. Methods* 1(2):e7 (1-9)(2014); Lamers et al., *Blood* 117(1):72-82 (2011); Reviere et al., *Proc. Natl. Acad. Sci. USA* 92:6733-6737 (1995)). In one embodiment, the vector is an SGF retroviral vector such as an SGF γ-retroviral vector, which is Moloney murine leukemia-based retroviral vector. SGF vectors have been described previously (see, for example, Wang et al., *Gene Therapy* 15:1454-1459 (2008)).

The vectors of the invention employ suitable promoters for expression in a particular host cell. The promoter can be an inducible promoter or a constitutive promoter. In a particular embodiment, the promoter of an expression vector provides expression in an immune cell, such as a T cell, or precursor cell thereof. Non-viral vectors can be used as well, so long as the vector contains suitable expression elements for expression in the immune cell or precursor cell thereof. Some vectors, such as retroviral vectors, can integrate into the host genome. If desired, targeted integration can be implemented using technologies such as a nuclease, transcription activator-like effector nucleases (TALENs), Zinc-finger nucleases (ZFNs), and/or clustered regularly interspaced short palindromic repeats (CRISPRs), by homologous recombination, and the like (Gersbach et al., *Nucl. Acids Res.* 39:7868-7878 (2011); Vasileva, et al. *Cell Death Dis.* 6:e1831. (Jul. 23, 2015); Sontheimer, *Hum. Gene Ther.* 26(7):413-424 (2015)).

The vectors and constructs can optionally be designed to include a reporter. For example, the vector can be designed to express a reporter protein, which can be useful to identify cells comprising the vector or nucleic acids provided on the vector, such as nucleic acids that have integrated into the host chromosome. In one embodiment, the reporter can be expressed as a bicistronic or multicistronic expression construct with the CAR or DN form. Exemplary reporter proteins include, but are not limited to, fluorescent proteins, such as mCherry, green fluorescent protein (GFP), blue fluorescent protein, for example, EBFP, EBFP2, Azurite, and mKalamal, cyan fluorescent protein, for example, ECFP, Cerulean, and CyPet, and yellow fluorescent protein, for example, YFP, Citrine, Venus, and YPet. In an additional embodiment, a vector construct can comprise a P2A sequence, which provides for optional co-expression of a reporter molecule. P2A is a self-cleaving peptide sequence, which can be used for bicistronic or multicistronic expression of protein sequences (see Szymczak et al., *Expert Opin. Biol. Therapy* 5(5):627-638 (2005)).

Assays can be used to determine the transduction efficiency of a CAR and/or DN form using routine molecular biology techniques. If a marker has been included in the construct, such as a fluorescent protein, gene transfer efficiency can be monitored by FACS analysis to quantify the fraction of transduced (for example, GFP$^+$) immune cells, such as T cells, or precursor cells thereof, and/or by quantitative PCR. Using a well-established cocultivation system (Gade et al., *Cancer Res.* 65:9080-9088 (2005); Gong et al., *Neoplasia* 1:123-127 (1999); Latouche et al., *Nat. Biotechnol.* 18:405-409 (2000)) it can be determined whether fibroblast AAPCs expressing cancer antigen (vs. controls) direct cytokine release from transduced immune cells, such as T cells, expressing a CAR (cell supernatant LUMINEX (Austin Tex.) assay for IL-2, IL-4, IL-10, IFN-γ, TNF-α, and GM-CSF), T cell proliferation (by carboxyfluorescein succinimidyl ester (CF SE) labeling), and T cell survival (by Annexin V staining). The influence of CD80 and/or 4-1BBL on T cell survival, proliferation, and efficacy can be evaluated. T cells can be exposed to repeated stimulation by cancer antigen positive target cells, and it can be determined whether T cell proliferation and cytokine response remain similar or diminished with repeated stimulation. The cancer antigen CAR constructs can be compared side by side under equivalent assay conditions. Cytotoxicity assays with multiple E:T ratios can be conducted using chromium-release assays.

In addition to providing a nucleic acid encoding a polypeptide that is a DN form or a CAR in a vector for expression in an immune cell or precursor cell thereof, a nucleic acid encoding the polypeptide can also be provided in other types of vectors more suitable for genetic manipulation, such as for expression of various constructs in a bacterial cell such as *E. coli*. Such vectors can be any of the well known expression vectors, including commercially available expression vectors (see in Sambrook et al., *Molecular Cloning: A Laboratory Manual*, Third Ed., Cold Spring Harbor Laboratory, New York (2001); and Ausubel et al., *Current Protocols in Molecular Biology*, John Wiley and Sons, Baltimore, Md. (1999).

If desired, a nucleic acid encoding a polypeptide for genetic engineering of a cell of the invention, such as a DN form or a CAR, can be codon optimized to increase efficiency of expression in an immune cell or precursor cell thereof. Codon optimization can be used to achieve higher levels of expression in a given cell. Factors that are involved in different stages of protein expression include codon adaptability, mRNA structure, and various cis-elements in transcription and translation. Any suitable codon optimization methods or technologies that are known to one skilled in the art can be used to modify the polynucleotides encoding the polypeptides. Such codon optimization methods are well known, including commercially available codon optimization services, for example, OptimumGene™ (GenScript; Piscataway, N.J.), Encor optimization (EnCor Biotechnology; Gainseville Fla.), Blue Heron (Blue Heron Biotech; Bothell, Wash.), and the like. Optionally, multiple codon optimizations can be performed based on different algorithms, and the optimization results blended to generate a codon optimized nucleic acid encoding a polypeptide.

Further modification can be introduced to the immune cells or precursor cells thereof of the invention. For example, the cells can be modified to address immunological complications and/or targeting by the CAR to healthy tissues that express the same target antigens as the tumor cells. For example, a suicide gene can be introduced into the cells to provide for depletion of the cells when desired. Suitable suicide genes include, but are not limited to, Herpes simplex virus thymidine kinase (hsv-tk), inducible Caspase 9 Suicide gene (iCasp-9), and a truncated human epidermal growth factor receptor (EGFRt) polypeptide. Agents are administered to the subject to which the cells containing the suicide genes have been administered, including but not limited to, ganciclovir (GCV) for hsv-tk (Greco et al., *Frontiers Pharmacol.* 6:95 (2015); Barese et al., *Mol. Therapy* 20:1932-1943 (2012)), AP1903 for iCasp-9 (Di Stasi et al., *N. Engl. J. Med.* 365:1673-1683 (2011), and cetuximab for EGFRt (U.S. Pat. No. 8,802,374), to promote cell death. In one embodiment, administration of a prodrug designed to activate the suicide gene, for example, a prodrug such as AP1903 that can activate iCasp-9, triggers apoptosis in the suicide gene-activated cells. In one embodiment, iCasp9 consists of the sequence of the human FK506-binding protein (FKBP12; GenBank number, AH002818 (AH002818.1, M92422.1, GI:182645; AH002818.2, GI:1036032368)) with an F36V mutation, connected through a Ser-Gly-Gly-Gly-Ser linker (SEQ ID NO:48) to the gene encoding human caspase 9 (CASP9; GenBank number, NM001229 (NM_001229.4, GI:493798577)), which has had its endogenous caspase activation and recruitment domain deleted. FKBP12-F36V binds with high affinity to an otherwise bioinert small-molecule dimerizing agent, AP1903. In the presence of AP1903, the iCasp9 promolecule dimerizes and activates the intrinsic apoptotic pathway, leading to cell death (Di Stasi et al., *N. Engl. J. Med.* 365:1673-1683 (2011)). In another embodiment, the suicide gene is an EGFRt polypeptide. The EGFRt polypeptide can provide for cell elimination by administering anti-EGFR monoclonal antibody, for example, cetuximab. The suicide gene can be expressed on a separate vector or, optionally, expressed within the vector encoding a CAR or DN form, and can be a bicistronic or multicistronic construct joined to a CAR or DN form encoding nucleic acid.

6.2 Chimeric Antigen Receptors (CARs)

The CAR that is recombinantly expressed by a cell of the invention has an antigen binding domain that binds to a cancer antigen. In specific embodiments, the CAR can be a "first generation," "second generation" or "third generation" CAR (see, for example, Sadelain et al., *Cancer Discov.* 3(4):388-398 (2013); Jensen et al., *Immunol. Rev.* 257:127-133 (2014); Sharpe et al., *Dis. Model Mech.* 8(4):337-350 (2015); Brentjens et al., *Clin. Cancer Res.* 13:5426-5435 (2007); Gade et al., *Cancer Res.* 65:9080-9088 (2005); Maher et al., *Nat. Biotechnol.* 20:70-75 (2002); Kershaw et al., *J. Immunol.* 173:2143-2150 (2004); Sadelain et al., *Curr. Opin. Immunol.* 21(2):215-223 (2009); Hollyman et al., *J. Immunother.* 32:169-180 (2009)).

"First generation" CARs are typically composed of an extracellular antigen binding domain, for example, a single-chain variable fragment (scFv), fused to a transmembrane domain, which is fused to a cytoplasmic/intracellular domain of the T cell receptor chain. "First generation" CARs typically have the intracellular domain from the CD3ζ-chain, which is the primary transmitter of signals from endogenous T cell receptors (TCRs) (see exemplary first generation CAR in FIG. 1A). "First generation" CARs can provide de novo antigen recognition and cause activation of both CD4$^+$ and CD8$^+$ T cells through their CD3ζ chain signaling domain in a single fusion molecule, independent of HLA-mediated antigen presentation. "Second-generation" CARs for use in the invention comprise a cancer antigen-binding domain fused to an intracellular signaling domain capable of activating immune cells such as T cells and a co-stimulatory domain designed to augment immune cell, such as T cell, potency and persistence (Sadelain et al., *Cancer Discov.* 3:388-398 (2013)). CAR design can therefore combine antigen recognition with signal transduction, two functions that are physiologically borne by two separate complexes, the TCR heterodimer and the CD3ζ complex. "Second generation" CARs include an intracellular domain from various co-stimulatory molecules, for example, CD28, 4-1BB, ICOS, OX40, and the like, in the cytoplasmic tail of the CAR to provide additional signals to the cell (see exemplary second generation CAR in FIG. 1A). "Second generation" CARs provide both co-stimulation, for example, by CD28 or 4-1BB domains, and activation, for example, by a CD3ζ signaling domain. Preclinical studies have indicated that "Second Generation" CARs can improve the anti-tumor activity of T cells. For example, robust efficacy of "Second Generation" CAR modified T cells was demonstrated in clinical trials targeting the CD19 molecule in patients with chronic lymphoblastic leukemia (CLL) and acute lymphoblastic leukemia (ALL) (Davila et al., *Oncoimmunol.* 1(9): 1577-1583 (2012)). "Third generation" CARs provide multiple co-stimulation, for example, by comprising both CD28 and 4-1BB domains, and activation, for example, by comprising a CD3ζ activation domain.

In the embodiments disclosed herein, the CARs generally comprise an extracellular antigen binding domain, a transmembrane domain and an intracellular domain, as described above, where the extracellular antigen binding domain binds to a cancer antigen. In a particular non-limiting embodiment, the extracellular antigen-binding domain is an scFv.

As disclosed herein, the methods of the invention involve administering cells that have been engineered to co-express a cancer antigen CAR and a dominant negative form ("DN form") of an inhibitor of a cell-mediated immune response. The extracellular antigen-binding domain of a CAR is usually derived from a monoclonal antibody (mAb) or from receptors or their ligands.

The design of CARs is well known in the art (see, for example, reviews by Sadelain et al., *Cancer Discov.* 3(4): 388-398 (2013); Jensen et al., *Immunol. Rev.* 257:127-133 (2014); Sharpe et al., *Dis. Model Mech.* 8(4):337-350 (2015), and references cited therein). A CAR directed to a desired cancer antigen can be generated using well known methods for designing a CAR, including those as described herein. A CAR, whether a first, second or third generation CAR, can be readily designed by fusing a cancer antigen binding activity, for example, an scFv antibody directed to the cancer antigen, to an immune cell signaling domain, such as a T cell receptor cytoplasmic/intracellular domain. As described above, the CAR generally has the structure of a cell surface receptor, with the cancer antigen binding activity, such as an scFv, as at least a portion of the extracellular domain, fused to a transmembrane domain, which is fused to an intracellular domain that has cell signaling activity in an immune cell, such as a T cell, or precursor cell thereof. The cancer antigen CAR can include co-stimulatory molecules, as described herein. One skilled in the art can readily select appropriate transmembrane domains, as described herein and known in the art, and intracellular domains to provide the desired signaling capability in the immune cell, such as a T cell, or precursor cell thereof.

A CAR for use in the present invention comprises an extracellular domain that includes an antigen binding domain that binds to a cancer antigen. The antigen binding domain binds to an antigen on the target cancer cell or tissue. Such an antigen binding domain is generally derived from an antibody. In one embodiment, the antigen binding domain can be an scFv or a Fab, or any suitable antigen binding fragment of an antibody (see Sadelain et al., *Cancer Discov.* 3:388-398 (2013)). Many antibodies or antigen binding domains derived from antibodies that bind to a cancer antigen are known in the art. Alternatively, such antibodies or antigen binding domains can be produced by routine methods. Methods of generating an antibody are well known in the art, including methods of producing a monoclonal antibody or screening a library to obtain an antigen binding polypeptide, including screening a library of human Fabs (Winter and Harris, *Immunol. Today* 14:243-246 (1993); Ward et al., *Nature* 341:544-546 (1989); Harlow and Lane, *Antibodies: A Laboratory Manual*, Cold Spring Harbor Laboratory Press (1988); Hilyard et al., Protein Engineering: A practical approach (IRL Press 1992); Borrabeck, Antibody Engineering, 2nd ed. (Oxford University Press 1995); Huse et al., *Science* 246:1275-1281 (1989)). For the CAR, the antigen binding domain derived from an antibody can be human, humanized, chimeric, CDR-grafted, and the like, as desired. For example, if a mouse monoclonal antibody is a source antibody for generating the antigen binding domain of a CAR, such an antibody can be humanized by grafting CDRs of the mouse antibody onto a human framework (see Borrabeck, supra, 1995), which can be beneficial for administering the CAR to a human subject. In a preferred embodiment, the antigen binding domain is an scFv. The generation of scFvs is well known in the art (see, for example, Huston, et al., *Proc. Nat. Acad. Sci. USA* 85:5879-5883 (1988); Ahmad et al., *Clin. Dev. Immunol.* 2012: ID980250 (2012); U.S. Pat. Nos. 5,091,513, 5,132,405 and 4,956,778; and U.S. Patent Publication Nos. 20050196754 and 20050196754)).

With respect to obtaining a cancer antigen binding activity, one skilled in the art can readily obtain a suitable cancer antigen binding activity, such as an antibody, using any of the well known methods for generating and screening for an antibody that binds to a desired antigen, as disclosed herein, including the generation of an scFv that binds to a cancer antigen, which is particularly useful in a CAR. In addition, a number cancer antigen antibodies, in particular monoclonal antibodies, are commercially available and can also be used as a source for a cancer antigen binding activity, such as an scFv, to generate a CAR.

Alternatively to using an antigen binding domain derived from an antibody, a CAR extracellular domain can comprise a ligand or extracellular ligand binding domain of a receptor (see Sadelain et al., *Cancer Discov.* 3:388-398 (2013); Sharpe et al., *Dis. Model Mech.* 8:337-350 (2015)). In this case, the ligand or extracellular ligand binding domain of a receptor provides to the CAR the ability to target the cell expressing the CAR to the corresponding receptor or ligand. The ligand or extracellular ligand binding domain is selected such that the cell expressing the CAR is targeted to a cancer cell or tumor (see Sadelain et al., *Cancer Discov.* 3:388-398 (2013); Sharpe et al., *Dis. Model Mech.* 8:337-350 (2015), and references cited therein). In an embodiment of the invention, the ligand or extracellular ligand binding domain is selected to bind to a cancer antigen that is the corresponding receptor or ligand (see Sadelain et al, *Cancer Discov.* 3:388-398 (2013)).

For a CAR directed to a cancer antigen, the antigen binding domain of the CAR is selected to bind to an antigen expressed on a cancer cell. Such a cancer antigen can be uniquely expressed on a cancer cell, or the cancer antigen can be overexpressed in a cancer cell relative to noncancerous cells or tissues. The cancer antigen to be bound by the CAR is chosen to provide targeting of the cell expressing the CAR over noncancerous cells or tissues. In one embodiment of the methods of the invention for treating a cancer, an immune cell or precursor cell thereof is designed to treat a cancer patient by expressing in the cell a CAR that binds to a suitable cancer antigen of the patient's cancer, along with a DN form, as described herein.

The cancer antigen can be a tumor antigen. Any suitable cancer antigen can be chosen based on the type of cancer exhibited by a subject (cancer patient) to be treated. It is understood that the selected cancer antigen is expressed in a manner such that the cancer antigen is accessible for binding by the CAR. Generally, the cancer antigen to be targeted by a cell expressing a CAR is expressed on the cell surface of a cancer cell. However, it is understood that any cancer antigen that is accessible for binding to a CAR is suitable for targeting the CAR expressing cell to the cancer cell. Exemplary cancer antigens and exemplary cancers are provided below in Table 1.

TABLE 1

Cancer Antigens and Corresponding Cancer Targets.

| Antigen targeted | Tumors investigated | References[1] |
| --- | --- | --- |
| B7-H3 CD276 | Sarcoma and Neuroblastoma | (1) |
| B7-H6 Nkp30 | Ovarian and several solid cancers | (2-4) |
| CAIX Carbonic Anhydrase IX | Renal cell carcinoma | (5) |
| CEA Carcinoembryonic Antigen | Liver metastasis from Colon cancer, Colon, Pancreas, Gastric and Lung cancers | (6-20) |
| CSPG4 Chondroitin sulfate proteoglycan-4 | Melanoma, Mesothelioma, Glioblastoma, Osteosarcoma, Breast, Head and Neck cancers | (21-24) |
| DNAM-1 DNAX Accessory Molecule | Melanoma | (25) |
| EpHA2 Ephrin type A Receptor 2 | Glioblastoma and Lung cancer | (26, 27) |
| EpCAM Epithelial Cell Adhesion Molecule | Prostate cancer | (28, 29) |
| ERBB family | Head and Neck and Breast cancers | (30, 31) |
| ERBB2 | Prostate, Breast, Ovarian and Pancreatic cancers, Glioblastoma, Meduloblastoma, Osteosarcoma, Ewing sarcoma, Neuroectodermal tumor, Desmoplastic small round cell tumor and Fibrosarcoma | (32-48) |
| EGFRvIII Epidermal Growth Factor Receptor vIII | Glioma/Glioblastoma | (49-56) |
| FAP Fibroblast Associated Protein | Tumor associated fibroblast in Lung cancer, Mesothelioma, Breast and Pancreatic cancers | (27, 57-59) |
| FRα and β Folate Receptor | Ovarian cancer | (60-64) |
| GD2 Disialoganglioside | Neuroblastoma, Edwing sarcoma, Melanoma | (65-71) |
| GD3 | Melanoma and other Neuroectodermal tumors | (72, 73) |
| Gp100/HLA-A2 | Melanoma | (74, 75) |
| GPC3 Glypican 3 | Hepatocellular carcinoma | (76) |
| HERK-V | Melanoma | (77) |
| MAGE-1/HLA-A1 Melanoma Antigen E | Melanoma | (78, 79) |
| IL-11Rα | Osteosarcoma | (80) |
| IL-13Rα2 | Glioma/Glioblastoma Medullobastoma | (81-87) |
| Lewis-Y | Ovarian | (88) (89, 90) |
| LMP1 Latent Membrane Protein 1 | Nasopharyngeal cancer | (91) |
| L1-CAM CD271 L1-Cellular Adhesion Molecule | Glioblastoma, Neuroblastoma, Ovarian, Lung and Renal carcinoma | (92, 93) |
| Muc-1 Mucin-1 | Prostate and Breast cancers | (43, 94-96) |
| Muc-16 Mucin-16 | Ovarian cancer | (97, 98) |
| MSLN Mesothelin | Ovarian, Mesothelioma, Lung cancers | (99-107) |
| N-cam CD56 Neural cell-adhesion molecule1 | Neuroblastoma | (108) |
| NKG2DL NKG2D Ligands | Ovarian | (109, 110) |
| PSCA Prostate Stem cell Antigen | Prostate cancer | (111-113) |
| PSMA Prostate Specific Membrane Antigen | Prostate | (114-117) |
| ROR1 Receptor tyrosine kinase-like Orphan Receptor | Epithelial solid tumors | (117, 118) |
| TAG72 Tumor Associated Glycoprotein 72 | Gastrointestinal, Colon and Breast cancers | (119-122) |
| TRAIL R Trail Receptor | Various type of cancer | (123) |

TABLE 1-continued

Cancer Antigens and Corresponding Cancer Targets.

| Antigen targeted | Tumors investigated | References[1] |
|---|---|---|
| VEGFR2<br>Vascular Endothelial Growth Factor Receptor-2 | Tumor associated vasculature | (124-127) |

[1]1. Cheung et al., *Hybrid Hybridomics*, 22: 209-18 (2003); 2. Zhang et al., *J Immunol.*, 189: 2290-9 (2012); 3. Wu et al., *Gene Ther.*, 22: 675-684 (2015); 4. Wu et al., *J Immunol.*, 194: 5305-11 (2015); 5. Lamers et al., *Mol Ther.*, 21: 904-12 (2013); 6. Darcy et al., *Eur J Immunol.*, 28: 1663-72 (1998); 7. Nolan et al., *Clin Cancer Res.*, 5: 3928-41 (1999); 8. Darcy et al., *J Immunol.*, 164: 3705-12 (2000); 9. Hombach et al., *Gene Ther.*, 6: 300-4 (1999); 10. Haynes et al., *J Immunol.*, 166: 182-7 (2001); 11. Haynes et al., *J Immunol.*, 169: 5780-6 (2002); 12. Schirrmann et al., *Cancer Gene Ther.*, 9: 390-8 (2002); 13. Arakawa et al., *Anticancer Res.* 2002; 22: 4285-9. 14. Gyobu et al., *Cancer Res.*, 64: 1490-5 (2004); 15. Shibaguchi et al., *Anticancer Res.*, 26: 4067-72 (2006); 16. Emtage et al., *Clin Cancer Res.* 14: 8112-22 (2008); 17. Chmielewski et al., *Gastroenterology*, 143: 1095-107 e2 (2012); 18. Chmielewski et al., *Gene Ther.*, 20: 177-86 (2013); 19. Burga et al., *Cancer Immunol Immunother.*, 64: 817-29 (2015); 20. Katz et al. *Clin Cancer Res.*, 21: 3149-59 (2015); 21. Beard et al., *J Immunother Cancer*, 2: 25 (2014); 22. Burns et al., *Cancer Res.*, 70: 3027-33 (2010); 23. Geldres et al., *Clin Cancer Res.*, 20: 962-71 (2014); 24. Schmidt et al., *Proc Natl Acad Sci USA*, 108: 2474-9(2011); 25. Wu et al., *Cancer Immunol Immunother.*, 64: 409-18 (2015); 26. Chow et al., *Mol Ther.*, 21: 629-37 (2013); 27. Kakarla et al., *Mol Ther.*, 21: 1611-20 (2013); 28. Shirasu et al., *J Biomed Biotechnol.*, 2012: 853879 (2012); 29. Deng et al., *BMC Immunol.*, 16: 1 (2015); 30. Davies et al., *Mol Med.*, 18: 565-76 (2012); 31. Papa et al., *Methods Mol Biol.*, 1317: 365-82 (2015); 32. Stancovski et al., *J Immunol.*, 151: 6577-82 (1993); 33. Moritz et al., *Proc Natl Acad Sci USA*, 91: 4318-22 (1994); 34. Haynes et al., *Cancer Immunol Immunother.*, 47: 278-86 (1999); 35. Pinthus et al., *Cancer Res.*, 63: 2470-6 (2003); 36. Ahmed et al., *Cancer Res.*, 67: 5957-64 (2007); 37. Li et al., *Cancer Gene Ther.* 15: 382-92 (2008); 38. Wang et al., *Clin Cancer Res.*, 15: 943-50 (2009); 39. Ahmed et al., *Mol Ther.*, 17: 1779-87 (2009); 40. Zhao et al., *J Immunol.*, 183: 5563-74 (2009); 41. Ahmed et al., *Clin Cancer Res.*, 16: 474-85 (2010); 42. Duong et al., *Immunotherapy*, 3: 33-48 (2011); 43. Wilkie et al., *J Clin Immunol.*, 32: 1059-70 (2012); 44. Lanitis et al., *PLoS One*, 7: e49829 (2012); 45. Maliar et al., *Gastroenterology*, 143: 1375-84 e1-5 (2012); 46. Rainusso et al., *Cancer Gene Ther.*, 19: 212-7 (2012); 47. Sun et al., *Breast Cancer Res.*, 16: R61 (2014); 48. Ahmed et al., *J Clin Oncol.*, 33: 1688-96 (2015); 49. Ohno et al., *Cancer Sci.*, 101: 2518-24 (2010); 50. Morgan et al., *Hum Gene Ther.* , 23: 1043-53 (2012); 51. Choi et al., *J Clin Neurosci.*, 21: 189-90 (2014); 52. Ohno et al., *J Immunother Cancer*, 1: 21 (2013); 53. Shen et al., *J Hematol Oncol.*, 6: 33 (2013); 54. Sampson et al., *Clin Cancer Res.*, 20: 972-84 (2014); 55. Miao et al., *PLoS One*, 9: e94281 (2014); 56. Johnson et al., *Sci Transl Med.*, 7: 275ra22 (2015); 57. Petrausch et al., *BMC Cancer*, 12: 615 (2012); 58. Schuberth et al., *J Transl Med.*, 11: 187 (2013); 59. Wang et al., *Cancer Immunol Res.*, 2: 154-66 (2014); 60. Parker et al., *Hum Gene Ther.*, 11: 2377-87 (2000); 61. Kershaw et al., *Clin Cancer Res.*, 12: 6106-15 (2006); 62. Song et al., *Cancer Res.*, 71: 4617-27 (2011); 63. Kandalaft et al., *J Transl Med.*, 10: 157 (2012); 64. Song et al., *Oncotarget*, (2015); 65. Krause et al., *J Exp Med.*, 188: 619-26 (1998); 66. Rossig et al., *Int J Cancer*, 94: 228-36 (2001); 67. Pule et al., *Nat Med.*, 14: 1264-70 (2008); 68. Yvon et al., *Clin Cancer Res.*, 15: 5852-60 (2009); 69. Louis et al., *Blood*, 118: 6050-6 (2011); 70. Kailayangiri et al., *Br J Cancer*, 106: 1123-33 (2012); 71. Singh et al., *Cancer Immunol Res.*, 2: 1059-70 (2014); 72. Yun et al., *Neoplasia*, 2: 449-59 (2000); 73. Lo et al., *Clin Cancer Res.*, 16: 2769-80 (2010); 74. Zhang et al., *Immunol Cell Biol.*, 91: 615-24 (2013); 75. Zhang et al., *Sci Rep.*, 4: 3571 (2014); 76. Gao et al., *Clin Cancer Res.*, 20: 6418-28 (2014); 77. Krishnamurthy et al., *Clin Cancer Res.*, 21: 3241-51 (2015); 78. Willemsen et al., *Gene Ther.*, 8: 1601-8 (2001); 79. Willemsen et al., *J Immunol.*, 174: 7853-8 (2005); 80. Huang et al., *Cancer Res.*, 72: 271-81 (2012); 81. Stastny et al., *J Pediatr Hematol Oncol.*, 29: 669-77 (2007); 82. Chang et al., *Cytotherapy*, 9: 771-84 (2007); 83. Lazovic et al., *Clin Cancer Res.*, 14: 3832-9 (2008); 84. Kong et al., *Clin Cancer Res.*, 18: 5949-60 (2012); 85. Hegde et al., *Mol Ther.*, 21: 2087-101 (2013); 86. Krebs et al., *Cytotherapy*, 16: 1121-31 (2014); 87. Brown et al., *Clin Cancer Res.*, (2015); 88. Westwood et al., *Proc Natl Acad Sci USA*, 102: 19051-6 (2005); 89. Westwood et al., *J Immunother*, 32: 292-301 (2009); 90. Neeson et al., *Gene Ther.*, 17: 1105-16 (2010); 91. Tang et al., *J Biomed Res.*, 28: 468-75 (2014); 92. Park et al., *Mol Ther.*, 15: 825-33 (2007); 93. Hong et al., *J Immunother.*, 37: 93-104 (2014); 94. Wilkie et al., *J Immunol.*, 180: 4901-9 (2008); 95. Bakhtiari et al., *Hybridoma (Larchmt).*, 28: 85-92 (2009); 96. Sanchez et al., *Prostate Cancer Prostatic Dis.*, 16: 123-31, S1 (2013); 97. Chekmasova et al., *Discov Med.*, 9: 62-70 (2010); 98. Koneru et al., *Oncoimmunology*, 4: e994446 (2015); 99. Carpenito et al., *Proc Natl Acad Sci USA*, 106: 3360-5 (2009); 100. Zhao et al., *Cancer Res.*, 70: 9053-61 (2010); 101. Lanitis et al., *Mol Ther.*, 20: 633-43 (2012); 102. Riese et al., *Cancer Res.*, 73: 3566-77 (2013); 103. Moon et al., *Clin Cancer Res.*, 20: 4262-73 (2014); 104. Guedan et al., *Blood*, 124: 1070-80 (2014); 105. Beatty, *Oncoimmunology*, 3: e28327 (2014); 106. Adusumilli et al., *Sci Transl Med.*, 6: 261ra151 (2014); 107. Wang et al., *Cancer Immunol Res.*, 3: 815-26 (2015); 108. Gilham et al., *J Immunother.*, 25: 139-51 (2002); 109. Barber et al., *J Immunol.*, 183: 6939-47 (2009); 110. Song et al., *Hum Gene Ther.*, 24: 295-305 (2013); 111. Morgenroth et al., *Prostate*, 67: 1121-31 (2007); 112. Hillerdal et al., *BMC Cancer*, 14: 30 (2014); 113. Abate-Daga et al., *Hum Gene Ther.*, 25: 1003-12 (2014); 114. Maher et al., *Nat Biotechnol.*, 20: 70-5 (2002); 115. Ma et al., *Prostate*, 61: 12-25 (2004); 116. Gade et al., *Cancer Res.*, 65: 9080-8 (2005); 117. Hudecek et al., *Clin Cancer Res.*, 19: 3153-64 (2013); 118. Deniger et al., *PLoS One*, 10: e0128151 (2015); 119. Hombach et al., *Gastroenterology*, 113: 1163-70 (1997); 120. McGuinness et al., *Hum Gene Ther.*, 10: 165-73 (1999); 121. Patel et al., *Cancer Gene Ther.* 7: 1127-34 (2000); 122. Sharifzadeh et al., *Cancer Lett.*, 334: 237-44 (2013); 123. Kobayashi et al., *Biochem Biophys Res Commun.* 453: 798-803 (2014); 124. Chinnasamy et al., *Clin Cancer Res.*, 18: 1672-83 (2012); 125. Kanagawa et al., *Cancer Gene Ther.*, 20: 57-64 (2013); 126. Chinnasamy et al., *Cancer Res.*, 73: 3371-80 (2013); 127. Wang et al., *Gene Ther.*, 20: 970-8 (2013); references 128-175, additional references of cancer antigens and corresponding cancer antigen targets; 128. Ordonez, *Am J Surg Pathol.*, 27: 1418-28 (2003); 129. Dennis et al., *Clin Cancer Res.*, 11: 3766-72 (2005); 130. Alvarez et al., *Nanomedicine*, 4: 295-301 (2008); 131. Rizk et al., *Cancer Epidemiol Biomarkers Prev.*, 21: 482-6 (2012); 132. Ordonez, *Mod Pathol.*, 16: 192-7 (2003); 133. Frierson et al., *Hum Pathol.*, 34: 605-9 (2003); 134. Tchou et al., *Breast Cancer Res Treat.*, 33: 799-804 (2012); 135. Parinyanitikul et al., *Clin Breast Cancer*, 13: 378-84 (2013); 136. Wang et al., *J Int Med Res.*, 40: 909-16 (2012); 137. Li et al., *Breast Cancer Res Treat.*, 147: 675-84 (2014); 138. Ordonez et al., *Hum Pathol.*, 45: 1529-40 (2014); 139. Tozbikian et al., *PLoS One*, 9: e114900 (2014); 140. Bayoglu et al., *Biomed Pharmacother.*, 70: 190-5 (2015); 141. Einama et al., *Br J Cancer*, 107: 137-42 (2012); 142. Baba et al., *J Surg Oncol.*, 105: 195-9 (2012); 143. Ito et al., *Oncol Rep.*, 31: 27-33 (2014); 144. Hassan et al., *Am J Clin Pathol.*, 124: 838-45 (2005); 145. Yu et al., *J Cancer*, 1: 141-9 (2010); 146. Kawamata et al., *Int J Oncol.*, 41: 2109-18 (2012); 147. Nomura et al., *Int Surg.*, 98: 164-9 (2013); 148. Argani Pedram et al., *Clin Cancer Res.*, 7: 3862-8 (2001); 149. Swierczynski et al., *Hum Pathol.* 35: 357-66 (2004); 150. Inami et al., *Oncol Rep.*, 20: 1375-80 (2008); 151. Frank et al., *Am J Clin Pathol.*, 142: 313-9 (2014); 152. Scales et al., *Mol Cancer Ther.*, 13: 2630-40 (2014); 153. Liebig et al., *Cancer Lett.*, 223: 159-67 (2005); 154. Kawamata et al., *J Gastroenterol.*, 49: 81-92 (2014); 155. Miettinen et al., *Am J Surg Pathol.*, 27: 150-8 (2003); 156. Ordonez, *Am J Surg Pathol.*, 27: 1031-51 (2003); 157. Ordonez, *Mod Pathol.* 19: 417-28 (2006); 158. Kushitani et al., *Pathol Int.*, 57: 190-9 (2007); 159. Pu et al., *Diagn Cytopathol.*, 36: 20-5 (2008); 160. Kachala et al., *Clin Cancer Res.*, 20: 1020-8 (2014); 161. Anish et al., *Oncotarget*, (2015); 162. Pan et al., *Hum Pathol.*, 34: 1155-62 (2003); 163. Yuanbin et al., *2014 ASCO Annual Meeting*, (2014); 164. Ordonez, *Hum Pathol.*, 35: 697-710 (2004); 165. Galloway et al., *Histopathology*, 48: 767-9 (2006); 166. Roe et al., *Lung Cancer*, 61: 235-43 (2008); 167. Tan et al., *Hum Pathol.*, 41: 1330-8 (2010); 168. Servais et al., *Clin Cancer Res.*, 18: 2478-89 (2012); 169. Drapkin et al., *Hum Pathol.*, 35: 1014-21 (2004); 170. Rosen et al., *Gynecol Oncol.* 99: 267-77 (2005); 171. Hassan et al., *Appl Immunohistochem Mol Morphol.* 13: 243-7 (2005); 172. Cao et al., *Int J Gynecol Pathol*, 24: 67-72 (2005); 173. Yen et al., *Clin Cancer Res.*, 12: 827-31 (2006); 174. Dainty et al., *Gynecol Oncol.*, 105: 563-70 (2007); 175. Obulhasim et al., *Eur J Gynaecol Oncol.*, 31: 63-71 (2010).

Suitable antigens include, but are not limited to, mesothelin (MSLN), prostate specific membrane antigen (PSMA), prostate stem cell antigen (PCSA), carbonic anhydrase IX (CAIX), carcinoembryonic antigen (CEA), CD5, CD7, CD10, CD19, CD20, CD22, CD30, CD33, CD34, CD38, CD41, CD44, CD49f, CD56, CD74, CD123, CD133, CD138, epithelial glycoprotein2 (EGP 2), epithelial glycoprotein-40 (EGP-40), epithelial cell adhesion molecule (EpCAM), folate-binding protein (FBP), fetal acetylcholine receptor (AChR), folate receptor-α and β (FRα and β), Ganglioside G2 (GD2), Ganglioside G3 (GD3), human Epidermal Growth Factor Receptor 2 (HER-2/ERB2), Epidermal Growth Factor Receptor vIII (EGFRvIII), ERB3, ERB4, human telomerase reverse transcriptase (hTERT), Interleukin-13 receptor subunit alpha-2 (IL-13Rα2), κ-light chain, kinase insert domain receptor (KDR), Lewis A (CA19.9), Lewis Y (LeY), L1 cell adhesion molecule (L1CAM), melanoma-associated antigen 1 (melanoma antigen family A1, MAGE-A1), Mucin 16 (Muc-16), Mucin 1 (Muc-1), NKG2D ligands, cancer-testis antigen NY-ESO-1, oncofetal antigen (h5T4), tumor-associated glycoprotein 72 (TAG-72), vascular endothelial growth factor R2 (VEGF-R2), Wilms tumor protein (WT-1), type 1 tyrosine-protein kinase transmembrane receptor (ROR1), B7-H3 (CD276), B7-H6 (Nkp30), Chondroitin sulfate proteoglycan-4 (CSPG4), DNAX Accessory Molecule (DNAM-1), Ephrin type A Receptor 2 (EpHA2), Fibroblast Associated Protein (FAP), Gp100/HLA-A2, Glypican 3 (GPC3), HA-1H, HERK-V, IL-11Rα, Latent Membrane Protein 1 (LMP1), Neural cell-adhesion molecule (N-CAM/CD56), and Trail Receptor (TRAIL R). It is understood that these or other cancer antigens can be utilized for targeting by a cancer antigen CAR.

In some embodiments of the invention, the CAR is designed to bind to and target cancer cells expressing mesothelin. Mesothelin (MSLN) is an immunogenic cell surface antigen (Ho et al., *Clin. Cancer Res.* 11:3814-3820 (2005); Hassan et al., *Eur. J. Cancer* 44:46-53 (2008)) that is highly expressed in solid cancers (Hassan et al., R. & Ho, M. Mesothelin targeted cancer immunotherapy. *Eur. J. Cancer* 44, 46-53 (2008); Zervos et al., *Curr. Opin. Pulm. Med.* 14:303-309 (2008); Palumbo et al., *Curr. Med. Chem.* 15:855-867 (2008); Roe et al., *Lung Cancer* 61:235-243 (2008); Pass et al., *Ann. Thorac. Surg.* 85:265-272 (2008); Rodriguez Portal et al., *Cancer Epidemiol. Biomarkers Prev.* 18(2):646-650 (2009)). MSLN is involved in cell proliferation (Bharadwaj et al., *Mol. Cancer Res.* 6:1755-1765 (2008)), adhesion (Uehara et al., *Mol. Cancer Res.* 6:186-193 (2008); Kaneko et al., *J. Biol. Chem.* 284:3739-3749 (2009)), invasion (Servais et al., *Clin. Cancer Res.* 18:2478-2489 (2012); Wang et al., *J. Int. Med. Res.* 40:2109-2116 (2012); Wang et al., *J. Int. Med. Res.* 40:909-916 (2012)), cell signaling (Uehara et al., *N., Mol. Cancer Res.* 6:186-193 (2008)), and metastasis (Wu et al., *Clin. Cancer Res.* 14:1938-1946 (2008)). Studies have demonstrated that serum soluble MSLN-related peptide (SMRP) secreted by MSLN-expressing tumors can be measured in both humans (Pass et al., *Ann. Thorac. Surg.* 85:265-272 (2008); *Cancer Epidemiol. Biomarkers Prev.* 18(2):646-650 (2009); Robinson et al., *Lung Cancer* 49 Suppl 1:S109-5111 (2005); Tajima et al., *Anticancer Res.* 28:3933-3936 (2008); Park et al., *Am. J. Respir. Crit. Care Med.* 178:832-837 (2008); Segawa et al., *Biochem. Biophys. Res. Commun.* 369:915-918 (2008); Amati et al., *Cancer Epidemiol. Biomarkers Prev.* 17:163-170 (2008); van den Heuvel et al., *Lung Cancer* 59, 350-354 (2008); Rizk et al., *Cancer Epidemiol. Biomarkers Prev.* 21:482-486 (2012)) and mice, and has been shown to correlate with therapy response and prognosis. In normal tissues, MSLN is expressed only in the pleura, pericardium, and peritoneum, at low levels (Hassan et al., *Eur. J. Cancer* 44:46-53 (2008); Bera et al., *Mol. Cell. Biol.* 20:2902-2906 (2000)). The anti-MSLN recombinant immunotoxin SS1P has shown in vivo specificity and significant antitumor activity in patients (Kelly et al., *Mol. Cancer Ther.* 11:517-525 (2012); Hassan et al., *Clin. Cancer Res.* 13:5144-5149 (2007)). In a pancreatic cancer vaccine trial, patients with survival advantage had consistent CD8$^+$ T cell responses to MSLN associated with vaccine-induced delayed-type hypersensitivity response (Thomas et al., *J. Exp. Med.* 200:297-306 (2004)). Specific T cell epitopes derived from MSLN were shown to activate human T cells to efficiently lyse human tumors expressing MSLN (Yokokawa et al., *Clin. Cancer Res.* 11:6342-6351 (2005)).

MSLN-specific CARs have shown efficacy against ovarian cancer, malignant pleural mesothelioma (MPM), and triple-negative breast cancer (TNBC) in both in vitro and in vivo settings (Lanitis et al., *Mol. Ther.* 20:633-643 (2012); Moon et al., *Clin. Cancer Res.* 17:4719-4730 (2011); Zhao et al., *Cancer Res.* 70:9053-9061 (2010); Riese et al., *Cancer Res.* 73:3566-3577 (2013); Tchou et al., *Breast Cancer Res. Treat.* 133:799-804 (2012)). Two Phase I clinical trials have used anti-MSLN CAR-transduced T cells. An NCI Phase I clinical trial (ClinicalTrials.gov record NCT01583686) treats metastatic or unresectable cancers that express MSLN with CAR T cells, in combination with myeloablative chemotherapy and/or aldesleukin (an IL-2 analogue) to augment CAR T cell persistence. A University of Pennsylvania Phase I clinical trial (ClinicalTrials.gov record NCT01355965) gives mesothelioma patients 1 to 3 doses of MSLN-targeted CAR T cells. In the latter study, a human anti-mouse antibody (HAMA) response was observed in the third treated patient (Maus et al., *Cancer Immunol. Res.* 1(1):26-31 (2013)). In one embodiment, a MSLN-targeted CAR is derived from a human Fab (Feng et al., *Mol. Cancer Ther.* 8:1113-1118 (2009)), and thus, affords a much decreased risk of immunogenicity, compared with CARs derived from murine antibodies (see Maus et al., *Cancer Immunol. Res.* 1(1):26-31 (2013)).

In a specific embodiment, one or more nucleic acids encoding a CAR and a DN form are used to transduce both CD4$^+$ and CD8$^+$ T cells. In such an embodiment, administration of the transduced T cells to a subject should generate both helper and cytotoxic T lymphocyte (CTL) responses in the subject, resulting in a sustained anti-tumor response.

As described above, a CAR also contains a signaling domain that functions in the immune cell, or precursor cell thereof, expressing the CAR. Such a signaling domain can be, for example, derived from CD3ζ or Fc receptor γ (see Sadelain et al., *Cancer Discov.* 3:388-398 (2013)). In general, the signaling domain will induce persistence, trafficking and/or effector functions in the transduced immune cells such as T cells, or precursor cells thereof (Sharpe et al., *Dis. Model Mech.* 8:337-350 (2015); Finney et al., *J. Immunol.* 161:2791-2797 (1998); Krause et al., *J. Exp. Med.* 188:619-626 (1998)). In the case of CD3ζ or Fc receptor γ, the signaling domain corresponds to the intracellular domain of the respective polypeptides, or a fragment of the intracellular domain that is sufficient for signaling. Exemplary signaling domains are described below in more detail.

Exemplary polypeptides are described herein with reference to GenBank numbers, GI numbers and/or SEQ ID NOS. It is understood that one skilled in the art can readily identify homologous sequences by reference to sequence sources, including but not limited to GenBank (ncbi.nlm.nih.gov/genbank/) and EMBL (embl.org/).

CD3ζ.

In a non-limiting embodiment, a CAR can comprise a signaling domain derived from a CD3ζ polypeptide, for example, a signaling domain derived from the intracellular domain of CD3ζ, which can activate or stimulate an immune cell, for example, a T cell, or precursor cell thereof. CD3ζ comprises 3 Immune-receptor-Tyrosine-based-Activation-Motifs (ITAMs), and transmits an activation signal to the cell, for example, a cell of the lymphoid lineage such as a T cell, after antigen is bound. A CD3ζ polypeptide can have an amino acid sequence corresponding to the sequence having GenBank No. NP_932170 (NP_932170.1, GI:37595565; see below), or fragments thereof. In one embodiment, the CD3ζ polypeptide has an amino acid sequence of amino acids 52 to 164 of the CD3ζ polypeptide sequence provided below, or a fragment thereof that is sufficient for signaling activity. An exemplary CAR is Mz, which has an intracellular domain comprising a CD3ζ polypeptide comprising amino acids 52 to 164 of the CD3ζ polypeptide sequence provided below. Another exemplary CAR is M28z, which has an intracellular domain comprising a CD3ζ polypeptide comprising amino acids 52 to 164 of the CD3ζ polypeptide provided below. Still another exemplary CAR is MBBz, which has an intracellular domain comprising a CD3ζ polypeptide comprising amino acids 52 to 164 of the CD3ζ polypeptide provided below. Yet another exemplary CAR is P28z, which has an intracellular domain derived from a CD3ζ polypeptide. See GenBank NP_932170 for reference to domains within CD3ζ, for example, signal peptide, amino acids 1 to 21; extracellular domain, amino acids 22 to 30; transmembrane domain, amino acids 31 to 51; intracellular domain, amino acids 52 to 164.

(B7.1) and CD86 (B7.2) proteins. In one embodiment, a CAR can comprise a co-stimulatory signaling domain derived from CD28. For example, as disclosed herein, a CAR can include at least a portion of an intracellular/cytoplasmic domain of CD28, for example an intracellular/

```
                                                  (NP_932170; SEQ ID NO: 1)
  1 MKWKALFTAA ILQAQLPITE AQSFGLLDPK LCYLLDGILF IYGVILTALF LRVKFSRSAD

61 APAYQQGQNQ LYNELNLGRR EEYDVLDKRR GRDPEMGGKP QRRKNPQEGL YNELQKDKMA

121 EAYSEIGMKG ERRRGKGHDG LYQGLSTATK DTYDALHMQA LPPR
```

It is understood that a "CD3ζ nucleic acid molecule" refers to a polynucleotide encoding a CD3ζ polypeptide. In one embodiment, the CD3ζ nucleic acid molecule encoding the CD3ζ polypeptide comprised in the intracellular domain of a CAR, including exemplary CARs Mz, M28z, or MBBz, comprises a nucleotide sequence as set forth below.

```
                                                  (SEQ ID NO: 2)
AGAGTGAAGTTCAGCAGGAGCGCAGACGCCCCCGCGTACCAGCAGGGCCA

GAACCAGCTCTATAACGAGCTCAATCTAGGACGAAGAGAGGAGTACGATG

TTTTGGACAAGAGACGTGGCCGGGACCCTGAGATGGGGGGAAAGCCGAGA

AGGAAGAACCCTCAGGAAGGCCTGTACAATGAACTGCAGAAAGATAAGAT

GGCGGAGGCCTACAGTGAGATTGGGATGAAAGGCGAGCGCCGGAGGGGCA

AGGGGCACGATGGCCTTTACCAGGGTCTCAGTACAGCCACCAAGGACACC

TACGACGCCCTTCACATGCAGGCCCTGCCCCCTCGCTAA
```

In certain non-limiting embodiments, an intracellular domain of a CAR can further comprise at least one co-stimulatory signaling domain. Such a co-stimulatory signaling domain can provide increased activation of an immune cell or precursor cell thereof. A co-stimulatory signaling domain can be derived from a CD28 polypeptide, a 4-1BB polypeptide, an OX40 polypeptide, an ICOS polypeptide, a DAP10 polypeptide, a 2B4 polypeptide, and the like. CARs comprising an intracellular domain that comprises a co-stimulatory signaling region comprising 4-1BB, ICOS or DAP-10 have been described previously (see U.S. Pat. No. 7,446,190, which is incorporated herein by reference, which also describes representative sequences for 4-1BB, ICOS and DAP-10). In some embodiments, the intracellular domain of a CAR can comprise a co-stimulatory signaling region that comprises two co-stimulatory molecules, such as CD28 and 4-1BB (see Sadelain et al., *Cancer Discov.* 3(4):388-398 (2013)), or CD28 and OX40, or other combinations of co-stimulatory ligands, as disclosed herein.

cytoplasmic domain that can function as a co-stimulatory signaling domain (see FIG. 1B). A CD28 polypeptide can have an amino acid sequence corresponding to the sequence having GenBank No. P10747 (P10747.1, GI:115973) or NP_006130 (NP_006130.1, GI:5453611), as provided below, or fragments thereof. If desired, CD28 sequences additional to the intracellular domain can be included in a CAR of the invention. For example, a CAR can comprise the transmembrane of a CD28 polypeptide. In one embodiment, a CAR can have an amino acid sequence comprising the intracellular domain of CD28 corresponding to amino acids 180 to 220 of CD28, or a fragment thereof. In another embodiment, a CAR can have an amino acid sequence comprising the transmembrane domain of CD28 corresponding to amino acids 153 to 179, or a fragment thereof. M28z is an exemplary CAR, which comprises a co-stimulatory signaling domain corresponding to an intracellular domain of CD28 (see FIG. 1B). M28z also comprises a transmembrane domain derived from CD28 (see FIG. 1B). Thus, M28z exemplifies a CAR that comprises two domains from CD28, a co-stimulatory signaling domain and a transmembrane domain. In one embodiment, a CAR has an amino acid sequence comprising the transmembrane domain and the intracellular domain of CD28 and comprises amino acids 153 to 220 of CD28. In another embodiment, a CAR is exemplified by M28z CAR and comprises amino acids 117 to 220 of CD28. Another exemplary CAR having a transmembrane domain and intracellular domain of CD28 is P28z (see FIG. 1B). In one embodiment, a CAR can comprise a transmembrane domain derived from a CD28 polypeptide comprising amino acids 153 to 179 of the CD28 polypeptide provided below. See GenBank NP_006130 for reference to domains within CD28, for example, signal peptide, amino acids 1 to 18; extracellular domain, amino acids 19 to 152; transmembrane domain, amino acids 153 to 179; intracellular domain, amino acids 180 to 220. It is understood that sequences of CD28 that are shorter or longer than a specific delineated domain can be included in a CAR, if desired.

```
                                                  (NP_006130; SEQ ID NO: 3)
  1 MLRLLLALNL FPSIQVTGNK ILVKQSPMLV AYDNAVNLSC KYSYNLFSRE FRASLHKGLD

61 SAVEVCVVYG NYSQQLQVYS KTGFNCDGKL GNESVTFYLQ NLYVNQTDIY FCKIEVMYPP

121 PYLDNEKSNG TIIHVKGKHL CPSPLFPGPS KPFWVLVVVG GVLACYSLLV TVAFIIFWVR

181 SKRSRLLHSD YMNMTPRRPG PTRKHYQPYA PPRDFAAYRS
```

CD28.

Cluster of Differentiation 28 (CD28) is a protein expressed on T cells that provides co-stimulatory signals for T cell activation and survival. CD28 is the receptor for CD80

It is understood that a "CD28 nucleic acid molecule" refers to a polynucleotide encoding a CD28 polypeptide. In one embodiment, the CD28 nucleic acid molecule encoding the CD28 polypeptide of M28z comprising the transmembrane domain and the intracellular domain, for example, the co-stimulatory signaling region, comprises a nucleotide sequence as set forth below.

(SEQ ID NO: 4)
```
ATTGAAGTTATGTATCCTCCTCCTTACCTAGACAATGAGAAGAGCAATGG

AACCATTATCCATGTGAAAGGGAAACACCTTTGTCCAAGTCCCCTATTTC

CCGGACCTTCTAAGCCCTTTTGGGTGCTGGTGGTGGTTGGTGGAGTCCTG

GCTTGCTATAGCTTGCTAGTAACAGTGGCCTTTATTATTTTCTGGGTGAG

GAGTAAGAGGAGCAGGCTCCTGCACAGTGACTACATGAACATGACTCCCC

GCCGCCCCGGGCCCACCCGCAAGCATTACCAGCCCTATGCCCCACCACGC

GACTTCGCAGCCTATCGCTCC
```

4-1BB.

4-1BB, also referred to as tumor necrosis factor receptor superfamily member 9, can act as a tumor necrosis factor (TNF) ligand and have stimulatory activity. In one embodiment, a CAR can comprise a co-stimulatory signaling domain derived from 4-1BB. A 4-1BB polypeptide can have an amino acid sequence corresponding to the sequence having GenBank No. P41273 (P41273.1, GI:728739) or NP_001552 (NP_001552.2, GI:5730095) or fragments thereof. In one embodiment, a CAR can have a co-stimulatory domain comprising the intracellular domain of 4-1BB corresponding to amino acids 214 to 255, or a fragment thereof. In another embodiment, a CAR can have a transmembrane domain of 4-1BB corresponding to amino acids 187 to 213, or a fragment thereof. An exemplary CAR is MBBz, which has an intracellular domain comprising a 4-1BB polypeptide (for example, amino acids 214 to 255 of NP_001552, SEQ ID NO:5) (see FIG. 1B). See GenBank NP_001552 for reference to domains within 4-1BB, for example, signal peptide, amino acids 1 to 17; extracellular domain, amino acids 18 to 186; transmembrane domain, amino acids 187 to 213; intracellular domain, amino acids 214 to 255. It is understood that sequences of 4-1BB that are shorter or longer than a specific delineated domain can be included in a CAR, if desired. It is also understood that a "4-1BB nucleic acid molecule" refers to a polynucleotide encoding a 4-1BB polypeptide.

OX40.

OX40, also referred to as tumor necrosis factor receptor superfamily member 4 precursor or CD134, is a member of the TNFR-superfamily of receptors. In one embodiment, a CAR can comprise a co-stimulatory signaling domain derived from OX40. An OX40 polypeptide can have an amino acid sequence corresponding to the sequence having GenBank No. P43489 (P43489.1, GI:1171933) or NP_003318 (NP_003318.1, GI:4507579), provided below, or fragments thereof. In one embodiment, a CAR can have a co-stimulatory domain comprising the intracellular domain of OX40 corresponding to amino acids 236 to 277, or a fragment thereof. In another embodiment, a CAR can have an amino acid sequence comprising the transmembrane domain of OX40 corresponding to amino acids 215 to 235 of OX40, or a fragment thereof. See GenBank NP_003318 for reference to domains within OX40, for example, signal peptide, amino acids 1 to 28; extracellular domain, amino acids 29 to 214; transmembrane domain, amino acids 215 to 235; intracellular domain, amino acids 236 to 277. It is understood that sequences of OX40 that are shorter or longer than a specific delineated domain can be included in a CAR, if desired. It is also understood that an "OX40 nucleic acid molecule" refers to a polynucleotide encoding an OX40 polypeptide.

(NP_003318; SEQ ID NO: 6)
```
  1 MCVGARRLGR GPCAALLLLG LGLSTVTGLH CVGDTYPSND RCCHECRPGN GMVSRCSRSQ

61 NTVCRPCGPG FYNDVVSSKP CKPCTWCNLR SGSERKQLCT ATQDTVCRCR AGTQPLDSYK

121 PGVDCAPCPP GHFSPGDNQA CKPWTNCTLA GKHTLQPASN SSDAICEDRD PPATQPQETQ

181 GPPARPITVQ PTEAWPRTSQ GPSTRPVEVP GGRAVAAILG LGLVLGLLGP LAILLALYLL

241 RRDQRLPPDA HKPPGGGSFR TPIQEEQADA HSTLAKI
```

ICOS.

Inducible T-cell costimulator precursor (ICOS), also referred to as CD278, is a CD28-superfamily costimulatory molecule that is expressed on activated T cells. In one embodiment, a CAR can comprise a co-stimulatory signaling domain derived from ICOS. An ICOS polypeptide can have an amino acid sequence corresponding to the sequence having GenBank No. NP_036224 (NP_036224.1, GI:15029518), provided below, or fragments thereof. In one embodiment, a CAR can have a co-stimulatory domain comprising the intracellular domain of ICOS corresponding to amino acids 162 to 199 of ICOS. In another embodiment, a CAR can have an amino acid sequence comprising the transmembrane domain of ICOS corresponding to amino acids 141 to 161 of ICOS, or a fragment thereof. See GenBank NP_036224 for reference to domains within ICOS, for example, signal peptide, amino acids 1 to 20; extracellular domain, amino acids 21 to 140; transmembrane domain, amino acids 141 to 161; intracellular domain, (NP_001552; SEQ ID NO: 5)
```
  1 MGNSCYNIVA TLLLVLNFER TRSLQDPCSN CPAGTFCDNN RNQICSPCPP NSFSSAGGQR

61 TCDICRQCKG VFRTRKECSS TSNAECDCTP GFHCLGAGCS MCEQDCKQGQ ELTKKGCKDC

121 CFGTFNDQKR GICRPWTNCS LDGKSVLVNG TKERDVVCGP SPADLSPGAS SVTPPAPARE

181 PGHSPQIISF FLALTSTALL FLLFFLTLRF SVVKRGRKKL LYIFKQPFMR PVQTTQEEDG

241 CSCRFPEEEE GGCEL
``` amino acids 162 to 199. It is understood that sequences of ICOS that are shorter or longer than a specific delineated domain can be included in a CAR, if desired. It is also understood that an "ICOS nucleic acid molecule" refers to a polynucleotide encoding an ICOS polypeptide.

```
                                              (NP_036224; SEQ ID NO: 7)
  1 MKSGLWYFFL FCLRIKVLTG EINGSANYEM FIFHNGGVQI LCKYPDIVQQ FKMQLLKGGQ

61 ILCDLTKTKG SGNTVSIKSL KFCHSQLSNN SVSFFLYNLD HSHANYYFCN LSIFDPPPFK

121 VTLTGGYLHI YESQLCCQLK FWLPIGCAAF VVVCILGCIL ICWLTKKKYS SSVHDPNGEY

181 MFMRAVNTAK KSRLTDVTL
```

DAP10.

DAP10, also referred to as hematopoietic cell signal transducer, is a signaling subunit that associates with a large family of receptors in hematopoietic cells. In one embodiment, a CAR can comprise a co-stimulatory domain derived from DAP10. A DAP10 polypeptide can have an amino acid sequence corresponding to the sequence having GenBank No. NP_055081.1 (GI:15826850), provided below, or fragments thereof. In one embodiment, a CAR can have a co-stimulatory domain comprising the intracellular domain of DAP10 corresponding to amino acids 70 to 93, or a fragment thereof. In another embodiment, a CAR can have a transmembrane domain of DAP10 corresponding to amino acids 49 to 69, or a fragment thereof. See GenBank NP_055081.1 for reference to domains within DAP10, for example, signal peptide, amino acids 1 to 19; extracellular domain, amino acids 20 to 48; transmembrane domain, amino acids 49 to 69; intracellular domain, amino acids 70 to 93. It is understood that sequences of DAP10 that are shorter or longer than a specific delineated domain can be included in a CAR, if desired. It is also understood that a "DAP10 nucleic acid molecule" refers to a polynucleotide encoding an DAP10 polypeptide.

peptide comprises a CD8 polypeptide comprising amino acids MALPVTALLLPLALLLHAARP (SEQ ID NO:9). It is understood that use of a CD8 signal peptide is exemplary. Any suitable signal peptide, as are well known in the art, can be applied to a CAR to provide cell surface expression in an immune cell (see Gierasch *Biochem.* 28:923-930 (1989); von Heijne, *J. Mol. Biol.* 184 (1):99-105 (1985)). Particularly useful signal peptides can be derived from cell surface proteins naturally expressed in the immune cell or precursor cell thereof, including any of the signal peptides of the polypeptides disclosed herein. Thus, any suitable signal peptide can be utilized to direct a CAR to be expressed at the cell surface of an immune cell or precursor cell thereof.

In certain non-limiting embodiments, an extracellular antigen-binding domain of a CAR can comprise a linker sequence or peptide linker connecting the heavy chain variable region and light chain variable region of the extracellular antigen-binding domain. In one non-limiting example, the linker comprises amino acids having the sequence set forth in GGGGSGGGGSGGGGS (SEQ ID NO:10).

In certain non-limiting embodiments, a CAR can also comprise a spacer region or sequence that links the domains of the CAR to each other. For example, a spacer can be

```
                                              (NP_055081.1; SEQ ID NO: 8)
  1 MIHLGHILFL LLLPVAAAQT TPGERSSLPA FYPGTSGSCS GCGSLSLPLL AGLVAADAVA

61 SLLIVGAVFL CARPRRSPAQ EDGKVYINMP GRG
```

The extracellular domain of a CAR can be fused to a leader or a signal peptide that directs the nascent protein into the endoplasmic reticulum and subsequent translocation to the cell surface. It is understood that, once a polypeptide containing a signal peptide is expressed at the cell surface, the signal peptide has generally been proteolytically removed during processing of the polypeptide in the endoplasmic reticulum and translocation to the cell surface. Thus, a polypeptide such as a CAR is generally expressed at the cell surface as a mature protein lacking the signal peptide, whereas the precursor form of the polypeptide includes the signal peptide. A signal peptide or leader can be essential if a CAR is to be glycosylated and/or anchored in the cell membrane. The signal sequence or leader is a peptide sequence generally present at the N-terminus of newly synthesized proteins that directs their entry into the secretory pathway. The signal peptide is covalently joined to the N-terminus of the extracellular antigen-binding domain of a CAR as a fusion protein. In one embodiment, the signal included between a signal peptide and an antigen binding domain, between the antigen binding domain and the transmembrane domain, between the transmembrane domain and the intracellular domain, and/or between domains within the intracellular domain, for example, between a stimulatory domain and a co-stimulatory domain. The spacer region can be flexible enough to allow interactions of various domains with other polypeptides, for example, to allow the antigen binding domain to have flexibility in orientation in order to facilitate antigen recognition. The spacer region can be, for example, the hinge region from an IgG, the $CH_2CH_3$ (constant) region of an immunoglobulin, and/or portions of CD3ζ (cluster of differentiation 3) or some other sequence suitable as a spacer.

The transmembrane domain of a CAR generally comprises a hydrophobic alpha helix that spans at least a portion of the membrane. Different transmembrane domains result in different receptor stability. After antigen recognition, receptors cluster and a signal is transmitted to the cell. In an embodiment, the transmembrane domain of a CAR can be derived from another polypeptide that is naturally expressed in the immune cell or precursor cell thereof. In one embodiment, a CAR can have a transmembrane domain derived from CD8, CD28, CD3ζ, CD4, 4-1BB, OX40, ICOS, CTLA-4, PD-1, LAG-3, 2B4, BTLA, or other polypeptides expressed in the immune cell, or precursor cell thereof, having a transmembrane domain, including others as disclosed herein. Optionally, the transmembrane domain can be derived from a polypeptide that is not naturally expressed in the immune cell or precursor cell thereof, so long as the transmembrane domain can function in transducing signal from antigen bound to the CAR to the intracellular signaling and/or co-stimulatory domains. It is understood that the portion of the polypeptide that comprises a transmembrane domain of the polypeptide can include additional sequences from the polypeptide, for example, additional sequences adjacent on the N-terminal or C-terminal end of the transmembrane domain, or other regions of the polypeptide, as desired.

CD8.

Cluster of differentiation 8 (CD8) is a transmembrane glycoprotein that serves as a co-receptor for the T cell receptor (TCR). CD8 binds to a major histocompatibility complex (MHC) molecule and is specific for the class I MHC protein. In one embodiment, a CAR can comprise a transmembrane domain derived from CD8. A CD8 polypeptide can have an amino acid sequence corresponding to the sequence having GenBank No. NP_001139345.1 (GI: 225007536), as provided below, or fragments thereof. In one embodiment, a CAR can have an amino acid sequence comprising the transmembrane domain of CD8 corresponding to amino acids 183 to 203, or fragments thereof. In one embodiment, an exemplary CAR is Mz, which has a transmembrane domain derived from a CD8 polypeptide (see FIG. 1B). In another embodiment, an exemplary CAR is MBBz, which has a transmembrane domain derived from a CD8 polypeptide (see FIG. 1B). In one non-limiting embodiment, a CAR can comprise a transmembrane domain derived from a CD8 polypeptide comprising amino acids 183 to 203. In addition, a CAR can comprise a hinge domain comprising amino acids 137-182 of the CD8 polypeptide provided below. In another embodiment, a CAR can comprise amino acids 137-203 of the CD8 polypeptide provided below. In yet another embodiment, a CAR can comprise amino acids 137 to 209 of the CD8 polypeptide provided below. See GenBank NP_001139345.1 for reference to domains within CD8, for example, signal peptide, amino acids 1 to 21; extracellular domain, amino acids 22 to 182; transmembrane domain amino acids, 183 to 203; intracellular domain, amino acids 204 to 235. It is understood that additional sequence of CD8 beyond the transmembrane domain of amino acids 183 to 203 can be included in a CAR, if desired. It is further understood that sequences of CD8 that are shorter or longer than a specific dilineated domain can be included in a CAR, if desired. It also is understood that a "CD8 nucleic acid molecule" refers to a polynucleotide encoding a CD8 polypeptide.

```
                                        (NP_001139345.1; SEQ ID NO: 11)
  1 MALPVTALLL PLALLLHAAR PSQFRVSPLD RTWNLGETVE LKCQVLLSNP TSGCSWLFQP

61 RGAAASPTFL LYLSQNKPKA AEGLDTQRFS GKRLGDTFVL TLSDFRRENE GYYFCSALSN

121 SIMYFSHFVP VFLPAKPTTT PAPRPPTPAP TIASQPLSLR PEACRPAAGG AVHTRGLDFA

181 CDIYIWAPLA GTCGVLLLSL VITLYCNHRN RRRVCKCPRP VVKSGDKPSL SARYV
```

CD4.

Cluster of differentiation 4 (CD4), also referred to as T-cell surface glycoprotein CD4, is a glycoprotein found on the surface of immune cells such as T helper cells, monocytes, macrophages, and dendritic cells. In one embodiment, a CAR can comprise a transmembrane domain derived from CD4. CD4 exists in various isoforms. It is understood that any isoform can be selected to achieve a desired function. Exemplary isoforms include isoform 1 (NP_000607.1, GI:10835167), isoform 2 (NP_001181943.1, GI:303522479), isoform 3 (NP_001181944.1, GI:303522485; or NP_001181945.1, GI:303522491; or NP_001181946.1, GI:303522569), and the like. One exemplary isoform sequence, isoform 1, is provided below. In one embodiment, a CAR can have an amino acid sequence comprising the transmembrane domain of CD4 corresponding to amino acids 397 to 418, or fragments thereof. See GenBank NP_000607.1 for reference to domains within CD4, for example, signal peptide, amino acids 1 to 25; extracellular domain, amino acids 26 to 396; transmembrane domain amino acids, 397 to 418; intracellular domain, amino acids 419 to 458. It is understood that additional sequence of CD4 beyond the transmembrane domain of amino acids 397 to 418 can be included in a CAR, if desired. It is further understood that sequences of CD4 that are shorter or longer than a specific dilineated domain can be included in a CAR, if desired. It also is understood that a "CD4 nucleic acid molecule" refers to a polynucleotide encoding a CD4 polypeptide.

```
                                         (NP_000607.1; SEQ ID NO: 12)
  1 MNRGVPFRHL LLVLQLALLP AATQGKKVVL GKKGDTVELT CTASQKKSIQ FHWKNSNQIK

61 ILGNQGSFLT KGPSKLNDRA DSRRSLWDQG NFPLIIKNLK IEDSDTYICE VEDQKEEVQL

121 LVFGLTANSD THLLQGQSLT LTLESPPGSS PSVQCRSPRG KNIQGGKTLS VSQLELQDSG

181 TWTCTVLQNQ KKVEFKIDIV VLAFQKASSI VYKKEGEQVE FSFPLAFTVE KLTGSGELWW

241 QAERASSSKS WITFDLKNKE VSVKRVTQDP KLQMGKKLPL HLTLPQALPQ YAGSGNLTLA
```

```
301 LEAKTGKLHQ EVNLVVMRAT QLQKNLTCEV WGPTSPKLML SLKLENKEAK VSKREKAVWV

361 LNPEAGMWQC LLSDSGQVLL ESNIKVLPTW STPVQPMALI VLGGVAGLLL FIGLGIFFCV

421 RCRHRRRQAE RMSQIKRLLS EKKTCQCPHR FQKTCSPI
```

```
ATFMKLRTDA VLPLTVAEVQ KLLGPHVEGL KAEERHRPVR

DWILRQRQDD LDTLGLGLQG GIPNGYLVLD LSVQEALSGT

PCLLGPGPVL TVLALLLAST LA
```

As disclosed herein, mesothelin CARs exemplify CARs that can target a cancer antigen, and CARs directed to other cancer antigens can be generated using similar methods and others well known in the art, as described above. It is understood that domains of the polypeptides described herein can be used in a cancer antigen CAR, as useful to provide a desired function such as a signal peptide, antigen binding domain, transmembrane domain, intracellular signaling domain and/or co-stimulatory domain. For example, a domain can be selected such as a signal peptide, a transmembrane domain, an intracellular signaling domain, or other domain, as desired, to provide a particular function to a CAR of the invention. Possible desirable functions can include, but are not limited to, providing a signal peptide and/or transmembrane domain.

In one embodiment, the invention provides CARs directed to mesothelin. In certain non-limiting embodiments, MSLN is human mesothelin having the sequence with an NCBI Reference No: AAV87530.1 (GI:56406362), or fragments thereof, as provided below:

```
                    (GenBank AAV87530.1; SEQ ID NO: 13)
MALPTARPLL GSCGTPALGS LLFLLFSLGW VQPSRTLAGE

TGQEAAPLDG VLANPPNISS LSPRQLLGFP CAEVSGLSTE

RVRELAVALA QKNVKLSTEQ LRCLAHRLSE PPEDLDALPL

DLLLFLNPDA FSGPQACTHF FSRITKANVD LLPRGAPERQ

RLLPAALACW GVRGSLLSEA DVRALGGLAC DLPGRFVAES

AEVLLPRLVS CPGPLDQDQQ EAARAALQGG GPPYGPPSTW

SVSTMDALRG LLPVLGQPII RSIPQGIVAA WRQRSSRDPS

WRQPERTILR PRFRREVEKT ACPSGKKARE IDESLIFYKK

WELEACVDAA LLATQMDRVN AIPFTYEQLD VLKHKLDELY

PQGYPESVIQ HLGYLFLKMS PEDIRKWNVT SLETLKALLE

VNKGHEMSPQ VATLIDRFVK GRGQLDKDTL DTLTAFYPGY

LCSLSPEELS SVPPSSIWAV RPQDLDTCDP RQLDVLYPKA

RLAFQNMNGS EYFVKIQSFL GGAPTEDLKA LSQQNVSMDL
```

In certain embodiments, the extracellular antigen-binding domain of the anti-mesothelin CAR comprises a human anti-mesothelin antibody or an antigen-binding portion thereof described in U.S. Pat. No. 8,357,783, which is herein incorporated by reference in its entirety. In some embodiments, the extracellular antigen-binding domain is derived from a heavy chain variable region and a light chain variable region of an antibody that binds to human mesothelin, for example, antibody m912 as disclosed in Feng et al., *Mol. Cancer Therapy* 8(5):1113-1118 (2009), which is herein incorporated by reference in its entirety. Antibody m912 was isolated from a human Fab library by panning against recombinant mesothelin. In other embodiments, the extracellular antigen-binding domain is derived from an Fab, for example, from human or mouse Fab libraries.

In certain embodiments, the extracellular antigen-binding domain or an MSLN CAR comprises a heavy chain variable region comprising amino acids having the sequence set forth below.

```
                                       (SEQ ID NO: 14)
QVQLQESGPGLVKPSETLSLTCTVSGGSVSSGSYYWSWIRQPPGKGLE

WIGYIYYSGSTNYNPSLKSRVTISVDTSKNQFSLKLSSVTAADTAVYY

CAREGKNGAFDIWGQGTMVTVSSASTKGPSVFPLAPSSKSTSGGTAAL

GCLVKDYFPEPVTVSWNSGALTSGVHTFPAVLQSSGLYSLSSVVTVPS

SSLGTQTYICNVNHKPSNTKVDKKVEPKSCDKTSGQAG
```

The nucleic acid sequence encoding the amino acid sequence above is set forth below.

```
                                                   (SEQ ID NO: 15)
caggtgcagctgcaggagtccggcccaggactggtgaagccttcggagaccctgtccctc        60 acctgcactgtctctggtggctccgtcagcagtggtagttactactggagctggatccgg       120 cagcccccagggaagggactggagtggattgggtatatctattacagtgggagcaccaac       180 tacaaccnctccctcaagagtcgagtcaccatatcagtagacacgtccaagaaccagttc       240 tccctgaagctgagctctgtgaccgctgcggacacggccgtgtattactgtgcgagagag       300 gggaagaatggggcttttgatatctggggccaagggacaatggtcaccgtctcttcagcc       360 tccaccaagggcccatcggtcttccccctggcaccctcctccaagagcacctctggggc        420
```

-continued
```
acagcggccctgggctgcctggtcaaggactacttccccgaaccggtgacggtgtcgtgg    480 aactcaggcgccctgaccagcggcgtgcacaccttcccggctgtcctacagtcctcagga    540 ctctactccctcagcagcgtggtgaccgtgccctccagcagcttgggcacccagacctac    600 atctgcaacgtgaatcacaagcccagcaacaccaaggtggacaagaaagttgagcccaaa    660 tcttgtgacaaaactagtggccaggccggccac                              693
```

In some embodiments, the extracellular antigen-binding domain comprises a light chain variable region comprising amino acids having the sequence set forth below.

```
                                              (SEQ ID NO: 16)
DIQMTQSPSSLSASVGDRVTITCRASQSISSYLNWYQQKPGKAPKLLI

YAASSLQSGVPSGFSGSGSGTDFTLTISSLQPEDFATYYCQQSYSTPL

TFGGGTKVEIKRTVAAPSVFIFPPSDEQLKSGTASVVCLLNNFYPREA

KVQWKVDNALQSGNSQESVTEQDSKDSTYSLSSTLTLSKADYEKHKVY

ACEVTHQGLSSPVTKSFNRGEC
```

The nucleic acid sequence encoding the amino acid sequence above is set forth below.

```
                                              (SEQ ID NO: 17)
gacatccagatgacccagtctccatcctccctgtctgcatctgtaggagacagagtcacc     60 atcacttgccgggcaagtcagagcattagcagctatttaaattggtatcagcagaaacca   120 gggaaagcccctaagctcctgatctatgctgcatccagtttgcaaagtggggtcccatca   180 gggttcagtggcagtggatctgggacagatttcactctcaccatcagcagtctgcaacct   240 gaagattttgcaacttactactgtcaacagagttacagtaccccgctcactttcggcgga   300 gggaccaaggtggagatcaaacgaactgtggctgcaccatctgtcttcatcttcccgcca   360 tctgatgagcagttgaaatctggaactgcctctgttgtgtgcctgctgaataacttctat   420 cccagagaggccaaagtacagtggaaggtggataacgccctccaatcgggtaactcccag   480 gagagtgtcacagagcaggacagcaaggacagcacctactgcctcagcagcaccctgacg   540 ctgagcaaagcagactacgagaaacacaaactctacgcctgcgaagtcacccatcagggc   600 ctgagctcgcccgtcacaaagagcttcaacaggggagagt
```

In some embodiments, the extracellular antigen-binding domain comprises a light chain variable region comprising amino acids having the sequence set forth below.

```
                                              (SEQ ID NO: 18)
RHQMTQSPSSLSASVGDRVTITCRASQSISSYLNWYQQKPGKAPKLLIYA

ASSLQSGVPSGFSGSGSGTDFTLTISSLQPEDFATYYCQQSYSTPLTFGG

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC
```

In certain embodiments, the extracellular antigen-binding domain of an MSLN CAR comprises a single-chain variable fragment (scFv). In one specific embodiment, the extracellular antigen-binding domain of a CAR comprises a human scFV. In one embodiment, the human scFV comprises a heavy chain variable region comprising amino acids 1-119 of the MSLN CAR described above (SEQ ID NO:14). In another embodiment, the human scFV of an MSLN CAR comprises a heavy chain variable region comprising amino acids having the sequence set forth below.

```
                                              (SEQ ID NO: 19)
QVQLQESGPGLVKPSETLSLTCTVSGGSVSSGSYYWSWIRQPPGKGLEWI

GYIYYSGSTNYNPSLKSRVTISVDTSKNQFSLKLSSVTAADTAVYYCARE

GKNGAFDIWGQGTMVTVSSS
```

In one embodiment, the human scFV comprises a light chain variable region comprising amino acids 1-107 of SEQ ID NO:16. In one embodiment, the human scFV comprises a light chain variable region comprising amino acids 1-107 of SEQ ID NO:18.

In certain embodiments, the human scFV comprises amino acids having the sequence set forth below.

```
                                              (SEQ ID NO: 20)
Q V Q L Q E S G P G L V K P S E T L S L T C T V S

G G S V S S G S Y Y W S W I R Q P P G K G L E W I

G Y I Y Y S G S T N Y N P S L K S R V T I S V D T

S K N Q F S L K L S S V T A A D T A V Y Y C A R E

G K N G A F D I W G Q G T M V T V S S S G G G G S

G G G G S G G G G S R H Q M T Q S P S S L S A S V

G D R V T I T C R A S Q S I S S Y L N W Y Q Q K P

G K A P K L L I Y A A S S L Q S G V P S R F S G S

G S G T D F T L T I S S L Q P E D F A T Y Y C Q Q
```

SYSTPLTFGGGTKVEIKGQAGHHHH

HHGDYKDDDDKG

In one embodiment, the nucleic acid sequence encoding the amino acid sequence above is set forth below.

(SEQ ID NO: 21)
atggccttaccagtgaccgccttgctcctgccgctggccttgctgctcca cgccgccaggccgcaggtgcagctgcaggagtccggcccaggactggtga agccttcggagaccctgtccctcacctgcactgtctctggtggctccgtc agcagtggtagttactactggagctggatccggcagccccagggaaggg actggagtggattgggtatatctattacagtgggagcaccaactacaacc cctccctcaagagtcgagtcaccatatcagtagacacgtccaagaaccag ttctccctgaagctgagctctgtgaccgctgcggacacggccgtgtatta ctgtgcgagagaggggaagaatggggcttttgatatctggggccaaggga caatggtcaccgtctcttcaggtggaggcggttcaggcggaggtggctct ggcggtggcggatcacgacatcagatgacccagtctccatcctccctgtc tgcatctgtaggagacagagtcaccatcacttgccgggcaagtcagagca ttagcagctatttaaattggtatcagcagaaaccagggaaagcccctaag ctcctgatctatgctgcatccagtttgcaaagtggggtcccatcaaggtt cagtggcagtggatctgggacagatttcactctcaccatcagcagtctgc aacctgaagattttgcaacttactactgtcaacagagttacagtaccccg ctcactttcggcggagggaccaaggtggagatcaaacggactgcggcc gca In another embodiment, a nucleic acid sequence encoding the amino acid sequence of SEQ ID NO:20 is as provided below. The nucleic acid sequence set forth below is synthetically optimized for codon usage, which can increase the expression of the CAR, as disclosed herein.

(SEQ ID NO: 22)
ATGGCGCTGCCGGTGACCGCGCTGCTGCTGCCGCTGGCGCTGCTGCTGCA

TGCGGCGCGCCCGCAGGTGCAGCTGCAGGAAAGCGGCCCGGGCCTGGTGA

AACCGAGCGAAACCCTGAGCCTGACCTGCACCGTGAGCGGCGGCAGCGTG

AGCAGCGGCAGCTATTATTGGAGCTGGATTCGCCAGCCGCCGGGCAAAGG

CCTGGAATGGATTGGCTATATTTATTATAGCGGCAGCACCAACTATAACC

CGAGCCTGAAAAGCCGCGTGACCATTAGCGTGGATACCAGCAAAAACCAG

TTTAGCCTGAAACTGAGCAGCGTGACCGCGGCGGATACCGCGGTGTATTA

TTGCGCGCGCGAAGGCAAAAACGGCGCGTTTGATATTTGGGGCCAGGGCA

CCATGGTGACCGTGAGCAGCGGCGGCGGCGGCAGCGGCGGCGGCGGCAGC

GGCGGCGGCGGCAGCCGCCATCAGATGACCCAGAGCCCGAGCAGCCTGAG

CGCGAGCGTGGGCGATCGCGTGACCATTACCTGCCGCGCGAGCCAGAGCA

TTAGCAGCTATCTGAACTGGTATCAGCAGAAACCGGGCAAAGCGCCGAAA

CTGCTGATTTATGCGGCGAGCAGCCTGCAGAGCGGCGTGCCGAGCCGCTT

TAGCGGCAGCGGCAGCGGCACCGATTTTACCCTGACCATTAGCAGCCTGC

AGCCGGAAGATTTTGCGACCTATTATTGCCAGCAGAGCTATAGCACCCCG

CTGACCTTTGGCGGCGGCACCAAAGTGGAAATTAAACGCACCGCGGCGGC

G

In yet another embodiment, a nucleic acid sequence encoding the amino acid sequence of SEQ ID NO:20 is as provided below. The nucleic acid sequence as set forth below is synthetically optimized for codon usage, which can increase the expression of the CAR (SEQ ID NO: 23)
atggccCTCCCGGTAACGGCTCTGCTGCTTCCACTCGCACTGCTCTTGCA

TGCTGCCAGACCACAGGTCCAGCTGCAGGAGAGTGGGCCTGGACTGGTTA

AGCCGAGTGAGACACTTTCCTTGACGTGCACTGTGAGCGGGGGAAGTGTG

TCCTCAGGTAGTTATTACTGGTCCTGGATTCGCCAGCCACCAGGAAAGGG

ACTGGAGTGGATAGGTTATATCTATTATTCTGGCAGCACTAATTACAATC

CTTCTCTCAAAAGTAGGGTGACAATTTCAGTGGATACTTCCAAAAATCAG

TTTAGTCTGAAGCTCAGCTCTGTGACAGCTGCTGATACTGCAGTTTACTA

CTGCGCCAGGGAGGGGAAGAATGGCGCCTTCGATATTTGGGGACAGGGCA

CTATGGTGACTGTATCAAGCGGAGGCGGTGGCAGCGGCGGGGAGGGAGT

GGAGGCGGCGGGTCTCGACATCAGATGACACAGAGCCCATCATCACTTAG

CGCCAGCGTTGGCGACCGGGTTACGATAACATGCAGGGCTTCCCAATCTA

TCAGTTCTTATCTGAACTGGTATCAGCAGAAACCAGGTAAGGCCCCCAAG

CTGCTCATCTACGCAGCCTCATCCCTGCAGAGCGGCGTCCCTAGTCGATT

TTCCGGTAGTGGGTCAGGGACAGATTTTACCCTGACTATCAGTTCACTGC

AGCCCGAGGACTTCGCGACATACTATTGCCAACAGTCCTATAGTACACCC

TTGACATTTGGCGGCGGGACTAAAGTAGAAATTAAACGCACCgcggccgc a

In certain embodiments, the extracellular antigen-binding domain of a CAR comprises a heavy chain variable region CDR1 comprising the amino acids GGSVSSGSYY (SEQ ID NO:24), a heavy chain variable region CDR2 comprising the amino acids IYYSGST (SEQ ID NO:25), and a heavy chain variable region CDR3 comprising the amino acids AREGKNGAFDIW (SEQ ID NO:26). In some embodiments, the extracellular antigen-binding domain comprises a light chain variable region CDR1 comprising the amino acids QSISSY (SEQ ID NO:27), a light chain variable region CDR2 comprising the amino acids AASS (SEQ ID NO:28), and a light chain variable region CDR3 comprising the amino acids QQSYSTPLTF (SEQ ID NO:29). In one non-limiting, exemplary embodiment, the extracellular antigen-binding domain is a human scFv derived from a fully human anti-MSLN antibody m912 as disclosed in Feng et al., *Mol. Cancer Therapy* 8(5):1113-1118 (2009), which is incorporated herein by reference.

In one embodiment, an exemplary CAR is Mz, which comprises an extracellular antigen binding domain that specifically binds to human mesothelin, a transmembrane domain comprising a CD8 polypeptide, and an intracellular domain comprising a CD3ζ polypeptide (see FIG. 1B). Mz also comprises a signal peptide covalently joined to the N-terminus of the extracellular antigen-binding domain. The signal peptide comprises a CD8 polypeptide comprising amino acids having the sequence MALPVTALLLPLALLL-HAARP (SEQ ID NO:30).

In one embodiment, an exemplary CAR is M28z, which comprises an extracellular antigen binding domain that specifically binds to human mesothelin, a transmembrane domain comprising a CD28 polypeptide, and an intracellular domain comprising a CD3ζ polypeptide and a co-stimulatory signaling region comprising a CD28 polypeptide (see FIG. 1B). M28z also comprises a signal peptide covalently joined to the N-terminus of the extracellular antigen-binding domain. The signal peptide comprises a CD8 polypeptide comprising amino acids having the sequence MALPVTALLLPLALLLHAARP (SEQ ID NO:31).

In one embodiment, an exemplary CAR is MBBz, which comprises an extracellular antigen binding domain that specifically binds to human mesothelin, a transmembrane domain comprising a CD8 polypeptide, and an intracellular domain comprising a CD3ζ polypeptide and a co-stimulatory signaling region comprising a 4-1BB polypeptide (see FIG. 1B). MBBz also comprises a signal peptide covalently joined to the N-terminus of the extracellular antigen-binding domain. The signal peptide comprises a CD8 polypeptide comprising amino acids having the sequence MALPVTALLLPLALLLHAARP (SEQ ID NO:32).

6.3. Dominant Negative Forms of an Inhibitor of a Cell-Mediated Immune Response

According to the invention, an immune cell, such as a T cell, or a precursor cell thereof, is engineered to express a dominant negative form (DN form) of an inhibitor of a cell-mediated immune response.

Malignant cells adapt to generate an immunosuppressive microenvironment that protects the cells from immune recognition and elimination (Sharpe et al., *Dis. Model Mech.* 8:337-350 (2015)). The immunosuppressive microenvironment puts limitations on immunotherapy methods. The present invention addresses this limitation by expressing in an immune cell, or precursor cell thereof, a DN form of an inhibitor of a cell-mediated immune response.

An inhibitor of a cell-mediated immune response of the immune cell or precursor cell thereof refers to a molecule that acts to inhibit or suppress the immune response effected by the immune cell or precursor cell thereof. In one embodiment, the inhibitor of a cell-mediated immune response is an immune checkpoint inhibitor, also referred to as a checkpoint blockade.

In one embodiment, the invention provides immune cells, such as T cells, or precursor cells thereof, that co-express a cancer antigen CAR and a dominant negative form of an inhibitor of a cell-mediated immune response of the immune cell, for example, a receptor that functions in an immune checkpoint inhibitor pathway. Immune checkpoint pathways are inhibitory pathways that suppress the immune response of an immune cell. The pathways deliver negative signals to the immune cells, such as T cells, and attenuate TCR-mediated signals, leading to decreased cell proliferation, cytokine production and cell cycle progression (see Pardoll, *Nat. Rev.* 12:252-264 (2012); Wu et al., *Int. J. Biol. Sci.* 8:1420-1430 (2012)). The immune checkpoint inhibitor pathway generally involves a ligand-receptor pair. Exemplary immune checkpoint inhibitor pathway receptors include, for example, PD-1, CTLA-4, BTLA, TIM-3, LAG-3, CD160, TIGIT, LAIR1, 2B4, and the like (see Chen et al., *Nat. Rev. Immunol.* 13(4):227-242 (2013)). The corresponding ligands for these receptors include, for example, PD-L1 (for PD-1); PD-L2 (for PD-1); CD80, CD86 (for CTLA-4); HVEM (for BTLA); Galectin-9, HMGB1 (for TIM-3); MHC II (for LAG-3); HVEM (for CD160); CD155, CD112, CD113 (for TIGIT); C1q, collagen (for LAIR1); CD48 (for 2B4), and the like (Chen et al., supra, 2013). Expression of a DN form in the immune cell, such as a T cell, or precursor cell thereof, provides for inhibition of a checkpoint inhibitor pathway that is intrinsic to the cell.

In one embodiment of the invention, a dominant negative form ("DN form") of an immune checkpoint inhibitor pathway receptor is provided, as disclosed herein.

A DN form of an inhibitor of a cell-mediated immune response that is a cell-surface receptor such as an immune checkpoint inhibitor pathway receptor can be generated by deleting some portion of the receptor to prevent intracellular signaling, thereby suppressing the immune checkpoint pathway and sustaining activation of the immune cell, such as a T cell. A DN form of the invention is a polypeptide comprising (a) at least a portion of an extracellular domain of an immune checkpoint inhibitor, where the portion comprises the ligand binding region, and (b) a transmembrane domain, where the polypeptide is a dominant negative form of the immune checkpoint inhibitor. Generally, a DN form of an inhibitor of an immune checkpoint inhibitor pathway receptor retains most or all of an extracellular domain of the receptor such that the extracellular domain retains sufficient protein interaction activity to bind to its respective ligand. Thus, in a specific embodiment, a polypeptide encoding a DN form comprises substantially all of an extracellular domain of an immune checkpoint inhibitor. It is understood that a polypeptide comprising "substantially all" of an extracellular domain includes a polypeptide that comprises the entire extracellular domain or a portion of the extracellular domain in which one to a few amino acids have been deleted from the N-terminus and/or C-terminus of the extracellular domain, for example deletion of 1, 2, 3, 4, or 5 amino acids from the N-terminus and/or C-terminus, so long as the remaining portion of the extracellular domain retains sufficient protein interaction activity to bind to its respective ligand. A DN form of the invention generally also lacks some portion or all of a signaling domain, such as the intracellular/cytoplasmic domain, such that the DN form has reduced activity or is inactive for signaling in the immune checkpoint pathway. Without being bound by a particular mechanism or theory, binding of the ligand to the DN form decreases binding of the ligand to the intact endogenous receptor, and/or the DN form complexes with signaling molecules, including the endogenous receptor, resulting in decreased signaling of an immune checkpoint pathway.

A DN form of the invention generally has certain functional characteristics including, but not limited to, the ability to be expressed at the cell surface of an immune cell such as a T cell, or precursor cell thereof, the ability to bind to its respective ligand, and the inability or reduced ability to propagate an intracellular signal of an immune checkpoint pathway. One skilled in the art can readily generate a DN form of an inhibitor of a cell-mediated immune response by engineering the inhibitor to have such functional characteristics. In one embodiment, a DN form is constructed to retain the extracellular domain of inhibitor of a cell-mediated immune response, or at least a sufficient portion of the extracellular domain to retain ligand binding activity. In an exemplary embodiment, a DN form can be constructed using the extracellular domain of an inhibitor of a cell-mediated immune response, including, but not limited to, the extracellular domains of PD-1, CTLA-4, BTLA, TIM-3, LAG-3, CD160, TIGIT, LAIR1, 2B4, as disclosed herein. One skilled in the art will readily understand that it is not required to retain the entire extracellular domain of an inhibitor of a cell-mediated immune response, and that deletions from the N-terminus and/or C-terminus of the extracellular domain can be introduced so long as ligand binding activity is retained. One skilled in the art can readily determine the appropriateness of such N-terminal and/or C-terminal deletions based on the analysis of the receptor sequence to identify protein motifs known to provide ligand binding activity (see, for example, ExPASy (expasy.org), in particular PROSITE (prosite.expasy.org)). In addition or alternatively, suitable N-terminal and/or C-terminal deletions can be determined empirically by introducing deletions in a polypeptide and measuring binding activity for the respective ligand. Thus, one skilled in the art can readily determine an appropriate sequence of an inhibitor of a cell-mediated immune response to provide ligand binding activity to a DN form of the invention.

It is understood that, whether an entire extracellular domain or a portion of the extracellular domain of a receptor is used in a DN form, additional sequences can optionally be included in the extracellular domain of the DN form. Such additional sequences can be derived from the parent polypeptide of the DN form, or the additional sequences can be derived from a different polypeptide. Such a polypeptide comprising sequences from a parent polypeptide and a different polypeptide is a non-naturally occurring, chimeric polypeptide. For example, a signal peptide or leader peptide is generally included so that the DN form will be expressed at the cell surface of the immune cell such as a T cell, or precursor cell thereof. It is understood that, once a polypeptide containing a signal peptide is expressed at the cell surface, the signal peptide has generally been proteolytically removed during processing of the polypeptide in the endoplasmic reticulum and translocation to the cell surface. Thus, a polypeptide such as a DN form is generally expressed at the cell surface as a mature protein lacking the signal peptide, whereas the precursor form of the polypeptide includes the signal peptide. The signal peptide can be the naturally occurring signal peptide of the receptor, or alternatively can be derived from a different protein. Exemplary signal peptides are described herein, including those described herein as being suitable for a CAR. To additionally provide expression at the cell surface, the DN form will generally include a transmembrane domain that provides for retention of the DN form at the cell surface. The transmembrane domain can be the naturally occurring transmembrane of the receptor, or alternatively can be derived from a different protein. In a particular embodiment, the transmembrane domain derived from another protein is derived from another receptor expressed on the cell surface of the immune cell such as a T cell, or precursor cell thereof. Exemplary transmembrane domains are described herein, including those described herein as being suitable for a CAR.

In the case of an immune checkpoint pathway receptor, generally the signaling domain resides within the intracellular/cytoplasmic domain. The signaling activity of an immune checkpoint pathway receptor is generally mediated by protein-protein interactions with cell surface receptor(s) and/or intracellular signaling molecules. In one embodiment, a DN form lacks the entire intracellular domain, or a portion thereof, that functions in propagating the signal of an immune checkpoint pathway. It is understood that it is not necessary to delete the entire intracellular domain of the receptor so long as a sufficient portion of the intracellular signaling domain is deleted to inhibit or reduce signaling from the DN form. In addition or alternatively, mutations can be introduced into the intracellular signaling domain to inhibit or reduce signaling from the DN form. In addition or alternatively, a heterologous sequence with no signaling activity can be substituted for the intracellular signaling domain of the receptor to generate a DN form. One skilled in the art will readily understand that these and other well known methods can be utilized to generate a DN form of the invention.

One exemplary embodiment of a dominant negative form of an immune checkpoint inhibitor is a dominant negative form of PD-1. As disclosed herein, a dominant negative form of PD-1 was co-expressed in a CAR T cell with a mesothelin CAR and found to increase tumor elimination and prolong mouse survival (see Example). A dominant negative form of PD-1 is exemplary of a DN form of an inhibitor of a cell-mediated immune response, including an immune checkpoint inhibitor. The results disclosed herein indicate that co-expressing a dominant negative form of an inhibitor of a cell-mediated immune response can enhance the effectiveness of a CAR T cell, or other immune cell or precursor cell thereof, expressing a cancer antigen CAR. It is understood that a PD-1 DN form as disclosed herein is exemplary. Based on the teachings disclosed herein, one skilled in the art can readily prepare a DN form of an inhibitor of a cell-mediated immune response, including an immune checkpoint pathway receptor.

As described herein, a DN form of an inhibitor of a cell-mediated immune response is designed to have reduced or inhibited intracellular signaling. The DN forms of the invention are generally based on inhibiting a receptor of an immune checkpoint pathway, which function to inhibit activation of an immune cell, such as T cell, for example, cell proliferation, cytokine production and/or cell cycle progression. The DN forms of the invention are designed to remove the intracellular signaling domain, or a portion thereof, so that the signaling ability of the receptor is reduced or inhibited. The DN form also functions to inhibit signaling of the endogenous receptor. In a particular embodiment, the reduced or inhibited signaling overcomes the checkpoint blockade, resulting in sustained signaling and activation of the immune cell, such as a T cell, or precursor cell thereof. It is understood that the signaling activity of the DN form can be completely knocked out or partially knocked out, so long as the partial reduction in activity is sufficient for the effect of providing enhanced activation of the immune cell, or precursor cell thereof, in comparison to the absence of the DN form. Also, the DN form is not required to result in complete inactivation of signaling from the endogenous receptor but can reduce the activation of the endogenous receptor sufficient to overcome the checkpoint blockade and allow activation of the immune cell, such as a T cell, or precursor cell thereof. One skilled in the art can readily determine the effect of a DN form on the activity of a parent receptor using assay methods well known in the art, including assays using in vivo models, such as animal models, to assess the effect of the DN form on the effectiveness of CAR expressing cells, as disclosed herein.

As with a CAR for use in the invention, optional linker or spacer sequences can be included in a DN form, for example, a linker or spacer between a signal peptide and the extracellular ligand binding domain, particularly when heterologous sequences are fused. A linker or spacer can also optionally be included between the extracellular ligand binding domain and the transmembrane domain. Similarly, a linker or spacer can optionally be included between the transmembrane domain and any remaining intracellular domain. Such optional linkers or spacers are described herein. In addition, such linkers or spacers can be derived from a heterologous sequence. For example, as described above, a transmembrane domain derived from a heterologous polypeptide can optionally include additional sequences at the N-terminus and/or C-terminus derived from the heterologous polypeptide. Such additional sequences can function as a linker or spacer.

Exemplary DN forms of immune checkpoint inhibitors are described below in more detail. DN forms consisting essentially of the described sequences are also envisioned.

PD-1.

Programmed cell death protein 1 (PD-1) is a negative immune regulator of activated T cells upon engagement with its corresponding ligands, PD-L1 and PD-L2, expressed on endogenous macrophages and dendritic cells. PD-1 is a type I membrane protein of 268 amino acids. PD-1 has two ligands, PD-L1 and PD-L2, which are members of the B7 family. The protein's structure comprises an extracellular IgV domain followed by a transmembrane region and an intracellular tail. The intracellular tail contains two phosphorylation sites located in an immunoreceptor tyrosine-based inhibitory motif and an immunoreceptor tyrosine-based switch motif. PD-1 negatively regulates TCR signals. SHP-1 and SHP-2 phosphatases bind to the cytoplasmic tail of PD-1 upon ligand binding. Upregulation of PD-L1 is one mechanism tumor cells use to evade the host immune system. In pre-clinical and clinical trials, PD-1 blockade by antagonistic antibodies induced anti-tumor responses mediated through the host endogenous immune system.

A PD-1 polypeptide can have an amino acid corresponding to GenBank No. NP_005009.2 (GI:167857792), as provided below, or fragments thereof. See GenBank NP_005009.2 for reference to domains within PD-1, for example, signal peptide, amino acids 1 to 20; extracellular domain, amino acids 21 to 170; transmembrane domain, amino acids 171 to 191; intracellular domain, amino acids 192 to 288. It is understood that an "PD-1 nucleic acid molecule" refers to a polynucleotide encoding an PD-1 polypeptide.

a transmembrane domain that is optionally a heterologous transmembrane domain, including any of various transmembrane domains described herein. Although the PD-1 DN form exemplified in the Example herein comprises heterologous sequences fused to the extracellular domain of PD-1, it is understood that a PD-1 DN form can comprise PD-1 sequence only.

In one embodiment, the invention provides a PD-1 DN form that comprises the extracellular domain, or a ligand binding portion thereof, of PD-1, for example, amino acids 21 to 170 corresponding to the extracellular domain of PD-1 (GenBank NP_005009.2; SEQ ID NO:33). A cell expressing such a PD-1 DN form should lack the ability or have reduced ability to signal in a PD-1 immune checkpoint pathway. In one embodiment, a PD-1 DN form is a deletion mutant having a deletion of the intracellular domain, for example, amino acids 192 to 288 of PD-1 (GenBank NP_005009.2; SEQ ID NO:33), or a portion thereof, such that intracellular signaling of the immune checkpoint pathway mediated by PD-1 is reduced or inhibited. Additional embodiments of a DN form of PD-1 are described below.

In one embodiment, a PD-1 DN form comprises an amino acid sequence comprising the extracellular domain of PD-1 fused to the transmembrane and hinge domains of CD8. In one embodiment, a PD-1 DN form comprises amino acids 21 to 165 of a PD-1 sequence (NP_005009.2; SEQ ID NO:33). Such a PD-1 DN form comprises the extracellular domain of PD-1. In another embodiment, the invention provides a PD-1 DN form comprising amino acids 1 to 165 (precursor form) or amino acids 21 to 165 (mature form) of a PD-1 sequence (NP_005009.2; SEQ ID NO:33). Such a DN form comprises the signal peptide of PD-1, amino acids 1 to 20, and extracellular domain amino acids 21 to 165, whereas the mature form lacks the signal peptide. In one embodiment, a PD-1 DN form comprises amino acids 21 to 151 of a PD-1 sequence (NP_005009.2; SEQ ID NO:33). In another embodiment, the invention provides a PD-1 DN

```
                                         (NP_005009.2; SEQ ID NO: 33)
  1 MQIPQAPWPV VWAVLQLGWR PGWFLDSPDR PWNPPTFSPA LLVVTEGDNA TFTCSFSNTS

61 ESFVLNWYRM SPSNQTDKLA AFPEDRSQPG QDCRFRVTQL PNGRDFHMSV VRARRNDSGT

121 YLCGAISLAP KAQIKESLRA ELRVTERRAE VPTAHPSPSP RPAGQFQTLV VGVVGGLLGS

181 LVLLVWVLAV ICSRAARGTI GARRTGQPLK EDPSAVPVFS VDYGELDFQW REKTPEPPVP

241 CVPEQTEYAT IVFPSGMGTS SPARRGSADG PRSAQPLRPE DGHCSWPL
```

In one embodiment, the invention provides an inhibitor of a cell-mediated immune response that is a PD-1 dominant negative form (DN form). In one embodiment, the PD-1 DN form comprises the extracellular ligand binding domain of PD-1. In one embodiment, the PD-1 DN form comprises the extracellular ligand binding domain of PD-1 and a transmembrane domain (e.g., mature form). In another embodiment, the PD-1 DN form comprises the extracellular ligand binding domain of PD-1, a transmembrane domain and a signal peptide (e.g., precursor form). The invention also provides encoding polypeptides and nucleic acids of the PD-1 DN forms of the invention. In a particular embodiment, the PD-1 extracellular ligand binding domain is fused to one or more heterologous polypeptide sequences, that is, the PD-1 DN form is a chimeric sequence. For example, the PD-1 extracellular ligand binding domain can be fused at its N-terminus to a signal peptide that is optionally a heterologous signal peptide, including various signal peptides described herein. In addition, a PD-1 DN form can comprise form comprising amino acids 1 to 151 (precursor form) or amino acids 21 to 151 (mature form) of a PD-1 sequence (NP_005009.2; SEQ ID NO:33). Optionally, a PD-1 DN form comprises an extracellular ligand binding domain starting at amino acid 21 through an amino acid between amino acids 151 to 165 of a PD-1 sequence (NP_005009.2; SEQ ID NO:33). In another embodiment, a PD-1 DN form comprises the transmembrane domain of CD8, amino acids 183 to 203 of a CD8 sequence (NP_001139345.1; SEQ ID NO:11). Such an embodiment is representative of a chimeric DN form comprising a transmembrane domain from a different (heterologous) polypeptide. As described above, a DN form comprising a heterologous domain such as a transmembrane domain can optionally include additional sequence from the heterologous polypeptide. In one such embodiment, a DN form is provided that comprises additional sequence from the heterologous polypeptide N-terminal of the transmembrane domain. In one embodiment, the DN form comprises the hinge domain of CD8. In a particular embodiment, the heterologous sequence comprises additional N-terminal sequence of amino acids 137 to 182, or optionally starting at amino acids 138 or 139, of a CD8 sequence (NP_001139345.1; SEQ ID NO:11). In another embodiment, a DN form is provided that comprises additional sequence from the heterologous polypeptide C-terminal of the transmembrane domain. In a particular embodiment, the heterologous sequence comprises additional C-terminal sequence from amino acids 204 to 209 of a CD8 sequence (NP_001139345.1; SEQ ID NO:11). In one embodiment, the PD-1 DN form comprises the transmembrane domain of CD8, amino acids 183 to 203, optionally a hinge domain comprising amino acids 137 to 182 (or optionally starting at amino acids 138 or 139), and/or additional C-terminal sequence comprising amino acids 204 to 209. In a particular embodiment of the invention, a PD-1 DN form is provided that comprises amino acids 1 to 165 of a PD-1 sequence (NP_005009.2; SEQ ID NO:33), and amino acids 137 to 209, optionally starting at amino acids 138 or 139, of a CD8 sequence (NP_001139345.1; SEQ ID NO:11).

In a further particular embodiment, the invention provides a PD-1 DN form comprising the sequence provided below, where the underlined sequence is derived from PD-1 and the italicized sequence is derived from CD8.

(SEQ ID NO: 43)
MQIPQAPWPVVWAVLQLGWRPGWFLDSPDRPWNPPTFSPALLVVTEGDNA

TFTCSFSNTSESFVLNWYRMSPSNQTDKLAAFPEDRSQPGQDCRFRVTQL

PNGRDFHMSVVRARRNDSGTYLCGAISLAPKAQIKESLRAELRVTERRAE

VPTAHPSPSPRPAGQAAA*PTTTPAPRPPTPAPTIASQPLSLRPEACRPAA*

*GGAVHTRGLDFACDIYIWAPLAGTCGVLLLSLVITLYCNHRRIQ*

In an additional embodiment, a DN form of the invention optionally comprises a P2A sequence, which provides for optional co-expression of a reporter molecule. P2A is a sequence used for bicistronic or multicistronic expression of protein sequences (see Szymczak et al., *Expert Opin. Biol. Therapy* 5(5):627-638 (2005)). An exemplary P2A sequence is GSGATNFSLLKQAGDVEENPGPM (SEQ ID NO:44). In a further embodiment, a DN form of the invention is co-expressed with a reporter protein. In a particular embodiment, the reporter protein is mCherry fluorescent protein. In a particular embodiment, the mCherry polypeptide sequence is as provided below. It is understood that mCherry is merely exemplary and that any desired reporter molecule, such as a fluorescent protein can be included as a reporter, as described herein.

(SEQ ID NO: 45)
MVSKGEEDNMAIIKEFMRFKVHMEGSVNGHEFEIEGEGEGRPYEGTQTAK

LKVTKGGPLPFAWDILSPQFMYGSKAYVKHPADIPDYLKLSFPEGFKWER

VMNFEDGGVVTVTQDSSLQDGEFIYKVKLRGTNFPSDGPVMQKKTMGWEA

SSERMYPEDGALKGEIKQRLKLKDGGHYDAEVKTTYKAKKPVQLPGAYNV

NIKLDITSHNEDYTIVEQYERAEGRHSTGGMDELYK

In a further particular embodiment, a PD-1 DN form is expressed as a polypeptide construct as provided below, where the underlined sequence is derived from PD-1, the italicized sequence is derived from CD8, the P2A sequence is double underlined, and the mCherry sequence is underlined and italicized.

(SEQ ID NO: 46)
MQIPQAPWPVVWAVLQLGWRPGWFLDSPDRPWNPPTFSPALLVVTEGDNA

TFTCSFSNTSESFVLNWYRMSPSNQTDKLAAFPEDRSQPGQDCRFRVTQL

PNGRDFHMSVVRARRNDSGTYLCGAISLAPKAQIKESLRAELRVTERRAE

VPTAHPSPSPRPAGQAAA*PTTTPAPRPPTPAPTIASQPLSLRPEACRPAA*

*GGAVHTRGLDFACDIYIWAPLAGTCGVLLLSLVITLYCNHRRI*QGSGATN

FSLLKQAGDVEENPGP*MVSKGEEDNMAIIKEFMRFKVHMEGSVNGHEFEI*

*EGEGEGRPYEGTQTAKLKVTKGGPLPFAWDILSPQFMYGSKAYVKHPADI*

*PDYLKLSFPEGFKWERVMNFEDGGVVTVTQDSSLQDGEFIYKVKLRGTNF*

*PSDGPVMQKKTMGWEASSERMYPEDGALKGEIKQRLKLKDGGHYDAEVKT*

*TYKAKKPVQLPGAYNVNIKLDITSHNEDYTIVEQYERAEGRHSTGGMDEL*

*YK*

In a particular embodiment, a nucleic acid encoding a PD-1 DNR form construct is provided below, where the underlined sequence encodes amino acids derived from PD-1 DN, the italicized sequence encodes amino acids derived from CD8, the P2A encoding sequence is double underlined, the mCherry encoding sequence is underlined and italicized, a Kozak sequence is bolded with a dashed underline, and restriction sites Age I and Xho I are underlined with a dotted line at the 5' and 3' ends, respectively.

(SEQ ID NO:47)
ACCGGTGGTACCTCACCCTTACCGAGTCGGCGACACAGTGTGGGTCCGCCG

ACACCAGACTAAGAACCTAGAACCTCGCTGGAAAGGACCTTACACAGTCCT

GCTGACCACCCCCACCGCCCTCAAAGTAGACGGCATCGCAGCTTGGATACA

CGCCGCCCACGTGAAGGCTGCCGACCCCGGGGGTGGACCATCCTCTAGACT

GGCCACCATGCAGATCCCACAGGCGCCCTGGCCAGTCGTCTGGGCGGTGCT

ACAACTGGGCTGGCGGCCAGGATGGTTCTTAGACTCCCCAGACAGGCCCTG

GAACCCCCCCACCTTCTCCCCAGCCCTGCTCGTGGTGACCGAAGGGGACAA

CGCCACCTTCACCTGCAGCTTCTCCAACACATCGGAGAGCTTCGTGCTAAA

CTGGTACCGCATGAGCCCCAGCAACCAGACGGACAAGCTGGCCGCTTTCCC

CGAGGACCGCAGCCAGCCCGGCCAGGACTGCCGCTTCCGTGTCACACAACT

GCCCAACGGGCGTGACTTCCACATGAGCGTGGTCAGGGCCCGGCGCAATGA

CAGCGGCACCTACCTCTGTGGGGCCATCTCCCTGGCCCCCAAGGCGCAGAT

CAAAGAGAGCCTGCGGGCAGAGCTCAGGGTGACAGAGAGAAGGGCAGAAGT

GCCCACAGCCCACCCCAGCCCCTCACCCAGGCCAGCCGGCCAGGCGGCCGC

*ACCCACCACGACGCCAGCGCCGCGACCACCAACCCCGGCGCCCACGATCGC*

*GTCGCAGCCCCTGTCCCTGCGCCCAGAGGCGTGCCGGCCAGCGGCGGGGGG*

*CGCAGTGCACACGAGGGGGCTGGACTTCGCCTGTGATATCTACATCTGGGC*

*GCCCCTGGCCGGGACTTGTGGGGTCCTTCTCCTGTCACTGGTTATCACCCT*

*TTACTGCAACCACAGGCGGATCCAA*GGATCTGGAGCAACAAACTTCTCACT

ACTCAAACAAGCAGGTGACGTGGAGGAGAATCCCGGCCCCATGGTGAGCAA

GGGCGAGGAGGATAACATGGCCATCATCAAGGAGTTCATGCGCTTCAAGGT

GCACATGGAGGGCTCCGTGAACGGCCACGAGTTCGAGATCGAGGGCGAGGG

-continued
CGAGGGCCGCCCCTACGAGGGCACCCAGACCGCCAAGCTGAAGGTGACCAA

GGGTGGCCCCCTGCCCTTCGCCTGGGACATCCTGTCCCCTCAGTTCATGTA

CTLA-4.

Cytotoxic T-lymphocyte-associated protein 4 (CTLA-4) is an inhibitory receptor expressed by activated T cells, which when engaged by its corresponding ligands (CD80 and CD86; B7-1 and B7-2, respectively), mediates activated T cell inhibition or anergy. In both preclinical and clinical studies, CTLA-4 blockade by systemic antibody infusion enhanced the endogenous anti-tumor response albeit, in the clinical setting, with significant unforeseen toxicities. CTLA-4 contains an extracellular V domain, a transmembrane domain, and a cytoplasmic tail. Alternate splice variants, encoding different isoforms, have been characterized. The membrane-bound isoform functions as a homodimer interconnected by a disulfide bond, while the soluble isoform functions as a monomer. The intracellular domain is similar to that of CD28, in that it has no intrinsic catalytic activity and contains one YVKM motif able to bind PI3K, PP2A and SHP-2 and one proline-rich motif able to bind SH3 containing proteins. One role of CTLA-4 in inhibiting T cell responses seems to be directly via SHP-2 and PP2A dephosphorylation of TCR-proximal signaling proteins such as CD3ζ and LAT. CTLA-4 can also affect signaling indirectly via competing with CD28 for CD80/86 binding. CTLA-4 has also been shown to bind and/or interact with PI3K, CD80, AP2M1, and PPP2R5A.

A CTLA-4 polypeptide can have an amino acid sequence corresponding to GenBank No. AAH69566.1 (GI: 46854814) or NP_005205.2 (GI:21361212), sequence as provided below, or fragments thereof. See GenBank NP_005205.2 for reference to domains within CTLA-4, for example, signal peptide, amino acids 1 to 35; extracellular domain, amino acids 36 to 161; transmembrane domain, amino acids 162 to 182; intracellular domain, amino acids 183 to 223. It is understood that a "CTLA-4 nucleic acid molecule" refers to a polynucleotide encoding a CTLA-4 polypeptide.

(NP_005205.2; SEQ ID NO: 34)
1 MACLGFQRHK AQLNLATRTW PCTLLFFLLF IPVFCKAMHV AQPAVVLASS RGIASFVCEY

61 ASPGKATEVR VTVLRQADSQ VTEVCAATYM MGNELTFLDD SICTGTSSGN QVNLTIQGLR

121 AMDTGLYICK VELMYPPPYY LGIGNGTQIY VIDPEPCPDS DFLLWILAAV SSGLFFYSFL

181 LTAVSLSKML KKRSPLTTGV YVKMPPTEPE CEKQFQPYFI PIN

-continued
CGGCTCCAAGGCCTACGTGAAGCACCCCGCCGACATCCCCGACTACTTGAA

GCTGTCCTTCCCCGAGGGCTTCAAGTGGGAGCGCGTGATGAACTTCGAGGA

CGGCGGCGTGGTGACCGTGACCCAGGACTCCTCCCTGCAGGACGGCGAGTT

CATCTACAAGGTGAAGCTGCGCGGCACCAACTTCCCCTCCGACGGCCCCGT

AATGCAGAAGAAGACCATGGGCTGGGAGGCCTCCTCCGAGCGGATGTACCC

CGAGGACGGCGCCCTGAAGGGCGAGATCAAGCAGAGGCTGAAGCTGAAGGA

CGGCGGCCACTACGACGCTGAGGTCAAGACCACCTACAAGGCCAAGAAGCC

CGTGCAGCTGCCCGGCGCCTACAACGTCAACATCAAGTTGGACATCACCTC

CCACAACGAGGACTACACCATCGTGGAACAGTACGAACGCGCCGAGGGCCG

CCACTCCACCGGCGGCATGGACGAGCTGTACAAGTAACTCGAG

In one embodiment, the invention provides a CTLA-4 DN form. In one embodiment, the CTLA-4 DN form comprises the extracellular ligand binding domain of CTLA-4. In one embodiment, the CTLA-4 DN form comprises the extracellular ligand binding domain of CTLA-4 and a transmembrane domain (e.g., mature form). In another embodiment, the CTLA-4 DN form comprises the extracellular ligand binding domain of CTLA-4, a transmembrane domain and a signal peptide (e.g., precursor form). The invention also provides encoding polypeptides and nucleic acids of the CTLA-4 DN forms of the invention. In a particular embodiment, the CTLA-4 extracellular ligand binding domain is fused to one or more heterologous polypeptide sequences, that is, the CTLA-4 DN form is chimeric. For example, the CTLA-4 extracellular ligand binding domain can be fused at its N-terminus to a signal peptide that is optionally a heterologous signal peptide, including various signal peptides described herein. In addition, a CTLA-4 DN form can comprise a transmembrane domain that is optionally a heterologous transmembrane domain, including any of various transmembrane domains described herein.

In an embodiment of the invention, the CTLA-4 DN form can comprise the extracellular domain, or a ligand binding portion thereof, of CTLA-4, for example, amino acids 36 to 161 corresponding to the extracellular domain of CTLA-4 (GenBank NP_005205.2; SEQ ID NO:34). A cell expressing such a CTLA-4 DN form should lack the ability or have reduced ability to signal in a CTLA-4 immune checkpoint pathway. In one embodiment, a CTLA-4 DN form is a deletion mutant having a deletion of the intracellular domain, for example, amino acids 183 to 223 of CTLA-4 (GenBank NP_005205.2; SEQ ID NO:34), or a portion thereof, such that intracellular signaling of the immune checkpoint pathway mediated by CTLA-4 is reduced or inhibited.

BTLA.

B- and T-lymphocyte attenuator (BTLA) expression is induced during activation of T cells, and BTLA remains expressed on Th1 cells but not Th2 cells. BTLA interacts with a B7 homolog, B7H4. BTLA displays T-Cell inhibition via interaction with tumor necrosis family receptors (TNF-R), not just the B7 family of cell surface receptors. BTLA is a ligand for tumor necrosis factor (receptor) superfamily, member 14 (TNFRSF14), also known as herpes virus entry mediator (HVEM). BTLA-HVEM complexes negatively regulate T-cell immune responses. BTLA activation has been shown to inhibit the function of human CD8$^+$ cancer-specific T cells. BTLA has also been designated as CD272 (cluster of differentiation 272).

A BTLA polypeptide can have an amino acid sequence corresponding to GenBank No. AAP44003.1 (GI:31880027) or NP_861445.3 (GI:145580621), sequence provided below, or fragments thereof. See GenBank NP_861445.3 for reference to domains within BTLA, for example, signal peptide, amino acids 1 to 30; extracellular domain, amino acids 31 to 157; transmembrane domain, amino acids 158 to 178; intracellular domain, amino acids 179 to 289. It is understood that a "BTLA nucleic acid molecule" refers to a polynucleotide encoding a BTLA polypeptide.

that intracellular signaling of the immune checkpoint pathway mediated by BTLA is reduced or inhibited.

TIM-3.

T cell immunoglobulin mucin-3 (TIM-3), also referred to as hepatitis A virus cellular receptor 2 precursor, is a Th1-specific cell surface protein that regulates macrophage activation. Tim-3 was first identified as a molecule selectively expressed on IFN-γ-producing CD4+ T helper 1 (Th1)

```
                                                     (NP_861445.3; SEQ ID NO: 35)
  1 MKTLPAMLGT GKLFWVFFLI PYLDIWNIHG KESCDVQLYI KRQSEHSILA GDPFELECPV

61 KYCANRPHVT WCKLNGTTCV KLEDRQTSWK EEKNISFFIL HFEPVLPNDN GSYRCSANFQ

121 SNLIESHSTT LYVTDVKSAS ERPSKDEMAS RPWLLYSLLP LGGLPLLITT CFCLFCCLRR

181 HQGKQNELSD TAGREINLVD AHLKSEQTEA STRQNSQVLL SETGIYDNDP DLCFRMQEGS

241 EVYSNPCLEE NKPGIVYASL NHSVIGPNSR LARNVKEAPT EYASICVRS
```

In one embodiment, the invention provides a BTLA DN form. In one embodiment, the BTLA DN form comprises the extracellular ligand binding domain of BTLA. In one embodiment, the BTLA DN form comprises the extracellular ligand binding domain of BTLA and a transmembrane domain (e.g., mature form). In another embodiment, the BTLA DN form comprises the extracellular ligand binding domain of BTLA, a transmembrane domain and a signal peptide (e.g., precursor form). The invention also provides encoding polypeptides and nucleic acids of the BTLA DN forms of the invention. In a particular embodiment, the BTLA extracellular ligand binding domain is fused to one or more heterologous polypeptide sequences, that is, the BTLA DN form is chimeric. For example, the BTLA extracellular ligand binding domain can be fused at its N-terminus to a signal peptide that is optionally a heterologous signal peptide, including various signal peptides described herein. In addition, a BTLA DN form can comprise a transmembrane domain that is optionally a heterologous transmembrane domain, including any of various transmembrane domains described herein.

In an embodiment of the invention, the BTLA DN form can comprise the extracellular domain, or a ligand binding portion thereof, of BTLA, for example, amino acids 31 to 157 corresponding to the extracellular domain of BTLA (GenBank NP_861445.3; SEQ ID NO:35). A cell expressing such a BTLA DN form should lack the ability or have reduced ability to signal in a BTLA immune checkpoint pathway. In one embodiment, a BTLA DN form is a deletion mutant having a deletion of the intracellular domain, for example, amino acids 179 to 289 of BTLA (GenBank NP_861445.3; SEQ ID NO:35), or a portion thereof, such and CD8+ T cytotoxic 1 (Tc1) T cells. TIM-3 possess an N-terminal Ig domain of the V type, followed by a mucin domain.

A TIM-3 polypeptide can have an amino acid sequence corresponding to GenBank No. NP_116171.3 (GI: 49574534), sequence provided below, or fragments thereof. See GenBank NP_116171.3 for reference to domains within TIM-3, for example, signal peptide, amino acids 1 to 21; extracellular domain, amino acids 22 to 202; transmembrane domain, amino acids 203 to 223; intracellular domain, amino acids 224 to 301. It is understood that a "TIM-3 nucleic acid molecule" refers to a polynucleotide encoding a TIM-3 polypeptide.

```
                                                     (NP_116171.3; SEQ ID NO: 36)
  1 MFSHLPFDCV LLLLLLLLTR SSEVEYRAEV GQNAYLPCFY TPAAPGNLVP VCWGKGACPV

61 FECGNVVLRT DERDVNYWTS RYWLNGDFRK GDVSLTIENV TLADSGIYCC RIQIPGIMND

121 EKFNLKLVIK PAKVTPAPTR QRDFTAAFPR MLTTRGHGPA ETQTLGSLPD INLTQISTLA

181 NELRDSRLAN DLRDSGATIR IGIYIGAGIC AGLALALIFG ALIFKWYSHS KEKIQNLSLI

241 SLANLPPSGL ANAVAEGIRS EENIYTIEEN VYEVEEPNEY YCYVSSRQQP SQPLGCRFAM

301 P
```

In one embodiment, the invention provides a TIM-3 DN form. In one embodiment, the TIM-3 DN form comprises the extracellular ligand binding domain of TIM-3. In one embodiment, the TIM-3 DN form comprises the extracellular ligand binding domain of TIM-3 and a transmembrane domain (e.g., mature form). In another embodiment, the TIM-3 DN form comprises the extracellular ligand binding domain of TIM-3, a transmembrane domain and a signal peptide (e.g., precursor form). The invention also provides encoding polypeptides and nucleic acids of the TIM-3 DN forms of the invention. In a particular embodiment, the TIM-3 extracellular ligand binding domain is fused to one or more heterologous polypeptide sequences, that is, the TIM-3 DN form is chimeric. For example, the TIM-3 extracellular ligand binding domain can be fused at its N-terminus to a signal peptide that is optionally a heterologous signal peptide, including various signal peptides described herein. In addition, a TIM-3 DN form can comprise a transmembrane domain that is optionally a heterologous transmembrane domain, including any of various transmembrane domains described herein.

In an embodiment of the invention, the TIM-3 DN form can comprise the extracellular domain, or a ligand binding portion thereof, of TIM-3, for example, amino acids 22 to 202 corresponding to the extracellular domain of TIM-3 (GenBank NP_116171.3; SEQ ID NO:36). A cell expressing such a TIM-3 DN form should lack the ability or have reduced ability to signal in a TIM-3 immune checkpoint pathway. In one embodiment, a TIM-3 DN form is a deletion mutant having a deletion of the intracellular domain, for example, amino acids 224 to 301 of TIM-3 (GenBank NP_116171.3; SEQ ID NO:36), or a portion thereof, such that intracellular signaling of the immune checkpoint pathway mediated by TIM-3 is reduced or inhibited.

LAG-3.

Lymphocyte-activation protein 3 (LAG-3) is a negative immune regulator of immune cells. LAG-3 belongs to the immunoglobulin (Ig) superfamily and contains 4 extracellular Ig-like domains. The LAG3 gene contains 8 exons. The sequence data, exon/intron organization, and chromosomal localization all indicate a close relationship of LAG-3 to CD4. LAG-3 has also been designated CD223 (cluster of differentiation 223).

A LAG-3 polypeptide can have an amino acid sequence corresponding to GenBank No. CAA36243.3 (GI: 15617341) or NP_002277.4 (GI:167614500), sequence provided below, or fragments thereof. See GenBank NP_002277.4 for reference to domains within LAG-3, for example, signal peptide, amino acids 1 to 22; extracellular domain, amino acids 23 to 450; transmembrane domain, amino acids 451 to 471; intracellular domain, amino acids 472 to 525. It is understood that a "LAG-3 nucleic acid molecule" refers to a polynucleotide encoding a LAG-3 polypeptide.

In one embodiment, the invention provides a LAG-3 DN form. In one embodiment, the LAG-3 DN form comprises the extracellular ligand binding domain of LAG-3. In one embodiment, the LAG-3 DN form comprises the extracellular ligand binding domain of LAG-3 and a transmembrane domain (e.g., mature form). In another embodiment, the LAG-3 DN form comprises the extracellular ligand binding domain of LAG-3, a transmembrane domain and a signal peptide (e.g., precursor form). The invention also provides encoding polypeptides and nucleic acids of the LAG-3 DN forms of the invention. In a particular embodiment, the LAG-3 extracellular ligand binding domain is fused to one or more heterologous polypeptide sequences, that is, the LAG-3 DN form is chimeric. For example, the LAG-3 extracellular ligand binding domain can be fused at its N-terminus to a signal peptide that is optionally a heterologous signal peptide, including various signal peptides described herein. In addition, a LAG-3 DN form can comprise a transmembrane domain that is optionally a heterologous transmembrane domain, including any of various transmembrane domains described herein.

In an embodiment of the invention, the LAG-3 DN form can comprise the extracellular domain, or a ligand binding portion thereof, of LAG-3, for example, amino acids 23 to 450 corresponding to the extracellular domain of LAG-3 (GenBank NP_002277.4; SEQ ID NO:37). A cell expressing such a LAG-3 DN form should lack the ability or have reduced ability to signal in a LAG-3 immune checkpoint pathway. In one embodiment, a LAG-3 DN form is a deletion mutant having a deletion of the intracellular domain, for example, amino acids 472 to 525 of LAG-3 (GenBank NP_002277.4; SEQ ID NO:37), or a portion thereof, such that intracellular signaling of the immune checkpoint pathway mediated by LAG-3 is reduced or inhibited.

TIGIT.

T-cell immunoreceptor with Ig and ITIM domains (TIGIT) is a cell surface protein that suppresses T-cell activation. It belongs to the poliovirus receptor (PVR) family of immunoglobulin (Ig) proteins that share 3 conserved sequence motifs in their N-terminal Ig domains. A TIGIT polypeptide can have an amino acid sequence cor-

```
                                                (NP_002277.4; SEQ ID NO: 37)
  1 MWEAQFLGLL FLQPLWVAPV KPLQPGAEVP VVWAQEGAPA QLPCSPTIPL QDLSLLRRAG

61 VTWQHQPDSG PPAAAPGHPL APGPHPAAPS SWGPRPRRYT VLSVGPGGLR SGRLPLQPRV

121 QLDERGRQRG DFSLWLRPAR RADAGEYRAA VHLRDRALSC RLRLRLGQAS MTASPPGSLR

181 ASDWVILNCS FSRPDRPASV HWFRNRGQGR VPVRESPHHH LAESFLFLPQ VSPMDSGPWG

241 CILTYRDGFN VSIMYNLTVL GLEPPTPLTV YAGAGSRVGL PCRLPAGVGT RSFLTAKWTP

301 PGGGPDLLVT GDNGDFTLRL EDVSQAQAGT YTCHIHLQEQ QLNATVTLAI ITVTPKSFGS

361 PGSLGKLLCE VTPVSGQERF VWSSLDTPSQ RSFSGPWLEA QEAQLLSQPW QCQLYQGERL

421 LGAAVYFTEL SSPGAQRSGR APGALPAGHL LLFLILGVLS LLLLVTGAFG FHLWRRQWRP

481 RRFSALEQGI HPPQAQSKIE ELEQEPEPEP EPEPEPEPEP EPEQL
``` responding to GenBank No. NP_776160.2 (GI:256600228), sequence provided below, or fragments thereof. See GenBank NP_776160.2 for reference to domains within TIGIT, for example, signal peptide, amino acids 1 to 21; extracellular domain, amino acids 22 to 141; transmembrane domain, amino acids 142 to 162; intracellular domain, amino acids 163 to 244. It is understood that a "TIGIT nucleic acid molecule" refers to a polynucleotide encoding a TIGIT polypeptide.

```
                                        (NP_776160.2; SEQ ID NO: 38)
 1 MRWCLLLIWA QGLRQAPLAS GMMTGTIETT GNISAEKGGS IILQCHLSST TAQVTQVNWE

61 QQDQLLAICN ADLGWHISPS FKDRVAPGPG LGLTLQSLTV NDTGEYFCIY HTYPDGTYTG
```

```
121 RIFLEVLESS VAEHGARFQI PLLGAMAATL VVICTAVIVV VALTRKKKAL RIHSVEGDLR

181 RKSAGQEEWS PSAPSPPGSC VQAEAAPAGL CGEQRGEDCA ELHDYFNVLS YRSLGNCSFF

241 TETG
```

In one embodiment, the invention provides a TIGIT DN form. In one embodiment, the TIGIT DN form comprises the extracellular ligand binding domain of TIGIT. In one embodiment, the TIGIT DN form comprises the extracellular ligand binding domain of TIGIT and a transmembrane domain (e.g., mature form). In another embodiment, the TIGIT DN form comprises the extracellular ligand binding domain of TIGIT, a transmembrane domain and a signal peptide (e.g., precursor form). The invention also provides encoding polypeptides and nucleic acids of the TIGIT DN forms of the invention. In a particular embodiment, the TIGIT extracellular ligand binding domain is fused to one or more heterologous polypeptide sequences, that is, the TIGIT DN form is chimeric. For example, the TIGIT extracellular ligand binding domain can be fused at its N-terminus to a signal peptide that is optionally a heterologous signal peptide, including various signal peptides described herein. In addition, a TIGIT DN form can comprise a transmembrane domain that is optionally a heterologous transmembrane domain, including any of various transmembrane domains described herein.

In an embodiment of the invention, the TIGIT DN form can comprise the extracellular domain, or a ligand binding portion thereof, of TIGIT, for example, amino acids 22 to 141 corresponding to the extracellular domain of TIGIT (GenBank NP_776160.2; SEQ ID NO:38). A cell expressing such a TIGIT DN form should lack the ability or have reduced ability to signal in a TIGIT immune checkpoint pathway. In one embodiment, a TIGIT DN form is a deletion mutant having a deletion of the intracellular domain, for example, amino acids 163 to 244 of TIGIT (GenBank NP_776160.2; SEQ ID NO:38), or a portion thereof, such that intracellular signaling of the immune checkpoint pathway mediated by TIGIT is reduced or inhibited.

LAIR1.

Leukocyte-associated immunoglobulin-like receptor 1 (LAIR1) is an inhibitory receptor that plays a constitutive negative regulatory role on cytolytic function of natural killer (NK) cells, B-cells and T-cells. LAIR exists in various isoforms. It is understood that any isoform can be selected to achieve a desired function. Exemplary isoforms include isoform a (NP_002278.2, GI:612407859), isoform b (NP_068352.2, GI:612407861), isoform c (NP_001275952.2, GI:612407867), isoform e (NP_001275954.2, GI:612407869), isoform f (NP_001275955.2, GI:612407863), isoform g (NP_001275956.2, GI:612407865), and the like. One exemplary isoform sequence, isoform a, is provided below. In one embodiment, a LAIR1 polypeptide can have an amino acid sequence corresponding to NP_002278.2, sequence provided below, or fragments thereof. See GenBank NP_002278.2 for reference to domains within LAIR1, for example, signal peptide, amino acids 1 to 21; extracellular domain, amino acids 22 to 165; transmembrane domain, amino acids 166 to 186; intracellular domain, amino acids 187 to 287. It is understood that a "LAIR1 nucleic acid molecule" refers to a polynucleotide encoding a LAIR1 polypeptide.

```
                                            (NP_002278.2; SEQ ID NO: 39)
  1 MSPHPTALLG LVLCLAQTIH TQEEDLPRPS ISAEPGTVIP LGSHVTFVCR GPVGVQTFRL

61 ERDSRSTYND TEDVSQASPS ESEARFRIDS VREGNAGLYR CIYYKPPKWS EQSDYLELLV

121 KESSGGPDSP DTEPGSSAGP TQRPSDNSHN EHAPASQGLK AEHLYILIGV SVVFLFCLLL

181 LVLFCLHRQN QIKQGPPRSK DEEQKPQQRP DLAVDVLERT ADKATVNGLP EKDRETDTSA

241 LAAGSSQEVT YAQLDHWALT QRTARAVSPQ STKPMAESIT YAAVARH
```

In one embodiment, the invention provides a LAIR1 DN form. In one embodiment, the LAIR1 DN form comprises the extracellular ligand binding domain of LAIR1. In one embodiment, the LAIR1 DN form comprises the extracellular ligand binding domain of LAIR1 and a transmembrane domain (e.g., mature form). In another embodiment, the LAIR1 DN form comprises the extracellular ligand binding domain of LAIR1, a transmembrane domain and a signal peptide (e.g., precursor form). The invention also provides encoding polypeptides and nucleic acids of the LAIR1 DN forms of the invention. In a particular embodiment, the LAIR1 extracellular ligand binding domain is fused to one or more heterologous polypeptide sequences, that is, the LAIR1 DN form is chimeric. For example, the LAIR1 extracellular ligand binding domain can be fused at its N-terminus to a signal peptide that is optionally a heterologous signal peptide, including various signal peptides described herein. In addition, a LAIR1 DN form can comprise a transmembrane domain that is optionally a heterologous transmembrane domain, including any of various transmembrane domains described herein.

In an embodiment of the invention, the LAIR1 DN form can comprise the extracellular domain, or a ligand binding portion thereof, of LAIR1, for example, amino acids 22 to 165 corresponding to the extracellular domain of LAIR1 (GenBank NP_002278.2; SEQ ID NO:39). A cell expressing such a LAIR1 DN form should lack the ability or have reduced ability to signal in a LAIR1 immune checkpoint pathway. In one embodiment, a LAIR1 DN form is a deletion mutant having a deletion of the intracellular domain, for example, amino acids 187 to 287 of LAIR1 (GenBank NP_002278.2; SEQ ID NO:39), or a portion thereof, such that intracellular signaling of the immune checkpoint pathway mediated by LAIR1 is reduced or inhibited.

2B4.

Natural Killer Cell Receptor 2B4 (2B4) mediates non-MHC restricted cell killing on NK cells and subsets of T cells. The 2B4-S isoform is believed to be an activating receptor, and the 2B4-L isoform is believed to be a negative immune regulator of immune cells. 2B4 becomes engaged upon binding its high-affinity ligand, CD48. 2B4 contains a tyrosine-based switch motif, a molecular switch that allows the protein to associate with various phosphatases. 2B4 has also been designated CD244 (cluster of differentiation 244).

A 2B4 polypeptide can have an amino acid sequence corresponding to GenBank No. NP_001160135.1 (GI: 262263435), sequence provided below, or fragments thereof. See GenBank NP_001160135.1 for reference to domains within 2B4, for example, signal peptide, amino acids 1 to 18; extracellular domain, amino acids 19 to 229; transmembrane domain, amino acids 230 to 250; intracellular domain, amino acids 251 to 370. It is understood that a "2B4 nucleic acid molecule" refers to a polynucleotide encoding a 2B4 polypeptide.

portion thereof, of 2B4, for example, amino acids 19 to 229 corresponding to the extracellular domain of 2B4 (GenBank NP_001160135.1; SEQ ID NO:40). A cell expressing such a 2B4 DN form should lack the ability or have reduced ability to signal in a 2B4 immune checkpoint pathway. In one embodiment, a 2B4 DN form is a deletion mutant having a deletion of the intracellular domain, for example, amino acids 251 to 370 of 2B4 (GenBank NP_001160135.1; SEQ ID NO:40), or a portion thereof, such that intracellular signaling of the immune checkpoint pathway mediated by 2B4 is reduced or inhibited.

CD160.

CD160 is a glycosylphosphatidylinositol-anchored molecule containing a single IgV-like domain that binds to HVEM and functions as a co-inhibitory receptor on T cells. A CD160 polypeptide can have an amino acid sequence corresponding to GenBank NP_008984.1 (GI:5901910),

```
                                                (NP_001160135.1; SEQ ID NO: 40)
  1 MLGQVVTLIL LLLLKVYQGK GCQGSADHVV SISGVPLQLQ PNSIQTKVDS IAWKKLLPSQ

61 NGFHHILKWE NGSLPSNTSN DRFSFIVKNL SLLIKAAQQQ DSGLYCLEVT SISGKVQTAT

121 FQVFVFESLL PDKVEKPRLQ GQGKILDRGR CQVALSCLVS RDGNVSYAWY RGSKLIQTAG

181 NLTYLDEEVD INGTHTYTCN VSNPVSWESH TLNLTQDCQN AHQEFRFWPF LVIIVILSAL

241 FLGTLACFCV WRRKRKEKQS ETSPKEFLTI YEDVKDLKTR RNHEQEQTFP GGGSTIYSMI

301 QSQSSAPTSQ EPAYTLYSLI QPSRKSGSRK RNHSPSFNST IYEVIGKSQP KAQNPARLSR

361 KELENFDVYS
```

In one embodiment, the invention provides a 2B4 DN form. In one embodiment, the 2B4 DN form comprises the extracellular ligand binding domain of 2B4. In one embodiment, the 2B4 DN form comprises the extracellular ligand binding domain of 2B4 and a transmembrane domain (e.g., mature form). In another embodiment, the 2B4 DN form comprises the extracellular ligand binding domain of 2B4, a transmembrane domain and a signal peptide (e.g., precursor form). The invention also provides encoding polypeptides and nucleic acids of the 2B4 DN forms of the invention. In a particular embodiment, the 2B4 extracellular ligand binding domain is fused to one or more heterologous polypeptide sequences, that is, the 2B4 DN form is chimeric. For example, the 2B4 extracellular ligand binding domain can be fused at its N-terminus to a signal peptide that is optionally a heterologous signal peptide, including various signal peptides described herein. In addition, a 2B4 DN form can comprise a transmembrane domain that is optionally a heterologous transmembrane domain, including any of various transmembrane domains described herein.

In an embodiment of the invention, the 2B4 DN form can comprise the extracellular domain, or a ligand binding sequence provided below, or fragments thereof. See GenBank NP_008984.1 for reference to domains within CD160, for example, signal peptide, amino acids 1 to 26; extracellular domain, amino acids 27 to 159. It is understood that a "CD160 nucleic acid molecule" refers to a polynucleotide encoding a CD160 polypeptide.

```
                                                (NP_008984.1; SEQ ID NO: 41)
  1 MLLEPGRGCC ALAILLAIVD IQSGGCINIT SSASQEGTRL NLICTVWHKK EEAEGFVVFL

61 CKDRSGDCSP ETSLKQLRLK RDPGIDGVGE ISSQLMFTIS QVTPLHSGTY QCCARSQKSG

121 IRLQGHFFSI LFTETGNYTV TGLKQRQHLE FSHNEGTLSS GFLQEKVWVM LVTSLVALQA

181 L
```

In one embodiment, the invention provides a CD160 DN form. In one embodiment, the CD160 DN form comprises the extracellular ligand binding domain of CD160. In one embodiment, the CD160 DN form comprises the extracellular ligand binding domain of CD160 and a transmembrane domain (e.g., mature form). In another embodiment, the CD160 DN form comprises the extracellular ligand binding domain of CD160, a transmembrane domain and a signal peptide (e.g., precursor form). The invention also provides encoding polypeptides and nucleic acids of the CD160 DN forms of the invention. In a particular embodiment, the CD160 extracellular ligand binding domain is fused to one or more heterologous polypeptide sequences, that is, the CD160 DN form is chimeric. For example, the CD160 extracellular ligand binding domain can be fused at its N-terminus to a signal peptide that is optionally a heterologous signal peptide, including various signal peptides described herein. In addition, a CD160 DN form can comprise a transmembrane domain that is a heterologous transmembrane domain, including any of various transmembrane domains described herein.

In an embodiment of the invention, the CD160 DN form can comprise the extracellular domain, or a ligand binding portion thereof, of CD160, for example, amino acids 27 to 159 corresponding to the extracellular domain of CD160 (GenBank NP_008984.1; SEQ ID NO:41). A cell expressing such a CD160 DN form should lack the ability or have reduced ability to signal in an immune checkpoint pathway. In one embodiment, the CD160 DN form comprises the extracellular domain of CD160, or a ligand binding portion thereof, and a transmembrane domain derived from a heterologous polypeptide, including but not limited to one of the transmembrane domains described herein. In one non-limiting embodiment, the CD160 DN form comprises the transmembrane domain of CD8. In a cell expressing the CD160 DN form, intracellular signaling of the immune checkpoint pathway mediated by CD160 should be reduced or inhibited.

TGF-β Receptor Type 2.

TGF-β receptor type 2 binds to TGF-β and a type I receptor dimer forming a heterotetrameric complex with the ligand. A TGF-β receptor type 2 polypeptide can have an amino acid sequence corresponding to GenBank No. NP_001020018.1 (GI:67782326), sequence provided below, or fragments thereof. See GenBank NP_001020018.1 for reference to domains within TGF-β receptor type 2, for example, signal peptide, amino acids 1 to 22; extracellular domain, amino acids 23 to 191; transmembrane domain, amino acids 192 to 212; intracellular domain, amino acids 213 to 592 (see also annotation in UniProtKB—P37173). It is understood that a "TGF-β receptor type 2 nucleic acid molecule" refers to a polynucleotide encoding a TGF-β receptor type 2 polypeptide.

receptor extracellular ligand binding domain is fused to one or more heterologous polypeptide sequences, that is, the TGFβ receptor DN form is chimeric. For example, the TGFβ receptor extracellular ligand binding domain can be fused at its N-terminus to a signal peptide that is optionally a heterologous signal peptide, including various signal peptides described herein. In addition, a TGFβ receptor DN form can comprise a transmembrane domain that is a heterologous transmembrane domain, including any of various transmembrane domains described herein.

TGFβ receptor DN forms have been described previously (see, for example, Bottinger et al., *EMBO J.* 16:2621-2633 (1997), describing a DN form comprising TGFβ receptor extracellular and transmembrane domains; Foster et al., *I Immunother.* 31:500-505 (2008); Bollard et al., *Blood* 99:3179-3187 (2002); Wieser et al., *Mol. Cell. Biol.* 13:7239-7247 (1993)). In an embodiment of the invention, the TGFβ receptor DN form can comprise the extracellular domain, or a ligand binding portion thereof, of TGFβ receptor, for example, amino acids 23 to 191 corresponding to the extracellular domain of TGFβ receptor (GenBank NP_001020018.1, SEQ ID NO:42). A cell expressing such a TGFβ receptor DN form lacks the ability or has reduced ability to signal in the cell. In one embodiment, a TGFβ receptor DN form is a deletion mutant having a deletion of the intracellular domain, for example, amino acids 213 to 592 of TGFβ receptor (GenBank NP_001020018.1, SEQ ID NO:42), or a portion thereof, such that intracellular signaling of mediated by TGFβ receptor is reduced or inhibited (see also Bottinger et al., *EMBO 1* 16:2621-2633 (1997); Foster et al., *I Immunother.* 31:500-505 (2008); Bollard et al., *Blood* 99:3179-3187 (2002); Wieser et al., *Mol. Cell. Biol.* 13:7239-7247 (1993)).

It is understood that, optionally, a second DN form of an inhibitor of a cell-mediated immune response, such as an immune checkpoint inhibitor, can be expressed in a cell of

```
                                                     (NP_001020018.1, SEQ ID NO: 42)
   1 MGRGLLRGLW PLHIVLWTRI ASTIPPHVQK SDVEMEAQKD EIICPSCNRT AHPLRHINND

61 MIVTDNNGAV KFPQLCKFCD VRFSTCDNQK SCMSNCSITS ICEKPQEVCV AVWRKNDENI

121 TLETVCHDPK LPYHDFILED AASPKCIMKE KKKPGETFFM CSCSSDECND NIIFSEEYNT

181 SNPDLLLVIF QVTGISLLPP LGVAISVIII FYCYRVNRQQ KLSSTWETGK TRKLMEFSEH

241 CAIILEDDRS DISSTCANNI NHNTELLPIE LDTLVGKGRF AEVYKAKLKQ NTSEQFETVA

301 VKIFPYEEYA SWKTEKDIFS DINLKHENIL QFLTAEERKT ELGKQYWLIT AFHAKGNLQE

361 YLTRHVISWE DLRKLGSSLA RGIAHLHSDH TPCGRPKMPI VHRDLKSSNI LVKNDLTCCL

421 CDFGLSLRLD PTLSVDDLAN SGQVGTARYM APEVLESRMN LENVESFKQT DVYSMALVLW

481 EMTSRCNAVG EVKDYEPPFG SKVREHPCVE SMKDNVLRDR GRPEIPSFWL NHQGIQMVCE

541 TLTECWDHDP EARLTAQCVA ERFSELEHLD RLSGRSCSEE KIPEDGSLNT TK
```

In one embodiment, the invention provides a TGFβ receptor DN form. In one embodiment, the TGFβ receptor DN form comprises the extracellular ligand binding domain of TGFβ receptor. In one embodiment, the TGFβ receptor DN form comprises the extracellular ligand binding domain of TGFβ receptor and a transmembrane domain (e.g., mature form). In another embodiment, the TGFβ receptor DN form comprises the extracellular ligand binding domain of TGFβ receptor, a transmembrane domain and a signal peptide (e.g., precursor form). The invention also provides encoding polypeptides and nucleic acids of the TGF-β receptor DN forms of the invention. In a particular embodiment, the TGFβ the invention. In this case, it can be desirable to inhibit more than one cell-mediated immune response in the same cell. Thus, a cell can express two or more DN forms, each directed to a different inhibitor of a cell-mediated immune response, including those described above. For example, a DN form of PD-1 can be co-expressed in a cell with a DN form of TGF-β receptor, a DN form of PD-1 can be co-expressed with a DN form of CTLA-4, a CTLA-4 DN form can be co-expressed with a DN form of TGF-β, and so forth, as desired, including combinations of any of the DN forms described above In addition to immune cells or precursor cells thereof, the invention also provides a cell comprising a DN form polypeptide. The invention additionally provides a cell comprising a nucleic acid of the invention, which encodes a DN form polypeptide of the invention. Further provided is a cell comprising the vector of the invention. The cells of the invention can express a DN form of the invention, or an encoding nucleic acid.

Additionally provided are recombinant cells expressing polypeptides, nucleic acids and/or vectors of the invention. Such a recombinant cell can be an immune cell, such as a T cell, or a precursor cell thereof, that is used to express a cancer antigen CAR and/or a DN form of the invention. Such recombinant immune cells are described in more detail above. Recombinant cells can be used for genetic manipulations prior to transduction of the immune cells or precursor cells thereof to be used therapeutically, such as generating constructs of the polypeptides and encoding nucleic acids of the invention, and/or for generating nucleic acid material for incorporation into a vector for expression in an immune cell. Such cells can include, but are not limited to, bacterial cells, in particular *Escherichia coli*, yeast cells, such as *Saccharomyces cerevisiae, Pichia pastoris*, and the like. Such recombinant cells can be used to produce polypeptides and/or encoding nucleic acids of the invention encoding a DN form, which can be isolated or purified, if desired, from said cells using routine molecular biology and protein purification techniques.

6.4. Methods of Treatment

The invention also relates to methods of treating cancer using the cells of the invention. In one embodiment, the methods can include administering an immune cell, or precursor cell thereof, expressing a cancer antigen CAR and a DN form of an inhibitor of a cell-mediated immune response. The cancer antigen is chosen to target a cancer of the subject. In another embodiment, the methods can include administering a cancer-antigen specific immune cell, such as a T cell, or precursor cell thereof, where the cell recombinantly expresses a DN form of an inhibitor of a cell-mediated immune response.

The invention relates to various methods of using the immune cells, for example, T cells, or precursor cells thereof, expressing a DN form of an inhibitor of a cell-mediated immune response, or expressing a cancer antigen-specific CAR and a DN form of an inhibitor of a cell-mediated immune response. The cells are administered as a population of cells expressing a DN form or expressing a cancer antigen-specific CAR and a DN form. Optionally, the cells to be administered can be purified or enriched for the cells of the invention. For example, the methods of the invention can be used to treat cancer or reduce tumor burden in a subject. In one embodiment, the methods of the invention are used to treat cancer. It is understood that a method of treating cancer can include any effect that ameliorates a sign or symptom associated with cancer. Such signs or symptoms include, but are not limited to, reducing tumor burden, including inhibiting growth of a tumor, slowing the growth rate of a tumor, reducing the size of a tumor, reducing the number of tumors, eliminating a tumor, all of which can be measured using routine tumor imaging techniques well known in the art. Other signs or symptoms associated with cancer include, but are not limited to, fatigue, pain, weight loss, and other signs or symptoms associated with various cancers. In one non-limiting example, the methods of the invention can reduce tumor burden. Thus, administration of the cells of the invention can reduce the number of tumor cells, reduce tumor size, and/or eradicate the tumor in the subject. The tumor can be a solid tumor. Non-limiting examples of a solid tumor include mesothelioma, lung cancer, pancreatic cancer, ovarian cancer, breast cancer, colon cancer, pleural tumor, glioblastoma, esophageal cancer, gastric cancer, and synovial sarcoma. The methods of the invention can also provide for increased or lengthened survival of a subject having cancer. Additionally, methods of the invention can provide for an increased immune response in the subject against the cancer.

In the methods of the invention, the immune cells or precursor cells thereof are administered to a subject in need of cancer treatment. The subject can be a mammal, in particular a human. Preferably, the subject is a human. Suitable human subjects for therapy include those with "advanced disease" or "high tumor burden" who bear a clinically measurable tumor. A clinically measurable tumor is one that can be detected on the basis of tumor mass, for example, by palpation, CAT scan, sonogram, mammogram, X-ray, and the like. Positive biochemical or histopathologic markers can also be used to identify this population. A pharmaceutical composition comprising a cell of the invention is administered to a subject to elicit an anti-cancer response, with the objective of palliating the subject's condition. Reduction in tumor mass of a subject having a tumor can occur, but any clinical improvement constitutes a benefit. Clinical improvement comprises decreased risk or rate of progression or reduction in pathological consequences of the tumor.

Another group of suitable subjects can be a subject who has a history of cancer, but has been responsive to another mode of therapy. The prior therapy can have included, but is not restricted to, surgical resection, radiotherapy, and traditional chemotherapy. As a result, these individuals have no clinically measurable tumor. However, they are suspected of being at risk for progression of the disease, either near the original tumor site, or by metastases. This group can be further subdivided into high-risk and low-risk individuals. The subdivision is made on the basis of features observed before or after the initial treatment. These features are known in the clinical arts, and are suitably defined for different types of cancers. Features typical of high-risk subgroups are those in which the tumor has invaded neighboring tissues, or who show involvement of lymph nodes. Optionally, a cell of the invention can be administered for treatment prophylactically to prevent the occurrence of cancer in a subject suspected of having a predisposition to a cancer, for example, based on family history and/or genetic testing.

The subject can have an advanced form of disease, in which case the treatment objective can include mitigation or reversal of disease progression, and/or amelioration of side effects. The subjects can have a history of the condition, for which they have already been treated, in which case the therapeutic objective can be to decrease or delay the risk of recurrence. Additionally, refractory or recurrent malignancies can be treated using the cells of the invention.

The cells of the invention are administered to a subject, such as a human subject, in need of cancer treatment. The cancer can involve a solid tumor or a blood cancer not involving a solid tumor. Cancers to be treated using the cells of the invention comprise cancers typically responsive to immunotherapy. Exemplary types of cancers include, but are not limited to, carcinomas, sarcoma, leukemia, lymphoma, multiple myeloma, melanoma, brain and spinal cord tumors, germ cell tumors, neuroendocrine tumors, carcinoid tumors, and the like. The cancer can be a solid tumor or a blood cancer that does not form a solid tumor. In the case of a solid tumor, the tumor can be a primary tumor or a metastatic tumor.

Examples of other neoplasias or cancers that can be treated using the methods of the invention include bone cancer, intestinal cancer, liver cancer, skin cancer, cancer of the head or neck, melanoma (cutaneous or intraocular malignant melanoma), renal cancer (for example, clear cell carcinoma), throat cancer, prostate cancer (for example, hormone refractory prostate adenocarcinoma), blood cancers (for example, leukemias, lymphomas, and myelomas), uterine cancer, rectal cancer, cancer of the anal region, bladder cancer, brain cancer, stomach cancer, testicular cancer, carcinoma of the fallopian tubes, carcinoma of the endometrium, carcinoma of the cervix, carcinoma of the vagina, carcinoma of the vulva, leukemias (for example, acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (Hodgkin's disease, non-Hodgkin's disease, Waldenstrom's macroglobulinemia), cancer of the small intestine, cancer of the endocrine system, cancer of the thyroid gland, cancer of the parathyroid gland, cancer of the adrenal gland, sarcoma of soft tissue, cancer of the urethra, cancer of the penis, solid tumors of childhood, lymphocytic lymphoma, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, heavy chain disease, and solid tumors such as sarcomas and carcinomas, for example, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, hepatoma, bile duct carcinoma, choriocarcinoma, seminoma, embryonal carcinoma, Wilm's tumor, cervical cancer, uterine cancer, testicular cancer, bladder carcinoma, epithelial carcinoma, glioma, astrocytoma, medulloblastoma, craniopharyngioma, ependymoma, pinealoma, hemangioblastoma, acoustic neuroma, oligodenroglioma, schwannoma, meningioma, melanoma, neuroblastoma, and retinoblastoma.

In one embodiment, the methods of the invention are used to treat a cancer selected from malignant pleural disease, mesothelioma, lung cancer (for example, non-small cell lung cancer), pancreatic cancer, ovarian cancer, breast cancer (for example, metastatic breast cancer, metastatic triple-negative breast cancer), colon cancer, pleural tumor, glioblastoma, esophageal cancer, gastric cancer, and synovial sarcoma. The invention provides therapies that are particularly useful for treating solid tumors, for example, malignant pleural disease, mesothelioma, lung cancer, pancreatic cancer, ovarian cancer, breast cancer, colon cancer, pleural tumor, glioblastoma, esophageal cancer, gastric cancer, and synovial sarcoma. Solid tumors can be primary tumors or tumors in a metastatic state. In the case of a mesothelin directed CAR, mesothelin expressing tumors, include, for example, breast cancer, lung cancer, ovarian cancer, pancreatic cancer, esophagus cancer, colon cancer, gastric cancer, and malignant pleural mesothelioma (MPM).

In a specific embodiment, the cells recombinantly expressing a CAR and DN form that are administered to the subject comprise both $CD4^+$ and $CD8^+$ T cells, with the aim of generating both helper and cytotoxic T lymphocyte (CTL) responses in the subject.

For treatment, the amount administered is an amount effective for producing the desired effect. An effective amount or therapeutically effective amount is an amount sufficient to provide a beneficial or desired clinical result upon treatment. An effective amount can be provided in a single administration or a series of administrations (one or more doses). An effective amount can be provided in a bolus or by continuous perfusion. In terms of treatment, an effective amount is an amount that is sufficient to palliate, ameliorate, stabilize, reverse or slow the progression of the disease, or otherwise reduce the pathological consequences of the disease. The effective amount can be determined by the physician for a particular subject. Several factors are typically taken into account when determining an appropriate dosage to achieve an effective amount. These factors include age, sex and weight of the subject, the condition being treated, the severity of the condition and the form and effective concentration of the cells of the invention being administered.

The cells of the invention are generally administered as a dose based on cells per kilogram (cells/kg) of body weight of the subject to which the cells are administered. Generally the cell doses are in the range of about $10^4$ to about $10^{10}$ cells/kg of body weight, for example, about $10^5$ to about $10^9$, about $10^5$ to about $10^8$, about $10^5$ to about $10^7$, or about $10^5$ to $10^6$, depending on the mode and location of administration. In general, in the case of systemic administration, a higher dose is used than in regional administration, where the immune cells of the invention are administered in the region of a tumor. Exemplary dose ranges include, but are not limited to, $1\times10^4$ to $1\times10^8$, $2\times10^4$ to $1\times10^8$, $3\times10^4$ to $1\times10^8$, $4\times10^4$ to $1\times10^8$, $5\times10^4$ to $1\times10^8$, $6\times10^4$, to $1\times10^8$, $7\times10^4$ to $1\times10^8$, $8\times10^4$ to $1\times10^8$, $9\times10^4$ to $1\times10^8$, $1\times10^5$ to $1\times10^8$, for example, $1\times10^5$ to $9\times10^7$, $1\times10^5$ to $8\times10^7$, $1\times10^5$ to $7\times10^7$, $1\times10^5$ to $6\times10^7$, $1\times10^5$ to $5\times10^7$, $1\times10^5$ to $4\times10^7$, $1\times10^5$ to $3\times10^7$, $1\times10^5$ to $2\times10^7$, $1\times10^5$ to $1\times10^7$, $1\times10^5$ to $9\times10^6$, $1\times10^5$ to $8\times10^6$, $1\times10^5$ to $7\times10^6$, $1\times10^5$ to $6\times10^6$, $1\times10^5$ to $5\times10^6$, $1\times10^5$ to $4\times10^6$, $1\times10^5$ to $3\times10^6$, $1\times10^5$ to $2\times10^6$, $1\times10^5$ to $1\times10^6$, $2\times10^5$ to $9\times10^7$, $2\times10^5$ to $8\times10^7$, $2\times10^5$ to $7\times10^7$, $2\times10^5$ to $6\times10^7$, $2\times10^5$ to $5\times10^7$, $2\times10^5$ to $4\times10^7$, $2\times10^5$ to $3\times10^7$, $2\times10^5$ to $2\times10^7$, $2\times10^5$ to $1\times10^7$, $2\times10^5$ to $9\times10^6$, $2\times10^5$ to $8\times10^6$, $2\times10^5$ to $7\times10^6$, $2\times10^5$ to $6\times10^6$, $2\times10^5$ to $5\times10^6$, $2\times10^5$ to $4\times10^6$, $3\times10^5$ to $3\times10^6$ cells/kg, and the like. Such dose ranges can be particularly useful for regional administration. In a particular embodiment, cells are provided in a dose of $1\times10^5$ to $1\times10^8$, for example $1\times10^5$ to $1\times10^7$, $1\times10^5$ to $1\times10^6$, $1\times10^6$ to $1\times10^8$, $1\times10^6$ to $1\times10^7$, $1\times10^7$ to $1\times10^8$, $1\times10^5$ to $5\times10^6$, in particular $1\times10^5$ to $3\times10^6$ or $3\times10^5$ to $3\times10^6$ cells/kg for regional administration, for example, intrapleural administration. Exemplary dose ranges also can include, but are not limited to, $5\times10^5$ to $1\times10^8$, for example, $6\times10^5$ to $1\times10^8$, $7\times10^5$ to $1\times10^8$, $8\times10^5$ to $1\times10^8$, $9\times10^5$ to $1\times10^8$, $1\times10^6$ to $1\times10^8$, $1\times10^6$ to $9\times10^7$, $1\times10^6$ to $8\times10^7$, $1\times10^6$ to $7\times10^7$, $1\times10^6$ to $6\times10^7$, $1\times10^6$ to $5\times10^7$, $1\times10^6$ to $4\times10^7$, $1\times10^6$ to $3\times10^7$ cells/kg, and the like. Such does can be particularly useful for systemic administration. In a particular embodiment, cells are provided in a dose of $1\times10^6$ to $3\times10^7$ cells/kg for systemic administration. Exemplary cell doses include, but are not limited to, a dose of $1\times10^4$, $2\times10^4$, $3\times10^4$, $4\times10^4$, $5\times10^4$, $6\times10^4$, $7\times10^4$, $8\times10^4$, $9\times10^4$, $1\times10^5$, $2\times10^5$, $3\times10^5$, $4\times10^5$, $5\times10^5$, $6\times10^5$, $7\times10^5$, $8\times10^5$, $9\times10^5$, $1\times10^6$, $2\times10^6$, $3\times10^6$, $4\times10^6$, $5\times10^6$, $6\times10^6$, $7\times10^6$, $8\times10^6$, $9\times10^7$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$ and so forth in the range of about $10^4$ to about $10^{10}$ cells/kg. In addition, the dose can also be adjusted to account for whether a single dose is being administered or whether multiple doses are being administered. The precise determination of what would be considered an effective dose can be based on factors individual to each subject, including their size, age, sex, weight, and condition of the particular subject, as described above. Dosages can be readily determined by those skilled in the art based on the disclosure herein and knowledge in the art.

The cells of the invention can be administered by any methods known in the art, including, but not limited to, pleural administration, intravenous administration, subcutaneous administration, intranodal administration, intratumoral administration, intrathecal administration, intrapleural administration, intraperitoneal administration, intracranial administration, and direct administration to the thymus. In one embodiment, the cells of the invention can be delivered regionally to a tumor using well known methods, including but not limited to, hepatic or aortic pump; limb, lung or liver perfusion; in the portal vein; through a venous shunt; in a cavity or in a vein that is nearby a tumor, and the like. In another embodiment, the cells of the invention can be administered systemically. In a preferred embodiment, the cells are administered regionally at the site of a tumor. The cells can also be administered intratumorally, for example, by direct injection of the cells at the site of a tumor and/or into the tumor vasculature. For example, in the case of malignant pleural disease, mesothelioma or lung cancer, administration is preferably by intrapleural administration (see Adusumilli et al., *Science Translational Medicine* 6(261):261ra151 (2014)). One skilled in the art can select a suitable mode of administration based on the type of cancer and/or location of a tumor to be treated. The cells can be introduced by injection or catheter. In one embodiment, the cells are pleurally administered to the subject in need, for example, using an intrapleural catheter. Optionally, expansion and/or differentiation agents can be administered to the subject prior to, during or after administration of cells to increase production of the cells of the invention in vivo.

Proliferation of the cells of the invention is generally done ex vivo, prior to administration to a subject, and can be desirable in vivo after administration to a subject (see Kaiser et al., *Cancer Gene Therapy* 22:72-78 (2015)). Cell proliferation should be accompanied by cell survival to permit cell expansion and persistence, such as with T cells.

The methods of the invention can further comprise adjuvant therapy in combination with, either prior to, during, or after treatment with the cells of the invention. Thus, the cell therapy methods of the invention can be used with other standard cancer care and/or therapies that are compatible with administration of the cells of the invention.

The methods of the invention relate to generating cancer-targeted immune cells, or precursor cells thereof, for adoptive therapy to enhance immune cell function through the design of improved antigen receptors and inclusion of cell intrinsic inhibition of immune checkpoint pathways, such as with co-expression of DN forms of an inhibitor of a cell-mediated immune response. Optionally, the methods of administering cells of the invention can additionally include immunomodulation of the host to facilitate the effectiveness of the administered cells of the invention in combination therapy. In an embodiment of the invention, the methods of the invention can further comprise administering at least one immunomodulatory agent. Non-limiting examples of immunomodulatory agents include immunostimulatory agents, checkpoint immune blockade agents, radiation therapy agents, and chemotherapy agents. In certain embodiments, the immunomodulatory agent is an immunostimulatory agent. In one embodiment, the immunostimulatory agent is a cytokine, including but not limited to, IL-2, IL-3, IL-6, IL-7, IL-11, IL-12, IL-15, IL-17, and IL-21. Other exemplary immunostimulatory agents include, but are not limited to, colony stimulating factors, such as G-, M- and GM-CSF, interferons, for example, γ-interferon, and the like. In one embodiment, the methods of the invention further comprise administering IL-2 or GM-CSF to the subject. In a specific embodiment, IL-2 is administered to the subject. The IL-2 or GM-CSF can be administered before, during or after cell therapy using cells of the invention (i.e., concurrently or sequentially), as desired. In a specific embodiment the cytokine (e.g., IL-2 or GM-CSF) is administered on the same day, or during the same week, or within 2 weeks, of the cell therapy using cells of the invention. In a particular embodiment, IL-2 is administered in a dose of about 50,000 to 800,000 international units (IU) per kilogram of body weight, for example, about 50,000 to 720,000, 50,000 to 500,000, 50,000 to 250,000, 50,000 to 200,000, 50,000 to 150,000, 50,000 to 100,000, or about 720,000 IU/kg (Robbins et al., *J. Clin. Oncol.* 29:917-924 (2011)). In a non-limiting embodiment, IL-2 is administered in a dose of about 50,000, 55,000, 60,000, 61,000, 62,000, 63,000, 64,000, 65,000, 66,000, 67,000, 68,000, 69,000, 70,000, 71,000, 72,000, 73,000, 74,000, 75,000, 76,000, 77,000, 78,000, 79,000, 80,000, 85,000, 90,000, 95,000, 100,000, 110,000, 120,000, 130,000, 140,000, 150,000, 160,000, 170,000, 180,000, 190,000, 200,000, 210,000, 220,000, 230,000, 240,000, 250,000, 260,000, 270,000, 280,000, 290,000, 300,000, 320,000, 340,000, 360,000, 380,000, 400,000, 420,000, 440,000, 460,000, 480,000, 500,000, 520,000, 540,000, 560,000, 580,000, 600,000, 620,000, 640,000, 660,000, 680,000, 700,000, 720,000, 740,000, 760,000, 780,000 or 800,000 IU/kg. Given the improved efficacy of immune cell therapy using cells of the invention expressing a CAR and DN form, it is expected that the doses of cytokines, such as IL-2, suitable as combination therapy with a cell of the invention can be lower than that used with other therapies using cytokines. Administering a cytokine, for example, IL-2 or GM-CSF, is particularly useful if the CAR expressed in the immune cell results in reduced expression of an immune cell stimulatory cytokine, such as IL-2 or GM-CSF. The cytokine can be administered to enhance the efficacy of the immune cells of the invention expressing the CAR and DN form. As described in the Example hereinafter, T cells expressing a PD-1 DN form and MBBz CAR, having 4-1BB as a co-stimulatory signaling domain, exhibit decreased expression of IL-2, whereas T cells expressing a PD-1 DN form and M28z CAR, having CD28 as a co-stimulatory signaling domain, have increased expression of IL-2 (see Example). Accordingly, the invention provides for treating cancer in a subject having cancer by administering to the subject T cells expressing a PD-1 DN form and a MBBz CAR, which CAR has 4-1BB as a co-stimulatory signaling domain, and administering to the subject IL-2. A person skilled in the art can readily assay an immune cell of the invention for expression of immunostimulatory cytokines and, if desired, optionally administer an immunostimulatory cytokine that is deficiently expressed by the cells to a subject being treated with the cells. Such a combination therapy including an immunostimulatory cytokine can be used to increase the efficacy of immune cell therapy using such cells, for example, cells expressing a DN form of an immune checkpoint inhibitor with reduced immunostimulatory cytokine production.

Additional immunostimulatory agents include agonist costimulatory monoclonal antibodies, such as anti-4-1BB antibodies, anti-OX40 antibodies, and anti-ICOS antibodies. In one embodiment, the agonist costimulatory monoclonal antibody is an anti-4-1BB antibody.

Among all immunotherapeutic approaches, IL-12, a multifunctional cytokine, has been considered to be one of the most promising approaches to treat breast cancer (Boggio et al., *Cancer Res.* 60:359-364 (2000); Czerniecki et al., *Cancer Res.* 67:1842-1852 (2007); Nanni et al., *J. Exp. Med.* 194:1195-1205 (2001)). IL-12 is considered a master regulator of adaptive type 1 cell-mediated immunity, the critical pathway involved in antitumor responses (Del Vecchio et al., *Clin. Cancer Res.* 13:4677-4685 (2007)). IL-12 modulates antitumor responses at various levels, including polarization of CD4 T cells toward a Th1 phenotype (Wesa et al., *J. Immunother.* 30, 75-82 (2007)), boosting of T cell and NK effector functions (Curtsinger et al., *J. Exp. Med.* 197:1141-1151 (2003)), remodeling the innate immune response (Chmielewski et al., *Cancer Res.* 71:5697-5706 (2011)), and regulating tumor angiogenesis (Voest et al., *J. Natl. Cancer. Inst.* 87:581-586 (1995)). Among 148 clinical trials including administration of IL-12 to patients with cancer, successful phase II studies with intraperitoneal (Lenzi et al., *Clin. Cancer Res.* 8:3686-3695 (2002); Lenzi et al., *J. Transl. Med.* 5:66 (2007)) or subcutaneous (Mahvi et al., *Cancer Gene Ther.* 14:717-723 (2007); Kang et al., *Hum. Gene Ther.* 12:671-684 (2001)) IL-12 have shown that paracrine secretion of IL-12, generated by gene transfer, can induce immunity against the tumor locally and at a distant site. Although several studies have documented the anticancer effectiveness of IL-12 in preclinical models of breast cancer (Boggio et al., *Cancer Res.* 60:359-364 (2000); Nanni et al., *J. Exp. Med.* 194:1195-1205 (2001); Brunda et al., *J. Exp. Med.* 178:1223-1230 (1993)), the significant toxicity resulting from administration of recombinant human IL-12 observed in several clinical trials in advanced cancers precludes its clinical use. To overcome this limitation, a number of groups have demonstrated that intratumoral delivery of IL-12, using adenoviral vectors, induces tumor regression and T cell activation in preclinical models of breast cancer (Gyorffy et al., *J. Immunol.* 166:6212-6217 (2001); Bramson et al., *Hum. Gene Ther.* 7:1995-2002 (1996)). More recently, polylactic acid microspheres were used to release IL-12 into the tumor, and it was found that the antitumor response was mediated primarily by NK cells (Sabel et al., *Breast Cancer Res. Treat.* 122:325-336 (2010)). Others have used mesenchymal stromal cells to locally deliver IL-12 to mouse breast cancer (Eliopoulos et al., *Cancer Res.* 68, 4810-4818 (2008)). A phase I trial of paclitaxel and trastuzumab, in combination with IL-12, in patients with HER2/neu-expressing malignancies showed an impressive synergy between IL-12 and trastuzumab for stimulation of NK-cell cytokine secretion (Bekaii-Saab et al., *Mol. Cancer Ther.* 8:2983-2991 (2009)). Therefore, IL-12 is particularly useful as an anticancer agent to be used as a co-stimulant in an adoptive immune cell therapy approach, including the methods of the invention disclosed herein. The immunomodulating and antiangiogenic functions of IL-12 support the use of this cytokine in combination with a cell of the invention for treating cancers.

In another embodiment, the immunomodulatory agent is a co-stimulatory ligand. Co-stimulatory ligands include, without limitation, members of the tumor necrosis factor (TNF) superfamily, and immunoglobulin (Ig) superfamily ligands. TNF is a cytokine involved in systemic inflammation and stimulates the acute phase reaction. Its primary role is in the regulation of immune cells. Members of TNF superfamily share a number of common features. The majority of TNF superfamily members are synthesized as type II transmembrane proteins (extracellular C-terminus) containing a short cytoplasmic segment and a relatively long extracellular region. TNF superfamily members include, without limitation, nerve growth factor (NGF), CD40L/CD154, CD137L/4-1BBL, TNF-α, CD134L/OX40L/CD252, CD27L/CD70, Fas ligand (FasL), CD30L/CD153, tumor necrosis factor beta (TNFβ)/lymphotoxin-alpha (LTα), lymphotoxin-beta (LTβ), CD257/B cell-activating factor (BAFF)/Blys/THANK/Ta11-1, glucocorticoid-induced TNF Receptor ligand (GITRL), TNF-related apoptosis-inducing ligand (TRAIL), and LIGHT (TNFSF14). The immunoglobulin (Ig) superfamily is a large group of cell surface and soluble proteins that are involved in the recognition, binding, or adhesion processes of cells. These proteins share structural features with immunoglobulins, that is, they possess an immunoglobulin domain (fold). Immunoglobulin superfamily ligands include, without limitation, CD80 and CD86, both ligands for CD28. In some embodiments, the at least one co-stimulatory ligand is selected from the group consisting of 4-1BBL, CD80, CD86, CD70, OX40L, CD48, TNFRSF14, and the like.

In another embodiment, the immunomodulatory agent can be an immune checkpoint blockade agent. The administration of an immune checkpoint blockade agent supplements the inhibition of immune checkpoint blockade provided by expressing a DN form of an immune checkpoint inhibitor in a cell of the invention. Non-limiting examples of immune checkpoint blockade agents include anti-PD-L1 antibodies, anti-CTLA-4 antibodies, anti-PD-1 antibodies, anti-LAG3 antibodies, anti-B7-H3 antibodies, anti-TIM3 antibodies, and the like. Such immune checkpoint blockade agents include, but are not limited to, antibodies to PD-1, CTLA-4, BTLA, TIM-3, LAG-3, CD160, TIGIT, LAIR1, 2B4, and the like, or antibodies to the corresponding ligands for these receptors including, for example, PD-L1 (for PD-1); PD-L2 (for PD-1); CD80, CD86 (for CTLA-4); HVEM (for BTLA); Galectin-9, HMGB1 (for TIM-3); MHC II (for LAG-3); HVEM (for CD160); CD155, CD112, CD113 (for TIGIT); C1q, collagen (for LAIR1); CD48 (for 2B4), and the like. In one embodiment, the checkpoint immune blockade agent is an anti-PD-L1 antibody. It is understood that an antibody that inhibits the activity of an immune checkpoint inhibitor by binding to the immune checkpoint inhibitor receptor or its corresponding ligand, including receptors and ligands as disclosed herein, can be used as an immunomodulatory agent to further suppress the immunoinhibitory effect in an immune cell of the invention expressing a DN form. In a particular embodiment, the antibody will be to the immune checkpoint inhibitor, or its ligand, that corresponds to the DN form being expressed in the immune cell of the invention, which can be useful to further suppress any residual activity in the immune cell expressing the DN form. In certain embodiments, the methods of the invention can optionally include administration of an immune checkpoint blockade agent such as antibodies directed to the ligand and/or receptor of an immune checkpoint pathway.

In some embodiments, the immunomodulatory agent can be a radiation therapy agent. The localized, radiation-induced immunological milieu can provide the preconditions to enhance the engraftment of cells of the invention at the site of the tumor, thereby eliminating the need for systemic lymphodepleting regimens. The immunological responses resulting from a combination of radiation therapy, particularly low dose radiation therapy, and cell therapy methods of the invention also can enhance abscopal antitumor efficacy. In some embodiments, the immunomodulatory agent is a chemotherapy agent, including, but not limited to, cisplatin, cyclophosphamide, and the like. Cisplatin-induced secretion of chemokines and cytokines can promote cancer antigen-targeted cells of the invention and endogenous immune cell responses such as T-cell responses. Cyclophosphamide can function as a lymphodepleting agent, for example, as a preparatory lymphodepleting agent.

Tumor irradiation- and cisplatin therapy-induced tumoral and abscopal immunomodulation can provide the preconditioning required for better engraftment of cells f the invention. Co-stimulatory strategies, as described above, can potentiate the antitumor efficacy of both endogenous T cells and the cells of the invention.

In another embodiment, an immunomodulatory agent can be a "switch receptor." The methods of the invention can additionally include administering immune cells expressing a CAR and a "switch receptor." The switch receptor comprises at least a ligand binding domain of the extracellular region of an immune checkpoint inhibitor, fused to a transmembrane domain, fused to a cytoplasmic signaling domain (i.e., co-stimulatory domain) of an immunostimulatory molecule, thereby switching the activity upon ligand binding from immunoinhibitory to immunostimulatory (see e.g., Liu et al., Cancer Res. 76:1578-1590 (2016)). In one embodiment, the immune checkpoint inhibitor extracellular domain is derived from an immune checkpoint inhibitor including, but not limited to, programmed death 1 (PD-1), cytotoxic T lymphocyte antigen-4 (CTLA-4), B- and T-lymphocyte attenuator (BTLA), T cell immunoglobulin mucin-3 (TIM-3), lymphocyte-activation protein 3 (LAG-3), T cell immunoreceptor with Ig and ITIM domains (TIGIT), leukocyte-associated immunoglobulin-like receptor 1 (LAIR1), natural killer cell receptor 2B4 (2B4), and CD160. The ligand binding domains that can be used for generation of such a switch receptor include those ligand binding domains described above for generating a DN form of an immune checkpoint inhibitor. In the case of a switch receptor, a cytoplasmic signaling domain (i.e., co-stimulatory domain) is fused to the extracellular ligand binding domain of the immune checkpoint inhibitor via a transmembrane domain. A cytoplasmic signaling domain that is a co-stimulatory domain can be derived, for example, from a receptor such as the co-stimulatory molecules described herein for use in a CAR, including but not limited to a 4-1BB polypeptide, a CD28 polypeptide, an OX40 polypeptide, an ICOS polypeptide, a DAP10 polypeptide, and a 2B4 polypeptide. A switch receptor also includes a transmembrane domain, which can be derived from the polypeptide from which the co-stimulatory domain is derived, from the polypeptide from which the extracellular ligand binding domain of the immune checkpoint inhibitor is derived, or it can be a transmembrane domain from another polypeptide, similar to the description herein of the transmembrane domains that can be utilized to generate a CAR or DN form.

The invention provides for recombinant expression by an immune cell of both a CAR and a switch receptor, which switch receptor comprises (i) at least the extracellular ligand binding domain of an immune checkpoint inhibitor, (ii) a transmembrane domain, and (iii) a co-stimulatory signaling domain. In a particular embodiment, the co-stimulatory signaling domain of the switch receptor is the intracellular signaling domain of 4-1BB. In another particular embodiment of the invention, the immune cell expressing the switch receptor expresses a CAR, where the co-stimulatory signaling domain of the CAR is the intracellular signaling domain of CD28. In another particular embodiment, the invention provides an immune cell expressing a switch receptor and a CAR, where the co-stimulatory signaling domain of the switch receptor is the intracellular signaling domain of 4-1BB and the co-stimulatory signaling domain of the CAR is the intracellular signaling domain of CD28.

In a method utilizing a switch receptor, the switch receptor can be transduced into the same cell in which the CAR and DN form are transduced, so that the cell recombinantly expresses all three constructs. Alternatively and preferably, the switch receptor is transduced into a cell in which the CAR, but not DN form is transduced, so as to produce a cell expressing both the switch receptor and CAR, which can be used in combination therapy with cells that express both the CAR and DN form but not the switch receptor. In this case, both types of cells, cells expressing a CAR and DN form, and cells expressing a CAR and a switch receptor, are administered to the subject. Generally, the two types of cells are administered concurrently, but can also be administered sequentially, for example, within 1 or 2 hours, or within 1 or 2 days, or on the same day, as each other, as desired. In a particular embodiment, the co-stimulatory signaling domain of the CAR is different than the co-stimulatory signaling domain of the switch receptor being expressed in the same cell. This should result in two co-stimulatory signaling domains in the same cell and enhanced efficacy of the cells for immune cell therapy. In the case where it is believed that the administered immune cells will proliferate sufficiently in the subject being treated such that additional doses of cells need not be administered, it may be suitable to administer the immune cells of the invention at the initiation of immune cell therapy. Optionally, the immune cells of the invention, including optionally immune cells that express a switch receptor, can be administered more than once, as needed.

Optionally, a cell of the invention can express a co-stimulatory receptor (CCR) that binds to an antigen different than the cancer antigen of the target cancer (see Sadelain, et al., Cancer Discovery 3(4):388-398 (2013), Chicaybam, et al., Int. Rev. Immunol. 30(5-6):294-311 (2011), Brentjens et al., Nature Medicine 9:279-286 (2003); U.S. Pat. No. 7,446,190 and U.S. 2013/0071414 (CD19-targeted CARs); Ahmed, et al., Clin. Cancer Res. 16(2):474-485 (2010) (HER2-targeted CARs); Chekmasova, et al., Clin. Cancer Res. 16(14):3594-606 (2010) (MUC16-targeted CARs); Zhong, et al., Molecular Therapy, 18(2):413-420 (2010) and U.S. Pat. No. 7,446,190 (prostate-specific membrane antigen (PSMA)-targeted CARs), all of which are herein incorporated by reference. CCRs mimic co-stimulatory signals but, unlike CARs, do not provide a T cell activation signal (see Sadelain, et al., Cancer Discovery 3(4):388-398 (2013)). Immune cells expressing two or more antigen recognizing receptors are described in WO 2014/055668, which is herein incorporated by reference.

Administering an immunomodulatory agent in a combination therapy with an immune cell of the invention can occur concurrently with administration of the immune cells of the invention, for example, when immune cell therapy is initiated, or can occur sequentially at any time during the immune cell therapy, as desired. A person skilled in the art can readily determine appropriate regimens for administering cells of the invention and an immunomodulatory agent in a combination therapy, including the timing and dosing of an immunomodulatory agent to be used in a combination therapy, based on the needs of the subject being treated.

6.5. Pharmaceutical Compositions

The invention additionally provides pharmaceutical compositions comprising the cells of the invention. The pharmaceutical composition comprises an effective amount of a cell of the invention and a pharmaceutically acceptable carrier. The cells of the invention and compositions comprising the cells can be conveniently provided in sterile liquid preparations, for example, typically isotonic aqueous solutions with cell suspensions, or optionally as emulsions, dispersions, or the like, which are typically buffered to a selected pH. The compositions can comprise carriers, for example, water, saline, phosphate buffered saline, and the like, suitable for the integrity and viability of the cells, and for administration of a cell composition.

Sterile injectable solutions can be prepared by incorporating cells of the invention in a suitable amount of the appropriate solvent with various amounts of the other ingredients, as desired. Such compositions can include a pharmaceutically acceptable carrier, diluent, or excipient such as sterile water, physiological saline, glucose, dextrose, or the like, that are suitable for use with a cell composition and for administration to a subject such as a human. Suitable buffers for providing a cell composition are well known in the art. Any vehicle, diluent, or additive used is compatible with preserving the integrity and viability of the cells of the invention.

The compositions will generally be isotonic, that is, they have the same osmotic pressure as blood and lacrimal fluid. The desired isotonicity of the cell compositions of the invention can be accomplished using sodium chloride, or other pharmaceutically acceptable agents such as dextrose, boric acid, sodium tartrate, or other inorganic or organic solutes. Sodium chloride is preferred particularly for buffers containing sodium ions. One particularly useful buffer is saline, for example, normal saline. Those skilled in the art will recognize that the components of the compositions should be selected to be chemically inert and will not affect the viability or efficacy of the cells of the invention and will be compatible for administration to a subject, such as a human. The skilled artisan can readily determine the amount of cells and optional additives, vehicles, and/or carrier in compositions to be administered in methods of the invention.

The cells of the invention can be administered in any physiologically acceptable vehicle. Suitable doses for administration are described herein. A cell population comprising cells of the invention can comprise a purified population of cells. Those skilled in the art can readily determine the percentage of cells in a cell population using various well-known methods, as described herein. The ranges of purity in cell populations comprising genetically modified cells of the invention can be from about 50% to about 55%, from about 55% to about 60%, from about 65% to about 70%, from about 70% to about 75%, from about 75% to about 80%, from about 80% to about 85%; from about 85% to about 90%, from about 90% to about 95%, or from about 95 to about 100%. Dosages can be readily adjusted by those skilled in the art; for example, a decrease in purity may require an increase in dosage.

The invention also provides kits for preparation of cells of the invention. In one embodiment, the kit comprises one or more vectors for generating a genetically engineered immune cell, such as a T cell, or precursor cell thereof, that expresses a DN form or co-expresses a cancer antigen CAR and DN form of an inhibitor of a cell-mediated immune response. The kits can be used to generate genetically engineered immune cells from autologous cells derived from a subject or from non-autologous cells to be administered to a compatible subject. In another embodiment, the kits can comprise cells of the invention, for example, autologous or non-autologous cells, for administration to a subject. In specific embodiments, the kits comprise the immune cells of the invention in one or more containers.

It is understood that modifications which do not substantially affect the activity of the various embodiments of this invention are also provided within the definition of the invention provided herein. Accordingly, the following example is intended to illustrate but not limit the present invention.

7. EXAMPLE

7.1. Overview of Experiments

Following immune attack, solid tumors upregulate coinhibitory ligands that bind to and inhibit T cells. This adaptive resistance poses a hurdle for the treatment of solid tumors by chimeric antigen receptor (CAR) T-cell therapy, a promising treatment that has demonstrated complete remissions in patients with acute leukemia. As described below, it was investigated whether PD-1-mediated T-cell exhaustion could affect mesothelin-targeted CAR T cells in a mesothelioma model and whether cell-intrinsic strategies could be utilized to overcome checkpoint blockade. Using a clinically relevant, orthotopic mouse model of pleural mesothelioma, it was demonstrated that T cells expressing CD28 or 4-1BB-based second generation CARs, although persistent, are functionally inhibited within the tumor microenvironment (see below). While CD28 and 4-1BB CARs conferred similar proliferation and persistence of CAR T cells, the latter more durably retained their cytotoxic and cytokine secretion functions, resulting in improved survival in mice given low T-cell doses. CAR T cells that additionally expressed a PD-1 dominant negative receptor demonstrated functional persistence, induced superior tumor elimination and prolonged mouse survival. The results disclosed herein provide insights into CAR T-cell exhaustion in solid tumors and provide a strategy for combining CAR therapy with immune checkpoint blockade, for example, PD-1/PD-L1 blockade or other molecules involved in checkpoint blockade (see below).

The studies described below characterized the mechanisms of tumor-mediated T-cell inhibition in order to enhance the efficacy of T-cell immunotherapy for solid malignancies. As described below, MSLN-targeted CARs were designed that, when transduced into human T cells, provided tumor antigen recognition and antigen-specific effector function activation. Signaling domains were also designed that provide costimulatory signaling and/or coinhibitory blockade. In vitro, cytotoxicity, cytokine secretion, and T-cell proliferation were analyzed. In vivo experiments were performed to analyze strategies for optimizing T-cell therapy using clinically relevant mouse models of orthotopic MPM and metastatic lung cancer. Human cancer cells and human T cells were used to validate and facilitate the translation of M28z CAR to the clinic, as previously demonstrated for CD19 (Brentj ens et al., *Nat. Med.* 9(3):279-286 (2003)) and PSMA (Gade et al., *Cancer Res.* 65(19): 9080-9088 (2005)) CART cells.

As described below in more detail, low-level tumor infiltration was modeled, and it was found that CAR T cells can be susceptible to tumor cell-mediated immune-inhibition, resulting in impaired T-cell function and diminished tumor rejection. T cells engineered to resist PD-1 signaling displayed enhanced anti-tumor potency. As described below, following a single low-dose CAR T-cell therapy of advanced tumors, it was observed that, in response to CAR T-cell secreted cytokines, tumor cells upregulate PD-L1 leading to CAR T-cell inhibition and tumor relapse. To directly overcome the PD-L1-mediated immunosuppression, a PD-1 dominant negative receptor (PD-1 DNR) lacking the intracellular inhibitory signaling domain was designed. The cotransduction of PD-1 DNR with a CAR enhanced CAR T-cell function, resulting in a long-term cancer free survival following a single low-dose of CAR T cells. There is no previous disclosure of co-expressing a cancer antigen CAR with an immune checkpoint pathway receptor dominant negative, as is disclosed herein. The coexpression of an immune checkpoint pathway receptor DNR with a cancer antigen CAR is immediately translatable to the clinic since a DNR can be added to any CAR without inhibiting CAR function or adding toxicity. Without being bound by a particular theory, it is believed that the DNR simply binds (consumes) negative signal induced by its corresponding ligand (for example, PD-L1 in the case of PD-1) and avoids downstream signaling.

As described below, the presence and kinetics of tumor-mediated inhibition of CAR T cells were determined. By performing a comprehensive serial analysis of T-cell effector functions, it was established that even costimulated CAR T cells currently in clinical trials are subject to inhibition of their cytolytic and cytokine secretion functions upon repeated antigen encounter in vivo. The differing abilities of alternative costimulatory strategies (4-1BB vs. CD28) to withstand immuno inhibition was determined, as well as one of the mechanisms of tolerance (that is, PD-1 receptor/PD-1 ligand engagement). As further disclosed herein, it was found that a PD-1 dominant negative receptor (DNR) that, when cotransduced with a second-generation CAR, mediates enhanced T-cell persistence as well as T-cell resistance to tumor-mediated T-cell inhibition. The results disclosed herein demonstrate the benefit of optimizing signaling in an antigen-specific manner by simultaneously providing costimulation and check point blockade to counteract tumor-mediated T-cell inhibition. These results support using such an approach for improved tumor therapy, including but not limited to the treatment of MSLN-expressing solid tumors.

7.2. Methods and Procedures

The experimental procedures were approved by the Institutional Animal Care and Use Committee of Memorial Sloan Kettering Cancer Center (MSKCC). Each experiment was performed multiple times, using different donor T cells. To avoid confounding variables—such as differences due to transduction efficiencies, donor-related variability, and E:T ratios—data are presented using a representative experiment, with sample replicates of more than 3.

Cell Lines.

MSTO-211H human pleural mesothelioma cells (ATCC, Manassas, Va.) were retrovirally transduced to express GFP and firefly luciferase fusion protein (MSTO GFP-ffLuc$^+$). These cells were then transduced with the human MSLN variant 1 subcloned into an SFG retroviral vector to generate MSTO MSLN$^+$ GFP-ffLuc$^+$. Similarly, A549 cells and 3T3 murine fibroblasts were transduced with human MSLN variant 1 alone to generate A549 MSLN+ and 3T3 MSLN+ cell lines. 3T3 cells were also cotransduced with PD-L1 to generate 3T3 MSLN+ PDL1+ cells.

γ-Retroviral Vector Construction and Viral Production.

To generate MSLN-specific CARs, a cDNA encoding for a fully human scFv m912 specific for MSLN (provided by D. Dimitrov, National Cancer Institute at Frederick) (Feng et al., Mol. Cancer Ther. 8(5):1113-1118 (2009)), linked to the human CD8 leader domain and the CD8/CD3ζ, CD28/CD3ζ, or CD8/4-1BB/CD3ζ domain was engineered, as previously described (Zhong et al., Mol. Ther. 18(2):413-420 (2010)). The control PSMA-specific CAR was generated similarly, using a previously characterized PSMA-targeting scFv (Gade et al., Cancer Res. 65(19):9080-9088 (2005)). For construction of the PD-1 DNR, commercial gene synthesis was used to encode the extracellular portion of the PD-1 receptor (amino acids 1-151) fused to the CD8 transmembrane and hinge domains. The CAR sequence was inserted into the SFG γ-retroviral vector (provided by I. Riviere, MSKCC) and linked to a P2A sequence to induce coexpression of the LNGFR reporter (truncated low-affinity nerve growth factor receptor) or, in the case of the PD-1 DNR, the mCherry fluorescent protein reporter (Markley et al., Blood 115(17):3508-3519 (2010); Papapetrou et al., Proc. Natl. Acad. Sci. USA 106(31):12759-12764 (2009)). The CAR and PD-1 DNR encoding plasmids were then transfected into 293T H29 packaging cell lines to produce the retrovirus, as previously described (Hollyman et al., J. Immunother. 32(2):169-180 (2009)).

T-Cell Isolation, Gene Transfer, and CD4/CD8 Isolation.

Peripheral blood leukocytes were isolated from the blood of healthy volunteer donors under an institutional review board-approved protocol. Peripheral blood mononuclear cells (PBMCs) were isolated by low-density centrifugation on Lymphoprep (Stem Cell Technology, Vancouver, Canada) and activated with phytohemagglutinin (2 µg/mL; Remel, Lenexa, Kans.). Two days after isolation, PBMCs were transduced with 293T RD114-produced retroviral particles encoding for CARs and PD-1 DNR and spinoculated for 1 h at 3000 rpm on plates coated with retronectin (15 µg/mL; r-Fibronectin, Takara, Tokyo, Japan). After 1 day, transduced PBMCs were maintained in IL-2 (20 UI/mL; Novartis, Basel, Switzerland). Transduction efficiencies were determined by flow cytometric analysis. Pure populations of CD4+ and CD8+ CAR+ T cells, or mCherry-positive PD-1 DNR-expressing and mCherry-positive EV-expressing CAR+ T cells, were obtained by flow cytometric-based sorting (BD Aria Sorter; BD Biosciences, San Jose, Calif.).

Flow Cytometry.

Human MSLN expression was detected using a phyco-erythrin- or allophycocyanin-conjugated anti-human MSLN rat IgG2a (R&D Systems, Minneapolis, Minn.). Expression of costimulation or inhibitory proteins on tumor cells was analyzed using the following antibodies: 4-1BBL (PE, clone 5F4; BioLegend, San Diego, Calif.), MHC HLA-DR (PE, clone L203; R&D Systems), PD-L1 (APC, clone MIH1; eBioscience, San Diego, Calif.), PD-L2 (APC, clone MIH18; eBioscience), and galectin-9 (APC, clone 9M13; BioLegend). T-cell phenotype and transduction efficiency were determined with monoclonal antibodies for CD3, CD4, CD8, and CD69m LNGFR. Expression of T-cell inhibitory receptors was analyzed using PD1 (APC, eBioJIU5; eBioscience), TIM-3 (PE, clone 344823; R&D Systems), and Lag-3 (PE, clone C9B7W; BioLegend). Cell staining was analyzed using a BD LSRII flow cytometer (BD, Franklin Lakes, N.J.) and FlowJo analysis software (FlowJo, Ashland, Oreg.).

T-Cell Functional Assays.

The cytotoxicity of T cells transduced with a CAR or vector control was determined by standard $^{51}$Cr-release assays, as previously described (McCoy et al., *National Cancer Institute Monograph* 37:59-67 (1973)). To perform the luciferase-activity assay, CAR+ T cells and MSTO-211H cells expressing MSLN and firefly luciferase were incubated for 18 h at different E:T ratios. Tumor-cell quantity was determined by BLI using IVIS 100/lumina II, after the addition of 100 µL of D-luciferin (15 mg/mL) per well, and was compared to the signal emitted by the tumor cells alone. CD107a and intracellular staining were performed after incubation of effector cells and irradiated MSTO-211H MSLN tumor cells for 18 h in 24-well plates at a ratio of 5:1. For the CD107a assay, 5 µL of CD107a-PeCy7 antibody (BD Biosciences, San Jose, Calif.) and Golgi STOP (4 µL/6 mL; BD Biosciences) were added at the time of stimulation. For intracellular staining, Golgi Plug (1 µL/1 mL; BD Biosciences) was added at the time of stimulation. After incubation, effector cells were stained for CD4, CD8, LNGFR, and CD3ζ marker, then fixed and permeabilized in accordance with the manufacturer's instructions (Cytofix/Cytoperm Kit; BD Biosciences). Staining for intracellular cytokines was performed using granzyme B-APC, perforin-PE, and IFN-γ-FITC antibodies (BD Biosciences).

Cytokine-release assays were performed by coculturing $3\times10^4$ to $5\times10^3$ T cells with target cells in a 1:1 to 5:1 ratio, in 200 µL of medium, in 96-well round-bottomed plates as triplicates. After 6 to 24 h of coculture, supernatants were collected. Cytokine levels were determined using a multiplex bead Human Cytokine Detection kit, in accordance with the manufacturer's instructions (Millipore, Darmstadt, Germany).

To analyze the proliferation capacity of T cells, $1\times10^6$ CAR+ T cells were stimulated over irradiated MSTO-211H or 3T3 cells with or without MSLN expression (and, in the case of 3T3, with or without PD-L1). Proliferation assays were performed in the absence of exogenous IL-2. Cells were counted every 7 days and then overlaid on irradiated target cells for repeated stimulations. The CAR+ T cell number versus time was plotted for each T-cell group.

Orthotopic Pleural Mesothelioma Animal Model and Ex Vivo Experiments.

To develop the orthotopic mouse model of pleural mesothelioma, female NOD/SCIDy mice (The Jackson Laboratory, Bar Harbor, Me.) aged 4 to 6 weeks were used. All procedures were performed under approved Institutional Animal Care and Use Committee protocols. Mice were anesthetized using inhaled isoflurane and oxygen, with bupivacaine administered for analgesia. Direct intrapleural injection of $1\times10^5$ to $1\times10^6$ tumor cells in 200 µL of serum-free medium via a right thoracic incision was performed to establish orthotopic MPM tumors, as previously described (Adusumilli et al., *Science Translational Medicine* 6(261):261ra151 (2014); Servais et al., *Clin. Cancer Res.* 18(9):2478-2489 (2012); Servais et al., in *Current Protocols in Pharmacology*, Enna, ed., Chapter 14 (Unit14 21), John Wiley & Sons (2011)). In total, $3\times10^4$ to $1\times10^5$ transduced T cells (in 200 µL of serum-free medium) were adoptively transferred into tumor-bearing mice, either into the thoracic cavity by direct intrapleural injection or systemically by tail vein injection. Tumor growth was monitored and quantified in vivo by BLI performed 20 minutes after a single intraperitoneal dose of D-luciferin (150 mg/kg; Perkin Elmer, Waltham, Mass.). BLI data were analyzed using Living Image software (version 2.60; Perkin Elmer); BLI signal was reported as total flux (photons per second), which represents the average of ventral and dorsal flux. To analyze the functional capacity of CAR T cells ex vivo, tumor tissues and mouse spleen were processed as follows: Tissues were weighed and harvested into ice-cold RPMI 1640. The tissues were manually morselized with a scalpel and then mechanically disaggregated through 40- to 100-µm filters. Next, samples were analyzed by FACS (fluorescence activated cell sorting) for phenotyping, or CAR+CD4+ or CD8+ T cells were sorted using a FACS Aria sorter then rested for 24 h in RPMI with IL-2 (60 UI/mL), and $^{51}$Cr-release and cytokine-release assays were performed as described above.

Histologic Analysis and Immunostaining.

Histopathologic evaluation of tumors was performed after hematoxylin and eosin (H&E) staining of paraffin-embedded, 4% paraformaldehyde-fixed tissue samples. Immunohistochemical analysis for human MSLN was performed with mouse anti-human MSLN immunoglobulin G, as previously described (Kachala et al., *Clin. Cancer Res.* 20(4): 1020-1028 (2014); Rizk et al., *Cancer Epidemiol. Biomarkers Prev.* 21(3):482-486 (2012); Tozbikian et al., *PLoS One* 9(12):e114900 (2014)).

Quantitative Real-Time PCR.

The mRNA from CD4+ LNGFR+ or CD8+ LNGFR+ sorted T cells were extracted and reverse transcribed into cDNA using µMACS One-Step cDNA kit (MACS molecular, Miltenyi Biotech Inc, Auburn, USA). Quantitative Real Time PCR (RT-PCR) was performed with the Taqman® method using Applied Biosystems® 7500 systems (Foster, Calif., USA), Taqman® Universal PCR Mastermix and Taqman® probes labeled with 6-carboxyfluorescein (FAM-MBG) and designed by Life Technologies (Carlsbad, Calif.): Tbet (Hs00203436_m1); Eomes (Hs00172872_m1); Granzyme B (Hs01554355_m1); IFN-γ (Hs00989291 m1); IL-2 (Hs00174114_m1); PD-1 (Hs01550088_m1). The comparative threshold cycle (CT) of the gene of interest was used and normalized to the β2m housekeeping gene using the following formula: ΔCt (sample)=Ct (gene of interest)–Ct (β2m). Then, the $2^{-\Delta\Delta Ct}$ method was used to analyze the relative fold change expression compared to control condition and calculated as follow: $2^{-\Delta\Delta Ct}=2^{\wedge}-(\Delta Ct(sample)-\Delta Ct(control))$.

Statistical Methods.

Data were analyzed using Prism (version 6.0; GraphPad Software, La Jolla, Calif.) software and are presented as mean±SEM, as stated in the figure legends. Results were analyzed using the unpaired Student's t test (two-tailed), with the Bonferroni correction used for multiple comparisons, when applicable. Survival curves were analyzed using the log-rank test. Statistical significance was defined as $P<0.05$. All statistical analyses were performed with Prism software.

7.3. CARs with CD28 or 4-1BB Costimulation Exhibit Equivalent Effector Cytokine Secretion and Proliferation In Vitro Upon Initial Antigen Stimulation Three CARs were constructed that incorporated a human MSLN-specific scFv (Feng et al., *Mol. Cancer Ther.* 8(5): 1113-1118 (2009)) and either CD3ζ, CD28/CD3ζ or 4-1BB/CD3ζ signaling domains (Mz, M28z, MBBz) (FIGS. 1A and 1B). The P28z CAR, which is specific for prostate-specific membrane antigen (PSMA), served as a negative effector to control for alloreactivity and xenoreactivity. Both CD4+ and CD8+ human peripheral blood T lymphocytes were effectively transduced using the SFG-retroviral vector (50%-70% transduction) (FIG. 9). MSLN-transduced MSTO-211H cells (MSLN+) and PSMA-transduced EL-4 mouse lymphoma cells (MSLN-) served as MSLN-positive and -negative targets in the in vitro experiments. Mz-, M28z-, and MBBz-transduced T cells demonstrated similar MSLN-specific lysis in vitro (FIG. 1C). P28z CAR T cells did not lyse MSTO MSLN+ cells, and MSLN-targeted CARs did not lyse EL4 PSMA+ cells, demonstrating that lysis is antigen specific. Validating the functionality of costimulatory signaling (Brentjens et al., *Clin. Cancer Res.* 13(18 Pt 1):5426-5435 (2007)), M28z and MBBz CART cells secreted 2- to 15-fold higher levels of Th1 cytokines (FIG. 1D) and achieved 14-fold greater T-cell accumulation upon repeated exposure to MSLN+ cells when compared to Mz in the absence of exogenous IL-2 (FIG. 1E). Having established antigen specificity and validated the functionality of costimulatory signaling domains, evaluation of the therapeutic potential of MSLN-targeted CAR T cells in mice bearing established pleural tumors was performed.

These results demonstrate that CARs with CD28 or 4-1BB costimulation exhibit equivalent effector cytokine secretion and proliferation in vitro upon initial antigen stimulation.

7.4. M28z is More Prone to Allowing Tumor Relapse than MBBz

In an orthotopic model of malignant pleural mesothelioma (MPM) previously established (Servais et al., *Clin. Cancer Res.* 18(9):2478-2489 (2012); Servais et al., in *Current Protocols in Pharmacology, Enna, ed.*, Chapter 14 (Unit14 21), John Wiley & Sons (2011); Servais et al., *PLoS One* 6(10):e26722 (2011); Adusumilli et al., *J. Gene Med.* 8(5): 603-615 (2006)), serial bioluminescence imaging (BLI) with firefly-luciferase (ffLuc)-transduced MSTO-211H cells was used to confirm the establishment of tumor, to equalize tumor burden across intervention groups before the initiation of T-cell therapy, and to measure the response to therapy. Both M28z and MBBz CAR T cells intrapleurally administered at a single dose of $1\times10^5$ (effector to target (E:T) ratio of 1:3000, estimated from tumor burden quantification) (Servais et al., *PLoS One* 6(10):e26722 (2011)) are able to eradicate established pleural tumors in the majority of mice (FIG. 2A, top).

Since the goal in this study was to investigate the effect of tumor-induced immuno inhibition on T-cell exhaustion, CAR T cells were administered to mice bearing established pleural tumors at successively lower doses. At these lower doses, it was expected that T cells would be especially susceptible to exhaustion as they must retain function upon repeated antigen encounters within an inhibitory environment in order to eliminate tumor. It is at these lower doses tumor relapse was begun to be observed, especially within the M28z cohort (FIG. 2A, middle and bottom). At the lowest dose tested of $4\times10^4$ (E:T, 1:7,500), mice treated with intrapleural Mz (first generation CAR, no costimulatory signaling included) CAR T cells showed an unsustainable response in terms of tumor burden (FIG. 2B), and median survival was 29 days longer than that in the P28z-treated controls (median survival, 45 vs. 16 days, P28z represents a xenoreactivity and alloreactivity control targeting the PSMA antigen) (FIG. 2B). Mice treated with M28z CAR T cells had a more uniform reduction in tumor burden and survived longer (median survival, 64 days) than mice treated with first-generation CAR T cells; however, all mice treated with M28z CAR T cells eventually died of progressing tumor. It was confirmed that tumor outgrowth was not caused by tumor antigen escape (recurring tumors in all tested mice were found to be MSLN+ by flow cytometric and histologic analysis). In contrast, intrapleurally administered MBBz CAR T cells induced tumor eradication within 20 days of treatment, and the vast majority of mice (7 of 8) remained tumor free for >100 days (median survival was not reached by day 100).

These results demonstrate that M28z is more prone to allowing tumor relapse than MBB.

7.5. MBBz Surpasses M28z CAR T Cells at Low T-Cell Doses

Improvements in CAR T-cell efficacy afforded by costimulatory signaling are typically attributed to improvements in CAR T-cell proliferation and/or persistence (Sadelain et al., *Cancer Discovery* 3(4):388-398 (2013)). As expected, M28z and MBBz CART cells achieved enhanced intratumoral T-cell accumulation, compared with Mz CAR T cells (9-fold greater for M28z, 12-fold greater for MBBz) (FIG. 3A). Surprisingly, despite the differences in efficacy between M28z and MBBz CAR T cells, similar numbers of tumor-infiltrating T cells were observed between the two groups (FIG. 3A). Furthermore, M28z and MBBz CAR T cells were equally persistent at long-term time points (FIG. 3B). Tumor tissue and spleen from M28z-treated mice that initially had a treatment response but then died of progressing tumor contained circulating T cells as well as tumor-infiltrating T cells, including CAR positive cells (FIG. 3C). This finding demonstrates that the mere persistence of T cells that can effectively traffic to the tumor is not sufficient to eliminate tumor and that the T-cell functional status within the tumor microenvironment may be the more critical determinant of clinical outcome. These results suggested that even costimulated T cells may become exhausted within a tumor, especially at low T-cell doses that correspond to low effector:target ratios. Furthermore, MBBz CAR T cells, which were as persistent as M28z CAR T cells, may be better able to resist exhaustion and retain T-cell effector function in order to eliminate a large tumor burden.

These results demonstrate that MBBz surpasses M28z CAR T cells at low T-cell doses.

7.6. Mesothelin CAR T Cells Become Exhausted Following In Vivo Antigen Exposure

To assess whether there is ongoing immuno inhibition of CAR T cells and to compare the relative abilities of M28z and MBBz CAR T cells to overcome tumor-mediated immuno inhibition, $1\times10^6$ CAR T cells were injected into the pleural cavities of MSTO MSLN+ tumor-bearing mice, allowed sufficient time for repeated antigen encounter and T-cell activation (confirmed by forward- and side-scatter and upregulation of the activation marker CD69), and then performed ex vivo stimulation of harvested CD4 or CD8 CAR tumor-infiltrating or splenic T cells with MSLN+ targets (schematic shown in FIG. 4A). Uninjected in vitro resting T cells ("preinfusion cells") were used to establish the baseline level of function (before antigen exposure). Compared with resting M28z CD8+ CAR T cells, T cells exposed to MSLN antigen in vivo had lower levels of cytolytic function (FIG. 4A) (preinfusion cell lysis, 20.5%; tumor-infiltrating T-cell lysis, 13.1%; splenic T-cell lysis, 8.7%). In contrast, MBBz CAR T cells retained cytolytic function (preinfusion cell lysis, 18.3%; tumor-infiltrating T-cell lysis, 37.2%; splenic T-cell lysis, 22.2%). Sorted CD4+ CAR T cells demonstrated a similar pattern of results.

Cytokine levels were also measured upon ex vivo stimulation of tumor-infiltrating and splenic CAR T cells, and a decrease in Th1 cytokine secretion was observed for CD4+ M28z CAR T cells exposed in vivo to MSLN+ antigen. CD4+ MBBz CAR T cells also demonstrated a decrease in Th1 cytokine secretion, although these cells were better able to retain cytokine secretion when compared with M28z CAR T cells (FIG. 4B). CD8+ T cell supernatants contained significantly lower levels of cytokines, compared with CD4+ T cell supernatants (a finding previously observed Adusumilli et al., *Science Translational Medicine* 6(261): 261ra151 (2014)). CD8+ T cells also had a decreased ability to secrete cytokines upon in vivo antigen exposure; CD8+

MBBz CAR T cells preferentially retained their ability to secrete IFN-γ. The mRNA levels of T cells harvested from tumor and spleen on day 3 after administration were assessed, and it was found that the in vivo expression levels of GzB, IL-2, and IFN-γ were mostly greater for CD4+ and CD8+ MBBz CAR T cells than for M28z CAR T cells, with the exception of IL-2 expression in the CD8+ subset (FIG. 4C).

These results demonstrate that mesothelin CAR T cells become exhausted following in vivo antigen exposure.

7.7. MBBz CAR T Cells Show Delayed Exhaustion In Vivo

The below describes experimental results showing that MBBz CAR T cells show delayed exhaustion in vivo.

Having demonstrated inhibition of both the cytolytic function and effector cytokine secretion in costimulated CAR T cells exposed to antigen in vivo (see above), it was reasoned that repeated antigen stimulation may, similar to models of chronic infection, play a role in T-cell inhibition and that differing abilities to retain function upon repeated antigen encounter might explain enhanced efficacy of MBBz CAR T cells. Therefore, Mz, M28z, and MBBz CAR T cells were tested for their ability to withstand repeated antigen encounter in an in vitro model system, wherein cells were assessed for proliferation, cytolytic function, and cytokine secretion upon MSLN+ antigen stimulation every 7 days. M28z and MBBz CAR T cells had similar abilities to expand upon serial MSLN+ stimulation, expanding to levels 14-fold greater than those of Mz CAR T cells; they lost the ability to expand following the third stimulation (FIG. 5A). Both MBBz and M28z CAR T cells lost cytolytic function upon repeated antigen stimulation, although MBBz CAR T cells were better able to retain lytic function. Whereas lysis was equal among the three T-cell groups at the first stimulation, by the third stimulation, M28z lytic function was inhibited to a more pronounced level, such that MBBz CAR T cells had enhanced tumor lysis at multiple E:T ratios (FIG. 5B, right). Lytic function (as assessed by a degranulation assay measuring CD107a expression) at the third stimulation correlated with the results of chromium-release assays (FIG. 5C).

Next, Th1 cytokine secretion was measured. Similar levels between M28z and MBBz CAR T cells were noted at the first stimulation, as well as a successive decrease with each stimulation. As with cytotoxicity, MBBz CAR T cells preferentially retained cytokine secretion; cytokine concentrations decreased >30-fold for M28z and only around 2-fold for MBBz CAR T cells, when levels at the first and second stimulations were compared (FIG. 5D). The differences in cytokine production were confirmed by measuring intracellular levels of cytokines at the second stimulation. Reverse-transcriptase PCR analysis of CAR T cells at the time of antigen stimulation revealed that MBBz CAR T cells expressed markers that correlate with lower levels of exhaustion and inhibition, compared with M28z CAR T cells; MBBz CAR T cells expressed higher levels of Tbet and Eomesodermin and lower levels of PD1 and FoxP3 (FIG. 10). The in vivo function of persisting CAR T cells that had already been exposed to tumor antigen was tested. Although quantitative persistence is equal between M28z and MBBz CAR T cells, it was thought that MBBz CAR T cells would demonstrate enhanced function upon tumor rechallenge. Mice with established MSLN+ pleural tumors were administered intrapleural M28z or MBBz CAR T cells (at a dose of $1 \times 10^5$, E:T ratio 1:3000) to eradicate pleural tumor (FIG. 5E). Twenty days after the initial T-cell injection, tumor rechallenge was performed by injecting MSLN+ tumor cells ($1 \times 10^6$) into the pleural cavity of survivors; tumor burden was monitored using BLI. Persisting MBBz CAR T cells were better able to control tumor burden (4 of 4 MBBz-treated mice had a BLI signal at baseline levels vs. 2 of 4 M28z-treated mice) (FIG. 5E).

These results demonstrate that MBBz CAR T cells show delayed exhaustion in vivo.

7.8. Tumor Cell PD-L1 Inhibits Mesothelin CAR T-Cell Effector Functions

Having established that CAR T cells are inhibited by the in vivo tumor environment and that MBBz CAR T cells are better able to overcome this inhibition, at least in part because of their ability to retain function upon repeated antigen encounter (see above), it was next sought to assess the role that inhibitory receptor and ligand pathways play in the model. Tumor-infiltrating T cells, in M28z-treated mice with tumor progression, were stained for the expression of well-known pathways of inhibition. High levels of expression of PD-1, Tim-3, and LAG-3 were found (FIG. 6A). Tumor-infiltrating MBBz CAR T cells harvested 6 days after administration demonstrated upregulation of inhibitory receptors as well, although they expressed significantly lower levels of PD-1 receptor at both the protein and the mRNA level (FIG. 6B-D). CD4+ T cells expressed higher levels of PD-1, compared with CD8+ T cells. It was also observed that a significant fraction of both M28z and MBBz CAR T cells coexpressed PD-1 and LAG-3 or PD-1 and Tim-3, suggesting that multiple inhibitory pathways could be functioning simultaneously (FIG. 11). Next, tumor-expressed ligands were assessed: PD-L1 and PD-L2 (ligands for PD-1), galectin-9 (ligand for Tim-3), and MHC class II (ligand for LAG-3). Only PD-1 ligands were expressed on pleural tumor cells harvested after intrapleural administration of M28z CAR T cells (FIG. 6E). As reported elsewhere (McGray et al., *Mol. Ther.* 22(1):206-218 (2014); Spranger et al., *Science Translational Medicine* 5(200):200ra116 (2013)), coculture of tumor cells with IFN-γ and TNF-α (at concentrations similar to those secreted by T cells in FIGS. 1 and 5) resulted in a similar level of upregulation of PD-L1 and PD-L2 expression on tumor cells (FIG. 6F), reflecting an adaptation of tumor cells to resist immune attack ("adaptive immunoresistance"). The unique presence of expression of both PD-1 receptor and ligand in vivo suggests that this pathway may play a significant inhibitory role.

As some studies have suggested that costimulation may be sufficient to overcome inhibition by PD-1 (Carter et al., *Eur. J. Immunol.* 32(3):634-643 (2002); Freeman et al., *J. Exp. Med.* 192(7):1027-1034 (2000); Koehler et al., *Cancer Res.* 67(5):2265-2273 (2007)), it was next assessed whether overexpressed PD-L1 can inhibit CAR T-cell function in an in vitro model of PD-L1-mediated immuno inhibition (using 3T3 mouse fibroblasts transduced with either MSLN alone (MSLN+) or both MSLN and PD-L1 (MSLN+ PD-L1+)) (FIG. 7A). In both M28z and MBBz CAR T cells, PD-L1 overexpression resulted in decreased accumulation upon successive stimulation (FIG. 7B) and Th1 effector cytokine secretion (FIG. 7D). Although tumor-cell lysis was not inhibited upon initial stimulation, chromium release assay performed with 3T3s as targets following two stimulations against MSTO MSLN+ tumor cells demonstrates decreased lytic function in both M28z and MBBz CAR T cells, a higher extent of decrease in M28z CAR T cells (FIG. 7C). This result may be due to the differential upregulation of PD-1 on M28z and MBBz CAR T cells following exposure to MSTO MSLN+ tumor cells.

These results demonstrate that tumor cell PD-L1 inhibits mesothelin CAR T-cell effector functions.

7.9. Cell Intrinsic PD-1 Resistance Rescues M28z CAR T-Cell Function In Vivo The above results indicate that the PD-1 pathway is a functioning mechanism of tumor-mediated immuno inhibition and that PD-1 upregulation following repeated antigen stimulation decreases CAR T-cell efficacy. Therefore, checkpoint blockade was combined with CD28 costimulatory signaling. Since the goal was to provide CAR T-cell-specific checkpoint blockade that was not reliant on repeated dosing of systemically administered antibodies, the studies were focused on genetically engineered methods of overcoming immuno inhibition. A PD-1 dominant negative receptor (DNR) was constructed that contained the extracellular ligand binding domain of the receptor fused to a CD8 transmembrane domain. Since the PD-1 DNR lacks any signaling domain, it was thought that sufficiently overexpressed receptor would enhance T-cell efficacy by saturating PD-1 ligands and thereby blocking signaling through the endogenous PD-1 receptor. M28z CAR T cells were cotransduced with either the PD-1 DNR linked by a P2A element to an mCherry reporter (PD-1 DNR) or an empty vector containing only the reporter (EV) (FIG. 8A). M28z CAR T cells cotransduced with the PD-1 DNR had slight but statistically significant advantages in proliferative ability (FIG. 8B), enhanced cytotoxicity (FIG. 8C) at multiple E:T ratios, as well as augmented levels of IL-2 and IFN-γ secretion (FIG. 8D).

Next, it was assessed whether intrapleural administration of M28z CAR T cells cotransduced with a genetically engineered PD-1 resistance would provide an in vivo advantage. Mice with established pleural MSLN+-expressing tumors were administered a single intrapleural dose of $5 \times 10^4$ CAR+ M28z EV or M28z PD-1 DNR T cells, and treatment response was monitored by tumor burden measurements (using serial BLI) and median survival. Mice treated with M28z PD-1 DNR T cells had significantly enhanced tumor burden control and prolonged median survival (FIG. 8E); however, only some mice (7/16, 44%) had long-term tumor-free survival, suggesting that there are redundant mechanisms of immuno inhibition that must be overcome. A cohort of the mice (M28z PD-1 DNR) in this experiment survived beyond 450 days in spite of repeated tumor rechallenge, demonstrating the "functional persistence" of CAR T cells transduced with PD-1 DNR. These results demonstrate that, with an injection of 50,000 CAR T cells, not only was a large tumor burden eradicated but tumor relapse was prevented in spite of multiple tumor rechallenge over more than 15 months.

To investigate an alternative genetic strategy for overcoming PD-1-mediated immuno inhibition, M28z CAR T cells were cotransduced with vectors expressing PD-1-targeting shRNAs (FIG. 12A), which generated >60% PD-1 receptor knockdown at the protein level (FIG. 12B). In M28z CAR T cells, cotransduction with PD-1 shRNAs enhanced proliferative function upon MSLN+ antigen stimulation (FIG. 12C), augmented cytotoxicity (FIG. 12D), and enhanced cytokine secretion upon stimulation with either mesothelioma cells or MSLN+ PDL1+ 3T3 mouse fibroblasts (FIG. 12E), compared with cotransduction with an shRNA targeting a non-mammalian gene (M28z KanR). M28z PD-1 shRNA-transduced T cells did not achieve greater in vivo tumor rejection efficacy than M28z KanR T cells, but it is noteworthy that the level of knockdown was significantly lower in vivo than in vitro. Thus, the PD1 DNR proved to be the more effective strategy in vivo than the RNA interference approach.

These results demonstrate that cell intrinsic PD-1 resistance rescues M28z CAR T-cell function in vivo.

7.10. MBBz CAR T Cells Prolong Tumor-free Survival in a Mouse Model of Metastatic Lung Cancer in which PD-1 Receptor and Complementary Ligands are Expressed To confirm that the results were not limited to one cell line or mouse model, experiments were conducted to reproduce the results in a mouse model of metastatic lung cancer. The A549 lung cancer cell line was used, which expresses PD-L1 in vivo following M28z CAR T-cell therapy (FIG. 13A) as well as both PD-1 ligands following in vitro treatment with IFN-γ (FIG. 13B). Similar to the results of the mouse model of orthotopic mesothelioma, a single low dose of MBBz CAR T cells was better able to control tumor burden (FIG. 13C) and prolong tumor-free survival (median survival, 103 days for MBBz vs. 73 days for M28z CAR T cells) (FIG. 13D).

These results demonstrate that MBBz CAR T cells prolong tumor-free survival in a mouse model of metastatic lung cancer in which PD-1 receptor and complementary ligands are expressed.

7.11 Effect of PD-1 Dominant Negative Receptor (DNR) and PD-1 Switch Receptor on Tumors As described above, cells expressing 4-1BB mesothelin CARs (MBBz) retain functional efficiency better than CD28 mesothelin CARs (M28z) when subjected to repeated antigen stimulation, as they are relatively resistant to PD1/PDL1-2 induced inhibition. PD1 DNR transduced into cells expressing M28z retain functional persistence due to the DNR.

In order to further characterize the effect of PD1 DNR in CAR T cells, PD1 DNR was transduced into cells expressing MBBz CARs, with the expectation that the transduction would increase their efficiency even further, as seen with cells expressing M28z. To test PD1 DNR transduction into MBBz transduced CAR T cells, T cells from two human donors were used. Human T cells were isolated and transduced with MBBz or MBBzPD1DNR CAR, both with a mcherry marker to identify CAR transduced T cells. The transduced cells were analyzed by FACS analysis essentially as described above. The results for donor 1 are shown in FIGS. 14A-14C. Both CARs were successfully transduced at 62-75% transduction efficiency in both CD4 and CD8 T cells. Staining with PD-1 antibody showed the transduction of PD1 DNR in T cells (FIG. 14C). A similar analysis was performed on cells from donor 2, except that M28z was the CAR used. The results for donor 2 are shown in FIGS. 15A-15C. Both CARs were successfully transduced at 68-74% transduction in both CD4 and CD8 T cells. Staining with PD-1 antibody showed the transduction of PD1 DNR in T cells (FIG. 15B). These results show that PD1 DNR can be effectively transduced into MBBz transduced CAR T cells with 50-60% efficiency with double transduction of CAR and PD1 DNR, similar to the transduction efficiency seen with M28z CAR co-transduction with PD1 DNR.

The efficacy of cells transduced with MBBz versus MBBz PD1 DNR was tested in vitro. Human T cells were isolated from two donors. In human T cells isolated from donor 1, both MBBz and MBBz PD1DNR transduced cells were exposed to antigen-expressing (mesothelin) targets and analyzed for T-cell accumulation, cytokine secretion and cytotoxicity essentially as described above. As shown in FIGS. 16A-16D, although T-cell accumulation (FIG. 16A), CAR T-cell percentage (FIG. 16B) and cytotoxicity (FIG. 16D) remained the same between both CARs, cytokine secretion was relatively lower in MBBzPD1DNR transduced CAR T cells (FIG. 16C). The results are shown in FIGS. 16A-16D.

In cells isolated from donor 2, both MBBz and MBBz PD1DNR transduced cells were exposed to antigen-expressing (mesothelin) targets and analyzed for T-cell accumulation, cytokine secretion and cytotoxicity. In this experiment, the cytotoxicity assay was measured repeatedly after repeated antigen exposure. As shown in FIGS. 17A-17D, although T-cell accumulation (FIG. 17A), CAR T-cell percentage (FIG. 17B) and cytotoxicity (FIG. 17C) remained the same between both CARs, cytokine secretion (IL-2 and IFN-γ) was relatively lower in MBBzPD1DNR transduced CAR T cells (FIG. 17D). Upon repeated antigen exposure, although the cytotoxicity decreased, there were no differences between the two constructs (FIG. 17C).

The effect of PD1 DNR transduction into MBBz transduced CAR T cells was tested. From donor 3, human T cells were isolated and transduced with MBBz or MBBzPD1DNR CAR, both with a mcherry marker to identify CAR transduced T cells. Cells were analyzed by FACS analysis, before and after stimulation. As shown in FIGS. 18A and 18B, both CARs were successfully transduced at 55-56% transduction efficiency in both CD4 and CD8 T cells. Staining with PD-1 antibody showed the transduction of PD1 DNR in T cells (FIG. 18B).

PD1 DNR transduction into MBBz transduced CAR T cells was further characterized. MBBz or MBBzPD1DNR CAR T cell accumulation was tested without or with IL-2 in the media. Cells transduced with MBBz or MBBz PD1 DNR were treated with or without 20 IU (international units)/mL IL-2, 40 IU IL-2/mL, or PD1 antibody (10 μg/mL). Cells transduced with MBBz PD1 DNR were tested without or with 20 IU/mL IL-2. As shown in FIGS. 19A-19C, IL-2 supplementation rescued MBBzPD1DNR CAR T-cell accumulation upon antigen stimulation. These results show that IL-2 supplementation improved the effect of using the PD1 DNR transduced into MBBz transduced CAR T cells, unlike in M28z CAR T cells, where expression of PD1 DNR in M28z was effective without IL-2 (see above).

The results described above indicate that transduction of PD1 DNR into cells expressing MBBz CAR reduced the efficacy of the MBBz CAR T cells. Experiments were performed showing that unlike, M28z CARs that can produce higher amounts of IL-2, the ability of cells expressing MBBz CAR to secrete IL-2 is limited. Therefore, PD1 DNR transduction resulted in apoptosis. The effectiveness of MBBz PD-1 DNR T cells was rescued by addition of IL-2.

The efficacy of T cells expressing MBBz or MBBz PD1 DNR was examined in vivo. Mice with established pleurla tumor were treated with a single dose of MBBz or MBBzPD1DNR CAR T cells. Following tumor eradication, mice were rechallenged with either pleural or peritoneal tumor, and CAR T-cell functional persistence was assessed by tumor regression and eradication as assessed by BLI for the presence of tumor (FIG. 20A). As shown in FIGS. 20B-20D, three groups of mice (each group represented in a separate graph) were treated with a single low dose of cells expressing MBBz, cells expressing MBBz PD1 DNR, or cells expressing MBBz+PD1 blocking antibody. Each line in the graph indicates one mouse. Cells expressing both CARs successfully eradicated initial and subsequent rechallenge tumor burden with one small dose of CAR T cells. Both MBBz and MBBz PD1 DNR transduced CAR T cells effectively retained functional persistence in spite of 3 tumor rechallaneges, including one challenge with PD-L1 transduced cancer cells. The overall result is that mice in all 3 groups successfully eradicated tumor burden, even with multiple tumor rechallenges.

To assess the functional persistence of MBBz and mBBz PD1 DNR transduced CART cells, cytokines were analyzed in the serum of mice. As shown in FIG. 21, human interferon gamma and human GM-CSF in the serum of mice transduced with human T cells was assessed. Analysis of mouse serum following re-challenge at about 100 days (day 104) shows the functional persistence of both MBBz and MBBz PD1 DNR transduced CAR T cells by detection of human cytokines (IFN-γ and GM-CSF) in mouse serum (FIG. 21).

The results described above indicate that differences between M28z and MBBz CARs when cotransduced with PD1 DNR can be identified, and therapies, such as additionally administering cytokines such as IL-2, can be utilized to improve the efficacy of immune cells expressing a CAR and immune checkpoint inhibitor dominant negative. Such results can be applied to clinical trial translation of the therapies.

Experiments were also performed to strengthen M28z CAR T cell therapy. Human T cells were transduced with M28z or M28z PD1 4-1BB CAR, both with a mcherry marker, and were flow sorted and tested for cytokine secretion and T-cell accumulation. PD1 4-1BB is a "switch receptor" construct (see Liu et al., Cancer Res. 76:1578-1590 (2016)), with the extracellular PD-1 ligand binding domain fused to a transmembrane domain fused to the cytoplasmic signaling domain (co-stimulatory domain) of 4-1BB (shown schematically in FIG. 22). As shown in FIG. 22, T cells were isolated, and cells were transduced with M28z mcherry or M28z PD1 4-1BB mcheery on day 2 or 3. Cells were sorted by mcherry expression on day 5 or 6. On day 7 or 8, the first stimulation was initiated, MGM (mesothelin expressing cells) (see WO 2015/188141) pretreated (3:1). CART cell accumulation and cytokine secretion (IL-2 and IFN-γ) were measured essentially as described above. As shown in FIG. 22, PD1 4-1BB cotransduced CAR T cells showed higher cytokine secretion and accumulation compared to M28z transduced CAR T cells. PD1 4-1BB acted as a third signal to enhance the efficacy of cells transduced with M28z. The results show that, to rescue the PD-1/PD-L1 mediated inhibition, PD-1 4-1BB cotransducted into M28z CAR T cells induced a third stimulation, via PD-1 4-1BB following PD-L1 engagement, thus increasing M28z potency.

7.12. Converting Tumor-Mediated PD-L1 Inhibition into CAR T-Cell Costimulation to Potentiate Thoracic Cancers Immunotherapy To overcome tumor-mediated inhibition of chimeric antigen receptor (CAR) T cells, the impact of tumor PD-L1 upregulation on CAR T-cell exhaustion and anti-tumor efficacy was investigated. In addition, experiments were performed to further develop clinically translatable T-cell extrinsic as well as intrinsic strategies to overcome PD-L1 inhibition in models of lung cancer (LC) and malignant pleural mesothelioma (MPM).

Human T cells were transduced with MSLN-specific CAR with CD28 and CD3zeta domains (M28z) and were tested in vitro and in clinically-relevant LC and MPM mouse models by bioluminescence imaging (BLI) of tumor burden progression. To counteract PD-1/PD-L1 inhibition in vivo, the efficacy of PD-1 blocking antibody or cell-intrinsic genetic-engineering strategies were evaluated by cotranducing M28z CAR T cells with a PD-1 dominant negative receptor (PD1-DNR) or with PD-1/4-1BB fusion protein.

A single, low-dose of M28z CAR T cells was able to resist the progression of established tumor for 40 days, but mice eventually died with progressing tumor. Tumor harvest analysis demonstrated the PD-1 and PD-L1 upregulation on CAR T cells and tumor cells (FIG. 23A). It was then confirmed in vitro that PD-L1 inhibits M28z T-cell effector functions (proliferation, cytotoxicity and cytokine secretion).

The ability of a PD-1-blocking antibody (clone EH12.2H7) to rescue M28z CAR T cells was evaluated in vivo. For this purpose, a single, very low dose of M28z CAR T cells ($5\times10^4$, E:T ratio, 1:6,000) was injected into mice with large established tumor burdens with the objective of inducing the exhaustion of CAR T cells. In these conditions, CAR T cells were able to stabilize the tumor for 30 days (FIG. 23B). At day 30, the PD-1 antibody was administered intraperitoneally at 10 mg/kg 3 times every 5 days (Curran et al., *Proc. Natl. Acad. Sci. USA* 107(9):4275-4280 (2010); Moon et al., *Clin. Cancer Res.* 22(2):436-447 (2016); Seung et al., *PLoS ONE,* 8(10):e77780 (2013)). There was a marked decrease in tumor BLI following 3 doses of the antibody. However, tumor relapses observed following cessation of treatment suggest that efficacy is short lived and reliant upon repeated PD-1 antibody administration. The addition of PD-1 blocking potentiates CAR T-cell therapy in vivo, but its efficacy requires multiple injections (FIG. 23B). As shown in FIG. 23B, multiple, long-term injections of the PD-1 antibody are able to control tumor burden but unable to eradicate the tumor.

In contrast to the results described above using the PD-1 blocking antibody, a single dose of M28z T cells coexpressing PD1-DNR restored effector functions and enhanced tumor burden control (FIG. 23C). This experiment is also described above, with the schematic diagram and the results of FIG. 23C shown in FIGS. 8A and 8E, respectively. A single dose of M28z T cells coexpressing PD1-DNR also prolonged median survival (56 vs 82 days, p=0.001).

PD-L1 inhibition was converted into a positive costimulatory signal by a PD-1/4-1BB switch receptor construct cotransducted into M28z CAR T cells. These cells exhibited enhanced cytokine secretion (IL-2 and IFN-γ) and T-cell accumulation (FIG. 23D). This experiment is also described above and the results shown in FIG. 22.

These results demonstrated the therapeutic benefit of providing optimized costimulation and coinhibitory blockade to counteract PD-L1/PD-1 immunosuppression, thus potentiating CAR T-cell therapy for lung cancer and mesothelioma.

7.13. Overview and Discussion of Experimental Results

As described above, CAR T-cell therapy and PD-1 checkpoint blockade have been demonstrated to be a rational combination in a solid tumor model. In vitro and ex vivo stimulation assays were performed to assess the impact of PD-1/PD-L1 inhibition on mesothelin CAR T-cell function. To directly counteract PD-1-mediated inhibition, retroviral vectors were used to combine CAR-mediated costimulation with a PD-1 DNR. Optimal signaling provided by this combinatorial strategy (costimulation and checkpoint blockade) enhanced T-cell function in the presence of tumor-encoded PD-L1 expression, resulting in long-term tumor-free survival following a single low dose of CAR T cells. These studies are relevant to the clinical practice of adoptive T-cell therapy and are immediately translational for the following reasons: (1) the costimulatory signaling domains tested—CD28 and 4-1BB—are the two costimulatory domains used in ongoing clinical trials (NCT02414269, NCT02159716, NCT01583686), (2) the models of pleural mesothelioma recapitulate human disease and uses large, clinically relevant tumor burdens that elucidate the relevance of T-cell exhaustion (Adusumilli et al., *Science Translational Medicine* 6(261): 261ra151 (2014); Servais et al., *Clin. Cancer Res.* 18(9):2478-2489 (2012); Servais et al., in *Current Protocols in Pharmacology*, Enna, ed., Chapter 14 (Unit14 21), John Wiley & Sons (2011); Servais et al., *PLoS One* 6(10):e26722 (2011)), and (3) the strategy of potentiating CAR T cells by genetically encoded checkpoint blockade uses human sequences that can be readily applied in the clinic (Adusumilli et al., *Science Translational Medicine* 6(261):261ra151 (2014); Feng et al., *Mol. Cancer Ther.* 8(5):1113-1118 (2009)).

The studies described above demonstrate that even T cells expressing second generation CARs are inhibited upon in vivo antigen exposure within the tumor microenvironment. That several other studies report that costimulation alone can overcome tumor-expressed inhibitory signaling may be explained by their reliance on in vitro studies, their use of immuno sensitive in vivo models, and their administration of high T-cell doses that do not reflect the burdens of established solid tumors seen in patients (Carter et al., *Eur. J. Immunol.* 32(3):634-643 (2002); Freeman et al., *J. Exp. Med.* 192(7):1027-1034 (2000); Koehler et al., *Cancer Res.* 67(5):2265-2273 (2007)). In the experiments described above, higher T-cell doses result in tumor eradication regardless of a CD28 or 4-1BB costimulatory domain. It is at the lower T-cell doses (and resulting lower effector:target ratios) that the effect of exhaustion becomes apparent. These findings illustrate the importance of using clinically relevant in vivo models and T-cell doses that are similar to those used in patient trials. The intrapleural T-cell doses used in the studies described above ($4\times10^4$ to $1\times10^5$ per mouse equivalent to $1.2\times10^5$ to $3\times10^6$/Kg in human) are markedly lower doses than used in other mesothelioma xenografts studies (Carpenito et al., *Proc. Natl. Acad. Sci. USA* 106(9):3360-3365 (2009); Zhao et al., *Cancer Res.* 70(22):9053-9061 (2010)) and is comparable to doses used in current clinical trials for hematologic malignancies (Brentj ens et al., *Science Translational Medicine* 5(177):177ra38 (2013); Grupp et al., *N. Engl. J. Med.* 368(16):1509-1518 (2013)) and solid tumors (Louis et al., *Blood* 118(23):6050-6056 (2011); Beatty et al., *Cancer Immunol. Res.* 2(2):112-120 (2014)). Therefore, the experimental strategy is particularly suited to characterize the role of exhaustion in CAR T-cell therapy.

In the results described above, although both 4-1BB and CD28 costimulatory signaling enhanced T-cell persistence to a similar degree, at lower E:T ratios, only treatment with 4-1BB-costimulated T cells eradicated tumor. 4-1BB-costimulated T cells, while still sensitive to tumor-mediated inhibition, were relatively resistant to decline in T-cell cytolytic function and cytokine secretion both following in vivo antigen exposure and upon repeated antigen stimulation in vitro. The resistance of 4-1BB signaling to immuno inhibition is associated with a more potent phenotype (PD-$1^{lo}$Tbet$^{hi}$, Eomesodermin$^{hi}$) (Curran et al., *J. Exp. Med.* 210(4):743-755 (2013); Hirschhorn-Cymerman et al., *J. Exp. Med.* 209(11):2113-2126 (2012); Song et al., *Oncoimmunology* 3(1):e27680 (2014); Schietinger et al., *Science* 335(6069):723-727 (2012); Kao et al., *Nat. Immunol.* 12(7): 663-671 (2011)), which has been linked to less exhaustion and a more robust cytotoxic effector response in other tumor models and the analogous model of chronic viral infection. This suggests that the criteria for selecting a particular costimulatory signaling strategy among the options available, that is, 4-1BB, CD28, OX40L, 4-1BBL, CD27, and the like, should extend beyond T-cell persistence to "functional persistence," which is the ability of T cells to function upon repeated antigen stimulation either initially within the tumor microenvironment or as may occur upon antigen rechallenge after control of primary tumor burden. As with previous studies supporting regional CAR T-cell therapy (Adusumilli et al., *Science Translational Medicine* 6(261):261ra151 (2014)), administering T cells with high functional persistence allows for single administrations of low T-cell doses, which can serve to limit cytokine release syndromes yet still eradicate primary tumor. It is important to note that these experiments do not mean that 4-1BB is the de facto costimulation agent to be used for patient therapy. The superior signaling pathway will depend on the unique patterns of costimulatory and coinhibitory ligand expression by the tumor, the antigen expression level or density, the affinity of scFv for the tumor antigen, the distance of the tumor epitope from the membrane, and variations in construct design (such as spacer and transmembrane domains) (Sadelain et al., *Cancer Discovery* 3(4):388-398 (2013); James et al., *J. Immunol.* 180(10):7028-7038 (2008); James et al., *J. Immunol.* 184(8):4284-4294 (2010); Watanabe et al., *J. Immunol.* 194(3):911-920 (2015); Hombach et al., *J. Immunol.* 178 (7):4650-4657 (2007); Chmielewski et al., *J. Immunol.* 173(12):7647-7653 (2004)). These variables, and not qualitative differences in signaling, may ultimately explain the variability seen in preclinical trials, which alternately conclude that 4-1BB or CD28 is superior, depending on the context. Indeed, the 4-1BB and CD28 constructs used in the experiments described above are sufficiently different in their transmembrane domains that conclusions determining the optimal costimulatory domain should not be made from these results, but can be determined using models such as those described above.

The relatively higher expression of PD-1 in M28z CAR T cells led to the focus on CD28-stimulated CAR T cells. On the basis of this analysis, genetic strategies were pursued for counteracting PD-1 inhibitory signaling, such as generating a PD-1 dominant negative receptor (PD-1 DNR) and shRNAs targeting PD-1. When expressed at sufficient levels, the PD-1 DNR competes with the endogenous PD-1 receptor for binding PD-1 ligands (PD-L1 and PD-L2). CD28-costimulated T cells cotransduced with PD-1 DNR demonstrated enhanced in vitro T-cell functions and in vivo T-cell efficacy, suggesting PD-1 signaling as a significant mechanism by which tumor cells evade CAR T cells in the tumor model. Although only in vitro efficacy was demonstrated for PD-1-targeting shRNAs, the absence of in vivo efficacy is likely related to saturation of shRNA machinery by the high volume of PD-1 transcripts induced following multiple in vivo antigen encounters, a conclusion supported by the finding that PD-1 knockdown was significantly lower in vivo than in vitro. The findings described above point to the therapeutic usefulness of adoptively transferred T cells that are genetically engineered to resist tumor-mediated immune inhibition. A DNR that targets TGF-β has been validated in preclinical models and is currently being tested in clinical trials (Foster et al., *J. Immunother.* 31(5):500-505 (2008); Bollard et al., *Blood* 99(9):3179-3187 (2002)).

Whereas others have combined T-cell therapy with PD-1-blocking antibodies either in vivo or in vitro, the addition of a genetic strategy for coinhibitory blockade described in the experiments above overcomes several major obstacles limiting antibody therapy, including (1) the reliance on repeated administrations of antibodies and (2) the incidence of immune-related adverse events. T-cell therapy, then, has advantages over antibody therapy because it can establish long-term engraftment of T cells programmed for resistance to inhibition after a single dose and because it provides blockade of inhibitory pathways that is limited to a tumor-targeted T-cell repertoire, which may limit the autoimmunity that results from a more broadly applied antibody checkpoint blockade. Furthermore, it is possible that perhaps PD-L1 blocking antibodies can further prolong the efficacy of M28z and M28z PD-1 DNR CAR T cells.

The studies described above are unique when compared to other reports characterizing CAR T-cell exhaustion. Moon et al. characterized T-cell hypofunction within an immunoresistant mesothelioma tumor (Moon et al., *Clin. Cancer Res.* 20(16):4262-4273 (2014)); however, their characterization of inhibition rested on ex vivo experiments and they did not demonstrate a therapeutic strategy that enhances survival in vivo. In contrast, the studies described above confirm the presence of PD-1 mediated inhibition in vivo and demonstrate gene-engineered checkpoint blockade that can be employed in clinical settings. Long et al. recently described CAR T-cell exhaustion in a model of osteosarcoma (Long et al., *Nat. Med.* 21(6):581-590 (2015)). Their characterization, however, is fundamentally different in that they describe an antigen-independent phenomenon that results from tonic signaling of aggregated CAR receptors. The T cells in this model of Long et al., supra, become exhausted during ex vivo expansion, even prior to T-cell transfer. The results described above characterize a model of T-cell exhaustion more akin to that developed in the chronic viral infection literature, in which T-cell exhaustion is antigen-dependent and results from exposure to repeated antigen encounters in an environment rich with inhibitory signaling (Barber et al., *Nature* 439(7077):682-687 (2006); Mueller et al., *Proc. Natl. Acad. Sci. USA* 106(21):8623-8628 (2009)).

The studies described above have identified one of the inhibitory mechanisms responsible for CAR T-cell and highlighted differences in the ability of costimulatory strategies to withstand immuno inhibition. Other inhibitory pathways may also function to potentially limit T-cell function. That a proportion of mice treated with PD-1 DNR-cotransduced M28z CAR T cells died of tumor progression suggests the action of other inhibitory mechanisms. Furthermore, the literature on chronic infection suggests the existence of other mechanisms of inhibition, both cell intrinsic and cell extrinsic, which are being assessed in tumor-targeted T-cell therapies (Moon et al., *Clin. Cancer Res.* 20(16):4262-4273 (2014); Riese et al., *Cancer Res.* 73(12):3566-3577 (2013)). Additional studies on inhibitory signaling can use an immunocompetent model that includes elements such as myeloid-derived suppressor cells and endogenous T cells, which have been shown to play important roles in tumor immune evasion.

The results described above have established the importance of tumor-mediated inhibition of CAR T-cell effector functions. By performing a comprehensive analysis of T-cell effector functions, it has been established that even costimulated CAR T cells, although they demonstrate enhanced persistence, are subject to inhibition upon repeated antigen encounter, both in vitro and within the tumor microenvironment. The results described demonstrate that CAR T-cell therapy can be used to counteract inhibitory signaling and provides the flexibility to engineer signaling domains that provide optimal costimulation and directly counteract inhibitory signals such as PD-1. Furthermore, in ongoing CAR T-cell therapy clinical trials in patients who show T-cell infiltration but a limited clinical response, combining PD-1/PD-L1 blockade following CAR T-cell therapy can be utilized to improve the efficacy of CAR T-cell therapy.

The results described above also show that the effectiveness of an immune cell expressing a CAR and a dominant negative form of an immune checkpoint inhibitor can be enhanced for immunotherapy. For example, the effectiveness of a T cell expressing a CAR and PD-1 DNR was increased by administering a cytokine, IL-2. The administration of IL-2 was found to be effective when the immune cell expressing a CAR and PD-1 DNR was deficient in producing IL-2.

The transcription factor nuclear factor of activated T cells (NFATc), upon activation of T cells through the T cell receptor, becomes dephosphorylated and translocates to the nucleus in lymphocytes (Serfling et al., Science Signaling (*Sci. STKE*) 398:pe42 (2007)). The translocated NFATc targets the IL-2 promoter. Induction of the IL-2 promoter in T cells depends critically on the activity of NFATc factors (Serfling et al., supra, 2007). A threshold abundance of NFAT factors needs to be reached in order for the induction of the Il-2 promoter (Serfling et al., supra, 2007). In both CD8 and CD4 T cells, PD1 induction following TCR stimulation requires NFATc (Bally et al., *J. Immunol.* 194: 4545-4554 (2015)).

Unlike CD28 costimulation, which induces strong NF-κB, AP-1 and NFAT activity, 4-1BB costimulation reduces NFAT activity (Jutz et al., *J. Immunol. Methods* 430:10-20. doi: 10.1016/j.jim.2016.01.007 (2016)). PD-1 strongly reduces NFAT activity (Jutz, supra, 2016)). 4-1BB signaling is mediated by TRAF2, which in turn inhibits NFAT-mediated transcription via NFAT-interacting protein NIP45 (Jutz et al., supra, 2016)). While not being bound by theory, it is possible that MBBz and PD-1 DNR reduced NFAT activity in MBBz PD1 DNR CAR cells, thereby reducing IL-2 production, decreasing T-cell proliferation, and increasing apoptosis (Serfling et al., *Science Signaling* (Sci. STKE) 398:pe42 (2007); (Bally et al., *J. Immunol.* 194:4545-4554 (2015); (Jutz et al., *J. Immunol. Methods* 430:10-20. doi: 10.1016/j.jim.2016.01.007 (2016)), unlike in cells expressing M28z PD-1 DNR CARs, which have abundant NFATc. 4-1BB signaling synergizes with PD-L1 blockade to augment CD8 T cell responses, but only at low or single dose combinations (Vezys et al., *J. Immunol.* 187:1634-1642 (2011)). Excessive usage of both results in decreased proliferation and increased apoptosis (Vezys et al., supra, 2011).

The effectiveness of an immune cell expressing a CAR and a dominant negative of an immune checkpoint inhibitor can also be enhanced by expression of a switch receptor, in which an intracellular signaling domain is fused to the extracellular ligand binding domain of an immune checkpoint inhibitor, such as PD-1. The results described above show that expression of a PD-1 extracellular domain fused to the cytoplasmic domain of 4-1BB increased cytokine production of IL-2 and interferon-gamma, and increased accumulation of CAR T cells. Expression of a switch receptor in an immune cell expressing a CAR can improve the efficacy of the immune cell for immunotherapy. Immune cells expressing a CAR and a switch receptor can be administered, concurrently or sequentially, with immune cells expressing a CAR and a dominant negative form of an immune checkpoint inhibitor to enhance the effectiveness of immunotherapy using such immune cells expressing a CAR and DN form of an immune checkpoint inhibitor.

The knowledge acquired from the clinical trials and the strategies presented herein are highly valuable to improve immunotherapy methods using CAR T cells, which is particularly use for therapy of solid tumors. Thus, the results described above exemplify methods that can be applied in a clinical setting to improve the efficacy of CAR T-cell therapy.

8. REFERENCES CITED

All references cited herein are incorporated herein by reference in their entirety and for all purposes to the same extent as if each individual publication or patent or patent application was specifically and individually indicated to be incorporated by reference in its entirety for all purposes.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed is:

1. A cell that is an immune cell or precursor cell thereof, which cell recombinantly expresses (a) a chimeric antigen receptor (CAR), and (b) a dominant negative form of programmed death 1 (PD-1), wherein the CAR binds to a cancer antigen, and wherein the dominant negative form (i) lacks a signaling domain, and (ii) comprises a CD8 transmembrane domain, wherein the dominant negative form comprises an extracellular domain comprising the ligand binding domain of PD-1 fused to the CD8 transmembrane domain.

2. The cell of claim 1, wherein the cell is a T cell or precursor thereof.

3. The cell of claim 1, wherein the cell is a precursor cell that is a hematopoietic stem or hematopoietic progenitor cell.

4. The cell of claim 2, wherein the cell is a cytotoxic T lymphocyte (CTL).

5. The cell of claim 1, wherein the cell is a T cell.

6. The cell of claim 1, wherein the cell is a Natural Killer (NK) cell.

7. The cell of claim 1, wherein the cancer antigen is selected from the group consisting of mesothelin, prostate specific membrane antigen (PSMA), prostate stem cell antigen (PCSA), carbonic anhydrase IX (CAIX), carcinoembryonic antigen (CEA), CD5, CD7, CD10, CD19, CD20, CD22, CD30, CD33, CD34, CD38, CD41, CD44, CD49f, CD56, CD74, CD123, CD133, CD138, epithelial glycoprotein2 (EGP 2), epithelial glycoprotein-40 (EGP-40), epithelial cell adhesion molecule (EpCAM), folate-binding protein (FBP), fetal acetylcholine receptor (AChR), folate receptor-α and β(FRα and β), Ganglioside G2 (GD2), Ganglioside G3 (GD3), human Epidermal Growth Factor Receptor 2 (HER-2/ERB2), Epidermal Growth Factor Receptor vIII (EGFRvIII), ERB3, ERB4, human telomerase reverse transcriptase (hTERT), Interleukin-13 receptor subunit alpha-2 (IL-13Rα2), κ-light chain, kinase insert domain receptor (KDR), Lewis A (CA19.9), Lewis Y (LeY), L1 cell adhesion molecule (L1CAM), melanoma-associated antigen 1 (melanoma antigen family A1, MAGE-A1), Mucin 16 (Muc-16), Mucin 1 (Muc-1), NKG2D ligands, cancer-testis antigen NY-ESO-1, oncofetal antigen (h5T4), tumor-associated glycoprotein 72 (TAG-72), vascular endothelial growth factor R2 (VEGF-R2), Wilms tumor protein (WT-1), type 1 tyrosine-protein kinase transmembrane receptor (ROR1), B7-H3 (CD276), B7-H6 (Nkp30), Chondroitin sulfate proteoglycan-4 (CSPG4), DNAX Accessory Molecule (DNAM-1), Ephrin type A Receptor 2 (EpHA2), Fibroblast Associated Protein (FAP), Gp100/HLA-A2, Glypican 3 (GPC3), HA-1H, HERK-V, IL-11Rα, Latent Membrane Protein 1 (LMP1), Neural cell-adhesion molecule (N-CAM/CD56), and Trail Receptor (TRAIL R).

8. The cell of claim 7, wherein the cancer antigen is mesothelin.

9. A pharmaceutical composition comprising a therapeutically effective amount of the cell of claim 1; and a pharmaceutically acceptable carrier.

10. A method of treating a cancer in a subject in need thereof, comprising administering to the subject a therapeutically effective amount of the cell of claim 1, wherein the cancer antigen is an antigen of the cancer.

11. A method of treating a cancer in a subject in need thereof, comprising administering to the subject the pharmaceutical composition of claim 9, wherein the cancer antigen is an antigen of the cancer.

12. The cell of claim 5, wherein the cancer antigen is mesothelin.

13. The cell of claim 1, wherein the cell further recombinantly expresses a suicide gene.

14. The cell of claim 13, wherein the suicide gene comprises inducible Caspase 9.

15. The cell of claim 2, wherein the cancer antigen is selected from the group consisting of mesothelin, prostate specific membrane antigen (PSMA), prostate stem cell antigen (PCSA), carbonic anhydrase IX (CAIX), carcinoembryonic antigen (CEA), CD5, CD7, CD10, CD19, CD20, CD22, CD30, CD33, CD34, CD38, CD41, CD44, CD49f, CD56, CD74, CD123, CD133, CD138, epithelial glycoprotein2 (EGP 2), epithelial glycoprotein-40 (EGP-40), epithelial cell adhesion molecule (EpCAM), folate-binding protein (FBP), fetal acetylcholine receptor (AChR), folate receptor-α and β(FRα and β), Ganglioside G2 (GD2), Ganglioside G3 (GD3), human Epidermal Growth Factor Receptor 2 (HER-2/ERB2), Epidermal Growth Factor Receptor vIII (EGFRvIII), ERB3, ERB4, human telomerase reverse transcriptase (hTERT), Interleukin-13 receptor subunit alpha-2 (IL-13Rα2), K-light chain, kinase insert domain receptor (KDR), Lewis A (CA19.9), Lewis Y (LeY), L1 cell adhesion molecule (L1CAM), melanoma-associated antigen 1 (melanoma antigen family A1, MAGE-A1), Mucin 16 (Muc-16), Mucin 1 (Muc-1), NKG2D ligands, cancer-testis antigen NY-ESO-1, oncofetal antigen (h5T4), tumor-associated glycoprotein 72 (TAG-72), vascular endothelial growth factor R2 (VEGF-R2), Wilms tumor protein (WT-1), type 1 tyrosine-protein kinase transmembrane receptor (ROR1), B7-H3 (CD276), B7-H6 (Nkp30), Chondroitin sulfate proteoglycan-4 (CSPG4), DNAX Accessory Molecule (DNAM-1), Ephrin type A Receptor 2 (EpHA2), Fibroblast Associated Protein (FAP), Gp100/HLA-A2, Glypican 3 (GPC3), HA-1H, HERK-V, IL-11Rα, Latent Membrane Protein 1 (LMP1), Neural cell-adhesion molecule (N-CAM/CD56), and Trail Receptor (TRAIL R).

16. The cell of claim 15, wherein the cancer antigen is mesothelin.

17. The pharmaceutical composition of claim 9, wherein the cell is a T cell.

18. The pharmaceutical composition of claim 17, wherein the cancer antigen is selected from the group consisting of mesothelin, prostate specific membrane antigen (PSMA), prostate stem cell antigen (PCSA), carbonic anhydrase IX (CAIX), carcinoembryonic antigen (CEA), CD5, CD7, CD10, CD19, CD20, CD22, CD30, CD33, CD34, CD38, CD41, CD44, CD49f, CD56, CD74, CD123, CD133, CD138, epithelial glycoprotein2 (EGP 2), epithelial glycoprotein-40 (EGP-40), epithelial cell adhesion molecule (EpCAM), folate-binding protein (FBP), fetal acetylcholine receptor (AChR), folate receptor-α and β(FRα and β), Ganglioside G2 (GD2), Ganglioside G3 (GD3), human Epidermal Growth Factor Receptor 2 (HER-2/ERB2), Epidermal Growth Factor Receptor vIII (EGFRvIII), ERB3, ERB4, human telomerase reverse transcriptase (hTERT), Interleukin-13 receptor subunit alpha-2 (IL-13Rα2), K-light chain, kinase insert domain receptor (KDR), Lewis A (CA19.9), Lewis Y (LeY), L1 cell adhesion molecule (L1CAM), melanoma-associated antigen 1 (melanoma antigen family A1, MAGE-A1), Mucin 16 (Muc-16), Mucin 1 (Muc-1), NKG2D ligands, cancer-testis antigen NY-ESO-1, oncofetal antigen (h5T4), tumor-associated glycoprotein 72 (TAG-72), vascular endothelial growth factor R2(VEGF-R2), Wilms tumor protein (WT-1), type 1 tyrosine-protein kinase transmembrane receptor (ROR1), B7-H3 (CD276), B7-H6 (Nkp30), Chondroitin sulfate proteoglycan-4 (CSPG4), DNAX Accessory Molecule (DNAM-1), Ephrin type A Receptor 2 (EpHA2), Fibroblast Associated Protein (FAP), Gp100/HLA-A2, Glypican 3 (GPC3), HA-1H, HERK-V, IL-11Rα, Latent Membrane Protein 1 (LMP1), Neural cell-adhesion molecule (N-CAM/CD56), and Trail Receptor (TRAIL R).

19. The cell of claim 13, wherein the cell is a T cell.

20. The pharmaceutical composition of claim 18, wherein the cancer antigen is mesothelin.

21. The cell of claim 8, wherein the cell is a T cell.

22. The pharmaceutical composition of claim 20, wherein the cell is a cytotoxic T lymphocyte (CTL).

23. A method of treating a cancer in a subject in need thereof, comprising administering to the subject a therapeutically effective amount of the cell of claim 2, wherein the cancer antigen is an antigen of the cancer.

24. A method of treating a cancer in a subject in need thereof, comprising administering to the subject a therapeutically effective amount of the cell of claim 5, wherein the cancer antigen is an antigen of the cancer.

25. A method of treating a cancer in a subject in need thereof, comprising administering to the subject a therapeutically effective amount of the cell of claim 3, wherein the cancer antigen is an antigen of the cancer.

26. A method of treating a cancer in a subject in need thereof, comprising administering to the subject a therapeutically effective amount of the cell of claim 4, wherein the cancer antigen is an antigen of the cancer.

27. A method of treating a cancer in a subject in need thereof, comprising administering to the subject a therapeutically effective amount of the cell of claim 6, wherein the cancer antigen is an antigen of the cancer.

28. A method of treating a cancer in a subject in need thereof, comprising administering to the subject a therapeutically effective amount of the cell of claim 8, wherein the cancer antigen is an antigen of the cancer.

29. The method of claim 28, wherein the cell is a T cell.

30. The method of claim 29, wherein the cell is a cytotoxic T lymphocyte (CTL).

31. The cell of claim 1, wherein the CD8 transmembrane domain is fused to CD8 hinge domain.

32. The cell of claim 1, wherein the cell is transduced with one or more nucleic acids encoding the CAR and the dominant negative form, wherein the encoded dominant negative form comprises amino acids 1-151 of SEQ ID NO:33.

33. The cell of claim 1, wherein the cell is transduced with one or more nucleic acids encoding the CAR and the dominant negative form, wherein the encoded dominant negative form comprises amino acids 1-165 of SEQ ID NO:33.

34. The cell of claim 1, wherein the cell is transduced with one or more nucleic acids encoding the CAR and the dominant negative form, wherein the encoded dominant negative form comprises the sequence of SEQ ID NO:43.

35. The cell of claim 1, wherein the sequence of the extracellular domain of the dominant negative form in mature form lacking a signal peptide consists of amino acids 21-165 of SEQ ID NO:33.

36. The cell of claim 1, wherein the dominant negative form comprises amino acids 21-244 of SEQ ID NO:43.

37. The cell of claim 1, wherein the sequence of the dominant negative form in mature form lacking a signal peptide consists of amino acids 21-244 of SEQ ID NO:43.

38. The cell of claim 31, wherein the cell is a T cell.
39. The cell of claim 34, wherein the cell is a T cell.
40. The cell of claim 36, wherein the cell is a T cell.
41. The cell of claim 37, wherein the cell is a T cell.
42. A pharmaceutical composition comprising a therapeutically effective amount of the cell of claim 31; and a pharmaceutically acceptable carrier.
43. A pharmaceutical composition comprising a therapeutically effective amount of the cell of claim 34; and a pharmaceutically acceptable carrier.
44. A pharmaceutical composition comprising a therapeutically effective amount of the cell of claim 36; and a pharmaceutically acceptable carrier.
45. A pharmaceutical composition comprising a therapeutically effective amount of the cell of claim 37; and a pharmaceutically acceptable carrier.
46. A method of treating a cancer in a subject in need thereof, comprising administering to the subject a therapeutically effective amount of the cell of claim 39, wherein the cancer antigen is an antigen of the cancer.
47. A method of treating a cancer in a subject in need thereof, comprising administering to the subject a therapeutically effective amount of the cell of claim 34, wherein the cancer antigen is an antigen of the cancer.
48. A method of treating a cancer in a subject in need thereof, comprising administering to the subject a therapeutically effective amount of the cell of claim 36, wherein the cancer antigen is an antigen of the cancer.
49. A method of treating a cancer in a subject in need thereof, comprising administering to the subject a therapeutically effective amount of the cell of claim 37, wherein the cancer antigen is an antigen of the cancer.
50. The cell of claim 34, wherein the cancer antigen is selected from the group consisting of mesothelin, prostate specific membrane antigen (PSMA), prostate stem cell antigen (PCSA), carbonic anhydrase IX (CAIX), carcinoembryonic antigen (CEA), CDS, CD7, CD10, CD19, CD20, CD22, CD30, CD33, CD34, CD38, CD41, CD44, CD49f, CD56, CD74, CD123, CD133, CD138, epithelial glycoprotein2 (EGP 2), epithelial glycoprotein-40 (EGP-40), epithelial cell adhesion molecule (EpCAM), folate-binding protein (FBP), fetal acetylcholine receptor (AChR), folate receptor-α and β(FRα and β), Ganglioside G2 (GD2), Ganglioside G3 (GD3), human Epidermal Growth Factor Receptor 2 (HER-2/ERB2), Epidermal Growth Factor Receptor vIII (EGFRvIII), ERB3, ERB4, human telomerase reverse transcriptase (hTERT), Interleukin-13 receptor subunit alpha-2 (IL-13Rα2), κ-light chain, kinase insert domain receptor (KDR), Lewis A (CA19.9), Lewis Y (LeY), L1 cell adhesion molecule (L1CAM), melanoma-associated antigen 1 (melanoma antigen family A1, MAGE-A1), Mucin 16 (Muc-16), Mucin 1 (Muc-1), NKG2D ligands, cancer-testis antigen NY-ESO-1, oncofetal antigen (h5T4), tumor-associated glycoprotein 72 (TAG-72), vascular endothelial growth factor R2(VEGF-R2), Wilms tumor protein (WT-1), type 1 tyrosine-protein kinase transmembrane receptor (ROR1), B7-H3 (CD276), B7-H6 (Nkp30), Chondroitin sulfate proteoglycan-4 (CSPG4), DNAX Accessory Molecule (DNAM-1), Ephrin type A Receptor 2 (EphA2), Fibroblast Associated Protein (FAP), Gp100/HLA-A2, Glypican 3 (GPC3), HA-1H, HERK-V, IL-11Rα, Latent Membrane Protein 1 (LMP1), Neural cell-adhesion molecule (N-CAM/CD56), and Trail Receptor (TRAIL R).

51. The cell of claim 50, wherein the cancer antigen is mesothelin.

52. A pharmaceutical composition comprising a therapeutically effective amount of the cell of claim 2; and a pharmaceutically acceptable carrier.

53. A pharmaceutical composition comprising a therapeutically effective amount of the cell of claim 3; and a pharmaceutically acceptable carrier.

54. A pharmaceutical composition comprising a therapeutically effective amount of the cell of claim 4; and a pharmaceutically acceptable carrier.

55. A pharmaceutical composition comprising a therapeutically effective amount of the cell of claim 6; and a pharmaceutically acceptable carrier.

56. A pharmaceutical composition comprising a therapeutically effective amount of the cell of claim 8; and a pharmaceutically acceptable carrier.

57. A method of treating a cancer in a subject in need thereof, comprising administering to the subject a therapeutically effective amount of the cell of claim 50, wherein the cancer antigen is an antigen of the cancer.

58. A method of treating a cancer in a subject in need thereof, comprising administering to the subject a therapeutically effective amount of the cell of claim 51, wherein the cancer antigen is an antigen of the cancer.

* * * * *